US012390146B2

(12) United States Patent
Neitz et al.

(10) Patent No.: US 12,390,146 B2
(45) Date of Patent: Aug. 19, 2025

(54) REAGENTS AND METHODS FOR MODULATING CONE PHOTORECEPTOR ACTIVITY

(71) Applicants: UNIVERSITY OF FLORIDA RESEARCH FOUNDATION, INCORPORATED, Gainesville, FL (US); UNIVERSITY OF WASHINGTON, Seattle, WA (US)

(72) Inventors: Jay Neitz, Seattle, WA (US); Maureen Neitz, Seattle, WA (US); James A. Kuchenbecker, Seattle, WA (US); William W. Hauswirth, Gainesville, FL (US)

(73) Assignees: UNIVERSITY OF WASHINGTON, Seattle, WA (US); UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 948 days.

(21) Appl. No.: 17/500,426

(22) Filed: Oct. 13, 2021

(65) Prior Publication Data

US 2022/0183613 A1 Jun. 16, 2022

Related U.S. Application Data

(63) Continuation of application No. 15/939,674, filed on Mar. 29, 2018, now Pat. No. 11,160,488, which is a continuation of application No. 14/837,448, filed on Aug. 27, 2015, now abandoned, which is a continuation of application No. 14/075,415, filed on Nov. 8, 2013, now Pat. No. 9,198,595, which is a continuation of application No. 13/395,609, filed as application No. PCT/US2010/048964 on Sep. 15, 2010, now abandoned.

(60) Provisional application No. 61/242,587, filed on Sep. 15, 2009.

(51) Int. Cl.

| | |
|---|---|
| ***C12N 15/86*** | (2006.01) |
| ***A61B 5/00*** | (2006.01) |
| ***A61B 5/398*** | (2021.01) |
| ***A61K 48/00*** | (2006.01) |
| ***A61N 5/06*** | (2006.01) |
| ***C07K 14/005*** | (2006.01) |
| ***C12N 7/00*** | (2006.01) |
| ***C12N 15/85*** | (2006.01) |

(52) U.S. Cl.

CPC ............ *A61B 5/398* (2021.01); *A61B 5/0036* (2018.08); *A61B 5/0048* (2013.01); *A61B 5/4836* (2013.01); *A61B 5/4848* (2013.01); *A61B 5/6821* (2013.01); *A61B 5/7225* (2013.01); *A61K 48/0058* (2013.01); *A61K 48/0075* (2013.01); *A61N 5/0622* (2013.01); *C07K 14/005* (2013.01); *C12N 7/00* (2013.01); *C12N 15/85* (2013.01); *C12N 15/86* (2013.01); *A61N 2005/0652* (2013.01); *A61N 2005/0661* (2013.01); *A61N 2005/0663* (2013.01); *C12N 2750/14132* (2013.01); *C12N 2750/14143* (2013.01); *C12N 2799/025* (2013.01); *C12N 2830/008* (2013.01); *C12N 2830/42* (2013.01); *C12N 2840/44* (2013.01)

(58) Field of Classification Search

CPC ........ C07K 14/005; C12N 7/00; C12N 15/85; C12N 15/86

See application file for complete search history.

(56) References Cited

U.S. PATENT DOCUMENTS

| | | | |
|---|---|---|---|
| 4,874,237 | A | 10/1989 | Cringle |
| 5,436,146 | A | 7/1995 | Shenk et al. |
| 5,753,500 | A | 5/1998 | Shenk et al. |
| 6,040,183 | A | 3/2000 | Ferrari et al. |
| 6,093,570 | A | 7/2000 | Ferrari et al. |
| 6,153,436 | A | 11/2000 | Hermonat et al. |
| 6,482,634 | B1 | 11/2002 | Wilson et al. |
| 6,548,286 | B1 | 4/2003 | Samulski et al. |
| 7,972,278 | B2 | 7/2011 | Graham et al. |
| 8,075,137 | B2 | 12/2011 | Klistorner et al. |
| 8,118,752 | B2 | 2/2012 | Hetling et al. |
| 8,343,067 | B2 | 1/2013 | Jones et al. |
| 9,198,595 | B2 | 12/2015 | Neitz et al. |
| 2002/0168342 | A1 | 11/2002 | Wang et al. |
| 2007/0188710 | A1 | 8/2007 | Hetling et al. |
| 2009/0128776 | A1 | 5/2009 | Keating et al. |
| 2010/0091242 | A1 | 4/2010 | Baglini et al. |
| 2011/0001465 | A1 | 1/2011 | Sung et al. |
| 2011/0116046 | A1 | 5/2011 | Haeri et al. |
| 2012/0172419 | A1 | 7/2012 | Neitz et al. |

(Continued)

FOREIGN PATENT DOCUMENTS

| | | |
|---|---|---|
| JP | 2002363107 | 12/2002 |
| JP | 2002363107 A | 12/2002 |

(Continued)

OTHER PUBLICATIONS

Mancuso, et al., (2005) Annual Meeting of the Association for Research in Vision and Ophthalmology, Ft. Lauderdale, FL, 46(Supp S): 4565.

(Continued)

*Primary Examiner* — Evelyn Y Pyla
*Assistant Examiner* — Katherine R Small
(74) *Attorney, Agent, or Firm* — MCDONNELL BOEHNEN HULBERT & BERGHOFF LLP

(57) ABSTRACT

The present invention provides reagents and methods for modulating cone photoreceptor activity, and devices for assessment of cone photoreceptor activity.

10 Claims, 8 Drawing Sheets

Specification includes a Sequence Listing.

(56) References Cited

U.S. PATENT DOCUMENTS

2013/0031709 A1 2/2013 Chen et al.
2015/0025939 A1 1/2015 Chatterjee et al.

FOREIGN PATENT DOCUMENTS

WO 02/082904 10/2002
WO 2015/142941 9/2015
WO 2015/142941 A1 9/2015

OTHER PUBLICATIONS

Mancuso, et al. (2007) Journal of Optical Society of America A: Optics and Image Science and Vision, 24(5):1411-1416.
Mauck, et al. (2008) Visual Neurosceince, 25(3):273-282.
Li, et al. (2008) Cone-specific expression using a human red opsin promoter in recombinant AAV, Vision Research, 48(3):332-338.
Kuchenbecker, et al. (2008) Visual Neurosceince, 25 (3): 301-306.
Cai, et al., (2010) FASEB Journal, 24(4): 1178-1191.
Komaromy, et al. (2010) Human Molecular Genetics, 19(13): 2581-2593.
Mancuso, et al., (2009) Nature, 461(7265): 784.
Pang, et al. (2006) Molecular Therapy, 13(3): 565-572.
Lai, et al. (2007) Survey of ophthalmology, 52(1): 61-96.
Sutter, E. E. (1991). The Fast m-Transform: A Fast Computation of Cross-Correlations with Binary m-Sequences. SIAM Journal on Computing, 20(4),686-694.
Swanson, W. H., Ueno, T., Smith, V. C., & Pokorny, J. (1987). Temporal modulation sensitivity and pulse-detection thresholds for chromatic and luminance perturbations. Journal of the Optical Society of America A-Optics, Image Science and Vision, 4(10), 13.
Lindenberg, T., Horn, F. K., & Korth, M. (2003). Cyclic summation versus m-sequence technique in the multifocal ERG. Graefes Archive of Clinical Experimental Ophthalmology., 241(6),505-510.
Wiesel, T.N. & Hubel, D.H. Single-cell responses in striate cortex of kittens deprived of vision in one eye. J Neurophysiol. 26, 1003-1017 (1963).
Jacobs, G.H. A perspective on color vision in platyrrhine monkeys. Vision Res. 38, 3307-3313 (1998).
Reffin, J.P., Astell, S. & Mollon, J.D. Trials of a computer-controlled colour vision test that preserves the advantages of pseudo-isochromatic plates. in Colour Vision Deficiencies X69-76 (Kluwer Academic Publishers, Dordrecht, 1991).
Regan, B.C., Reffin, J.P. & Mollon, J.D. Luminance noise and the rapid determination of discrimination ellipses in colour deficiency. Vision Res. 34, 1279-1299 (1994).
Mancuso, K., Neitz, M. & Neitz, J. An adaptation of the Cambridge Colour Test for use with animals. Vis. Neurosci. (2006).
Nathans, J., Piantanida, T.P., Eddy, R.L., Shows, T.B. & Hogness, D.S. Molecular genetics of inherited variation in human color vision. Science 232, 203-210 (1986).
Shapley, R. Specificity of cone connections in the retina and color vision. Focus on "Specificity of cone inputs to macaque retinal ganglion cells". J Neurophysiol. 95, 587-588 (2006).
DeValois, R.L. & DeValois, K.K. A multi-stage color model. Vision Res. 33, 1053-1065 (1993).
Jacobs, G.H., Williams, G.A., Cahill, H. & Nathans, J. Emergence of Novel Color Vision in Mice Engineered to Express a Human Cone Photopigment. Science 315, 1723-1725 (2007).
Makous, W. Comment on "Emergence of Novel Color Vision in Mice Engineered to Express a Human Cone Photopigment". Science 318, 196 (2007).
Maguire, A.M. et al. Safety and efficacy of gene transfer for Leber's congenital amaurosis. N. Engl. J Med. 358, 2240-2248 (2008).
Bainbridge, J.W. & Ali, R.R. Success in sight: The eyes have it! Ocular gene therapy trials for LCA look promising. Gene Ther. 15, 1191-1192 (2008).
Cideciyan, A.V. et al. Human gene therapy for RPE65 isomerase deficiency activates the retinoid cycle of vision but with slow rod kinetics. Proc. Natl. Acad. Sci. USA 105, 15112-15117 (2008).
Wang, Y. et al. A locus control region adjacent to the human red and green visual pigment genes. Neuron 9, 429-440 (1992).
Nathans, J., Thomas, D. & Hogness, D.S. Molecular genetics of human color vision: the genes encoding blue, green, and red pigments. Science 232, 193-202 (1986).
Neitz, M., Neitz, J. & Jacobs, G.H. Spectral tuning of pigments underlying red green color vision. Science 252, 971-974 (1991).
Buning, H., Perabo, L., Coutelle, 0., Quadt-Humme, S. & Hallek, M. Recent developments in adeno-associated virus vector technology. J Gene Med. 10, 717-733 (2008).
ISR PCT/US2010/048964, mailed Jun. 17, 2011.
Mauck, et al. "Longitudinal in vivo Characterization of Expression of Viral Delivered Genes for L-opsin and Green Fluorescent Protein in Cone Photoreceptors of Gerbils," Invest Opthalmol Vis Sci 2006, 47:E-abstract 4071.
Mancuso, et al., "Colorblindness Cure: Gene Therapy Confers a New Sensation," Invest Opthalmol Vis Sci 2008, 49: E-abstract 3252.
International Search Report for PCT/US15/21087, mailed Aug. 12, 2015.
Written Opinion of the International Search Authority for PCT/US15/21087, mailed Aug. 12, 2015.
Alexander et al. (2007) "Restoration of cone vision in a mouse model of achromatopsia" Nature Medicine 13:685-687 [published online May 2007].
Chiu et al. (1994) "Blue cones and cone bipolar cells share transcriptional specificity as determined by expression of human blue visual pigment-derived transgenes" J. Neurosci. 14(6):3426-3436.
Glushakova et al. (2006) "Human Blue-Opsin Promoter Preferentially Targets Reporter Gene Expression to Rat S-Cone Photoreceptors" Invest. Opthalmol. Vis. Sci. 47:3505-3513.
Gunther et al. (2006) "A novel mutation in the short-wavelength-sensitive cone pigment gene associated with a tritan color vision defect" Vis. Neurosci. 23(3-4):403-409.
Komaromy et al. (2008) "Targeting gene expression to cones with human cone opsin promoters in recombinant AAV" Gene Therapy 15:1049-1055 [published online Mar. 13, 2008].
Shaaban et al. (1998) "Transgenic Mice Expressing a Functional Human Photopigment" Invest. Ophthalmol. Vis. Sci. 39:1036-1043.
Ueyama et al. (2009) "Analysis of introns and promoters of L/M visual pigment genes in relation to deutan color-vision deficiency with an array of normal gene orders" J. Hum. Genet. 54(9):525-530.
Khani et al., Inv. Opth. Vis. Sci. (2007) vol. 48(9), pp. 3954-3961.
Mancuso et al., 2007, [Abstract] Journal of Vision, vol. 7(15): 15a.
Khani et al., Inv. Opth. Vis. Sci. 2007, 48(9)3954-3961.
Mancuso et al., 2007, [Abstract] Journal of Vision, 7(15):15a.
International Search Report for PCTIUS15/21087, mailed Aug. 12, 2015.
Written Opinion of the International Search Authority for PCTIUS15/21087, mailed Aug. 12, 2015.
Gushakova et al. (2006) Human Blue-Opsin Promoter Preferentially Targets Reporter Gene Expression to Rat S-Cone Photoreceptorsn Invest. Opthalmol. Vis. Sci. 47:3505-3513.
Gunther et al. (2006) A novel mutation in the short-wavelength-sensitive cone pigment gene associated with a tritan color vision defecr Vis. Neurosci. 23(3-4):403-409.
Komaromy et al. (2008) "Targeting gene expression to cones with human cone opsin promoters in recombinant MV" Gene Therapy 15: 1049-1055 [published online Mar. 13, 2008].
Ueyama et al. (2009) "Analysis of intrans and promoters of LIM visual pigment genes in relation to deutan color-vision deficiency with an array of normal gene orders" J. Hum. Genet. 54(9):525-530.

| | | Typical SNR | Highest SNR |
|---|---|---|---|
| GRN | Ring 2 | 82.98129 | 139.6429 |
| | Ring 3 | 34.42575 | 47.00658 |
| | Ring 4 | 33.5582 | 49.9321 |
| | | | |
| RED | Ring 2 | 47.16825 | 87.55556 |
| | Ring 3 | 20.84694 | 34.38312 |
| | Ring 4 | 16.75357 | 20.45714 |

SEQUENCE LISTING

```
<160> NUMBER OF SEQ ID NOS: 51

<210> SEQ ID NO 1
<211> LENGTH: 494
<212> TYPE: DNA
<213> ORGANISM: Artificial Sequence
<220> FEATURE:
<223> OTHER INFORMATION: Synthetic

<400> SEQUENCE: 1

ggatccggtt ccaggcctcg gccctaaata gtctccctgg gctttcaaga gaaccacatg      60

agaaaggagg attcgggctc tgagcagttt caccacccac cccccagtct gcaaatcctg     120

acccgtgggt ccacctgccc caaaggcgga cgcaggacag tagaagggaa cagagaacac     180

ataaacacag agagggccac agcggctccc acagtcaccg ccaccttcct ggcggggatg     240

ggtggggcgt ctgagtttgg ttcccagcaa atccctctga gccgcccttg cgggctcgcc     300

tcaggagcag gggagcaaga ggtgggagga ggaggtctaa gtcccaggcc caattaagag     360

atcaggtagt gtagggtttg ggagctttta aggtgaagag gcccgggctg atcccacagg     420

ccagtataaa gcgccgtgac cctcaggtga tgcgccaggg ccggctgccg tcggggacag     480

ggctttccat agcc                                                       494


<210> SEQ ID NO 2
<211> LENGTH: 494
<212> TYPE: DNA
<213> ORGANISM: Artificial Sequence
<220> FEATURE:
<223> OTHER INFORMATION: Synthetic

<400> SEQUENCE: 2

ttatttagta gaaacggggt ttcaccatgt tagtcaggct ggtcgggaac tcctgacctc      60

aggagatcta cccgccttgg cctcccaaag tgctgggatt acaggcgtgt gccactgtgc     120

ccagccactt ttttttagac agagtcttgg tctgttgccc aggctagagt tcagtggcgc     180

catctcagct cactgcaacc tccgcctccc agattcaagc gattctcctg cctcgacctc     240

ccagtagctg ggattacagg tttccagcaa atccctctga gccgcccccg gggctcgcc      300

tcaggagcaa ggaagcaagg ggtgggagga ggaggtctaa gtcccaggcc caattaagag     360

atcagatggt gtaggatttg ggagctttta aggtgaagag gcccgggctg atcccactgg     420
```

```
ccggtataaa gcaccgtgac cctcaggtga cgcaccaggg ccggctgccg tcggggacag    480

ggctttccat agcc                                                      494


<210> SEQ ID NO 3
<211> LENGTH: 568
<212> TYPE: DNA
<213> ORGANISM: Artificial Sequence
<220> FEATURE:
<223> OTHER INFORMATION: Synthetic

<400> SEQUENCE: 3

ctaggcattg tcaagttgcc taagtcctgt tccatcaagg ctgtttactg atgtgcttcc     60

agggcactcc ccactcccag ccctttcctg cagcccaggg ctggttccta gcctctcagc    120

agacttaaga tgggcacctt ccacaaaggg gcagatgagt tgaggaaaac ttaactgata    180

cagttgtgcc agaagccaaa ataagaggcg tgccctttct atagccccat taaaagaaca    240

aaaaagtgga agcatcttca gtgaatatgg gtcagcacct cccagacctc agggagtcca    300

cttctgttca tcccagcacc cagcattgca tatccagatt atttgagccc aatctcttat    360

cctctgaaga acacaatcgg ctttggggcc acaaaaggtt taggtagtgg tttagggatt    420

tctaatccca aactttgtcc ttgggaggtt taggattagt attgatcatt cacagagccc    480

aagtgttttt agaggagggg ttttgtgggg tgggaggatc acctataaga ggactcagag    540

gggggtgtgg ggcatccatg agaaaaat                                       568


<210> SEQ ID NO 4
<211> LENGTH: 1555
<212> TYPE: DNA
<213> ORGANISM: Artificial Sequence
<220> FEATURE:
<223> OTHER INFORMATION: Synthetic

<400> SEQUENCE: 4

ccagggtgag attatgaggc tgagctgaga atatcaagac tgtaccgagt agggggcctt     60

ggcaagtgtg gagagcccgg cagctggggc agagggcgga gtacggtgtg cgtttacgga    120

cctcttcaaa cgaggtagga aggtcagaag tcaaaaaggg aacaaatgat gtttaaccac    180

acaaaaatga aaatccaatg gttggatatc cattccaaat acacaaaggc aacggataag    240

tgatccgggc caggcacaga aggccatgca cccgtaggat tgcactcaga gctcccaaat    300

gcataggaat agaagggtgg gtgcaggagg ctgaggggtg gggaaagggc atgggtgttt    360

catgaggaca gagcttccgt ttcatgcaat gaaaagagtt tggagacgga tggtggtgac    420

tggactatac acttacacac ggtagcgatg gtacactttg tattatgtat attttaccac    480

gatcttttta aagtgtcaaa ggcaaatggc caaatggttc cttgtcctat agctgtagca    540

gccatcggct gttagtgaca aagcccctga gtcaagatga cagcagcccc cataactcct    600

aatcggctct cccgcgtgga gtcatttagg agtagtcgca ttagagacaa gtccaacatc    660

taatcttcca ccctggccag ggccccagct ggcagcgagg gtgggagact ccgggcagag    720

cagagggcgc tgacattggg gcccggcctg gcttgggtcc ctctggcctt tccccagggg    780

ccctctttcc ttggggcttt cttgggccgc cactgctccc gctcctctcc ccccatccca    840

ccccctcacc ccctcgttct tcatatcctt ctctagtgct ccctccactt tcatccaccc    900

ttctgcaaga gtgtgggacc acaaatgagt tttcacctgg cctggggaca cacgtgcccc    960

cacaggtgct gagtgacttt ctaggacagt aatctgcttt aggctaaaat gggacttgat   1020
```

```
cttctgttag ccctaatcat caattagcag agccggtgaa ggtgcagaac ctaccgcctt   1080

tccaggcctc ctcccacctc tgccacctcc actctccttc ctgggatgtg ggggctggca   1140

cacgtgtggc ccagggcatt ggtgggattg cactgagctg ggtcattagc gtaatcctgg   1200

acaagggcag acagggcgag cggagggcca gctccggggc tcaggcaagg ctgggggctt   1260

cccccagaca ccccactcct cctctgctgg acccccactt catagggcac ttcgtgttct   1320

caaagggctt ccaaatagca tggtggcctt ggatgcccag ggaagcctca gagttgctta   1380

tctccctcta gacagaaggg gaatctcggt caagagggag aggtcgccct gttcaaggcc   1440

acccagccag ctcatggcgg taatgggaca aggctggcca gccatcccac cctcagaagg   1500

gacccggtgg ggcaggtgat ctcagaggag gctcacttct gggtctcaca ttctt        1555
```

<210> SEQ ID NO 5
<211> LENGTH: 189
<212> TYPE: DNA
<213> ORGANISM: Artificial Sequence
<220> FEATURE:
<223> OTHER INFORMATION: Synthetic

<400> SEQUENCE: 5

```
gatccggtac tcgaggaact gaaaaaccag aaagttaact ggtaagttta gtctttttgt     60

cttttatttc aggtcccgga tccggtggtg gtgcaaatca aagaactgct cctcagtgga    120

tgttgccttt acttctaggc ctgtacggaa gtgttacttc tgctctaaaa gctgcggaat    180

tgtacccgc                                                            189
```

<210> SEQ ID NO 6
<211> LENGTH: 1114
<212> TYPE: DNA
<213> ORGANISM: Homo sapiens

<400> SEQUENCE: 6

```
atgagaaaaa tgtcggagga agagttttat ctgttcaaaa atatctcttc agtggggccg     60

tgggatgggc ctcagtacca cattgcccct gtctgggcct tctacctcca ggcagctttc    120

atgggcactg tcttccttat agggttccca ctcaatgcca tggtgctggt ggccacactg    180

cgctacaaaa agttgcggca gcccctcaac tacattctgg tcaacgtgtc cttcggaggc    240

ttcctcctct gcatcttctc tgtcttccct gtcttcgtcg ccagctgtaa cggatacttc    300

gtcttcggtc gccatgtttg tgctttggag ggcttcctgg gcactgtagc aggtctggtt    360

acaggatggt cactggcctt cctggccttt gagcgctaca ttgtcatctg taagcccttc    420

ggcaacttcc gcttcagctc caagcatgca ctgacggtgg tcctggctac ctggaccatt    480

ggtattggcg tctccatccc acccttcttt ggctggagcc ggttcatccc tgagggcctg    540

cagtgttcct gtggccctga ctggtacacc gtgggcacca aataccgcag cgagtcctat    600

acgtggttcc tcttcatctt ctgcttcatt gtgcctctct ccctcatctg cttctcctac    660

actcagctgc tgagggccct gaaagctgtt gcagctcagc agcaggagtc agctacgacc    720

cagaaggctg aacgggaggt gagccgcatg gtggttgtga tggtaggatc cttctgtgtc    780

tgctacgtgc cctacgcggc cttcgccatg tacatggtca acaaccgtaa ccatgggctg    840

gacttacggc ttgtcaccat tccttcattc ttctccaaga gtgcttgcat ctacaatccc    900

atcatctact gcttcatgaa taagcagttc caagcttgca tcatgaagat ggtgtgtggg    960

aaggccatga cagatgaatc cgacacatgc agctcccaga aaacagaagt ttctactgtc   1020

tcgtctaccc aagttggccc caactgagga cccaatattg gcctgtttgc aacagctaga   1080
```

attaaatttt acttttaaaa aaaaaaaaaa aaaa 1114

<210> SEQ ID NO 7
<211> LENGTH: 348
<212> TYPE: PRT
<213> ORGANISM: Homo sapiens

<400> SEQUENCE: 7

Met Arg Lys Met Ser Glu Glu Glu Phe Tyr Leu Phe Lys Asn Ile Ser
1 5 10 15

Ser Val Gly Pro Trp Asp Gly Pro Gln Tyr His Ile Ala Pro Val Trp
20 25 30

Ala Phe Tyr Leu Gln Ala Ala Phe Met Gly Thr Val Phe Leu Ile Gly
35 40 45

Phe Pro Leu Asn Ala Met Val Leu Val Ala Thr Leu Arg Tyr Lys Lys
50 55 60

Leu Arg Gln Pro Leu Asn Tyr Ile Leu Val Asn Val Ser Phe Gly Gly
65 70 75 80

Phe Leu Leu Cys Ile Phe Ser Val Phe Pro Val Phe Val Ala Ser Cys
85 90 95

Asn Gly Tyr Phe Val Phe Gly Arg His Val Cys Ala Leu Glu Gly Phe
100 105 110

Leu Gly Thr Val Ala Gly Leu Val Thr Gly Trp Ser Leu Ala Phe Leu
115 120 125

Ala Phe Glu Arg Tyr Ile Val Ile Cys Lys Pro Phe Gly Asn Phe Arg
130 135 140

Phe Ser Ser Lys His Ala Leu Thr Val Val Leu Ala Thr Trp Thr Ile
145 150 155 160

Gly Ile Gly Val Ser Ile Pro Pro Phe Phe Gly Trp Ser Arg Phe Ile
165 170 175

Pro Glu Gly Leu Gln Cys Ser Cys Gly Pro Asp Trp Tyr Thr Val Gly
180 185 190

Thr Lys Tyr Arg Ser Glu Ser Tyr Thr Trp Phe Leu Phe Ile Phe Cys
195 200 205

Phe Ile Val Pro Leu Ser Leu Ile Cys Phe Ser Tyr Thr Gln Leu Leu
210 215 220

Arg Ala Leu Lys Ala Val Ala Ala Gln Gln Gln Glu Ser Ala Thr Thr
225 230 235 240

Gln Lys Ala Glu Arg Glu Val Ser Arg Met Val Val Val Met Val Gly
245 250 255

Ser Phe Cys Val Cys Tyr Val Pro Tyr Ala Ala Phe Ala Met Tyr Met
260 265 270

Val Asn Asn Arg Asn His Gly Leu Asp Leu Arg Leu Val Thr Ile Pro
275 280 285

Ser Phe Phe Ser Lys Ser Ala Cys Ile Tyr Asn Pro Ile Ile Tyr Cys
290 295 300

Phe Met Asn Lys Gln Phe Gln Ala Cys Ile Met Lys Met Val Cys Gly
305 310 315 320

Lys Ala Met Thr Asp Glu Ser Asp Thr Cys Ser Ser Gln Lys Thr Glu
325 330 335

Val Ser Thr Val Ser Ser Thr Gln Val Gly Pro Asn
340 345

<210> SEQ ID NO 8

<211> LENGTH: 1998
<212> TYPE: DNA
<213> ORGANISM: Homo sapiens

<400> SEQUENCE: 8

```
cccactggcc ggtataaagc accgtgaccc tcaggtgacg caccagggcc ggctgccgtc     60
ggggacaggg ctttccatag ccatggccca gcagtggagc ctccaaaggc tcgcaggccg    120
ccatccgcag gacagctatg aggacagcac ccagtccagc atcttcacct acaccaacag    180
caactccacc agaggcccct tcgaaggccc gaattaccac atcgctccca gatgggtgta    240
ccacctcacc agtgtctgga tgatctttgt ggtcattgca tccgtcttca caaatgggct    300
tgtgctggcg gccaccatga agttcaagaa gctgcgccac ccgctgaact ggatcctggt    360
gaacctggcg gtcgctgacc tggcagagac cgtcatcgcc agcactatca gcgttgtgaa    420
ccaggtctat ggctacttcg tgctgggcca ccctatgtgt gtcctggagg gctacaccgt    480
ctccctgtgt gggatcacag gtctctggtc tctggccatc atttcctggg agagatggat    540
ggtggtctgc aagccctttg gcaatgtgag atttgatgcc aagctggcca tcgtgggcat    600
tgccttctcc tggatctggg ctgctgtgtg gacagccccg cccatctttg gttggagcag    660
gtactggccc cacggcctga agacttcatg cggcccagac gtgttcagcg gcagctcgta    720
ccccggggtg cagtcttaca tgattgtcct catggtcacc tgctgcatca ccccactcag    780
catcatcgtg ctctgctacc tccaagtgtg gctggccatc cgagcggtgg caaagcagca    840
gaaagagtct gaatccaccc agaaggcaga gaaggaagtg acgcgcatgg tggtggtgat    900
ggtcctggca ttctgcttct gctggggacc atacgccttc ttcgcatgct ttgctgctgc    960
caaccctggc taccccttcc accctttgat ggctgccctg ccggccttct ttgccaaaag   1020
tgccactatc tacaaccccg ttatctatgt ctttatgaac cggcagtttc gaaactgcat   1080
cttgcagctt ttcgggaaga aggttgacga tggctctgaa ctctccagcg cctccaaaac   1140
ggaggtctca tctgtgtcct cggtatcgcc tgcatgaggt ctgcctccta cccatcccgc   1200
ccaccggggc tttggccacc tctcctttcc ccctccttct ccatccctgt aaaataaatg   1260
taatttatct ttgccaaaac caacaaagtc acagaggctt tcactgcagt gtgggaccac   1320
ctgagcctct gcgtgtgcag gcactgggtc tcgagagggt gcaaggggga taaagaggag   1380
agagcgcttc atagacttta agttttcccg agcctcatgt ctaccgatgg cgtgaaagga   1440
tcctggcaaa acagaagtgt gaggcaggtg ggcgtctata tccatttcac caggctggtg   1500
gttacataat cggcaagcaa gagctgtgga ggggcttgct ggatgccctc agcacccagg   1560
aggagggagg gagctagcaa gctaaggcag gtggccctcc tggcccctta aggtccatct   1620
gctggaggcc cagagtcctt ggagtacagt ctacacctgg aggggaccca ttcctgccag   1680
tctgtggcag ggatggcgcg ccacctctgc caggccagga ccccaagccc gatcagcatc   1740
agcatggtgc aggtgcacag gcgtgagctg atcagtgacg aggggcaggc acacaaggtg   1800
gagacaaaga ccaagaggac ggttgccagt gagaggcgcg gactcaggaa cttgaacaac   1860
atctgcgggg gacggctttg gaggtgctcc gctgcctcca gttgggtgac ttgctgtagc   1920
atctccagct tggatattcg gctcttgaag gtctccgtga tctcctgcag gagacgaaaa   1980
tgcacgcacc agaagtca                                                 1998
```

<210> SEQ ID NO 9
<211> LENGTH: 364
<212> TYPE: PRT
<213> ORGANISM: Homo sapiens

<400> SEQUENCE: 9

```
Met Ala Gln Gln Trp Ser Leu Gln Arg Leu Ala Gly Arg His Pro Gln
1               5                   10                  15

Asp Ser Tyr Glu Asp Ser Thr Gln Ser Ser Ile Phe Thr Tyr Thr Asn
            20                  25                  30

Ser Asn Ser Thr Arg Gly Pro Phe Glu Gly Pro Asn Tyr His Ile Ala
        35                  40                  45

Pro Arg Trp Val Tyr His Leu Thr Ser Val Trp Met Ile Phe Val Val
    50                  55                  60

Ile Ala Ser Val Phe Thr Asn Gly Leu Val Leu Ala Ala Thr Met Lys
65                  70                  75                  80

Phe Lys Lys Leu Arg His Pro Leu Asn Trp Ile Leu Val Asn Leu Ala
                85                  90                  95

Val Ala Asp Leu Ala Glu Thr Val Ile Ala Ser Thr Ile Ser Val Val
            100                 105                 110

Asn Gln Val Tyr Gly Tyr Phe Val Leu Gly His Pro Met Cys Val Leu
        115                 120                 125

Glu Gly Tyr Thr Val Ser Leu Cys Gly Ile Thr Gly Leu Trp Ser Leu
    130                 135                 140

Ala Ile Ile Ser Trp Glu Arg Trp Met Val Val Cys Lys Pro Phe Gly
145                 150                 155                 160

Asn Val Arg Phe Asp Ala Lys Leu Ala Ile Val Gly Ile Ala Phe Ser
                165                 170                 175

Trp Ile Trp Ala Ala Val Trp Thr Ala Pro Pro Ile Phe Gly Trp Ser
            180                 185                 190

Arg Tyr Trp Pro His Gly Leu Lys Thr Ser Cys Gly Pro Asp Val Phe
        195                 200                 205

Ser Gly Ser Ser Tyr Pro Gly Val Gln Ser Tyr Met Ile Val Leu Met
    210                 215                 220

Val Thr Cys Cys Ile Thr Pro Leu Ser Ile Ile Val Leu Cys Tyr Leu
225                 230                 235                 240

Gln Val Trp Leu Ala Ile Arg Ala Val Ala Lys Gln Gln Lys Glu Ser
                245                 250                 255

Glu Ser Thr Gln Lys Ala Glu Lys Glu Val Thr Arg Met Val Val Val
            260                 265                 270

Met Val Leu Ala Phe Cys Phe Cys Trp Gly Pro Tyr Ala Phe Phe Ala
        275                 280                 285

Cys Phe Ala Ala Ala Asn Pro Gly Tyr Pro Phe His Pro Leu Met Ala
    290                 295                 300

Ala Leu Pro Ala Phe Phe Ala Lys Ser Ala Thr Ile Tyr Asn Pro Val
305                 310                 315                 320

Ile Tyr Val Phe Met Asn Arg Gln Phe Arg Asn Cys Ile Leu Gln Leu
                325                 330                 335

Phe Gly Lys Lys Val Asp Asp Gly Ser Glu Leu Ser Ser Ala Ser Lys
            340                 345                 350

Thr Glu Val Ser Ser Val Ser Ser Val Ser Pro Ala
        355                 360
```

<210> SEQ ID NO 10
<211> LENGTH: 1234
<212> TYPE: DNA
<213> ORGANISM: Homo sapiens

<400> SEQUENCE: 10

```
cggctgccgt cggggacagg gctttccata gccatggccc agcagtggag cctccaaagg      60

ctcgcaggcc gccatccgca ggacagctat gaggacagca cccagtccag catcttcacc     120

tacaccaaca gcaactccac cagaggcccc ttcgaaggcc cgaattacca catcgctccc     180

agatgggtgt accacctcac cagtgtctgg atgatctttg tggtcactgc atccgtcttc     240

acaaatgggc ttgtgctggc ggccaccatg aagttcaaga agctgcgcca cccgctgaac     300

tggatcctgg tgaacctggc ggtcgctgac ctagcagaga ccgtcatcgc cagcactatc     360

agcattgtga accaggtctc tggctacttc gtgctgggcc accctatgtg tgtcctggag     420

ggctacaccg tctccctgtg tgggatcaca ggtctctggt ctctggccat catttcctgg     480

gagaggtggc tggtggtgtg caagcccttt ggcaatgtga gatttgatgc caagctggcc     540

atcgtgggca ttgccttctc ctggatctgg tctgctgtgt ggacagcccc gcccatcttt     600

ggttggagca ggtactggcc ccacggcctg aagacttcat gcggcccaga cgtgttcagc     660

ggcagctcgt accccggggt gcagtcttac atgattgtcc tcatggtcac ctgctgcatc     720

atcccactcg ctatcatcat gctctgctac ctccaagtgt ggctggccat ccgagcggtg     780

gcaaagcagc agaaagagtc tgaatccacc cagaaggcag agaaggaagt gacgcgcatg     840

gtggtggtga tgatctttgc gtactgcgtc tgctggggac cctacacctt cttcgcatgc     900

tttgctgctg ccaaccctgg ttacgccttc caccctttga tggctgccct gccggcctac     960

tttgccaaaa gtgccactat ctacaacccc gttatctatg tctttatgaa ccggcagttt    1020

cgaaactgca tcttgcagct tttcgggaag aaggttgacg atggctctga actctccagc    1080

gcctccaaaa cggaggtctc atctgtgtcc tcggtatcgc ctgcatgagg tctgcctcct    1140

acccatcccg cccaccgggg ctttggccac ctctcctttc cccctccttc tccatccctg    1200

taaaataaat gtaatttatc tttgccaaaa ccaa                                1234
```

```
<210> SEQ ID NO 11
<211> LENGTH: 364
<212> TYPE: PRT
<213> ORGANISM: Homo sapiens

<400> SEQUENCE: 11

Met Ala Gln Gln Trp Ser Leu Gln Arg Leu Ala Gly Arg His Pro Gln
1               5                   10                  15

Asp Ser Tyr Glu Asp Ser Thr Gln Ser Ser Ile Phe Thr Tyr Thr Asn
            20                  25                  30

Ser Asn Ser Thr Arg Gly Pro Phe Glu Gly Pro Asn Tyr His Ile Ala
        35                  40                  45

Pro Arg Trp Val Tyr His Leu Thr Ser Val Trp Met Ile Phe Val Val
    50                  55                  60

Thr Ala Ser Val Phe Thr Asn Gly Leu Val Leu Ala Ala Thr Met Lys
65                  70                  75                  80

Phe Lys Lys Leu Arg His Pro Leu Asn Trp Ile Leu Val Asn Leu Ala
                85                  90                  95

Val Ala Asp Leu Ala Glu Thr Val Ile Ala Ser Thr Ile Ser Ile Val
            100                 105                 110

Asn Gln Val Ser Gly Tyr Phe Val Leu Gly His Pro Met Cys Val Leu
        115                 120                 125

Glu Gly Tyr Thr Val Ser Leu Cys Gly Ile Thr Gly Leu Trp Ser Leu
    130                 135                 140

Ala Ile Ile Ser Trp Glu Arg Trp Leu Val Val Cys Lys Pro Phe Gly
```

-continued

```
145                 150                 155                 160

Asn Val Arg Phe Asp Ala Lys Leu Ala Ile Val Gly Ile Ala Phe Ser
                165                 170                 175

Trp Ile Trp Ser Ala Val Trp Thr Ala Pro Pro Ile Phe Gly Trp Ser
            180                 185                 190

Arg Tyr Trp Pro His Gly Leu Lys Thr Ser Cys Gly Pro Asp Val Phe
        195                 200                 205

Ser Gly Ser Ser Tyr Pro Gly Val Gln Ser Tyr Met Ile Val Leu Met
    210                 215                 220

Val Thr Cys Cys Ile Ile Pro Leu Ala Ile Ile Met Leu Cys Tyr Leu
225                 230                 235                 240

Gln Val Trp Leu Ala Ile Arg Ala Val Ala Lys Gln Gln Lys Glu Ser
                245                 250                 255

Glu Ser Thr Gln Lys Ala Glu Lys Glu Val Thr Arg Met Val Val Val
            260                 265                 270

Met Ile Phe Ala Tyr Cys Val Cys Trp Gly Pro Tyr Thr Phe Phe Ala
        275                 280                 285

Cys Phe Ala Ala Ala Asn Pro Gly Tyr Ala Phe His Pro Leu Met Ala
    290                 295                 300

Ala Leu Pro Ala Tyr Phe Ala Lys Ser Ala Thr Ile Tyr Asn Pro Val
305                 310                 315                 320

Ile Tyr Val Phe Met Asn Arg Gln Phe Arg Asn Cys Ile Leu Gln Leu
                325                 330                 335

Phe Gly Lys Lys Val Asp Asp Gly Ser Glu Leu Ser Ser Ala Ser Lys
            340                 345                 350

Thr Glu Val Ser Ser Val Ser Ser Val Ser Pro Ala
        355                 360
```

<210> SEQ ID NO 12
<211> LENGTH: 7326
<212> TYPE: DNA
<213> ORGANISM: Homo sapiens

<400> SEQUENCE: 12

```
aggacacagc gtccggagcc agaggcgctc ttaacggcgt ttatgtcctt tgctgtctga     60

ggggcctcag ctctgaccaa tctggtcttc gtgtggtcat tagcatgggc ttcgtgagac    120

agatacagct tttgctctgg aagaactgga ccctgcggaa aaggcaaaag attcgctttg    180

tggtggaact cgtgtggcct ttatctttat ttctggtctt gatctggtta aggaatgcca    240

acccgctcta cagccatcat gaatgccatt tccccaacaa ggcgatgccc tcagcaggaa    300

tgctgccgtg gctccagggg atcttctgca atgtgaacaa tccctgtttt caaagcccca    360

ccccaggaga atctcctgga attgtgtcaa actataacaa ctccatcttg gcaagggtat    420

atcgagattt tcaagaactc ctcatgaatg caccagagag ccagcacctt ggccgtattt    480

ggacagagct acacatcttg tcccaattca tggacaccct ccggactcac ccggagagaa    540

ttgcaggaag aggaatacga ataagggata tcttgaaaga tgaagaaaca ctgacactat    600

ttctcattaa aaacatcggc ctgtctgact cagtggtcta ccttctgatc aactctcaag    660

tccgtccaga gcagttcgct catggagtcc cggacctggc gctgaaggac atcgcctgca    720

gcgaggccct cctggagcgc ttcatcatct tcagccagag acgcggggca aagacggtgc    780

gctatgccct gtgctccctc tcccagggca ccctacagtg gatagaagac actctgtatg    840

ccaacgtgga cttcttcaag ctcttccgtg tgcttcccac actcctagac agccgttctc    900
```

```
aaggtatcaa tctgagatct tggggaggaa tattatctga tatgtcacca agaattcaag    960
agtttatcca tcggccgagt atgcaggact tgctgtgggt gaccaggccc ctcatgcaga   1020
atggtggtcc agagaccttt acaaagctga tgggcatcct gtctgacctc ctgtgtggct   1080
accccgaggg aggtggctct cgggtgctct ccttcaactg gtatgaagac aataactata   1140
aggcctttct ggggattgac tccacaagga aggatcctat ctattcttat gacagaagaa   1200
caacatcctt ttgtaatgca ttgatccaga gcctggagtc aaatccttta accaaaatcg   1260
cttggagggc ggcaaagcct ttgctgatgg gaaaaatcct gtacactcct gattcacctg   1320
cagcacgaag gatactgaag aatgccaact caacttttga agaactggaa cacgttagga   1380
agttggtcaa agcctgggaa gaagtagggc cccagatctg gtacttcttt gacaacagca   1440
cacagatgaa catgatcaga gataccctgg ggaacccaac agtaaaagac tttttgaata   1500
ggcagcttgg tgaagaaggt attactgctg aagccatcct aaacttcctc tacaagggcc   1560
ctcgggaaag ccaggctgac gacatggcca acttcgactg gagggacata tttaacatca   1620
ctgatcgcac cctccgcctg gtcaatcaat acctggagtg cttggtcctg gataagtttg   1680
aaagctacaa tgatgaaact cagctcaccc aacgtgccct ctctctactg gaggaaaaca   1740
tgttctgggc cggagtggta ttccctgaca tgtatccctg gaccagctct ctaccacccc   1800
acgtgaagta taagatccga atggacatag acgtggtgga gaaaaccaat aagattaaag   1860
acaggtattg ggattctggt cccagagctg atcccgtgga agatttccgg tacatctggg   1920
gcgggtttgc ctatctgcag gacatggttg aacaggggat cacaaggagc caggtgcagg   1980
cggaggctcc agttggaatc tacctccagc agatgcccta cccctgcttc gtggacgatt   2040
ctttcatgat catcctgaac cgctgtttcc ctatcttcat ggtgctggca tggatctact   2100
ctgtctccat gactgtgaag agcatcgtct tggagaagga gttgcgactg aaggagacct   2160
tgaaaaatca gggtgtctcc aatgcagtga tttggtgtac ctggttcctg gacagcttct   2220
ccatcatgtc gatgagcatc ttcctcctga cgatattcat catgcatgga agaatcctac   2280
attacagcga cccattcatc ctcttcctgt tcttgttggc tttctccact gccaccatca   2340
tgctgtgctt tctgctcagc accttcttct ccaaggccag tctggcagca gcctgtagtg   2400
gtgtcatcta tttcaccctc tacctgccac acatcctgtg cttcgcctgg caggaccgca   2460
tgaccgctga gctgaagaag gctgtgagct tactgtctcc ggtggcattt ggatttggca   2520
ctgagtacct ggttcgcttt gaagagcaag gcctggggct gcagtggagc aacatcggga   2580
acagtcccac ggaaggggac gaattcagct tcctgctgtc catgcagatg atgctccttg   2640
atgctgctgt ctatggctta ctcgcttggt accttgatca ggtgtttcca ggagactatg   2700
gaaccccact tccttggtac tttcttctac aagagtcgta ttggcttggc ggtgaagggt   2760
gttcaaccag agaagaaaga gccctggaaa agaccgagcc cctaacagag gaaacggagg   2820
atccagagca cccagaagga atacacgact ccttctttga acgtgagcat ccagggtggg   2880
ttcctggggt atgcgtgaag aatctggtaa agatttttga gccctgtggc cggccagctg   2940
tggaccgtct gaacatcacc ttctacgaga accagatcac cgcattcctg ggccacaatg   3000
gagctgggaa aaccaccacc ttgtccatcc tgacgggtct gttgccacca acctctggga   3060
ctgtgctcgt tgggggaagg gacattgaaa ccagcctgga tgcagtccgg cagagccttg   3120
gcatgtgtcc acagcacaac atcctgttcc accacctcac ggtggctgag cacatgctgt   3180
tctatgccca gctgaaagga aagtcccagg aggaggccca gctggagatg gaagccatgt   3240
tggaggacac aggcctccac cacaagcgga atgaagaggc tcaggaccta tcaggtggca   3300
```

-continued

```
tgcagagaaa gctgtcggtt gccattgcct ttgtgggaga tgccaaggtg gtgattctgg   3360
acgaacccac ctctggggtg gacccttact cgagacgctc aatctgggat ctgctcctga   3420
agtatcgctc aggcagaacc atcatcatgt ccactcacca catggacgag gccgacctcc   3480
ttggggaccg cattgccatc attgcccagg gaaggctcta ctgctcaggc accccactct   3540
tcctgaagaa ctgctttggc acaggcttgt acttaacctt ggtgcgcaag atgaaaaaca   3600
tccagagcca aaggaaaggc agtgagggga cctgcagctg ctcgtctaag ggtttctcca   3660
ccacgtgtcc agcccacgtc gatgacctaa ctccagaaca agtcctggat ggggatgtaa   3720
atgagctgat ggatgtagtt ctccaccatg ttccagaggc aaagctggtg gagtgcattg   3780
gtcaagaact tatcttcctt cttccaaata agaacttcaa gcacagagca tatgccagcc   3840
ttttcagaga gctggaggag acgctggctg accttggtct cagcagtttt ggaatttctg   3900
acactcccct ggaagagatt tttctgaagg tcacggagga ttctgattca ggacctctgt   3960
ttgcgggtgg cgctcagcag aaaagagaaa acgtcaaccc ccgacacccc tgcttgggtc   4020
ccagagagaa ggctggacag acaccccagg actccaatgt ctgctcccca ggggcgccgg   4080
ctgctcaccc agagggccag cctcccccag agccagagtg cccaggcccg cagctcaaca   4140
cggggacaca gctggtcctc cagcatgtgc aggcgctgct ggtcaagaga ttccaacaca   4200
ccatccgcag ccacaaggac ttcctggcgc agatcgtgct cccggctacc tttgtgtttt   4260
tggctctgat gctttctatt gttatccctc cttttggcga ataccccgct ttgacccttc   4320
acccctggat atatgggcag cagtacacct tcttcagcat ggatgaacca ggcagtgagc   4380
agttcacggt acttgcagac gtcctcctga ataagccagg ctttggcaac cgctgcctga   4440
aggaagggtg gcttccggag taccccctgtg gcaactcaac accctggaag actccttctg   4500
tgtccccaaa catcacccag ctgttccaga agcagaaatg gacacaggtc aacccttcac   4560
catcctgcag gtgcagcacc agggagaagc tcaccatgct gccagagtgc cccgagggtg   4620
ccgggggcct cccgcccccc cagagaacac agcgcagcac ggaaattcta caagacctga   4680
cggacaggaa catctccgac ttcttggtaa aaacgtatcc tgctcttata agaagcagct   4740
taaagagcaa attctgggtc aatgaacaga ggtatggagg aatttccatt ggaggaaagc   4800
tcccagtcgt ccccatcacg gggggaagcac ttgttgggtt tttaagcgac cttggccgga   4860
tcatgaatgt gagcgggggc cctatcacta gagaggcctc taaagaaata cctgatttcc   4920
ttaaacatct agaaactgaa gacaacatta aggtgtggtt taataacaaa ggctggcatg   4980
ccctggtcag ctttctcaat gtggcccaca acgccatctt acgggccagc ctgcctaagg   5040
acaggagccc cgaggagtat ggaatcaccg tcattagcca accccctgaac ctgaccaagg   5100
agcagctctc agagattaca gtgctgacca cttcagtgga tgctgtggtt gccatctgcg   5160
tgattttctc catgtccttc gtcccagcca gctttgtcct ttatttgatc caggagcggg   5220
tgaacaaatc caagcacctc cagtttatca gtggagtgag ccccaccacc tactgggtga   5280
ccaacttcct ctgggacatc atgaattatt ccgtgagtgc tgggctggtg gtgggcatct   5340
tcatcgggtt tcagaagaaa gcctacactt ctccagaaaa ccttcctgcc cttgtggcac   5400
tgctcctgct gtatggatgg gcggtcattc ccatgatgta cccagcatcc ttcctgtttg   5460
atgtccccag cacagcctat gtggctttat cttgtgctaa tctgttcatc ggcatcaaca   5520
gcagtgctat taccttcatc ttggaattat ttgagaataa ccggacgctg ctcaggttca   5580
acgccgtgct gaggaagctg ctcattgtct tcccccactt ctgcctgggc cggggcctca   5640
```

```
ttgaccttgc actgagccag gctgtgacag atgtctatgc ccggtttggt gaggagcact   5700

ctgcaaatcc gttccactgg gacctgattg ggaagaacct gtttgccatg gtggtggaag   5760

gggtggtgta cttcctcctg accctgctgg tccagcgcca cttcttcctc tcccaatgga   5820

ttgccgagcc cactaaggag cccattgttg atgaagatga tgatgtggct gaagaaagac   5880

aaagaattat tactggtgga aataaaactg acatcttaag gctacatgaa ctaaccaaga   5940

tttatccagg cacctccagc ccagcagtgg acaggctgtg tgtcggagtt cgccctggag   6000

agtgctttgg cctcctggga gtgaatggtg ccggcaaaac aaccacattc aagatgctca   6060

ctggggacac cacagtgacc tcaggggatg ccaccgtagc aggcaagagt attttaacca   6120

atatttctga agtccatcaa aatatgggct actgtcctca gtttgatgca attgatgagc   6180

tgctcacagg acgagaacat ctttaccttt atgcccggct tcgaggtgta ccagcagaag   6240

aaatcgaaaa ggttgcaaac tggagtatta agagcctggg cctgactgtc tacgccgact   6300

gcctggctgg cacgtacagt gggggcaaca agcggaaact ctccacagcc atcgcactca   6360

ttggctgccc accgctggtg ctgctggatg agcccaccac agggatggac ccccaggcac   6420

gccgcatgct gtggaacgtc atcgtgagca tcatcagaga agggagggct gtggtcctca   6480

catcccacag catggaagaa tgtgaggcac tgtgtacccg gctggccatc atggtaaagg   6540

gcgcctttcg atgtatgggc accattcagc atctcaagtc caaatttgga gatggctata   6600

tcgtcacaat gaagatcaaa tccccgaagg acgacctgct tcctgacctg aaccctgtgg   6660

agcagttctt ccaggggaac ttcccaggca gtgtgcagag ggagaggcac tacaacatgc   6720

tccagttcca ggtctcctcc tcctccctgg cgaggatctt ccagctcctc ctctccccaca   6780

aggacagcct gctcatcgag gagtactcag tcacacagac cacactggac caggtgtttg   6840

taaattttgc taaacagcag actgaaagtc atgacctccc tctgcaccct cgagctgctg   6900

gagccagtcg acaagcccag gactgatctt tcacaccgct cgttcctgca gccagaaagg   6960

aactctgggc agctggaggc gcaggagcct gtgcccatat ggtcatccaa atggactggc   7020

cagcgtaaat gaccccactg cagcagaaaa caaacacacg aggagcatgc agcgaattca   7080

gaaagaggtc tttcagaagg aaaccgaaac tgacttgctc acctggaaca cctgatggtg   7140

aaaccaaaca aatacaaaat ccttctccag accccagaac tagaaacccc gggccatccc   7200

actagcagct ttggcctcca tattgctctc atttcaagca gatctgcttt tctgcatgtt   7260

tgtctgtgtg tctgcgttgt gtgtgatttt catggaaaaa taaaatgcaa atgcactcat   7320

cacaaa                                                              7326
```

<210> SEQ ID NO 13
<211> LENGTH: 2273
<212> TYPE: PRT
<213> ORGANISM: Homo sapiens

<400> SEQUENCE: 13

```
Met Gly Phe Val Arg Gln Ile Gln Leu Leu Leu Trp Lys Asn Trp Thr
1               5                   10                  15

Leu Arg Lys Arg Gln Lys Ile Arg Phe Val Val Glu Leu Val Trp Pro
            20                  25                  30

Leu Ser Leu Phe Leu Val Leu Ile Trp Leu Arg Asn Ala Asn Pro Leu
        35                  40                  45

Tyr Ser His His Glu Cys His Phe Pro Asn Lys Ala Met Pro Ser Ala
    50                  55                  60

Gly Met Leu Pro Trp Leu Gln Gly Ile Phe Cys Asn Val Asn Asn Pro
```

```
65                  70                  75                  80

Cys Phe Gln Ser Pro Thr Pro Gly Glu Ser Pro Gly Ile Val Ser Asn
                85                  90                  95

Tyr Asn Asn Ser Ile Leu Ala Arg Val Tyr Arg Asp Phe Gln Glu Leu
            100                 105                 110

Leu Met Asn Ala Pro Glu Ser Gln His Leu Gly Arg Ile Trp Thr Glu
        115                 120                 125

Leu His Ile Leu Ser Gln Phe Met Asp Thr Leu Arg Thr His Pro Glu
    130                 135                 140

Arg Ile Ala Gly Arg Gly Ile Arg Ile Arg Asp Ile Leu Lys Asp Glu
145                 150                 155                 160

Glu Thr Leu Thr Leu Phe Leu Ile Lys Asn Ile Gly Leu Ser Asp Ser
                165                 170                 175

Val Val Tyr Leu Leu Ile Asn Ser Gln Val Arg Pro Glu Gln Phe Ala
            180                 185                 190

His Gly Val Pro Asp Leu Ala Leu Lys Asp Ile Ala Cys Ser Glu Ala
        195                 200                 205

Leu Leu Glu Arg Phe Ile Ile Phe Ser Gln Arg Arg Gly Ala Lys Thr
    210                 215                 220

Val Arg Tyr Ala Leu Cys Ser Leu Ser Gln Gly Thr Leu Gln Trp Ile
225                 230                 235                 240

Glu Asp Thr Leu Tyr Ala Asn Val Asp Phe Phe Lys Leu Phe Arg Val
                245                 250                 255

Leu Pro Thr Leu Leu Asp Ser Arg Ser Gln Gly Ile Asn Leu Arg Ser
            260                 265                 270

Trp Gly Gly Ile Leu Ser Asp Met Ser Pro Arg Ile Gln Glu Phe Ile
        275                 280                 285

His Arg Pro Ser Met Gln Asp Leu Leu Trp Val Thr Arg Pro Leu Met
    290                 295                 300

Gln Asn Gly Gly Pro Glu Thr Phe Thr Lys Leu Met Gly Ile Leu Ser
305                 310                 315                 320

Asp Leu Leu Cys Gly Tyr Pro Glu Gly Gly Gly Ser Arg Val Leu Ser
                325                 330                 335

Phe Asn Trp Tyr Glu Asp Asn Asn Tyr Lys Ala Phe Leu Gly Ile Asp
            340                 345                 350

Ser Thr Arg Lys Asp Pro Ile Tyr Ser Tyr Asp Arg Arg Thr Thr Ser
        355                 360                 365

Phe Cys Asn Ala Leu Ile Gln Ser Leu Glu Ser Asn Pro Leu Thr Lys
    370                 375                 380

Ile Ala Trp Arg Ala Ala Lys Pro Leu Leu Met Gly Lys Ile Leu Tyr
385                 390                 395                 400

Thr Pro Asp Ser Pro Ala Ala Arg Arg Ile Leu Lys Asn Ala Asn Ser
                405                 410                 415

Thr Phe Glu Glu Leu Glu His Val Arg Lys Leu Val Lys Ala Trp Glu
            420                 425                 430

Glu Val Gly Pro Gln Ile Trp Tyr Phe Phe Asp Asn Ser Thr Gln Met
        435                 440                 445

Asn Met Ile Arg Asp Thr Leu Gly Asn Pro Thr Val Lys Asp Phe Leu
    450                 455                 460

Asn Arg Gln Leu Gly Glu Glu Gly Ile Thr Ala Glu Ala Ile Leu Asn
465                 470                 475                 480

Phe Leu Tyr Lys Gly Pro Arg Glu Ser Gln Ala Asp Asp Met Ala Asn
                485                 490                 495
```

```
Phe Asp Trp Arg Asp Ile Phe Asn Ile Thr Asp Arg Thr Leu Arg Leu
            500                 505                 510

Val Asn Gln Tyr Leu Glu Cys Leu Val Leu Asp Lys Phe Glu Ser Tyr
        515                 520                 525

Asn Asp Glu Thr Gln Leu Thr Gln Arg Ala Leu Ser Leu Leu Glu Glu
    530                 535                 540

Asn Met Phe Trp Ala Gly Val Val Phe Pro Asp Met Tyr Pro Trp Thr
545                 550                 555                 560

Ser Ser Leu Pro Pro His Val Lys Tyr Lys Ile Arg Met Asp Ile Asp
                565                 570                 575

Val Val Glu Lys Thr Asn Lys Ile Lys Asp Arg Tyr Trp Asp Ser Gly
            580                 585                 590

Pro Arg Ala Asp Pro Val Glu Asp Phe Arg Tyr Ile Trp Gly Gly Phe
        595                 600                 605

Ala Tyr Leu Gln Asp Met Val Glu Gln Gly Ile Thr Arg Ser Gln Val
    610                 615                 620

Gln Ala Glu Ala Pro Val Gly Ile Tyr Leu Gln Gln Met Pro Tyr Pro
625                 630                 635                 640

Cys Phe Val Asp Asp Ser Phe Met Ile Ile Leu Asn Arg Cys Phe Pro
                645                 650                 655

Ile Phe Met Val Leu Ala Trp Ile Tyr Ser Val Ser Met Thr Val Lys
            660                 665                 670

Ser Ile Val Leu Glu Lys Glu Leu Arg Leu Lys Glu Thr Leu Lys Asn
        675                 680                 685

Gln Gly Val Ser Asn Ala Val Ile Trp Cys Thr Trp Phe Leu Asp Ser
    690                 695                 700

Phe Ser Ile Met Ser Met Ser Ile Phe Leu Leu Thr Ile Phe Ile Met
705                 710                 715                 720

His Gly Arg Ile Leu His Tyr Ser Asp Pro Phe Ile Leu Phe Leu Phe
                725                 730                 735

Leu Leu Ala Phe Ser Thr Ala Thr Ile Met Leu Cys Phe Leu Leu Ser
            740                 745                 750

Thr Phe Phe Ser Lys Ala Ser Leu Ala Ala Ala Cys Ser Gly Val Ile
        755                 760                 765

Tyr Phe Thr Leu Tyr Leu Pro His Ile Leu Cys Phe Ala Trp Gln Asp
    770                 775                 780

Arg Met Thr Ala Glu Leu Lys Lys Ala Val Ser Leu Leu Ser Pro Val
785                 790                 795                 800

Ala Phe Gly Phe Gly Thr Glu Tyr Leu Val Arg Phe Glu Glu Gln Gly
                805                 810                 815

Leu Gly Leu Gln Trp Ser Asn Ile Gly Asn Ser Pro Thr Glu Gly Asp
            820                 825                 830

Glu Phe Ser Phe Leu Leu Ser Met Gln Met Met Leu Leu Asp Ala Ala
        835                 840                 845

Val Tyr Gly Leu Leu Ala Trp Tyr Leu Asp Gln Val Phe Pro Gly Asp
    850                 855                 860

Tyr Gly Thr Pro Leu Pro Trp Tyr Phe Leu Leu Gln Glu Ser Tyr Trp
865                 870                 875                 880

Leu Gly Gly Glu Gly Cys Ser Thr Arg Glu Glu Arg Ala Leu Glu Lys
                885                 890                 895

Thr Glu Pro Leu Thr Glu Glu Thr Glu Asp Pro Glu His Pro Glu Gly
            900                 905                 910
```

```
Ile His Asp Ser Phe Phe Glu Arg Glu His Pro Gly Trp Val Pro Gly
        915                 920                 925

Val Cys Val Lys Asn Leu Val Lys Ile Phe Glu Pro Cys Gly Arg Pro
    930                 935                 940

Ala Val Asp Arg Leu Asn Ile Thr Phe Tyr Glu Asn Gln Ile Thr Ala
945                 950                 955                 960

Phe Leu Gly His Asn Gly Ala Gly Lys Thr Thr Thr Leu Ser Ile Leu
                965                 970                 975

Thr Gly Leu Leu Pro Pro Thr Ser Gly Thr Val Leu Val Gly Gly Arg
            980                 985                 990

Asp Ile Glu Thr Ser Leu Asp Ala  Val Arg Gln Ser Leu  Gly Met Cys
        995                 1000                1005

Pro Gln  His Asn Ile Leu Phe  His His Leu Thr Val  Ala Glu His
    1010                1015                1020

Met Leu  Phe Tyr Ala Gln Leu  Lys Gly Lys Ser Gln  Glu Glu Ala
    1025                1030                1035

Gln Leu  Glu Met Glu Ala Met  Leu Glu Asp Thr Gly  Leu His His
    1040                1045                1050

Lys Arg  Asn Glu Glu Ala Gln  Asp Leu Ser Gly Gly  Met Gln Arg
    1055                1060                1065

Lys Leu  Ser Val Ala Ile Ala  Phe Val Gly Asp Ala  Lys Val Val
    1070                1075                1080

Ile Leu  Asp Glu Pro Thr Ser  Gly Val Asp Pro Tyr  Ser Arg Arg
    1085                1090                1095

Ser Ile  Trp Asp Leu Leu Leu  Lys Tyr Arg Ser Gly  Arg Thr Ile
    1100                1105                1110

Ile Met  Ser Thr His His Met  Asp Glu Ala Asp Leu  Leu Gly Asp
    1115                1120                1125

Arg Ile  Ala Ile Ile Ala Gln  Gly Arg Leu Tyr Cys  Ser Gly Thr
    1130                1135                1140

Pro Leu  Phe Leu Lys Asn Cys  Phe Gly Thr Gly Leu  Tyr Leu Thr
    1145                1150                1155

Leu Val  Arg Lys Met Lys Asn  Ile Gln Ser Gln Arg  Lys Gly Ser
    1160                1165                1170

Glu Gly  Thr Cys Ser Cys Ser  Ser Lys Gly Phe Ser  Thr Thr Cys
    1175                1180                1185

Pro Ala  His Val Asp Asp Leu  Thr Pro Glu Gln Val  Leu Asp Gly
    1190                1195                1200

Asp Val  Asn Glu Leu Met Asp  Val Val Leu His His  Val Pro Glu
    1205                1210                1215

Ala Lys  Leu Val Glu Cys Ile  Gly Gln Glu Leu Ile  Phe Leu Leu
    1220                1225                1230

Pro Asn  Lys Asn Phe Lys His  Arg Ala Tyr Ala Ser  Leu Phe Arg
    1235                1240                1245

Glu Leu  Glu Glu Thr Leu Ala  Asp Leu Gly Leu Ser  Ser Phe Gly
    1250                1255                1260

Ile Ser  Asp Thr Pro Leu Glu  Glu Ile Phe Leu Lys  Val Thr Glu
    1265                1270                1275

Asp Ser  Asp Ser Gly Pro Leu  Phe Ala Gly Gly Ala  Gln Gln Lys
    1280                1285                1290

Arg Glu  Asn Val Asn Pro Arg  His Pro Cys Leu Gly  Pro Arg Glu
    1295                1300                1305

Lys Ala  Gly Gln Thr Pro Gln  Asp Ser Asn Val Cys  Ser Pro Gly
```

```
    1310                1315                1320

Ala Pro  Ala Ala His Pro Glu  Gly Gln Pro Pro Pro  Glu Pro Glu
    1325                1330                1335

Cys Pro  Gly Pro Gln Leu Asn  Thr Gly Thr Gln Leu  Val Leu Gln
    1340                1345                1350

His Val  Gln Ala Leu Leu Val  Lys Arg Phe Gln His  Thr Ile Arg
    1355                1360                1365

Ser His  Lys Asp Phe Leu Ala  Gln Ile Val Leu Pro  Ala Thr Phe
    1370                1375                1380

Val Phe  Leu Ala Leu Met Leu  Ser Ile Val Ile Pro  Pro Phe Gly
    1385                1390                1395

Glu Tyr  Pro Ala Leu Thr Leu  His Pro Trp Ile Tyr  Gly Gln Gln
    1400                1405                1410

Tyr Thr  Phe Phe Ser Met Asp  Glu Pro Gly Ser Glu  Gln Phe Thr
    1415                1420                1425

Val Leu  Ala Asp Val Leu Leu  Asn Lys Pro Gly Phe  Gly Asn Arg
    1430                1435                1440

Cys Leu  Lys Glu Gly Trp Leu  Pro Glu Tyr Pro Cys  Gly Asn Ser
    1445                1450                1455

Thr Pro  Trp Lys Thr Pro Ser  Val Ser Pro Asn Ile  Thr Gln Leu
    1460                1465                1470

Phe Gln  Lys Gln Lys Trp Thr  Gln Val Asn Pro Ser  Pro Ser Cys
    1475                1480                1485

Arg Cys  Ser Thr Arg Glu Lys  Leu Thr Met Leu Pro  Glu Cys Pro
    1490                1495                1500

Glu Gly  Ala Gly Gly Leu Pro  Pro Pro Gln Arg Thr  Gln Arg Ser
    1505                1510                1515

Thr Glu  Ile Leu Gln Asp Leu  Thr Asp Arg Asn Ile  Ser Asp Phe
    1520                1525                1530

Leu Val  Lys Thr Tyr Pro Ala  Leu Ile Arg Ser Ser  Leu Lys Ser
    1535                1540                1545

Lys Phe  Trp Val Asn Glu Gln  Arg Tyr Gly Gly Ile  Ser Ile Gly
    1550                1555                1560

Gly Lys  Leu Pro Val Val Pro  Ile Thr Gly Glu Ala  Leu Val Gly
    1565                1570                1575

Phe Leu  Ser Asp Leu Gly Arg  Ile Met Asn Val Ser  Gly Gly Pro
    1580                1585                1590

Ile Thr  Arg Glu Ala Ser Lys  Glu Ile Pro Asp Phe  Leu Lys His
    1595                1600                1605

Leu Glu  Thr Glu Asp Asn Ile  Lys Val Trp Phe Asn  Asn Lys Gly
    1610                1615                1620

Trp His  Ala Leu Val Ser Phe  Leu Asn Val Ala His  Asn Ala Ile
    1625                1630                1635

Leu Arg  Ala Ser Leu Pro Lys  Asp Arg Ser Pro Glu  Glu Tyr Gly
    1640                1645                1650

Ile Thr  Val Ile Ser Gln Pro  Leu Asn Leu Thr Lys  Glu Gln Leu
    1655                1660                1665

Ser Glu  Ile Thr Val Leu Thr  Thr Ser Val Asp Ala  Val Val Ala
    1670                1675                1680

Ile Cys  Val Ile Phe Ser Met  Ser Phe Val Pro Ala  Ser Phe Val
    1685                1690                1695

Leu Tyr  Leu Ile Gln Glu Arg  Val Asn Lys Ser Lys  His Leu Gln
    1700                1705                1710
```

```
Phe Ile  Ser Gly Val Ser Pro  Thr Thr Tyr Trp Val  Thr Asn Phe
    1715                 1720                 1725

Leu Trp  Asp Ile Met Asn Tyr  Ser Val Ser Ala Gly  Leu Val Val
    1730                 1735                 1740

Gly Ile  Phe Ile Gly Phe Gln  Lys Lys Ala Tyr Thr  Ser Pro Glu
    1745                 1750                 1755

Asn Leu  Pro Ala Leu Val Ala  Leu Leu Leu Leu Tyr  Gly Trp Ala
    1760                 1765                 1770

Val Ile  Pro Met Met Tyr Pro  Ala Ser Phe Leu Phe  Asp Val Pro
    1775                 1780                 1785

Ser Thr  Ala Tyr Val Ala Leu  Ser Cys Ala Asn Leu  Phe Ile Gly
    1790                 1795                 1800

Ile Asn  Ser Ser Ala Ile Thr  Phe Ile Leu Glu Leu  Phe Glu Asn
    1805                 1810                 1815

Asn Arg  Thr Leu Leu Arg Phe  Asn Ala Val Leu Arg  Lys Leu Leu
    1820                 1825                 1830

Ile Val  Phe Pro His Phe Cys  Leu Gly Arg Gly Leu  Ile Asp Leu
    1835                 1840                 1845

Ala Leu  Ser Gln Ala Val Thr  Asp Val Tyr Ala Arg  Phe Gly Glu
    1850                 1855                 1860

Glu His  Ser Ala Asn Pro Phe  His Trp Asp Leu Ile  Gly Lys Asn
    1865                 1870                 1875

Leu Phe  Ala Met Val Val Glu  Gly Val Val Tyr Phe  Leu Leu Thr
    1880                 1885                 1890

Leu Leu  Val Gln Arg His Phe  Phe Leu Ser Gln Trp  Ile Ala Glu
    1895                 1900                 1905

Pro Thr  Lys Glu Pro Ile Val  Asp Glu Asp Asp Asp  Val Ala Glu
    1910                 1915                 1920

Glu Arg  Gln Arg Ile Ile Thr  Gly Gly Asn Lys Thr  Asp Ile Leu
    1925                 1930                 1935

Arg Leu  His Glu Leu Thr Lys  Ile Tyr Pro Gly Thr  Ser Ser Pro
    1940                 1945                 1950

Ala Val  Asp Arg Leu Cys Val  Gly Val Arg Pro Gly  Glu Cys Phe
    1955                 1960                 1965

Gly Leu  Leu Gly Val Asn Gly  Ala Gly Lys Thr Thr  Thr Phe Lys
    1970                 1975                 1980

Met Leu  Thr Gly Asp Thr Thr  Val Thr Ser Gly Asp  Ala Thr Val
    1985                 1990                 1995

Ala Gly  Lys Ser Ile Leu Thr  Asn Ile Ser Glu Val  His Gln Asn
    2000                 2005                 2010

Met Gly  Tyr Cys Pro Gln Phe  Asp Ala Ile Asp Glu  Leu Leu Thr
    2015                 2020                 2025

Gly Arg  Glu His Leu Tyr Leu  Tyr Ala Arg Leu Arg  Gly Val Pro
    2030                 2035                 2040

Ala Glu  Glu Ile Glu Lys Val  Ala Asn Trp Ser Ile  Lys Ser Leu
    2045                 2050                 2055

Gly Leu  Thr Val Tyr Ala Asp  Cys Leu Ala Gly Thr  Tyr Ser Gly
    2060                 2065                 2070

Gly Asn  Lys Arg Lys Leu Ser  Thr Ala Ile Ala Leu  Ile Gly Cys
    2075                 2080                 2085

Pro Pro  Leu Val Leu Leu Asp  Glu Pro Thr Thr Gly  Met Asp Pro
    2090                 2095                 2100
```

```
Gln Ala  Arg Arg Met Leu Trp  Asn Val Ile Val Ser  Ile Ile Arg
    2105                 2110                 2115

Glu Gly  Arg Ala Val Val Leu  Thr Ser His Ser Met  Glu Glu Cys
    2120                 2125                 2130

Glu Ala  Leu Cys Thr Arg Leu  Ala Ile Met Val Lys  Gly Ala Phe
    2135                 2140                 2145

Arg Cys  Met Gly Thr Ile Gln  His Leu Lys Ser Lys  Phe Gly Asp
    2150                 2155                 2160

Gly Tyr  Ile Val Thr Met Lys  Ile Lys Ser Pro Lys  Asp Asp Leu
    2165                 2170                 2175

Leu Pro  Asp Leu Asn Pro Val  Glu Gln Phe Phe Gln  Gly Asn Phe
    2180                 2185                 2190

Pro Gly  Ser Val Gln Arg Glu  Arg His Tyr Asn Met  Leu Gln Phe
    2195                 2200                 2205

Gln Val  Ser Ser Ser Ser Leu  Ala Arg Ile Phe Gln  Leu Leu Leu
    2210                 2215                 2220

Ser His  Lys Asp Ser Leu Leu  Ile Glu Glu Tyr Ser  Val Thr Gln
    2225                 2230                 2235

Thr Thr  Leu Asp Gln Val Phe  Val Asn Phe Ala Lys  Gln Gln Thr
    2240                 2245                 2250

Glu Ser  His Asp Leu Pro Leu  His Pro Arg Ala Ala  Gly Ala Ser
    2255                 2260                 2265

Arg Gln  Ala Gln Asp
    2270
```

<210> SEQ ID NO 14
<211> LENGTH: 2608
<212> TYPE: DNA
<213> ORGANISM: Homo sapiens

<400> SEQUENCE: 14

```
tccttcttca ttctgcagtt ggtgccagaa ctctggatcc tgaactggaa gaaaatgtct     60

atccaggttg agcatcctgc tggtggttac aagaaactgt ttgaaactgt ggaggaactg    120

tcctcgccgc tcacagctca tgtaacaggc aggatccccc tctggctcac cggcagtctc    180

cttcgatgtg ggccaggact ctttgaagtt ggatctgagc cattttacca cctgtttgat    240

gggcaagccc tcctgcacaa gtttgacttt aaagaaggac atgtcacata ccacagaagg    300

ttcatccgca ctgatgctta cgtacgggca atgactgaga aaaggatcgt cataacagaa    360

tttggcacct gtgctttccc agatccctgc aagaatatat tttccaggtt tttttcttac    420

tttcgaggag tagaggttac tgacaatgcc cttgttaatg tctacccagt gggggaagat    480

tactacgctt gcacagagac caactttatt acaaagatta atccagagac cttggagaca    540

attaagcagg ttgatctttg caactatgtc tctgtcaatg gggccactgc tcacccccac    600

attgaaaatg atggaaccgt ttacaatatt ggtaattgct ttggaaaaaa tttttcaatt    660

gcctacaaca ttgtaaagat cccaccactg caagcagaca aggaagatcc aataagcaag    720

tcagagatcg ttgtacaatt cccctgcagt gaccgattca agccatctta cgttcatagt    780

tttggtctga ctcccaacta tatcgttttt gtggagacac cagtcaaaat taacctgttc    840

aagttccttt cttcatggag tctttgggga gccaactaca tggattgttt tgagtccaat    900

gaaaccatgg gggtttggct tcatattgct gacaaaaaaa ggaaaaagta cctcaataat    960

aaatacagaa cttctccttt caacctcttc catcacatca acacctatga agacaatggg   1020

tttctgattg tggatctctg ctgctggaaa ggatttgagt ttgtttataa ttacttatat   1080
```

```
ttagccaatt tacgtgagaa ctgggaagag gtgaaaaaaa atgccagaaa ggctccccaa   1140
cctgaagtta ggagatatgt acttcctttg aatattgaca aggctgacac aggcaagaat   1200
ttagtcacgc tccccaatac aactgccact gcaattctgt gcagtgacga gactatctgg   1260
ctggagcctg aagttctctt ttcagggcct cgtcaagcat ttgagtttcc tcaaatcaat   1320
taccagaagt attgtgggaa accttacaca tatgcgtatg gacttggctt gaatcacttt   1380
gttccagata ggctctgtaa gctgaatgtc aaaactaaag aaacttgggt ttggcaagag   1440
cctgattcat acccatcaga acccatcttt gtttctcacc cagatgcctt ggaagaagat   1500
gatggtgtag ttctgagtgt ggtggtgagc ccaggagcag gacaaaagcc tgcttatctc   1560
ctgattctga atgccaagga cttaagtgaa gttgcccggg ctgaagtgga gattaacatc   1620
cctgtcacct ttcatggact gttcaaaaaa tcttgagcat actccagcaa gatatgtttt   1680
tggtagcaaa actgagaaaa tcagcttcag gtctgcaatc aaattctgtt caattttagc   1740
ctgctatatg tcatggtttt aacttgcaga tgcgcacaat tttgcaatgt tttacagaaa   1800
gcactgagtt gagcaagcaa ttcctttatt taaaaaaaaa agtacgtatt tagataatca   1860
tacttcctct gtgagacagg ccataactga aaaactctta aatatttagc aatcaaatag   1920
gaaatgaatg tggacttact aaatggcttt taattcctat tataagagca tattttaggt   1980
acctatctgc tccaattata tttttaacat ttaaaaacca aagtcctcta cacttgattt   2040
atattatatg tggctttgct gagtcaagga agtatcatgc aataaggctt aattactaaa   2100
tgtcaaacca aactttttct caaaccaggg actatcatct aagattaatt acagtaatta   2160
ttttgcgtat acgtaactgc tcaaagatta tgaatcttat gaatgttaac ctttccgttt   2220
attacaagca agtactatta tttctgattt tataataaga aaatctgtgt ttaatcaact   2280
gaggcctctc aaccaaataa catctcagag attaagttat atattaaaag cttatgtaac   2340
ataaaagcaa gtacatatag tagtgactat atttaaaaaa acagcataaa atgcttaaaa   2400
atgtaatatt tactaaaatc agattatggg ataatgttgc aggattatac tttattgcat   2460
ctttttttgtt taattgtatt taagcattgt gcaatcactt gggaaaaata ttaaattatt   2520
aacattgagg tattaataca ttttaagcct tttgttttta aatttctttt cttccagaga   2580
ttgtttaaaa ataaatattg acaaaaat                                      2608
```

<210> SEQ ID NO 15
<211> LENGTH: 533
<212> TYPE: PRT
<213> ORGANISM: Homo sapiens

<400> SEQUENCE: 15

```
Met Ser Ile Gln Val Glu His Pro Ala Gly Gly Tyr Lys Lys Leu Phe
1               5                   10                  15

Glu Thr Val Glu Glu Leu Ser Ser Pro Leu Thr Ala His Val Thr Gly
            20                  25                  30

Arg Ile Pro Leu Trp Leu Thr Gly Ser Leu Leu Arg Cys Gly Pro Gly
        35                  40                  45

Leu Phe Glu Val Gly Ser Glu Pro Phe Tyr His Leu Phe Asp Gly Gln
    50                  55                  60

Ala Leu Leu His Lys Phe Asp Phe Lys Glu Gly His Val Thr Tyr His
65                  70                  75                  80

Arg Arg Phe Ile Arg Thr Asp Ala Tyr Val Arg Ala Met Thr Glu Lys
                85                  90                  95
```

```
Arg Ile Val Ile Thr Glu Phe Gly Thr Cys Ala Phe Pro Asp Pro Cys
            100                 105                 110

Lys Asn Ile Phe Ser Arg Phe Phe Ser Tyr Phe Arg Gly Val Glu Val
        115                 120                 125

Thr Asp Asn Ala Leu Val Asn Val Tyr Pro Val Gly Glu Asp Tyr Tyr
    130                 135                 140

Ala Cys Thr Glu Thr Asn Phe Ile Thr Lys Ile Asn Pro Glu Thr Leu
145                 150                 155                 160

Glu Thr Ile Lys Gln Val Asp Leu Cys Asn Tyr Val Ser Val Asn Gly
                165                 170                 175

Ala Thr Ala His Pro His Ile Glu Asn Asp Gly Thr Val Tyr Asn Ile
            180                 185                 190

Gly Asn Cys Phe Gly Lys Asn Phe Ser Ile Ala Tyr Asn Ile Val Lys
        195                 200                 205

Ile Pro Pro Leu Gln Ala Asp Lys Glu Asp Pro Ile Ser Lys Ser Glu
    210                 215                 220

Ile Val Val Gln Phe Pro Cys Ser Asp Arg Phe Lys Pro Ser Tyr Val
225                 230                 235                 240

His Ser Phe Gly Leu Thr Pro Asn Tyr Ile Val Phe Val Glu Thr Pro
                245                 250                 255

Val Lys Ile Asn Leu Phe Lys Phe Leu Ser Ser Trp Ser Leu Trp Gly
            260                 265                 270

Ala Asn Tyr Met Asp Cys Phe Glu Ser Asn Glu Thr Met Gly Val Trp
        275                 280                 285

Leu His Ile Ala Asp Lys Lys Arg Lys Lys Tyr Leu Asn Asn Lys Tyr
    290                 295                 300

Arg Thr Ser Pro Phe Asn Leu Phe His His Ile Asn Thr Tyr Glu Asp
305                 310                 315                 320

Asn Gly Phe Leu Ile Val Asp Leu Cys Cys Trp Lys Gly Phe Glu Phe
                325                 330                 335

Val Tyr Asn Tyr Leu Tyr Leu Ala Asn Leu Arg Glu Asn Trp Glu Glu
            340                 345                 350

Val Lys Lys Asn Ala Arg Lys Ala Pro Gln Pro Glu Val Arg Arg Tyr
        355                 360                 365

Val Leu Pro Leu Asn Ile Asp Lys Ala Asp Thr Gly Lys Asn Leu Val
    370                 375                 380

Thr Leu Pro Asn Thr Thr Ala Thr Ala Ile Leu Cys Ser Asp Glu Thr
385                 390                 395                 400

Ile Trp Leu Glu Pro Glu Val Leu Phe Ser Gly Pro Arg Gln Ala Phe
                405                 410                 415

Glu Phe Pro Gln Ile Asn Tyr Gln Lys Tyr Cys Gly Lys Pro Tyr Thr
            420                 425                 430

Tyr Ala Tyr Gly Leu Gly Leu Asn His Phe Val Pro Asp Arg Leu Cys
        435                 440                 445

Lys Leu Asn Val Lys Thr Lys Glu Thr Trp Val Trp Gln Glu Pro Asp
    450                 455                 460

Ser Tyr Pro Ser Glu Pro Ile Phe Val Ser His Pro Asp Ala Leu Glu
465                 470                 475                 480

Glu Asp Asp Gly Val Val Leu Ser Val Val Val Ser Pro Gly Ala Gly
                485                 490                 495

Gln Lys Pro Ala Tyr Leu Leu Ile Leu Asn Ala Lys Asp Leu Ser Glu
            500                 505                 510

Val Ala Arg Ala Glu Val Glu Ile Asn Ile Pro Val Thr Phe His Gly
```

515 520 525

Leu Phe Lys Lys Ser
530

<210> SEQ ID NO 16
<211> LENGTH: 1752
<212> TYPE: DNA
<213> ORGANISM: Homo sapiens

<400> SEQUENCE: 16
gagcccgatt taacggaaac tgtgggcggt gagaagttcc ttatgacaca ctaatcccaa 60
cctgctgacc ggaccacgcc tccagcggag ggaacctcta gagctccagg acattcaggt 120
accaggtagc cccaaggagg agctgccgac ctggcaggga acaaccaaga ctggggttaa 180
atctcacagc ctgcaagtgg aagagaagaa cttgaaccca ggtccaactt ttgcgccaca 240
gcaggctgcc tcttggtcct gacaggaagt cacaacttgg ccctgacttc ctatcctagg 300
gaaggggccg gctggagagg ccaggacaga gaaagcagat cccttctttt tccaaggact 360
ctgtgtcttc cataggcaac atgtcagaag gggtgggcac gttccgcatg gtacctgaag 420
aggaacagga gctccgtgcc caactggagc agctcacaac caaggaccat ggacctgtct 480
ttggcccgtg cagccagctg ccccgccaca ccttgcagaa ggccaaggat gagctgaacg 540
agagagagga gacccgggag gaggcagtgc gagagctgca ggagatggtg caggcgcagg 600
cggcctcggg ggaggagctg gcggtggccg tggcggagag ggtgcaagag aaggacagcg 660
gcttcttcct gcgcttcatc cgcgcacgga agttcaacgt gggccgtgcc tatgagctgc 720
tcagaggcta tgtgaatttc cggctgcagt accctgagct ctttgacagc ctgtccccag 780
aggctgtccg ctgcaccatt gaagctggct accctggtgt cctctctagt cgggacaagt 840
atggccgagt ggtcatgctc ttcaacattg agaactggca aagtcaagaa atcacctttg 900
atgagatctt gcaggcatat tgcttcatcc tggagaagct gctggagaat gaggaaactc 960
aaatcaatgg cttctgcatc attgagaact tcaagggctt taccatgcag caggctgcta 1020
gtctccggac ttcagatctc aggaagatgg tggacatgct ccaggattcc ttcccagccc 1080
ggttcaaagc catccacttc atccaccagc catggtactt caccacgacc tacaatgtgg 1140
tcaagccctt cttgaagagc aagctgcttg agagggtctt tgtccacggg gatgaccttt 1200
ctggtttcta ccaggagatc gatgagaaca tcctgccctc tgacttcggg ggcacgctgc 1260
ccaagtatga tggcaaggcc gttgctgagc agctctttgg cccccaggcc caagctgaga 1320
acacagcctt ctgaaaacat ctcctgccag ctgaactgta gttagaatct ctgggcctct 1380
cctcaactgt cctggaccca aggctaggaa agggctgctt gagatgactg tggtcccccc 1440
ttagactccc taagcccgag tgagctcagg tgtcaccctg ttctcaagtt gggggatggg 1500
taataaagga gggggaattc ccttgaacaa gaagaactgg ggatagttat atttccacct 1560
gcccttgaag ctttaagaca gtgatttttg tgtaaggttg tatttcaaag actcgaattc 1620
attttctcag tcatttcctt tgtaacagag ttttacgact tagagtctgt gaaaacaggc 1680
aaggagcccg ggttaaaata tccccctatt cgcccccaaa atgcaataaa agaagataaa 1740
agagagagga ta 1752

<210> SEQ ID NO 17
<211> LENGTH: 317
<212> TYPE: PRT
<213> ORGANISM: Homo sapiens

<400> SEQUENCE: 17

```
Met Ser Glu Gly Val Gly Thr Phe Arg Met Val Pro Glu Glu Glu Gln
1               5                   10                  15

Glu Leu Arg Ala Gln Leu Glu Gln Leu Thr Thr Lys Asp His Gly Pro
            20                  25                  30

Val Phe Gly Pro Cys Ser Gln Leu Pro Arg His Thr Leu Gln Lys Ala
        35                  40                  45

Lys Asp Glu Leu Asn Glu Arg Glu Glu Thr Arg Glu Glu Ala Val Arg
    50                  55                  60

Glu Leu Gln Glu Met Val Gln Ala Gln Ala Ala Ser Gly Glu Glu Leu
65                  70                  75                  80

Ala Val Ala Val Ala Glu Arg Val Gln Glu Lys Asp Ser Gly Phe Phe
                85                  90                  95

Leu Arg Phe Ile Arg Ala Arg Lys Phe Asn Val Gly Arg Ala Tyr Glu
            100                 105                 110

Leu Leu Arg Gly Tyr Val Asn Phe Arg Leu Gln Tyr Pro Glu Leu Phe
        115                 120                 125

Asp Ser Leu Ser Pro Glu Ala Val Arg Cys Thr Ile Glu Ala Gly Tyr
    130                 135                 140

Pro Gly Val Leu Ser Ser Arg Asp Lys Tyr Gly Arg Val Val Met Leu
145                 150                 155                 160

Phe Asn Ile Glu Asn Trp Gln Ser Gln Glu Ile Thr Phe Asp Glu Ile
                165                 170                 175

Leu Gln Ala Tyr Cys Phe Ile Leu Glu Lys Leu Leu Glu Asn Glu Glu
            180                 185                 190

Thr Gln Ile Asn Gly Phe Cys Ile Ile Glu Asn Phe Lys Gly Phe Thr
        195                 200                 205

Met Gln Gln Ala Ala Ser Leu Arg Thr Ser Asp Leu Arg Lys Met Val
    210                 215                 220

Asp Met Leu Gln Asp Ser Phe Pro Ala Arg Phe Lys Ala Ile His Phe
225                 230                 235                 240

Ile His Gln Pro Trp Tyr Phe Thr Thr Thr Tyr Asn Val Val Lys Pro
                245                 250                 255

Phe Leu Lys Ser Lys Leu Leu Glu Arg Val Phe Val His Gly Asp Asp
            260                 265                 270

Leu Ser Gly Phe Tyr Gln Glu Ile Asp Glu Asn Ile Leu Pro Ser Asp
        275                 280                 285

Phe Gly Gly Thr Leu Pro Lys Tyr Asp Gly Lys Ala Val Ala Glu Gln
    290                 295                 300

Leu Phe Gly Pro Gln Ala Gln Ala Glu Asn Thr Ala Phe
305                 310                 315
```

<210> SEQ ID NO 18
<211> LENGTH: 3027
<212> TYPE: DNA
<213> ORGANISM: Homo sapiens

<400> SEQUENCE: 18

```
cagcgttcag gctgcccctt cttggctggg aagggcgctg aagaaacaac gcccaggacc      60

aggactatcc cctgctcaag ctgtgattcc gagacccctg ccaccactac tgcattcacg     120

gggatcccag gctagtggga ctcgacatgg gtagccccca gggcagctcc ctacagcttg     180

ggccatctgc acttttccca aggccctaag tctccgcctc tgggctcgtt aaggtttggg     240

gtgggagctg tgctgtggga agcaacccgg actacacttg gcaagcatgg cgctactgaa     300
```

```
agtcaagttt gaccagaaga agcgggtcaa gttggcccaa gggctctggc tcatgaactg    360
gttctccgtg ttggctggca tcatcatctt cagcctagga ctgttcctga agattgaact    420
ccgaaagagg agcgatgtga tgaataattc tgagagccat tttgtgccca actcattgat    480
agggatgggg gtgctatcct gtgtcttcaa ctcgctggct gggaagatct gctacgacgc    540
cctggaccca gccaagtatg ccagatggaa gccctggctg aagccgtacc tggctatctg    600
tgttctcttc aacatcatcc tcttccttgt ggctctctgc tgctttctgc ttcggggctc    660
gctggagaac accctgggcc aagggctcaa gaacggcatg aagtactacc gggacacaga    720
cacccctggc aggtgtttca tgaagaagac catcgacatg ctgcagatcg agttcaaatg    780
ctgcggcaac aacggttttc gggactggtt tgagattcag tggatcagca atcgctacct    840
ggacttttcc tccaaagaag tcaaagatcg aatcaagagc aacgtggatg ggcggtacct    900
ggtggacggc gtccctttca gctgctgcaa tcctagctcg ccacggccct gcatccagta    960
tcagatcacc aacaactcag cacactacag ttacgaccac cagacggagg agctcaacct   1020
gtgggtgcgt ggctgcaggg ctgccctgct gagctactac agcagcctca tgaactccat   1080
gggtgtcgtc acgctcctca tttggctctt cgaggtgacc attacaattg ggctgcgcta   1140
cctacagacg tcgctggatg gtgtgtccaa ccccgaggaa tctgagagcg agagccaggg   1200
ctggctgctg gagaggagcg tgccggagac ctggaaggcc tttctggaga gtgtgaagaa   1260
gctgggcaag ggcaaccagg tggaagccga gggcgcagac gcaggccagg ccccagaggc   1320
tggctgaggg ccctggggcc cctcccctcc cgaacactga gaaatagtgc actccaagaa   1380
acgtggatct ccccctcatc caactccgaa agtctgaatc tcccaaggag ggcaccatct   1440
tacagagact ctccctgacg gtggaattta agtttagggt ccctaaaagc atttgacaca   1500
cagttgttga atgactgacc caaaatgtga atgaagctaa tgtgaatgtg agtgaagctc   1560
ccttcaggcc cgctgcccta ggatatgccc tcctggtgac tcgggggctg tctcagacga   1620
ctagcccagg acccatcttt ctcacacgga tttagtccca ccctatggcc actggccgta   1680
tctgagggct gctccccttt tagaatttac ctcttatgag ctccatgttg cttcactcta   1740
tccaaagtgt cacttggtgc ataagcacag aaatctgaaa aatggccatg ttgtcttttt   1800
ttttttttt taatgccaag attgacaggt tggccgtttg cttaatgcca gaagttgggg   1860
gaaagttacg cttttctaag aataatggac tcttaaggca ttgagggctc taaacaggat   1920
tctttaatca tggagcaaga gaatttcaag gcaggggatt ttatccccca ccaaaaacac   1980
agtgaaaggc ctgcttttgt gtcccattca catgccctcg gtcactgagt ctggagtgaa   2040
ccacgggttg aggaagtcag gctgttggcg tgtcccagca ccacaccacc cctaaagtgc   2100
caggtgatct cctgtggctc atcggtggaa gcagtggggt aggctgctgc cctgctgtgg   2160
aagaggagca acaatcagac atgagtccac cctttggaga ccaggcctca gctcttggtg   2220
ggcccaggga cacccacaca ggtggccatc acagccccat ggacaacact aattgtccac   2280
agcaaagggc aaggaatcct ctgggagctt cttccgtttc ttccccccag atacccatct   2340
tgaaaaacac tatttctgga atgcttctgc atcaaaggag attctttgag atagcccatc   2400
ttcctgagct agcaaataca ggagttttca ctttctttag gaaagagaag ctttcagggg   2460
aaggagagaa tgattttgct gacttcccaa gccctggtga ccagaccaag gcagggccca   2520
gcataattcc tccagttgga tgaacattca agagagctcg ttcctacctg gctggagacc   2580
gaggccagaa ggcaaaaacc agaaagggaa cagtccataa cttacctctg cttctgaccg   2640
```

```
atggtgtttg ggaataggtt actttggact gagtttgggt tctctgctgt cctaagaact   2700

tcagtgtaga gaaaataaga cttctggtgc tgctggggta tgttctgggc ttaattcccc   2760

caagcagaag accagatcca agatgtttgg acaccctgtc agacgttggt cccaagttta   2820

attagatttc tgaatctcgt tgaggccaag gaatgatcca tactgaaaaa atgctgagcc   2880

agccatcttt ggcaaaggtc cctgagctct tgctatctct caagagtgct gagaaccacg   2940

gtgaaagtgc tgctctaggc ccacaagtgt aactatgctg ttaacagctg tcaatagata   3000

attaaaattc atactgtatg aaaatca                                       3027


<210> SEQ ID NO 19
<211> LENGTH: 346
<212> TYPE: PRT
<213> ORGANISM: Homo sapiens

<400> SEQUENCE: 19

Met Ala Leu Leu Lys Val Lys Phe Asp Gln Lys Lys Arg Val Lys Leu
1               5                   10                  15

Ala Gln Gly Leu Trp Leu Met Asn Trp Phe Ser Val Leu Ala Gly Ile
            20                  25                  30

Ile Ile Phe Ser Leu Gly Leu Phe Leu Lys Ile Glu Leu Arg Lys Arg
        35                  40                  45

Ser Asp Val Met Asn Asn Ser Glu Ser His Phe Val Pro Asn Ser Leu
    50                  55                  60

Ile Gly Met Gly Val Leu Ser Cys Val Phe Asn Ser Leu Ala Gly Lys
65                  70                  75                  80

Ile Cys Tyr Asp Ala Leu Asp Pro Ala Lys Tyr Ala Arg Trp Lys Pro
                85                  90                  95

Trp Leu Lys Pro Tyr Leu Ala Ile Cys Val Leu Phe Asn Ile Ile Leu
            100                 105                 110

Phe Leu Val Ala Leu Cys Cys Phe Leu Leu Arg Gly Ser Leu Glu Asn
        115                 120                 125

Thr Leu Gly Gln Gly Leu Lys Asn Gly Met Lys Tyr Tyr Arg Asp Thr
    130                 135                 140

Asp Thr Pro Gly Arg Cys Phe Met Lys Lys Thr Ile Asp Met Leu Gln
145                 150                 155                 160

Ile Glu Phe Lys Cys Cys Gly Asn Asn Gly Phe Arg Asp Trp Phe Glu
                165                 170                 175

Ile Gln Trp Ile Ser Asn Arg Tyr Leu Asp Phe Ser Ser Lys Glu Val
            180                 185                 190

Lys Asp Arg Ile Lys Ser Asn Val Asp Gly Arg Tyr Leu Val Asp Gly
        195                 200                 205

Val Pro Phe Ser Cys Cys Asn Pro Ser Ser Pro Arg Pro Cys Ile Gln
    210                 215                 220

Tyr Gln Ile Thr Asn Asn Ser Ala His Tyr Ser Tyr Asp His Gln Thr
225                 230                 235                 240

Glu Glu Leu Asn Leu Trp Val Arg Gly Cys Arg Ala Ala Leu Leu Ser
                245                 250                 255

Tyr Tyr Ser Ser Leu Met Asn Ser Met Gly Val Val Thr Leu Leu Ile
            260                 265                 270

Trp Leu Phe Glu Val Thr Ile Thr Ile Gly Leu Arg Tyr Leu Gln Thr
        275                 280                 285

Ser Leu Asp Gly Val Ser Asn Pro Glu Glu Ser Glu Ser Glu Ser Gln
    290                 295                 300
```

```
Gly Trp Leu Leu Glu Arg Ser Val Pro Glu Thr Trp Lys Ala Phe Leu
305                 310                 315                 320

Glu Ser Val Lys Lys Leu Gly Lys Gly Asn Gln Val Glu Ala Glu Gly
                325                 330                 335

Ala Asp Ala Gly Gln Ala Pro Glu Ala Gly
            340                 345


<210> SEQ ID NO 20
<211> LENGTH: 1767
<212> TYPE: DNA
<213> ORGANISM: Homo sapiens

<400> SEQUENCE: 20

gtcagctggg tgactcatac atctgtgaga ccctccgtat ggagaccggg gcgggggtg      60

ttgcttaatg cttagaactg ctgaaactac cagttcactg tctcagcact aatccaactc    120

tgctccttaa gtgggatttg gcttttagac attgagacct ggatgctggg catcctcgct    180

agatccccta caaattcccc acatacgtag gccaggagcc tcagcggtgc cccttcaggc    240

tcatctggca agacggtacc agcttgctca gaacaggggc tggctattca tcatctcaga    300

gcatagagac cctctccttg ccacccggcc cttcccacct ggttggtgac aaatcacaag    360

gtggtagaag ttgccaggga cagataacat ggcagccagc gggaagacca gcaagtccga    420

accgaaccat gttatcttca agaagatctc ccgggacaaa tcggtgacca tctacctggg    480

gaacagagac tacatagacc atgtcagcca agtccagcct gtggatggtg tcgtgttggt    540

tgatcctgat cttgtgaagg gaaagaaagt gtatgtcact ctgacctgcg ccttccgcta    600

tggccaagag gacattgacg tgatcggctt gaccttccgc agggacctgt acttctcccg    660

ggtccaggtg tatcctcctg tgggggccgc gagcaccccc acaaaactgc aagagagcct    720

gcttaaaaag ctggggagca acacgtaccc ctttctcctg acgtttcctg actacttgcc    780

ctgttcagtg atgttgcagc cagctccaca agattcaggg aagtcctgtg gggttgactt    840

tgaggtcaaa gcattcgcca cagacagcac cgatgccgaa gaggacaaaa tccccaagaa    900

gagctccgtg cgattactga tccgcaaagt acagcatgcc ccacttgaga tgggtcccca    960

gccccgagct gaggcggcct ggcagttctt catgtctgac aagcccctgc accttgcggt   1020

ctctctcaac aaagagatct atttccatgg ggagcccatc cctgtgaccg tgactgtcac   1080

caataacaca gagaagaccg tgaagaagat taaagcattc gtggaacagg tggccaatgt   1140

ggttctctac tcgagtgatt attacgtcaa gcccgtggct atggaggaag cgcaagaaaa   1200

agtgccacca aacagcactt tgaccaagac gctgacgctg ctgcccttgc tggctaacaa   1260

tcgagaaagg agaggcattg ccctggatgg gaaaatcaag cacgaggaca caaaccttgc   1320

ctccagcacc atcattaagg agggcataga ccggaccgtc ctgggaatcc tggtgtctta   1380

ccagatcaag gtgaagctca cagtgtcagg ctttctggga gagctcacct ccagtgaagt   1440

cgccactgag gtcccattcc gcctcatgca ccctcagcct gaggacccag ctaaggaaag   1500

ttatcaggat gcaaatttag tttttgagga gtttgctcgc cataatctga aagatgcagg   1560

agaagctgag gaggggaaga gagacaagaa tgacgttgat gagtgaagat gtcggctcag   1620

gatgccggaa aatgacctgt agttaccagt gcaacgagca aagccccaca gtttagtcct   1680

ttggagttat gctgcgtatg aaaggatgag tcttcttccg agaaataaag cttgtttgtt   1740

ctcccctgga aaaaaaaaaa aaaaaaa                                       1767


<210> SEQ ID NO 21
```

<211> LENGTH: 405
<212> TYPE: PRT
<213> ORGANISM: Homo sapiens

<400> SEQUENCE: 21

```
Met Ala Ala Ser Gly Lys Thr Ser Lys Ser Glu Pro Asn His Val Ile
1               5                   10                  15

Phe Lys Lys Ile Ser Arg Asp Lys Ser Val Thr Ile Tyr Leu Gly Asn
            20                  25                  30

Arg Asp Tyr Ile Asp His Val Ser Gln Val Gln Pro Val Asp Gly Val
        35                  40                  45

Val Leu Val Asp Pro Asp Leu Val Lys Gly Lys Lys Val Tyr Val Thr
    50                  55                  60

Leu Thr Cys Ala Phe Arg Tyr Gly Gln Glu Asp Ile Asp Val Ile Gly
65                  70                  75                  80

Leu Thr Phe Arg Arg Asp Leu Tyr Phe Ser Arg Val Gln Val Tyr Pro
                85                  90                  95

Pro Val Gly Ala Ala Ser Thr Pro Thr Lys Leu Gln Glu Ser Leu Leu
            100                 105                 110

Lys Lys Leu Gly Ser Asn Thr Tyr Pro Phe Leu Leu Thr Phe Pro Asp
        115                 120                 125

Tyr Leu Pro Cys Ser Val Met Leu Gln Pro Ala Pro Gln Asp Ser Gly
    130                 135                 140

Lys Ser Cys Gly Val Asp Phe Glu Val Lys Ala Phe Ala Thr Asp Ser
145                 150                 155                 160

Thr Asp Ala Glu Glu Asp Lys Ile Pro Lys Lys Ser Ser Val Arg Leu
                165                 170                 175

Leu Ile Arg Lys Val Gln His Ala Pro Leu Glu Met Gly Pro Gln Pro
            180                 185                 190

Arg Ala Glu Ala Ala Trp Gln Phe Phe Met Ser Asp Lys Pro Leu His
        195                 200                 205

Leu Ala Val Ser Leu Asn Lys Glu Ile Tyr Phe His Gly Glu Pro Ile
    210                 215                 220

Pro Val Thr Val Thr Val Thr Asn Asn Thr Glu Lys Thr Val Lys Lys
225                 230                 235                 240

Ile Lys Ala Phe Val Glu Gln Val Ala Asn Val Val Leu Tyr Ser Ser
                245                 250                 255

Asp Tyr Tyr Val Lys Pro Val Ala Met Glu Glu Ala Gln Glu Lys Val
            260                 265                 270

Pro Pro Asn Ser Thr Leu Thr Lys Thr Leu Thr Leu Leu Pro Leu Leu
        275                 280                 285

Ala Asn Asn Arg Glu Arg Arg Gly Ile Ala Leu Asp Gly Lys Ile Lys
    290                 295                 300

His Glu Asp Thr Asn Leu Ala Ser Ser Thr Ile Ile Lys Glu Gly Ile
305                 310                 315                 320

Asp Arg Thr Val Leu Gly Ile Leu Val Ser Tyr Gln Ile Lys Val Lys
                325                 330                 335

Leu Thr Val Ser Gly Phe Leu Gly Glu Leu Thr Ser Ser Glu Val Ala
            340                 345                 350

Thr Glu Val Pro Phe Arg Leu Met His Pro Gln Pro Glu Asp Pro Ala
        355                 360                 365

Lys Glu Ser Tyr Gln Asp Ala Asn Leu Val Phe Glu Glu Phe Ala Arg
    370                 375                 380

His Asn Leu Lys Asp Ala Gly Glu Ala Glu Glu Gly Lys Arg Asp Lys
```

385 390 395 400

Asn Asp Val Asp Glu
405

<210> SEQ ID NO 22
<211> LENGTH: 2483
<212> TYPE: DNA
<213> ORGANISM: Homo sapiens

<400> SEQUENCE: 22
agttgattgc aggtcctcct ggggccagaa gggtgcctgg gaggccaggt tctggggatc 60
ccctccatcc agaagaacca cctgctcact ctgtcccttc gcctgctgct gggaccatgg 120
gggctggggc cagtgctgag gagaagcact ccagggagct ggaaaagaag ctgaaagagg 180
acgctgagaa ggatgctcga accgtgaagc tgctgcttct gggtgccggt gagtccggga 240
agagcaccat cgtcaagcag atgaagatta tccaccagga cgggtactcg ctggaagagt 300
gcctcgagtt tatcgccatc atctacggca acacgttgca gtccatcctg gccatcgtac 360
gcgccatgac cacactcaac atccagtacg gagactctgc acgccaggac gacgcccgga 420
agctgatgca catggcagac actatcgagg agggcacgat gcccaaggag atgtcggaca 480
tcatccagcg gctgtggaag gactccggta tccaggcctg ttttgagcgc gcctcggagt 540
accagctcaa cgactcggcg ggctactacc tctccgacct ggagcgcctg gtaaccccgg 600
gctacgtgcc caccgagcag gacgtgctgc gctcgcgagt caagaccact ggcatcatcg 660
agacgcagtt ctccttcaag gatctcaact tccggatgtt cgatgtgggc gggcagcgct 720
cggagcgcaa gaagtggatc cactgcttcg agggcgtgac ctgcatcatc ttcatcgcgg 780
cgctgagcgc ctacgacatg gtgctagtgg aggacgacga agtgaaccgc atgcacgaga 840
gcctgcacct gttcaacagc atctgcaacc accgctactt cgccacgacg tccatcgtgc 900
tcttccttaa caagaaggac gtcttcttcg agaagatcaa gaaggcgcac ctcagcatct 960
gtttcccgga ctacgatgga cccaacacct acgaggacgc cggcaactac atcaaggtgc 1020
agttcctcga gctcaacatg cggcgcgacg tgaaggagat ctattcccac atgacgtgcg 1080
ccaccgacac gcagaacgtc aaatttgtct tcgacgctgt caccgacatc atcatcaagg 1140
agaacctcaa agactgtggc ctcttctgag gccagggcct gtgctgcagt cggggacaag 1200
gagcttccgt ctggcaaggc cggggcacaa tttgcactcc cctcagctag acgcacagac 1260
tcagcaataa acctttgcat caggctccag ctgtcctttc ttggtggagg acttaattat 1320
cacaagtcat gggcatttat taagtgccca gtgctgggtt gggcatgaag tgggaagatg 1380
gcccctccca ggaagaagta cctggcctga caaggtgggg cactcttggg ggtatgggac 1440
caactcatgg cttttcacgg gagttgagga gagaggagct gtggaaaata ttcactggga 1500
cagtcttgga tcaagaggga gttttgaggt ggaggctcat tctggcaggg accgtagtgt 1560
ctaccagccc cagaaacatg ggcttatggc cacaggagtt cagtggagca agagcagggg 1620
aggagagacg tggacaggtg cccaaagcca gtcggagggc ctgggctttc tcagaaggtg 1680
atggagagtc ttggaagccc tcgaggcagg aacataattg cagggctggg attagggtga 1740
gggaagtgag gcacactcac cttgggtgca acatttaagg cgatgccaaa aaatttagta 1800
accaaggtaa ataatattag gataatattt ttaaaaatca aatgaatgca aaaccccaca 1860
atgaatgaaa tatcaaaatc caacagagga tcaaacagag gcatgctaag atatattggg 1920
gcttgaagca aagggaaaac tatttgttgc tatatgtttg tagggatttt ttgccagttt 1980

```
taaaaataca tgtatcataa agtttactat ctcagccact tgccggtgta tagtttggtg   2040

gtgttaagta cattcataat gttgtacaac caccgcaact gttcatctcc agaactcctt   2100

tcctcttgta aaactgtaac tctgtaccca tgaaaaaata accccccatt cctgccttcc   2160

cccggctcct ggcatccacc attctacttt ccatctctat gaatgtgact gctctaagtg   2220

cctcagatgt gtgggtccat gaagtctttg tctttttgca actggcttat ttcacttagc   2280

atcatgtctt caaggtttat tcatgtgtag catatggcag aatctccttc ctttttaagg   2340

ttgaataata ttccattgta tatattccac actttgttta tttattcatc tattgatgaa   2400

tggttacatc tgccttttgg ctattgtgaa taatgctgct atgaacatgg gtgtacaaat   2460

ctctcaaaaa aaaaaaaaaa aaa                                           2483
```

```
<210> SEQ ID NO 23
<211> LENGTH: 350
<212> TYPE: PRT
<213> ORGANISM: Homo sapiens

<400> SEQUENCE: 23

Met Gly Ala Gly Ala Ser Ala Glu Glu Lys His Ser Arg Glu Leu Glu
1               5                   10                  15

Lys Lys Leu Lys Glu Asp Ala Glu Lys Asp Ala Arg Thr Val Lys Leu
            20                  25                  30

Leu Leu Leu Gly Ala Gly Glu Ser Gly Lys Ser Thr Ile Val Lys Gln
        35                  40                  45

Met Lys Ile Ile His Gln Asp Gly Tyr Ser Leu Glu Glu Cys Leu Glu
    50                  55                  60

Phe Ile Ala Ile Ile Tyr Gly Asn Thr Leu Gln Ser Ile Leu Ala Ile
65                  70                  75                  80

Val Arg Ala Met Thr Thr Leu Asn Ile Gln Tyr Gly Asp Ser Ala Arg
                85                  90                  95

Gln Asp Asp Ala Arg Lys Leu Met His Met Ala Asp Thr Ile Glu Glu
            100                 105                 110

Gly Thr Met Pro Lys Glu Met Ser Asp Ile Ile Gln Arg Leu Trp Lys
        115                 120                 125

Asp Ser Gly Ile Gln Ala Cys Phe Glu Arg Ala Ser Glu Tyr Gln Leu
    130                 135                 140

Asn Asp Ser Ala Gly Tyr Tyr Leu Ser Asp Leu Glu Arg Leu Val Thr
145                 150                 155                 160

Pro Gly Tyr Val Pro Thr Glu Gln Asp Val Leu Arg Ser Arg Val Lys
                165                 170                 175

Thr Thr Gly Ile Ile Glu Thr Gln Phe Ser Phe Lys Asp Leu Asn Phe
            180                 185                 190

Arg Met Phe Asp Val Gly Gly Gln Arg Ser Glu Arg Lys Lys Trp Ile
        195                 200                 205

His Cys Phe Glu Gly Val Thr Cys Ile Ile Phe Ile Ala Ala Leu Ser
    210                 215                 220

Ala Tyr Asp Met Val Leu Val Glu Asp Asp Glu Val Asn Arg Met His
225                 230                 235                 240

Glu Ser Leu His Leu Phe Asn Ser Ile Cys Asn His Arg Tyr Phe Ala
                245                 250                 255

Thr Thr Ser Ile Val Leu Phe Leu Asn Lys Lys Asp Val Phe Phe Glu
            260                 265                 270

Lys Ile Lys Lys Ala His Leu Ser Ile Cys Phe Pro Asp Tyr Asp Gly
        275                 280                 285
```

```
Pro Asn Thr Tyr Glu Asp Ala Gly Asn Tyr Ile Lys Val Gln Phe Leu
    290                 295                 300

Glu Leu Asn Met Arg Arg Asp Val Lys Glu Ile Tyr Ser His Met Thr
305                 310                 315                 320

Cys Ala Thr Asp Thr Gln Asn Val Lys Phe Val Phe Asp Ala Val Thr
                325                 330                 335

Asp Ile Ile Ile Lys Glu Asn Leu Lys Asp Cys Gly Leu Phe
            340                 345                 350


<210> SEQ ID NO 24
<211> LENGTH: 201
<212> TYPE: PRT
<213> ORGANISM: Homo sapiens

<400> SEQUENCE: 24

Met Gly Asn Val Met Glu Gly Lys Ser Val Glu Glu Leu Ser Ser Thr
1               5                   10                  15

Glu Cys His Gln Trp Tyr Lys Lys Phe Met Thr Glu Cys Pro Ser Gly
            20                  25                  30

Gln Leu Thr Leu Tyr Glu Phe Arg Gln Phe Phe Gly Leu Lys Asn Leu
        35                  40                  45

Ser Pro Ser Ala Ser Gln Tyr Val Glu Gln Met Phe Glu Thr Phe Asp
    50                  55                  60

Phe Asn Lys Asp Gly Tyr Ile Asp Phe Met Glu Tyr Val Ala Ala Leu
65                  70                  75                  80

Ser Leu Val Leu Lys Gly Lys Val Glu Gln Lys Leu Arg Trp Tyr Phe
                85                  90                  95

Lys Leu Tyr Asp Val Asp Gly Asn Gly Cys Ile Asp Arg Asp Glu Leu
            100                 105                 110

Leu Thr Ile Ile Gln Ala Ile Arg Ala Ile Asn Pro Cys Ser Asp Thr
        115                 120                 125

Thr Met Thr Ala Glu Glu Phe Thr Asp Thr Val Phe Ser Lys Ile Asp
    130                 135                 140

Val Asn Gly Asp Gly Glu Leu Ser Leu Glu Glu Phe Ile Glu Gly Val
145                 150                 155                 160

Gln Lys Asp Gln Met Leu Leu Asp Thr Leu Thr Arg Ser Leu Asp Leu
                165                 170                 175

Thr Arg Ile Val Arg Arg Leu Gln Asn Gly Glu Gln Asp Glu Glu Gly
            180                 185                 190

Ala Asp Glu Ala Ala Glu Ala Ala Gly
        195                 200


<210> SEQ ID NO 25
<211> LENGTH: 1103
<212> TYPE: PRT
<213> ORGANISM: Homo sapiens

<400> SEQUENCE: 25

Met Thr Ala Cys Ala Arg Arg Ala Gly Gly Leu Pro Asp Pro Gly Leu
1               5                   10                  15

Cys Gly Pro Ala Trp Trp Ala Pro Ser Leu Pro Arg Leu Pro Arg Ala
            20                  25                  30

Leu Pro Arg Leu Pro Leu Leu Leu Leu Leu Leu Leu Leu Gln Pro Pro
        35                  40                  45

Ala Leu Ser Ala Val Phe Thr Val Gly Val Leu Gly Pro Trp Ala Cys
    50                  55                  60
```

```
Asp Pro Ile Phe Ser Arg Ala Arg Pro Asp Leu Ala Ala Arg Leu Ala
65                  70                  75                  80

Ala Ala Arg Leu Asn Arg Asp Pro Gly Leu Ala Gly Gly Pro Arg Phe
                85                  90                  95

Glu Val Ala Leu Leu Pro Glu Pro Cys Arg Thr Pro Gly Ser Leu Gly
            100                 105                 110

Ala Val Ser Ser Ala Leu Ala Arg Val Ser Gly Leu Val Gly Pro Val
        115                 120                 125

Asn Pro Ala Ala Cys Arg Pro Ala Glu Leu Leu Ala Glu Glu Ala Gly
    130                 135                 140

Ile Ala Leu Val Pro Trp Gly Cys Pro Trp Thr Gln Ala Glu Gly Thr
145                 150                 155                 160

Thr Ala Pro Ala Val Thr Pro Ala Ala Asp Ala Leu Tyr Ala Leu Leu
                165                 170                 175

Arg Ala Phe Gly Trp Ala Arg Val Ala Leu Val Thr Ala Pro Gln Asp
            180                 185                 190

Leu Trp Val Glu Ala Gly Arg Ser Leu Ser Thr Ala Leu Arg Ala Arg
        195                 200                 205

Gly Leu Pro Val Ala Ser Val Thr Ser Met Glu Pro Leu Asp Leu Ser
    210                 215                 220

Gly Ala Arg Glu Ala Leu Arg Lys Val Arg Asp Gly Pro Arg Val Thr
225                 230                 235                 240

Ala Val Ile Met Val Met His Ser Val Leu Leu Gly Gly Glu Glu Gln
                245                 250                 255

Arg Tyr Leu Leu Glu Ala Ala Glu Glu Leu Gly Leu Thr Asp Gly Ser
            260                 265                 270

Leu Val Phe Leu Pro Phe Asp Thr Ile His Tyr Ala Leu Ser Pro Gly
        275                 280                 285

Pro Glu Ala Leu Ala Ala Leu Ala Asn Ser Ser Gln Leu Arg Arg Ala
    290                 295                 300

His Asp Ala Val Leu Thr Leu Thr Arg His Cys Pro Ser Glu Gly Ser
305                 310                 315                 320

Val Leu Asp Ser Leu Arg Arg Ala Gln Glu Arg Arg Glu Leu Pro Ser
                325                 330                 335

Asp Leu Asn Leu Gln Gln Val Ser Pro Leu Phe Gly Thr Ile Tyr Asp
            340                 345                 350

Ala Val Phe Leu Leu Ala Arg Gly Val Ala Glu Ala Arg Ala Ala Ala
        355                 360                 365

Gly Gly Arg Trp Val Ser Gly Ala Ala Val Ala Arg His Ile Arg Asp
    370                 375                 380

Ala Gln Val Pro Gly Phe Cys Gly Asp Leu Gly Gly Asp Glu Glu Pro
385                 390                 395                 400

Pro Phe Val Leu Leu Asp Thr Asp Ala Ala Gly Asp Arg Leu Phe Ala
                405                 410                 415

Thr Tyr Met Leu Asp Pro Ala Arg Gly Ser Phe Leu Ser Ala Gly Thr
            420                 425                 430

Arg Met His Phe Pro Arg Gly Gly Ser Ala Pro Gly Pro Asp Pro Ser
        435                 440                 445

Cys Trp Phe Asp Pro Asn Asn Ile Cys Gly Gly Gly Leu Glu Pro Gly
    450                 455                 460

Leu Val Phe Leu Gly Phe Leu Leu Val Val Gly Met Gly Leu Ala Gly
465                 470                 475                 480
```

```
Ala Phe Leu Ala His Tyr Val Arg His Arg Leu Leu His Met Gln Met
                485                 490                 495

Val Ser Gly Pro Asn Lys Ile Ile Leu Thr Val Asp Asp Ile Thr Phe
            500                 505                 510

Leu His Pro His Gly Gly Thr Ser Arg Lys Val Ala Gln Gly Ser Arg
        515                 520                 525

Ser Ser Leu Gly Ala Arg Ser Met Ser Asp Ile Arg Ser Gly Pro Ser
    530                 535                 540

Gln His Leu Asp Ser Pro Asn Ile Gly Val Tyr Glu Gly Asp Arg Val
545                 550                 555                 560

Trp Leu Lys Lys Phe Pro Gly Asp Gln His Ile Ala Ile Arg Pro Ala
                565                 570                 575

Thr Lys Thr Ala Phe Ser Lys Leu Gln Glu Leu Arg His Glu Asn Val
            580                 585                 590

Ala Leu Tyr Leu Gly Leu Phe Leu Ala Arg Gly Ala Glu Gly Pro Ala
        595                 600                 605

Ala Leu Trp Glu Gly Asn Leu Ala Val Val Ser Glu His Cys Thr Arg
    610                 615                 620

Gly Ser Leu Gln Asp Leu Leu Ala Gln Arg Glu Ile Lys Leu Asp Trp
625                 630                 635                 640

Met Phe Lys Ser Ser Leu Leu Leu Asp Leu Ile Lys Gly Ile Arg Tyr
                645                 650                 655

Leu His His Arg Gly Val Ala His Gly Arg Leu Lys Ser Arg Asn Cys
            660                 665                 670

Ile Val Asp Gly Arg Phe Val Leu Lys Ile Thr Asp His Gly His Gly
        675                 680                 685

Arg Leu Leu Glu Ala Gln Lys Val Leu Pro Glu Pro Pro Arg Ala Glu
    690                 695                 700

Asp Gln Leu Trp Thr Ala Pro Glu Leu Leu Arg Asp Pro Ala Leu Glu
705                 710                 715                 720

Arg Arg Gly Thr Leu Ala Gly Asp Val Phe Ser Leu Ala Ile Ile Met
                725                 730                 735

Gln Glu Val Val Cys Arg Ser Ala Pro Tyr Ala Met Leu Glu Leu Thr
            740                 745                 750

Pro Glu Glu Val Val Gln Arg Val Arg Ser Pro Pro Pro Leu Cys Arg
        755                 760                 765

Pro Leu Val Ser Met Asp Gln Ala Pro Val Glu Cys Ile Leu Leu Met
    770                 775                 780

Lys Gln Cys Trp Ala Glu Gln Pro Glu Leu Arg Pro Ser Met Asp His
785                 790                 795                 800

Thr Phe Asp Leu Phe Lys Asn Ile Asn Lys Gly Arg Lys Thr Asn Ile
                805                 810                 815

Ile Asp Ser Met Leu Arg Met Leu Glu Gln Tyr Ser Ser Asn Leu Glu
            820                 825                 830

Asp Leu Ile Arg Glu Arg Thr Glu Glu Leu Glu Leu Glu Lys Gln Lys
        835                 840                 845

Thr Asp Arg Leu Leu Thr Gln Met Leu Pro Pro Ser Val Ala Glu Ala
    850                 855                 860

Leu Lys Thr Gly Thr Pro Val Glu Pro Glu Tyr Phe Glu Gln Val Thr
865                 870                 875                 880

Leu Tyr Phe Ser Asp Ile Val Gly Phe Thr Thr Ile Ser Ala Met Ser
                885                 890                 895

Glu Pro Ile Glu Val Val Asp Leu Leu Asn Asp Leu Tyr Thr Leu Phe
```

```
            900                 905                 910

Asp Ala Ile Ile Gly Ser His Asp Val Tyr Lys Val Glu Thr Ile Gly
        915                 920                 925

Asp Ala Tyr Met Val Ala Ser Gly Leu Pro Gln Arg Asn Gly Gln Arg
    930                 935                 940

His Ala Ala Glu Ile Ala Asn Met Ser Leu Asp Ile Leu Ser Ala Val
945                 950                 955                 960

Gly Thr Phe Arg Met Arg His Met Pro Glu Val Pro Val Arg Ile Arg
                965                 970                 975

Ile Gly Leu His Ser Gly Pro Cys Val Ala Gly Val Val Gly Leu Thr
            980                 985                 990

Met Pro Arg Tyr Cys Leu Phe Gly  Asp Thr Val Asn Thr  Ala Ser Arg
        995                 1000                1005

Met Glu  Ser Thr Gly Leu Pro  Tyr Arg Ile His Val  Asn Leu Ser
    1010                1015                1020

Thr Val  Gly Ile Leu Arg Ala  Leu Asp Ser Gly Tyr  Gln Val Glu
    1025                1030                1035

Leu Arg  Gly Arg Thr Glu Leu  Lys Gly Lys Gly Ala  Glu Asp Thr
    1040                1045                1050

Phe Trp  Leu Val Gly Arg Arg  Gly Phe Asn Lys Pro  Ile Pro Lys
    1055                1060                1065

Pro Pro  Asp Leu Gln Pro Gly  Ser Ser Asn His Gly  Ile Ser Leu
    1070                1075                1080

Gln Glu  Ile Pro Pro Glu Arg  Arg Arg Lys Leu Glu  Lys Ala Arg
    1085                1090                1095

Pro Gly  Gln Phe Ser
    1100


<210> SEQ ID NO 26
<211> LENGTH: 676
<212> TYPE: PRT
<213> ORGANISM: Homo sapiens

<400> SEQUENCE: 26

Met Ala Lys Ile Asn Thr Gln Tyr Ser His Pro Ser Arg Thr His Leu
1               5                   10                  15

Lys Val Lys Thr Ser Asp Arg Asp Leu Asn Arg Ala Glu Asn Gly Leu
            20                  25                  30

Ser Arg Ala His Ser Ser Ser Glu Glu Thr Ser Ser Val Leu Gln Pro
        35                  40                  45

Gly Ile Ala Met Glu Thr Arg Gly Leu Ala Asp Ser Gly Gln Gly Ser
    50                  55                  60

Phe Thr Gly Gln Gly Ile Ala Arg Leu Ser Arg Leu Ile Phe Leu Leu
65                  70                  75                  80

Arg Arg Trp Ala Ala Arg His Val His His Gln Asp Gln Gly Pro Asp
                85                  90                  95

Ser Phe Pro Asp Arg Phe Arg Gly Ala Glu Leu Lys Glu Val Ser Ser
            100                 105                 110

Gln Glu Ser Asn Ala Gln Ala Asn Val Gly Ser Gln Glu Pro Ala Asp
        115                 120                 125

Arg Gly Arg Arg Lys Lys Thr Lys Lys Lys Asp Ala Ile Val Val Asp
    130                 135                 140

Pro Ser Ser Asn Leu Tyr Tyr Arg Trp Leu Thr Ala Ile Ala Leu Pro
145                 150                 155                 160
```

```
Val Phe Tyr Asn Trp Tyr Leu Leu Ile Cys Arg Ala Cys Phe Asp Glu
                165                 170                 175

Leu Gln Ser Glu Tyr Leu Met Leu Trp Leu Val Leu Asp Tyr Ser Ala
            180                 185                 190

Asp Val Leu Tyr Val Leu Asp Val Leu Val Arg Ala Arg Thr Gly Phe
        195                 200                 205

Leu Glu Gln Gly Leu Met Val Ser Asp Thr Asn Arg Leu Trp Gln His
    210                 215                 220

Tyr Lys Thr Thr Thr Gln Phe Lys Leu Asp Val Leu Ser Leu Val Pro
225                 230                 235                 240

Thr Asp Leu Ala Tyr Leu Lys Val Gly Thr Asn Tyr Pro Glu Val Arg
                245                 250                 255

Phe Asn Arg Leu Leu Lys Phe Ser Arg Leu Phe Glu Phe Phe Asp Arg
            260                 265                 270

Thr Glu Thr Arg Thr Asn Tyr Pro Asn Met Phe Arg Ile Gly Asn Leu
        275                 280                 285

Val Leu Tyr Ile Leu Ile Ile Ile His Trp Asn Ala Cys Ile Tyr Phe
    290                 295                 300

Ala Ile Ser Lys Phe Ile Gly Phe Gly Thr Asp Ser Trp Val Tyr Pro
305                 310                 315                 320

Asn Ile Ser Ile Pro Glu His Gly Arg Leu Ser Arg Lys Tyr Ile Tyr
                325                 330                 335

Ser Leu Tyr Trp Ser Thr Leu Thr Leu Thr Thr Ile Gly Glu Thr Pro
            340                 345                 350

Pro Pro Val Lys Asp Glu Glu Tyr Leu Phe Val Val Val Asp Phe Leu
        355                 360                 365

Val Gly Val Leu Ile Phe Ala Thr Ile Val Gly Asn Val Gly Ser Met
    370                 375                 380

Ile Ser Asn Met Asn Ala Ser Arg Ala Glu Phe Gln Ala Lys Ile Asp
385                 390                 395                 400

Ser Ile Lys Gln Tyr Met Gln Phe Arg Lys Val Thr Lys Asp Leu Glu
                405                 410                 415

Thr Arg Val Ile Arg Trp Phe Asp Tyr Leu Trp Ala Asn Lys Lys Thr
            420                 425                 430

Val Asp Glu Lys Glu Val Leu Lys Ser Leu Pro Asp Lys Leu Lys Ala
        435                 440                 445

Glu Ile Ala Ile Asn Val His Leu Asp Thr Leu Lys Lys Val Arg Ile
    450                 455                 460

Phe Gln Asp Cys Glu Ala Gly Leu Leu Val Glu Leu Val Leu Lys Leu
465                 470                 475                 480

Arg Pro Thr Val Phe Ser Pro Gly Asp Tyr Ile Cys Lys Lys Gly Asp
                485                 490                 495

Ile Gly Lys Glu Met Tyr Ile Ile Asn Glu Gly Lys Leu Ala Val Val
            500                 505                 510

Ala Asp Asp Gly Val Thr Gln Phe Val Val Leu Ser Asp Gly Ser Tyr
        515                 520                 525

Phe Gly Glu Ile Ser Ile Leu Asn Ile Lys Gly Ser Lys Ser Gly Asn
    530                 535                 540

Arg Arg Thr Ala Asn Ile Arg Ser Ile Gly Tyr Ser Asp Leu Phe Cys
545                 550                 555                 560

Leu Ser Lys Asp Asp Leu Met Glu Ala Leu Thr Glu Tyr Pro Glu Ala
                565                 570                 575

Lys Lys Ala Leu Glu Glu Lys Gly Arg Gln Ile Leu Met Lys Asp Asn
```

```
            580                 585                 590

Leu Ile Asp Glu Glu Leu Ala Arg Ala Gly Ala Asp Pro Lys Asp Leu
        595                 600                 605

Glu Glu Lys Val Glu Gln Leu Gly Ser Ser Leu Asp Thr Leu Gln Thr
    610                 615                 620

Arg Phe Ala Arg Leu Leu Ala Glu Tyr Asn Ala Thr Gln Met Lys Met
625                 630                 635                 640

Lys Gln Arg Leu Ser Gln Leu Glu Ser Gln Val Lys Gly Gly Gly Asp
                645                 650                 655

Lys Pro Leu Ala Asp Gly Glu Val Pro Gly Asp Ala Thr Lys Thr Glu
            660                 665                 670

Asp Lys Gln Gln
        675


<210> SEQ ID NO 27
<211> LENGTH: 694
<212> TYPE: PRT
<213> ORGANISM: Homo sapiens

<400> SEQUENCE: 27

Met Ala Lys Ile Asn Thr Gln Tyr Ser His Pro Ser Arg Thr His Leu
1               5                   10                  15

Lys Val Lys Thr Ser Asp Arg Asp Leu Asn Arg Ala Glu Asn Gly Leu
            20                  25                  30

Ser Arg Ala His Ser Ser Ser Glu Glu Thr Ser Ser Val Leu Gln Pro
        35                  40                  45

Gly Ile Ala Met Glu Thr Arg Gly Leu Ala Asp Ser Gly Gln Gly Ser
    50                  55                  60

Phe Thr Gly Gln Gly Ile Ala Arg Leu Ser Arg Leu Ile Phe Leu Leu
65                  70                  75                  80

Arg Arg Trp Ala Ala Arg His Val His His Gln Asp Gln Gly Pro Asp
                85                  90                  95

Ser Phe Pro Asp Arg Phe Arg Gly Ala Glu Leu Lys Glu Val Ser Ser
            100                 105                 110

Gln Glu Ser Asn Ala Gln Ala Asn Val Gly Ser Gln Glu Pro Ala Asp
        115                 120                 125

Arg Gly Arg Ser Ala Trp Pro Leu Ala Lys Cys Asn Thr Asn Thr Ser
    130                 135                 140

Asn Asn Thr Glu Glu Glu Lys Lys Thr Lys Lys Lys Asp Ala Ile Val
145                 150                 155                 160

Val Asp Pro Ser Ser Asn Leu Tyr Tyr Arg Trp Leu Thr Ala Ile Ala
                165                 170                 175

Leu Pro Val Phe Tyr Asn Trp Tyr Leu Leu Ile Cys Arg Ala Cys Phe
            180                 185                 190

Asp Glu Leu Gln Ser Glu Tyr Leu Met Leu Trp Leu Val Leu Asp Tyr
        195                 200                 205

Ser Ala Asp Val Leu Tyr Val Leu Asp Val Leu Val Arg Ala Arg Thr
    210                 215                 220

Gly Phe Leu Glu Gln Gly Leu Met Val Ser Asp Thr Asn Arg Leu Trp
225                 230                 235                 240

Gln His Tyr Lys Thr Thr Thr Gln Phe Lys Leu Asp Val Leu Ser Leu
                245                 250                 255

Val Pro Thr Asp Leu Ala Tyr Leu Lys Val Gly Thr Asn Tyr Pro Glu
            260                 265                 270
```

-continued

```
Val Arg Phe Asn Arg Leu Leu Lys Phe Ser Arg Leu Phe Glu Phe Phe
        275                 280                 285

Asp Arg Thr Glu Thr Arg Thr Asn Tyr Pro Asn Met Phe Arg Ile Gly
    290                 295                 300

Asn Leu Val Leu Tyr Ile Leu Ile Ile Ile His Trp Asn Ala Cys Ile
305                 310                 315                 320

Tyr Phe Ala Ile Ser Lys Phe Ile Gly Phe Gly Thr Asp Ser Trp Val
                325                 330                 335

Tyr Pro Asn Ile Ser Ile Pro Glu His Gly Arg Leu Ser Arg Lys Tyr
            340                 345                 350

Ile Tyr Ser Leu Tyr Trp Ser Thr Leu Thr Leu Thr Thr Ile Gly Glu
        355                 360                 365

Thr Pro Pro Pro Val Lys Asp Glu Glu Tyr Leu Phe Val Val Val Asp
    370                 375                 380

Phe Leu Val Gly Val Leu Ile Phe Ala Thr Ile Val Gly Asn Val Gly
385                 390                 395                 400

Ser Met Ile Ser Asn Met Asn Ala Ser Arg Ala Glu Phe Gln Ala Lys
                405                 410                 415

Ile Asp Ser Ile Lys Gln Tyr Met Gln Phe Arg Lys Val Thr Lys Asp
            420                 425                 430

Leu Glu Thr Arg Val Ile Arg Trp Phe Asp Tyr Leu Trp Ala Asn Lys
        435                 440                 445

Lys Thr Val Asp Glu Lys Glu Val Leu Lys Ser Leu Pro Asp Lys Leu
    450                 455                 460

Lys Ala Glu Ile Ala Ile Asn Val His Leu Asp Thr Leu Lys Lys Val
465                 470                 475                 480

Arg Ile Phe Gln Asp Cys Glu Ala Gly Leu Leu Val Glu Leu Val Leu
                485                 490                 495

Lys Leu Arg Pro Thr Val Phe Ser Pro Gly Asp Tyr Ile Cys Lys Lys
            500                 505                 510

Gly Asp Ile Gly Lys Glu Met Tyr Ile Ile Asn Glu Gly Lys Leu Ala
        515                 520                 525

Val Val Ala Asp Asp Gly Val Thr Gln Phe Val Val Leu Ser Asp Gly
    530                 535                 540

Ser Tyr Phe Gly Glu Ile Ser Ile Leu Asn Ile Lys Gly Ser Lys Ser
545                 550                 555                 560

Gly Asn Arg Arg Thr Ala Asn Ile Arg Ser Ile Gly Tyr Ser Asp Leu
                565                 570                 575

Phe Cys Leu Ser Lys Asp Asp Leu Met Glu Ala Leu Thr Glu Tyr Pro
            580                 585                 590

Glu Ala Lys Lys Ala Leu Glu Glu Lys Gly Arg Gln Ile Leu Met Lys
        595                 600                 605

Asp Asn Leu Ile Asp Glu Glu Leu Ala Arg Ala Gly Ala Asp Pro Lys
    610                 615                 620

Asp Leu Glu Glu Lys Val Glu Gln Leu Gly Ser Ser Leu Asp Thr Leu
625                 630                 635                 640

Gln Thr Arg Phe Ala Arg Leu Leu Ala Glu Tyr Asn Ala Thr Gln Met
                645                 650                 655

Lys Met Lys Gln Arg Leu Ser Gln Leu Glu Ser Gln Val Lys Gly Gly
            660                 665                 670

Gly Asp Lys Pro Leu Ala Asp Gly Glu Val Pro Gly Asp Ala Thr Lys
        675                 680                 685

Thr Glu Asp Lys Gln Gln
```

690

<210> SEQ ID NO 28
<211> LENGTH: 354
<212> TYPE: PRT
<213> ORGANISM: Homo sapiens

<400> SEQUENCE: 28

Met Gly Ser Gly Ala Ser Ala Glu Asp Lys Glu Leu Ala Lys Arg Ser
1 5 10 15

Lys Glu Leu Glu Lys Lys Leu Gln Glu Asp Ala Asp Lys Glu Ala Lys
20 25 30

Thr Val Lys Leu Leu Leu Leu Gly Ala Gly Glu Ser Gly Lys Ser Thr
35 40 45

Ile Val Lys Gln Met Lys Ile Ile His Gln Asp Gly Tyr Ser Pro Glu
50 55 60

Glu Cys Leu Glu Phe Lys Ala Ile Ile Tyr Gly Asn Val Leu Gln Ser
65 70 75 80

Ile Leu Ala Ile Ile Arg Ala Met Thr Thr Leu Gly Ile Asp Tyr Ala
85 90 95

Glu Pro Ser Cys Ala Asp Asp Gly Arg Gln Leu Asn Asn Leu Ala Asp
100 105 110

Ser Ile Glu Glu Gly Thr Met Pro Pro Glu Leu Val Glu Val Ile Arg
115 120 125

Arg Leu Trp Lys Asp Gly Gly Val Gln Ala Cys Phe Glu Arg Ala Ala
130 135 140

Glu Tyr Gln Leu Asn Asp Ser Ala Ser Tyr Tyr Leu Asn Gln Leu Glu
145 150 155 160

Arg Ile Thr Asp Pro Glu Tyr Leu Pro Ser Glu Gln Asp Val Leu Arg
165 170 175

Ser Arg Val Lys Thr Thr Gly Ile Ile Glu Thr Lys Phe Ser Val Lys
180 185 190

Asp Leu Asn Phe Arg Met Phe Asp Val Gly Gly Gln Arg Ser Glu Arg
195 200 205

Lys Lys Trp Ile His Cys Phe Glu Gly Val Thr Cys Ile Ile Phe Cys
210 215 220

Ala Ala Leu Ser Ala Tyr Asp Met Val Leu Val Glu Asp Asp Glu Val
225 230 235 240

Asn Arg Met His Glu Ser Leu His Leu Phe Asn Ser Ile Cys Asn His
245 250 255

Lys Phe Phe Ala Ala Thr Ser Ile Val Leu Phe Leu Asn Lys Lys Asp
260 265 270

Leu Phe Glu Glu Lys Ile Lys Lys Val His Leu Ser Ile Cys Phe Pro
275 280 285

Glu Tyr Asp Gly Asn Asn Ser Tyr Asp Asp Ala Gly Asn Tyr Ile Lys
290 295 300

Ser Gln Phe Leu Asp Leu Asn Met Arg Lys Asp Val Lys Glu Ile Tyr
305 310 315 320

Ser His Met Thr Cys Ala Thr Asp Thr Gln Asn Val Lys Phe Val Phe
325 330 335

Asp Ala Val Thr Asp Ile Ile Ile Lys Glu Asn Leu Lys Asp Cys Gly
340 345 350

Leu Phe

```
<210> SEQ ID NO 29
<211> LENGTH: 858
<212> TYPE: PRT
<213> ORGANISM: Homo sapiens

<400> SEQUENCE: 29

Met Gly Glu Ile Asn Gln Val Ala Val Glu Lys Tyr Leu Glu Glu Asn
1               5                   10                  15

Pro Gln Phe Ala Lys Glu Tyr Phe Asp Arg Lys Leu Arg Val Glu Val
            20                  25                  30

Leu Gly Glu Ile Phe Lys Asn Ser Gln Val Pro Val Gln Ser Ser Met
        35                  40                  45

Ser Phe Ser Glu Leu Thr Gln Val Glu Glu Ser Ala Leu Cys Leu Glu
    50                  55                  60

Leu Leu Trp Thr Val Gln Glu Glu Gly Gly Thr Pro Glu Gln Gly Val
65                  70                  75                  80

His Arg Ala Leu Gln Arg Leu Ala His Leu Leu Gln Ala Asp Arg Cys
                85                  90                  95

Ser Met Phe Leu Cys Arg Ser Arg Asn Gly Ile Pro Glu Val Ala Ser
            100                 105                 110

Arg Leu Leu Asp Val Thr Pro Thr Ser Lys Phe Glu Asp Asn Leu Val
        115                 120                 125

Gly Pro Asp Lys Glu Val Val Phe Pro Leu Asp Ile Gly Ile Val Gly
    130                 135                 140

Trp Ala Ala His Thr Lys Lys Thr His Asn Val Pro Asp Val Lys Lys
145                 150                 155                 160

Asn Ser His Phe Ser Asp Phe Met Asp Lys Gln Thr Gly Tyr Val Thr
                165                 170                 175

Lys Asn Leu Leu Ala Thr Pro Ile Val Val Gly Lys Glu Val Leu Ala
            180                 185                 190

Val Ile Met Ala Val Asn Lys Val Asn Ala Ser Glu Phe Ser Lys Gln
        195                 200                 205

Asp Glu Glu Val Phe Ser Lys Tyr Leu Asn Phe Val Ser Ile Ile Leu
    210                 215                 220

Arg Leu His His Thr Ser Tyr Met Tyr Asn Ile Glu Ser Arg Arg Ser
225                 230                 235                 240

Gln Ile Leu Met Trp Ser Ala Asn Lys Val Phe Glu Glu Leu Thr Asp
                245                 250                 255

Val Glu Arg Gln Phe His Lys Ala Leu Tyr Thr Val Arg Ser Tyr Leu
            260                 265                 270

Asn Cys Glu Arg Tyr Ser Ile Gly Leu Leu Asp Met Thr Lys Glu Lys
        275                 280                 285

Glu Phe Tyr Asp Glu Trp Pro Ile Lys Leu Gly Glu Val Glu Pro Tyr
    290                 295                 300

Lys Gly Pro Lys Thr Pro Asp Gly Arg Glu Val Asn Phe Tyr Lys Ile
305                 310                 315                 320

Ile Asp Tyr Ile Leu His Gly Lys Glu Glu Ile Lys Val Ile Pro Thr
                325                 330                 335

Pro Pro Ala Asp His Trp Thr Leu Ile Ser Gly Leu Pro Thr Tyr Val
            340                 345                 350

Ala Glu Asn Gly Phe Ile Cys Asn Met Met Asn Ala Pro Ala Asp Glu
        355                 360                 365

Tyr Phe Thr Phe Gln Lys Gly Pro Val Asp Glu Thr Gly Trp Val Ile
    370                 375                 380
```

```
Lys Asn Val Leu Ser Leu Pro Ile Val Asn Lys Lys Glu Asp Ile Val
385                 390                 395                 400

Gly Val Ala Thr Phe Tyr Asn Arg Lys Asp Gly Lys Pro Phe Asp Glu
                405                 410                 415

His Asp Glu Tyr Ile Thr Glu Thr Leu Thr Gln Phe Leu Gly Trp Ser
            420                 425                 430

Leu Leu Asn Thr Asp Thr Tyr Asp Lys Met Asn Lys Leu Glu Asn Arg
        435                 440                 445

Lys Asp Ile Ala Gln Glu Met Leu Met Asn Gln Thr Lys Ala Thr Pro
    450                 455                 460

Glu Glu Ile Lys Ser Ile Leu Lys Phe Gln Glu Lys Leu Asn Val Asp
465                 470                 475                 480

Val Ile Asp Asp Cys Glu Glu Lys Gln Leu Val Ala Ile Leu Lys Glu
                485                 490                 495

Asp Leu Pro Asp Pro Arg Ser Ala Glu Leu Tyr Glu Phe Arg Phe Ser
            500                 505                 510

Asp Phe Pro Leu Thr Glu His Gly Leu Ile Lys Cys Gly Ile Arg Leu
        515                 520                 525

Phe Phe Glu Ile Asn Val Val Glu Lys Phe Lys Val Pro Val Glu Val
    530                 535                 540

Leu Thr Arg Trp Met Tyr Thr Val Arg Lys Gly Tyr Arg Ala Val Thr
545                 550                 555                 560

Tyr His Asn Trp Arg His Gly Phe Asn Val Gly Gln Thr Met Phe Thr
                565                 570                 575

Leu Leu Met Thr Gly Arg Leu Lys Lys Tyr Tyr Thr Asp Leu Glu Ala
            580                 585                 590

Phe Ala Met Leu Ala Ala Ala Phe Cys His Asp Ile Asp His Arg Gly
        595                 600                 605

Thr Asn Asn Leu Tyr Gln Met Lys Ser Thr Ser Pro Leu Ala Arg Leu
    610                 615                 620

His Gly Ser Ser Ile Leu Glu Arg His His Leu Glu Tyr Ser Lys Thr
625                 630                 635                 640

Leu Leu Gln Asp Glu Ser Leu Asn Ile Phe Gln Asn Leu Asn Lys Arg
                645                 650                 655

Gln Phe Glu Thr Val Ile His Leu Phe Glu Val Ala Ile Ile Ala Thr
            660                 665                 670

Asp Leu Ala Leu Tyr Phe Lys Lys Arg Thr Met Phe Gln Lys Ile Val
        675                 680                 685

Asp Ala Cys Glu Gln Met Gln Thr Glu Glu Glu Ala Ile Lys Tyr Val
    690                 695                 700

Thr Val Asp Pro Thr Lys Lys Glu Ile Ile Met Ala Met Met Met Thr
705                 710                 715                 720

Ala Cys Asp Leu Ser Ala Ile Thr Lys Pro Trp Glu Val Gln Ser Gln
                725                 730                 735

Val Ala Leu Met Val Ala Asn Glu Phe Trp Glu Gln Gly Asp Leu Glu
            740                 745                 750

Arg Thr Val Leu Gln Gln Gln Pro Ile Pro Met Met Asp Arg Asn Lys
        755                 760                 765

Arg Asp Glu Leu Pro Lys Leu Gln Val Gly Phe Ile Asp Phe Val Cys
    770                 775                 780

Thr Phe Val Tyr Lys Glu Phe Ser Arg Phe His Lys Glu Ile Thr Pro
785                 790                 795                 800

Met Leu Ser Gly Leu Gln Asn Asn Arg Val Glu Trp Lys Ser Leu Ala
```

```
                805                 810                 815

Asp Glu Tyr Asp Ala Lys Met Lys Val Ile Glu Glu Glu Ala Lys Lys
            820                 825                 830

Gln Glu Gly Gly Ala Glu Lys Ala Ala Glu Asp Ser Gly Gly Gly Asp
        835                 840                 845

Asp Lys Lys Ser Lys Thr Cys Leu Met Leu
    850                 855


<210> SEQ ID NO 30
<211> LENGTH: 83
<212> TYPE: PRT
<213> ORGANISM: Homo sapiens

<400> SEQUENCE: 30

Met Ser Asp Asn Thr Thr Leu Pro Ala Pro Ala Ser Asn Gln Gly Pro
1               5                   10                  15

Thr Thr Pro Arg Lys Gly Pro Pro Lys Phe Lys Gln Arg Gln Thr Arg
            20                  25                  30

Gln Phe Lys Ser Lys Pro Pro Lys Lys Gly Val Lys Gly Phe Gly Asp
        35                  40                  45

Asp Ile Pro Gly Met Glu Gly Leu Gly Thr Asp Ile Thr Val Ile Cys
    50                  55                  60

Pro Trp Glu Ala Phe Ser His Leu Glu Leu His Glu Leu Ala Gln Phe
65                  70                  75                  80

Gly Ile Ile


<210> SEQ ID NO 31
<211> LENGTH: 299
<212> TYPE: PRT
<213> ORGANISM: Homo sapiens

<400> SEQUENCE: 31

Met Met Ala Tyr Met Asn Pro Gly Pro His Tyr Ser Val Asn Ala Leu
1               5                   10                  15

Ala Leu Ser Gly Pro Ser Val Asp Leu Met His Gln Ala Val Pro Tyr
            20                  25                  30

Pro Ser Ala Pro Arg Lys Gln Arg Arg Glu Arg Thr Thr Phe Thr Arg
        35                  40                  45

Ser Gln Leu Glu Glu Leu Glu Ala Leu Phe Ala Lys Thr Gln Tyr Pro
    50                  55                  60

Asp Val Tyr Ala Arg Glu Glu Val Ala Leu Lys Ile Asn Leu Pro Glu
65                  70                  75                  80

Ser Arg Val Gln Val Trp Phe Lys Asn Arg Arg Ala Lys Cys Arg Gln
                85                  90                  95

Gln Arg Gln Gln Gln Lys Gln Gln Gln Gln Pro Pro Gly Gly Gln Ala
            100                 105                 110

Lys Ala Arg Pro Ala Lys Arg Lys Ala Gly Thr Ser Pro Arg Pro Ser
        115                 120                 125

Thr Asp Val Cys Pro Asp Pro Leu Gly Ile Ser Asp Ser Tyr Ser Pro
    130                 135                 140

Pro Leu Pro Gly Pro Ser Gly Ser Pro Thr Thr Ala Val Ala Thr Val
145                 150                 155                 160

Ser Ile Trp Ser Pro Ala Ser Glu Ser Pro Leu Pro Glu Ala Gln Arg
                165                 170                 175

Ala Gly Leu Val Ala Ser Gly Pro Ser Leu Thr Ser Ala Pro Tyr Ala
            180                 185                 190
```

```
Met Thr Tyr Ala Pro Ala Ser Ala Phe Cys Ser Ser Pro Ser Ala Tyr
        195                 200                 205

Gly Ser Pro Ser Ser Tyr Phe Ser Gly Leu Asp Pro Tyr Leu Ser Pro
    210                 215                 220

Met Val Pro Gln Leu Gly Gly Pro Ala Leu Ser Pro Leu Ser Gly Pro
225                 230                 235                 240

Ser Val Gly Pro Ser Leu Ala Gln Ser Pro Thr Ser Leu Ser Gly Gln
                245                 250                 255

Ser Tyr Gly Ala Tyr Ser Pro Val Asp Ser Leu Glu Phe Lys Asp Pro
            260                 265                 270

Thr Gly Thr Trp Lys Phe Thr Tyr Asn Pro Met Asp Pro Leu Asp Tyr
        275                 280                 285

Lys Asp Gln Ser Ala Trp Lys Phe Gln Ile Leu
    290                 295


<210> SEQ ID NO 32
<211> LENGTH: 809
<212> TYPE: PRT
<213> ORGANISM: Homo sapiens

<400> SEQUENCE: 32

Met Phe Lys Ser Leu Thr Lys Val Asn Lys Val Lys Pro Ile Gly Glu
1               5                   10                  15

Asn Asn Glu Asn Glu Gln Ser Ser Arg Arg Asn Glu Glu Gly Ser His
            20                  25                  30

Pro Ser Asn Gln Ser Gln Gln Thr Thr Ala Gln Glu Glu Asn Lys Gly
        35                  40                  45

Glu Glu Lys Ser Leu Lys Thr Lys Ser Thr Pro Val Thr Ser Glu Glu
    50                  55                  60

Pro His Thr Asn Ile Gln Asp Lys Leu Ser Lys Lys Asn Ser Ser Gly
65                  70                  75                  80

Asp Leu Thr Thr Asn Pro Asp Pro Gln Asn Ala Ala Glu Pro Thr Gly
                85                  90                  95

Thr Val Pro Glu Gln Lys Glu Met Asp Pro Gly Lys Glu Gly Pro Asn
            100                 105                 110

Ser Pro Gln Asn Lys Pro Pro Ala Ala Pro Val Ile Asn Glu Tyr Ala
        115                 120                 125

Asp Ala Gln Leu His Asn Leu Val Lys Arg Met Arg Gln Arg Thr Ala
    130                 135                 140

Leu Tyr Lys Lys Lys Leu Val Glu Gly Asp Leu Ser Ser Pro Glu Ala
145                 150                 155                 160

Ser Pro Gln Thr Ala Lys Pro Thr Ala Val Pro Pro Val Lys Glu Ser
                165                 170                 175

Asp Asp Lys Pro Thr Glu His Tyr Tyr Arg Leu Leu Trp Phe Lys Val
            180                 185                 190

Lys Lys Met Pro Leu Thr Glu Tyr Leu Lys Arg Ile Lys Leu Pro Asn
        195                 200                 205

Ser Ile Asp Ser Tyr Thr Asp Arg Leu Tyr Leu Leu Trp Leu Leu Leu
    210                 215                 220

Val Thr Leu Ala Tyr Asn Trp Asn Cys Trp Phe Ile Pro Leu Arg Leu
225                 230                 235                 240

Val Phe Pro Tyr Gln Thr Ala Asp Asn Ile His Tyr Trp Leu Ile Ala
                245                 250                 255

Asp Ile Ile Cys Asp Ile Ile Tyr Leu Tyr Asp Met Leu Phe Ile Gln
```

```
            260                 265                 270

Pro Arg Leu Gln Phe Val Arg Gly Gly Asp Ile Ile Val Asp Ser Asn
        275                 280                 285

Glu Leu Arg Lys His Tyr Arg Thr Ser Thr Lys Phe Gln Leu Asp Val
    290                 295                 300

Ala Ser Ile Ile Pro Phe Asp Ile Cys Tyr Leu Phe Phe Gly Phe Asn
305                 310                 315                 320

Pro Met Phe Arg Ala Asn Arg Met Leu Lys Tyr Thr Ser Phe Phe Glu
                325                 330                 335

Phe Asn His His Leu Glu Ser Ile Met Asp Lys Ala Tyr Ile Tyr Arg
            340                 345                 350

Val Ile Arg Thr Thr Gly Tyr Leu Leu Phe Ile Leu His Ile Asn Ala
        355                 360                 365

Cys Val Tyr Tyr Trp Ala Ser Asn Tyr Glu Gly Ile Gly Thr Thr Arg
    370                 375                 380

Trp Val Tyr Asp Gly Glu Gly Asn Glu Tyr Leu Arg Cys Tyr Tyr Trp
385                 390                 395                 400

Ala Val Arg Thr Leu Ile Thr Ile Gly Gly Leu Pro Glu Pro Gln Thr
                405                 410                 415

Leu Phe Glu Ile Val Phe Gln Leu Leu Asn Phe Phe Ser Gly Val Phe
            420                 425                 430

Val Phe Ser Ser Leu Ile Gly Gln Met Arg Asp Val Ile Gly Ala Ala
        435                 440                 445

Thr Ala Asn Gln Asn Tyr Phe Arg Ala Cys Met Asp Asp Thr Ile Ala
    450                 455                 460

Tyr Met Asn Asn Tyr Ser Ile Pro Lys Leu Val Gln Lys Arg Val Arg
465                 470                 475                 480

Thr Trp Tyr Glu Tyr Thr Trp Asp Ser Gln Arg Met Leu Asp Glu Ser
                485                 490                 495

Asp Leu Leu Lys Thr Leu Pro Thr Thr Val Gln Leu Ala Leu Ala Ile
            500                 505                 510

Asp Val Asn Phe Ser Ile Ile Ser Lys Val Asp Leu Phe Lys Gly Cys
        515                 520                 525

Asp Thr Gln Met Ile Tyr Asp Met Leu Leu Arg Leu Lys Ser Val Leu
    530                 535                 540

Tyr Leu Pro Gly Asp Phe Val Cys Lys Lys Gly Glu Ile Gly Lys Glu
545                 550                 555                 560

Met Tyr Ile Ile Lys His Gly Glu Val Gln Val Leu Gly Gly Pro Asp
                565                 570                 575

Gly Thr Lys Val Leu Val Thr Leu Lys Ala Gly Ser Val Phe Gly Glu
            580                 585                 590

Ile Ser Leu Leu Ala Ala Gly Gly Gly Asn Arg Arg Thr Ala Asn Val
        595                 600                 605

Val Ala His Gly Phe Ala Asn Leu Leu Thr Leu Asp Lys Lys Thr Leu
    610                 615                 620

Gln Glu Ile Leu Val His Tyr Pro Asp Ser Glu Arg Ile Leu Met Lys
625                 630                 635                 640

Lys Ala Arg Val Leu Leu Lys Gln Lys Ala Lys Thr Ala Glu Ala Thr
                645                 650                 655

Pro Pro Arg Lys Asp Leu Ala Leu Leu Phe Pro Pro Lys Glu Glu Thr
            660                 665                 670

Pro Lys Leu Phe Lys Thr Leu Leu Gly Gly Thr Gly Lys Ala Ser Leu
        675                 680                 685
```

```
Ala Arg Leu Leu Lys Leu Lys Arg Glu Gln Ala Ala Gln Lys Lys Glu
    690                 695                 700

Asn Ser Glu Gly Gly Glu Glu Glu Gly Lys Glu Asn Glu Asp Lys Gln
705                 710                 715                 720

Lys Glu Asn Glu Asp Lys Gln Lys Glu Asn Glu Asp Lys Gly Lys Glu
                725                 730                 735

Asn Glu Asp Lys Asp Lys Gly Arg Glu Pro Glu Glu Lys Pro Leu Asp
            740                 745                 750

Arg Pro Glu Cys Thr Ala Ser Pro Ile Ala Val Glu Glu Glu Pro His
        755                 760                 765

Ser Val Arg Arg Thr Val Leu Pro Arg Gly Thr Ser Arg Gln Ser Leu
    770                 775                 780

Ile Ile Ser Met Ala Pro Ser Ala Glu Gly Gly Glu Glu Val Leu Thr
785                 790                 795                 800

Ile Glu Val Lys Glu Lys Ala Lys Gln
                805


<210> SEQ ID NO 33
<211> LENGTH: 610
<212> TYPE: PRT
<213> ORGANISM: Homo sapiens

<400> SEQUENCE: 33

Met Pro Leu Thr Glu Tyr Leu Lys Arg Ile Lys Leu Pro Asn Ser Ile
1               5                   10                  15

Asp Ser Tyr Thr Asp Arg Leu Tyr Leu Leu Trp Leu Leu Leu Val Thr
            20                  25                  30

Leu Ala Tyr Asn Trp Asn Cys Cys Phe Ile Pro Leu Arg Leu Val Phe
        35                  40                  45

Pro Tyr Gln Thr Ala Asp Asn Ile His Tyr Trp Leu Ile Ala Asp Ile
    50                  55                  60

Ile Cys Asp Ile Ile Tyr Leu Tyr Asp Met Leu Phe Ile Gln Pro Arg
65                  70                  75                  80

Leu Gln Phe Val Arg Gly Gly Asp Ile Ile Val Asp Ser Asn Glu Leu
                85                  90                  95

Arg Lys His Tyr Arg Thr Ser Thr Lys Phe Gln Leu Asp Val Ala Ser
            100                 105                 110

Ile Ile Pro Phe Asp Ile Cys Tyr Leu Phe Phe Gly Phe Asn Pro Met
        115                 120                 125

Phe Arg Ala Asn Arg Met Leu Lys Tyr Thr Ser Phe Phe Glu Phe Asn
    130                 135                 140

His His Leu Glu Ser Ile Met Asp Lys Ala Tyr Ile Tyr Arg Val Ile
145                 150                 155                 160

Arg Thr Thr Gly Tyr Leu Leu Phe Ile Leu His Ile Asn Ala Cys Val
                165                 170                 175

Tyr Tyr Trp Ala Ser Asn Tyr Glu Gly Ile Gly Thr Thr Arg Trp Val
            180                 185                 190

Tyr Asp Gly Glu Gly Asn Glu Tyr Leu Arg Cys Tyr Tyr Trp Ala Val
        195                 200                 205

Arg Thr Leu Ile Thr Ile Gly Gly Leu Pro Glu Pro Gln Thr Leu Phe
    210                 215                 220

Glu Ile Val Phe Gln Leu Leu Asn Phe Phe Ser Gly Val Phe Val Phe
225                 230                 235                 240

Ser Ser Leu Ile Gly Gln Met Arg Asp Val Ile Gly Ala Ala Thr Ala
```

```
                245                 250                 255

Asn Gln Asn Tyr Phe Arg Ala Cys Met Asp Asp Thr Ile Ala Tyr Met
            260                 265                 270

Asn Asn Tyr Ser Ile Pro Lys Leu Val Gln Lys Arg Val Arg Thr Trp
        275                 280                 285

Tyr Glu Tyr Thr Trp Asp Ser Gln Arg Met Leu Asp Glu Ser Asp Leu
    290                 295                 300

Leu Lys Thr Leu Pro Thr Thr Val Gln Leu Ala Leu Ala Ile Asp Val
305                 310                 315                 320

Asn Phe Ser Ile Ile Ser Lys Val Asp Leu Phe Lys Gly Cys Asp Thr
                325                 330                 335

Gln Met Ile Tyr Asp Met Leu Leu Arg Leu Lys Ser Val Leu Tyr Leu
            340                 345                 350

Pro Gly Asp Phe Val Cys Lys Lys Gly Glu Ile Gly Lys Glu Met Tyr
        355                 360                 365

Ile Ile Lys His Gly Glu Val Gln Val Leu Gly Gly Pro Asp Gly Thr
    370                 375                 380

Lys Val Leu Val Thr Leu Lys Ala Gly Ser Val Leu Leu Ala Ala Gly
385                 390                 395                 400

Gly Gly Asn Arg Arg Thr Ala Asn Val Val Ala His Gly Phe Ala Asn
                405                 410                 415

Leu Leu Thr Leu Asp Lys Lys Thr Leu Gln Glu Ile Leu Val His Tyr
            420                 425                 430

Pro Asp Ser Glu Arg Ile Leu Met Lys Lys Ala Arg Val Leu Leu Lys
        435                 440                 445

Gln Lys Ala Lys Thr Ala Glu Ala Thr Pro Pro Arg Lys Asp Leu Ala
    450                 455                 460

Leu Leu Phe Pro Pro Lys Glu Glu Thr Pro Lys Leu Phe Lys Thr Leu
465                 470                 475                 480

Leu Gly Gly Thr Gly Lys Ala Ser Leu Ala Arg Leu Leu Lys Leu Lys
                485                 490                 495

Arg Glu Gln Ala Ala Gln Lys Lys Glu Asn Ser Glu Gly Gly Glu Glu
            500                 505                 510

Glu Gly Lys Glu Asn Glu Asp Lys Gln Lys Glu Asn Glu Asp Lys Gln
        515                 520                 525

Lys Glu Asn Glu Asp Lys Gly Lys Glu Asn Glu Asp Lys Asp Lys Gly
    530                 535                 540

Arg Glu Pro Glu Glu Lys Pro Leu Asp Arg Pro Glu Cys Thr Ala Ser
545                 550                 555                 560

Pro Ile Ala Val Glu Glu Glu Pro His Ser Val Arg Arg Thr Val Leu
                565                 570                 575

Pro Arg Gly Thr Ser Arg Gln Ser Leu Ile Ile Ser Met Ala Pro Ser
            580                 585                 590

Ala Glu Gly Gly Glu Glu Val Leu Thr Ile Glu Val Lys Glu Lys Ala
        595                 600                 605

Lys Gln
    610
```

<210> SEQ ID NO 34
<211> LENGTH: 7100
<212> TYPE: DNA
<213> ORGANISM: Homo sapiens

<400> SEQUENCE: 34

```
gacatactga gaataaatcc aaagacatta gtttctttgc acgaaatgag gttacatatc     60
cagtgacatt tatttgagct atttaaacaa cttaaacatc tttttctttt cttaataagg    120
gacgtttcaa gttgtggtct cagccaaaat gagtgatacc ccttctactg gtttttccat    180
cattcatcct acgtcttctg aaggtcaagt tccacccccct cgccatttga gcctcactca    240
tcctgttgtg gccaagcgaa tcagtttcta caagagcgga gacccccaat tcggcggggt    300
cagggtggtg gtcaaccctc gctcctttaa gtcctttgat gctctgctgg ataacttgtc    360
caggaaggtg cccctccctt ttggagtgag gaacatcagc acccctcggg gcaggcacag    420
catcacgcgc ctggaggagc tggaggacgg cgagtcctac ctatgttccc acggcaggaa    480
ggtgcagcct gtagacctgg acaaagcccg tcggcgcccg cggccctggc tcagcagccg    540
ggccattagc gcgcactcac cgccccaccc cgtagccgtc gctgctcccg gcatgccccg    600
ccccccacgg agcctagtgg tcttcaggaa tggcgacccg aagacgaggc gtgcggttct    660
tctgagcagg agggtcaccc agagcttcga ggcatttcta cagcacctga cagaggtcat    720
gcagcgccct gtggtcaagc tgtacgctac ggacggaagg agggttccca gcctccaggc    780
agtgatcctg agctctggag ctgtggtggc ggcaggaagg gagccattta aaccaggaaa    840
ttatgacatc caaaaatact tgcttcctgc tagattacca gggatctctc agcgtgtgta    900
ccccaaggga aatgcaaagt cagaaagcag aaagataagc acacatatgt cttcaagctc    960
aaggtcccag atttattctg tttcttctga gaaaacacat aataatgatt gctacttaga   1020
ctattctttt gttcctgaaa agtacttggc cttagaaaag aatgattctc agaatttacc   1080
aatatatcct tctgaagatg atattgagaa atcaattatt tttaatcaag acggcactat   1140
gacagttgag atgaaagttc gattcagaat aaaagaggaa gaaaccataa aatggacaac   1200
tactgtcagt aaaactggtc cttctaataa tgatgaaaag agtgagatga gttttccagg   1260
aagaacagaa agtcgatcat ctggtttaaa gcttgcagca tgttcattct ctgcagatgt   1320
gtcacctatg gagcgaagca gtaatcaaga gggcagtttg gcagaggaga taaacattca   1380
aatgacagat caagtggctg aaacttgcag ttctgctagt tgggagaatg ctactgtgga   1440
cacagatatc atccagggaa ctcaagacca agcaaagcat cgtttttata ggccccctac   1500
acctggacta agaagagtga gacaaaagaa atctgtgatt ggcagtgtga ccttagtatc   1560
tgaaactgag gttcaagaga aaatgattgg acagttttca tatagtgaag aaagggaaag   1620
tggggaaaac aagtctgagt atcacatgtt tacacattct tgcagtaaaa tgtcatcagt   1680
atctaacaaa ccagtacttg ttcagatcaa taacaatgat caaatggagg agtcatcatt   1740
agaaagaaaa aaggaaaaca gtctgcttaa gtcaagtgca ataagtgctg gtgttataga   1800
aattacaagt cagaagatgt tagagatgtc acataataat ggtttgccat caactatatc   1860
aaataactca attgtggagg aagatgtagt tgattgtgtg gtattggaca acaaaactgg   1920
tatcaagaac ttcaaaactt atggtaacac caatgatagg ttcagtccta tttcagcaga   1980
tgcaacccat ttttcaagta ataactctgg aactgacaaa aatatttctg aggctccagc   2040
ttcagaagca tcctctactg tcactgcaag aattgacaga ctaattaatg aatttgctca   2100
gtgtggttta acaaaacttc caaaaaatga aaagaagatt ttgtcatctg ttgccagcaa   2160
aaagaagaaa aaatctcgac agcaagcaat aaattccagg tatcaagatg gacagcttgc   2220
aaccaaagga attcttaata agaatgagag aataaacaca aaaggtagaa ttacaaagga   2280
aatgatagtg caagattcag atagtcccct taaaggaggg atactttgtg aggaagacct   2340
ccagaaaagt gatactgtaa ttgaatcaaa tacttttgt tccaaaagta atctcaattc    2400
```

```
cacgatttcc aagaatttcc atagaaataa attaaatact actcaaaatt ccaaggttca   2460
aggactttta accaaaagaa aatctagatc actaaataaa ataagcttag gagcacctaa   2520
aaaaagagaa atcggtcaaa gagataaagt gtttcctcac aatgaatcta aatattgcaa   2580
aagtactttt gaaaacaaaa gtttatttca tgtatttaac atccttgagc aaaaacccaa   2640
agatttttat gcaccgcaat ctcaagcaga agtggcatct gggtatttga gaggaatggc   2700
aaagaagagt ttagtttcaa aagttactga ttcacacata actttaaaaa gccagaaaaa   2760
acgtaaaggg gataaagtga aagcaagtgc tattttaagt aaacaacatg ctacaaccag   2820
ggcaaattct ttagcttctt tgaaaaaacc tgattttcct gaggctattg ctcatcattc   2880
aattcaaaat tatatacaga gttggttgca gaacataaat ccatatccaa ctttaaagcc   2940
tataaaatca gctccagtat gtagaaatga aacgagtgtg gtaaattgta gcaataatag   3000
tttttcaggg aatgatcccc atacaaattc tggaaaaata agtaattttg ttatggaaag   3060
taataagcac ataactaaaa ttgccggttt gacaggagat aatctatgta aagagggaga   3120
taagtctttt attgccaatg acactggtga agaagatctc catgagacac aggttggatc   3180
tctgaatgat gcttatttgg ttcccctgca tgaacactgt actttgtcac agtcagctat   3240
taatgatcat aatactaaaa gtcatatagc tgctgaaaaa tcaggaccag agaaaaaact   3300
tgtttaccag gaaataaacc tagctagaaa aaggcaaagt gtagaggctg ccattcaagt   3360
agatcctata gaagaggaaa ctccaaaaga cctcttacca gtcctgatgc ttcaccaatt   3420
gcaagcttca gttcctggta ttcacaagac tcagaatgga gttgttcaaa tgccaggttc   3480
acttgcaggt gttccctttc attctgcaat atgtaattca tccactaatc tccttctagc   3540
ttggctcttg gtgctaaacc taaagggaag tatgaatagc ttctgtcaag ttgatgctca   3600
caaggctacc aacaaatctt cagaaacact tgcattgttg gagattctaa agcacatagc   3660
tatcacagag gaagctgatg acttgaaagc tgctgttgcc aatttagtgg agtcaactac   3720
aagccacttt ggactcagtg agaaagaaca agacatggtt ccaatagatc tttctgcaaa   3780
ttgttccacg gtcaacattc agagtgttcc taagtgcagt gaaaatgaaa gaacacaagg   3840
aatctcctct ttggatggag gttgctctgc cagtgaggca tgtgcccctg aagtctgtgt   3900
tttggaagtg acttgctctc catgtgagat gtgcactgta aataaggctt attctccaaa   3960
agagacatgt aaccccagtg acactttttt tcctagtgat ggttatggtg tggatcagac   4020
ttctatgaat aaggcttgtt tcctaggaga ggtctgttca cttactgata ctgtgttttc   4080
tgataaggct tgtgctcaaa aggagaacca tacctatgag ggagcttgcc caattgatga   4140
gacctacgtt cctgtcaatg tctgcaatac cattgacttt ttaaactcca aagaaaacac   4200
atatactgat aacttggatt caactgaaga gttagaaaga ggtgatgaca ttcagaaaga   4260
tctaaatatt ttgacagacc ctgaatataa aaatggattt aatacattgg tgtcacatca   4320
aaatgtcagt aatttaagct cctgtggcct ttgcctaagt gaaaaagaag cagaacttga   4380
taagaaacat agttctctag atgattttga aaattgttca ctaaggaagt ttcaggatga   4440
aaatgcatat acttcctttg atatggaaga accacggact tctgaagaac caggctcaat   4500
aaccaacagc atgacatcaa gtgaaagaaa catttcagaa ttggaatctt ttgaagaatt   4560
agaaaaccat gacactgata tctttaatac agtggtaaat ggaggagagc aagccactga   4620
agaattaatc caagaagagg tagaggctag taaaacttta gaattgatag acatctctag   4680
taagaatatt atggaagaaa aaagaatgaa cggtataatt tatgaaataa tcagtaagag   4740
```

```
gctggcaaca ccaccatctt tagatttttg ctatgattct aagcaaaata gtgaaaagga   4800
gaccaatgaa ggagaaacta agatggtaaa aatgatggtg aaaactatgg aaactggaag   4860
ttattcagag tcctctcctg atttaaaaaa atgcatcaaa agtccagtga cttctgattg   4920
gtcagactat cggcctgaca gtgacagtga gcagccatat aaaacatcca gtgatgatcc   4980
caatgacagt ggcgaactta cccaagagaa agaatataac ataggatttg ttaaaagggc   5040
aatagaaaaa ctgtacggta aagcagatat tatcaaacca tctttttttc ctgggtctac   5100
ccgcaaatct caggtttgtc cttataattc tgtggaattt cagtgttcca ggaaagcaag   5160
tctttatgat tctgaagggc agtcatttgg ctcttctgaa caggtatcta gtagttcatc   5220
tatgttgcag gaattccagg aggaaagaca agataagtgt gatgttagtg ctgtgaggga   5280
caattattgt aggggtgaca ttgtagaacc tggtacaaaa caaaatgatg atagcagaat   5340
cctcacagac atagaggaag gagtactgat tgacaaaggc aaatggcttc tgaaagaaaa   5400
tcatttgcta aggatgtcat ctgaaaatcc tggcatgtgt ggcaatgcag acaccacatc   5460
agtggacacc ctacttgata ataacagcag tgaggtacca tattcacatt ttggtaattt   5520
ggccccaggc ccaacgatgg atgaactctc ctcttcagaa ctcgaggaac tgactcaacc   5580
ccttgaacta aaatgcaatt actttaacat gcctcatggt agtgactcag aacctttttca  5640
tgaggacttg ctggatgttc gcaatgaaac ctgtgccaag gaaagaatag caaatcatca   5700
tacagaggag aagggtagtc atcagtcaga aagagtatgc acatctgtca ctcattcctt   5760
tatttctgct ggtaacaaag tctaccctgt ctctgatgat gctattaaaa accaaccatt   5820
gcctggcagt aatatgattc atggtacact tcaggaagct gactctttgg ataaactgta   5880
tgctctttgt ggtcaacatt gcccaatact aactgttatt atccaaccca tgaatgagga   5940
agaccgagga tttgcatatc gcaaagaatc tgatattgaa aatttcttgg gtttttattt   6000
atggatgaaa atacacccat atttacttca gacagacaaa aatgtgttca gggaagagaa   6060
caataaagca agtatgagac aaaatcttat tgataatgcc attggtgata tatttgatca   6120
gttttatttc agtaacacat ttgacttgat gggtaaaaga agaaaacaaa aaagaattaa   6180
cttcttgggg ttagaggaag aaggtaattt aaagaaattt caaccagatt tgaaggaaag   6240
gttttgtatg aatttcttgc acacatcatt gttagttgtg ggtaatgtgg attcaaatac   6300
acaagacctc agcggtcaga caaatgaaat ctttaaagca gtcgatgaga ataacaactt   6360
attaaataac agattccagg gctcaagaac aaatctcaac caagtagtaa gagaaaatat   6420
caactgtcat tacttctttg aaatgcttgg tcaagcttgc ctcttagata tttgccaagt   6480
tgagacctcc ttaaatatta gcaacagaaa tattttagaa ctttgtatgt ttgagggtga   6540
aaatcttttc atttgggaag aggaagacat attaaattta actgatcttg aaagcagtag   6600
agaacaagaa gatttataat ttcaatatca gcacactcat tctttgtcaa ttcatttttt   6660
cccatgagat gaagcacatg tgacgaatac ggactagata acctctaaga attttccact   6720
tcttcaaaat gaacttactc tagaaagctt acccttggat aaccagtttg actttcataa   6780
tgtctctgtt ttttgttttt ccaacaatta cagactcagg ttctcttatt ttggaagttt   6840
ctatctggtt ttgttctgaa cttacatttt tttttttttt ggtatctatg atttttttttg  6900
ctcagggcat caaaatgtgc taaggacaag aattatatcc tttttaaaaa atgttgttag   6960
cttggtgtaa aatgtatatt gactgtattg gtgaataaat tgaatagaca taacctcaaa   7020
gtacttcact tattcttttt aactactgat ttgataaaaa gtatgattat aagatatcca   7080
cgacaatctc atagtttctt                                               7100
```

<210> SEQ ID NO 35
<211> LENGTH: 2156
<212> TYPE: PRT
<213> ORGANISM: Homo sapiens

<400> SEQUENCE: 35

```
Met Ser Asp Thr Pro Ser Thr Gly Phe Ser Ile Ile His Pro Thr Ser
1               5                   10                  15

Ser Glu Gly Gln Val Pro Pro Pro Arg His Leu Ser Leu Thr His Pro
            20                  25                  30

Val Val Ala Lys Arg Ile Ser Phe Tyr Lys Ser Gly Asp Pro Gln Phe
        35                  40                  45

Gly Gly Val Arg Val Val Val Asn Pro Arg Ser Phe Lys Ser Phe Asp
    50                  55                  60

Ala Leu Leu Asp Asn Leu Ser Arg Lys Val Pro Leu Pro Phe Gly Val
65                  70                  75                  80

Arg Asn Ile Ser Thr Pro Arg Gly Arg His Ser Ile Thr Arg Leu Glu
                85                  90                  95

Glu Leu Glu Asp Gly Glu Ser Tyr Leu Cys Ser His Gly Arg Lys Val
            100                 105                 110

Gln Pro Val Asp Leu Asp Lys Ala Arg Arg Arg Pro Arg Pro Trp Leu
        115                 120                 125

Ser Ser Arg Ala Ile Ser Ala His Ser Pro Pro His Pro Val Ala Val
    130                 135                 140

Ala Ala Pro Gly Met Pro Arg Pro Pro Arg Ser Leu Val Val Phe Arg
145                 150                 155                 160

Asn Gly Asp Pro Lys Thr Arg Arg Ala Val Leu Leu Ser Arg Arg Val
                165                 170                 175

Thr Gln Ser Phe Glu Ala Phe Leu Gln His Leu Thr Glu Val Met Gln
            180                 185                 190

Arg Pro Val Val Lys Leu Tyr Ala Thr Asp Gly Arg Arg Val Pro Ser
        195                 200                 205

Leu Gln Ala Val Ile Leu Ser Ser Gly Ala Val Val Ala Ala Gly Arg
    210                 215                 220

Glu Pro Phe Lys Pro Gly Asn Tyr Asp Ile Gln Lys Tyr Leu Leu Pro
225                 230                 235                 240

Ala Arg Leu Pro Gly Ile Ser Gln Arg Val Tyr Pro Lys Gly Asn Ala
                245                 250                 255

Lys Ser Glu Ser Arg Lys Ile Ser Thr His Met Ser Ser Ser Ser Arg
            260                 265                 270

Ser Gln Ile Tyr Ser Val Ser Ser Glu Lys Thr His Asn Asn Asp Cys
        275                 280                 285

Tyr Leu Asp Tyr Ser Phe Val Pro Glu Lys Tyr Leu Ala Leu Glu Lys
    290                 295                 300

Asn Asp Ser Gln Asn Leu Pro Ile Tyr Pro Ser Glu Asp Asp Ile Glu
305                 310                 315                 320

Lys Ser Ile Ile Phe Asn Gln Asp Gly Thr Met Thr Val Glu Met Lys
                325                 330                 335

Val Arg Phe Arg Ile Lys Glu Glu Glu Thr Ile Lys Trp Thr Thr Thr
            340                 345                 350

Val Ser Lys Thr Gly Pro Ser Asn Asn Asp Glu Lys Ser Glu Met Ser
        355                 360                 365

Phe Pro Gly Arg Thr Glu Ser Arg Ser Ser Gly Leu Lys Leu Ala Ala
```

```
    370                 375                 380

Cys Ser Phe Ser Ala Asp Val Ser Pro Met Glu Arg Ser Ser Asn Gln
385                 390                 395                 400

Glu Gly Ser Leu Ala Glu Glu Ile Asn Ile Gln Met Thr Asp Gln Val
                405                 410                 415

Ala Glu Thr Cys Ser Ser Ala Ser Trp Glu Asn Ala Thr Val Asp Thr
            420                 425                 430

Asp Ile Ile Gln Gly Thr Gln Asp Gln Ala Lys His Arg Phe Tyr Arg
        435                 440                 445

Pro Pro Thr Pro Gly Leu Arg Arg Val Arg Gln Lys Lys Ser Val Ile
    450                 455                 460

Gly Ser Val Thr Leu Val Ser Glu Thr Glu Val Gln Glu Lys Met Ile
465                 470                 475                 480

Gly Gln Phe Ser Tyr Ser Glu Glu Arg Glu Ser Gly Glu Asn Lys Ser
                485                 490                 495

Glu Tyr His Met Phe Thr His Ser Cys Ser Lys Met Ser Ser Val Ser
            500                 505                 510

Asn Lys Pro Val Leu Val Gln Ile Asn Asn Asn Asp Gln Met Glu Glu
        515                 520                 525

Ser Ser Leu Glu Arg Lys Lys Glu Asn Ser Leu Leu Lys Ser Ser Ala
    530                 535                 540

Ile Ser Ala Gly Val Ile Glu Ile Thr Ser Gln Lys Met Leu Glu Met
545                 550                 555                 560

Ser His Asn Asn Gly Leu Pro Ser Thr Ile Ser Asn Asn Ser Ile Val
                565                 570                 575

Glu Glu Asp Val Val Asp Cys Val Val Leu Asp Asn Lys Thr Gly Ile
            580                 585                 590

Lys Asn Phe Lys Thr Tyr Gly Asn Thr Asn Asp Arg Phe Ser Pro Ile
        595                 600                 605

Ser Ala Asp Ala Thr His Phe Ser Ser Asn Asn Ser Gly Thr Asp Lys
    610                 615                 620

Asn Ile Ser Glu Ala Pro Ala Ser Glu Ala Ser Ser Thr Val Thr Ala
625                 630                 635                 640

Arg Ile Asp Arg Leu Ile Asn Glu Phe Ala Gln Cys Gly Leu Thr Lys
                645                 650                 655

Leu Pro Lys Asn Glu Lys Lys Ile Leu Ser Ser Val Ala Ser Lys Lys
            660                 665                 670

Lys Lys Lys Ser Arg Gln Gln Ala Ile Asn Ser Arg Tyr Gln Asp Gly
        675                 680                 685

Gln Leu Ala Thr Lys Gly Ile Leu Asn Lys Asn Glu Arg Ile Asn Thr
    690                 695                 700

Lys Gly Arg Ile Thr Lys Glu Met Ile Val Gln Asp Ser Asp Ser Pro
705                 710                 715                 720

Leu Lys Gly Gly Ile Leu Cys Glu Glu Asp Leu Gln Lys Ser Asp Thr
                725                 730                 735

Val Ile Glu Ser Asn Thr Phe Cys Ser Lys Ser Asn Leu Asn Ser Thr
            740                 745                 750

Ile Ser Lys Asn Phe His Arg Asn Lys Leu Asn Thr Thr Gln Asn Ser
        755                 760                 765

Lys Val Gln Gly Leu Leu Thr Lys Arg Lys Ser Arg Ser Leu Asn Lys
    770                 775                 780

Ile Ser Leu Gly Ala Pro Lys Lys Arg Glu Ile Gly Gln Arg Asp Lys
785                 790                 795                 800
```

```
Val Phe Pro His Asn Glu Ser Lys Tyr Cys Lys Ser Thr Phe Glu Asn
                805                 810                 815

Lys Ser Leu Phe His Val Phe Asn Ile Leu Glu Gln Lys Pro Lys Asp
            820                 825                 830

Phe Tyr Ala Pro Gln Ser Gln Ala Glu Val Ala Ser Gly Tyr Leu Arg
        835                 840                 845

Gly Met Ala Lys Lys Ser Leu Val Ser Lys Val Thr Asp Ser His Ile
    850                 855                 860

Thr Leu Lys Ser Gln Lys Lys Arg Lys Gly Asp Lys Val Lys Ala Ser
865                 870                 875                 880

Ala Ile Leu Ser Lys Gln His Ala Thr Thr Arg Ala Asn Ser Leu Ala
                885                 890                 895

Ser Leu Lys Lys Pro Asp Phe Pro Glu Ala Ile Ala His His Ser Ile
            900                 905                 910

Gln Asn Tyr Ile Gln Ser Trp Leu Gln Asn Ile Asn Pro Tyr Pro Thr
        915                 920                 925

Leu Lys Pro Ile Lys Ser Ala Pro Val Cys Arg Asn Glu Thr Ser Val
    930                 935                 940

Val Asn Cys Ser Asn Asn Ser Phe Ser Gly Asn Asp Pro His Thr Asn
945                 950                 955                 960

Ser Gly Lys Ile Ser Asn Phe Val Met Glu Ser Asn Lys His Ile Thr
                965                 970                 975

Lys Ile Ala Gly Leu Thr Gly Asp Asn Leu Cys Lys Glu Gly Asp Lys
            980                 985                 990

Ser Phe Ile Ala Asn Asp Thr Gly  Glu Glu Asp Leu His  Glu Thr Gln
        995                 1000                1005

Val Gly  Ser Leu Asn Asp Ala  Tyr Leu Val Pro Leu  His Glu His
    1010                1015                1020

Cys Thr  Leu Ser Gln Ser Ala  Ile Asn Asp His Asn  Thr Lys Ser
    1025                1030                1035

His Ile  Ala Ala Glu Lys Ser  Gly Pro Glu Lys Lys  Leu Val Tyr
    1040                1045                1050

Gln Glu  Ile Asn Leu Ala Arg  Lys Arg Gln Ser Val  Glu Ala Ala
    1055                1060                1065

Ile Gln  Val Asp Pro Ile Glu  Glu Glu Thr Pro Lys  Asp Leu Leu
    1070                1075                1080

Pro Val  Leu Met Leu His Gln  Leu Gln Ala Ser Val  Pro Gly Ile
    1085                1090                1095

His Lys  Thr Gln Asn Gly Val  Val Gln Met Pro Gly  Ser Leu Ala
    1100                1105                1110

Gly Val  Pro Phe His Ser Ala  Ile Cys Asn Ser Ser  Thr Asn Leu
    1115                1120                1125

Leu Leu  Ala Trp Leu Leu Val  Leu Asn Leu Lys Gly  Ser Met Asn
    1130                1135                1140

Ser Phe  Cys Gln Val Asp Ala  His Lys Ala Thr Asn  Lys Ser Ser
    1145                1150                1155

Glu Thr  Leu Ala Leu Leu Glu  Ile Leu Lys His Ile  Ala Ile Thr
    1160                1165                1170

Glu Glu  Ala Asp Asp Leu Lys  Ala Ala Val Ala Asn  Leu Val Glu
    1175                1180                1185

Ser Thr  Thr Ser His Phe Gly  Leu Ser Glu Lys Glu  Gln Asp Met
    1190                1195                1200
```

```
Val Pro  Ile Asp Leu Ser Ala  Asn Cys Ser Thr Val  Asn Ile Gln
    1205                 1210                 1215

Ser Val  Pro Lys Cys Ser Glu  Asn Glu Arg Thr Gln  Gly Ile Ser
    1220                 1225                 1230

Ser Leu  Asp Gly Gly Cys Ser  Ala Ser Glu Ala Cys  Ala Pro Glu
    1235                 1240                 1245

Val Cys  Val Leu Glu Val Thr  Cys Ser Pro Cys Glu  Met Cys Thr
    1250                 1255                 1260

Val Asn  Lys Ala Tyr Ser Pro  Lys Glu Thr Cys Asn  Pro Ser Asp
    1265                 1270                 1275

Thr Phe  Phe Pro Ser Asp Gly  Tyr Gly Val Asp Gln  Thr Ser Met
    1280                 1285                 1290

Asn Lys  Ala Cys Phe Leu Gly  Glu Val Cys Ser Leu  Thr Asp Thr
    1295                 1300                 1305

Val Phe  Ser Asp Lys Ala Cys  Ala Gln Lys Glu Asn  His Thr Tyr
    1310                 1315                 1320

Glu Gly  Ala Cys Pro Ile Asp  Glu Thr Tyr Val Pro  Val Asn Val
    1325                 1330                 1335

Cys Asn  Thr Ile Asp Phe Leu  Asn Ser Lys Glu Asn  Thr Tyr Thr
    1340                 1345                 1350

Asp Asn  Leu Asp Ser Thr Glu  Glu Leu Glu Arg Gly  Asp Asp Ile
    1355                 1360                 1365

Gln Lys  Asp Leu Asn Ile Leu  Thr Asp Pro Glu Tyr  Lys Asn Gly
    1370                 1375                 1380

Phe Asn  Thr Leu Val Ser His  Gln Asn Val Ser Asn  Leu Ser Ser
    1385                 1390                 1395

Cys Gly  Leu Cys Leu Ser Glu  Lys Glu Ala Glu Leu  Asp Lys Lys
    1400                 1405                 1410

His Ser  Ser Leu Asp Asp Phe  Glu Asn Cys Ser Leu  Arg Lys Phe
    1415                 1420                 1425

Gln Asp  Glu Asn Ala Tyr Thr  Ser Phe Asp Met Glu  Glu Pro Arg
    1430                 1435                 1440

Thr Ser  Glu Glu Pro Gly Ser  Ile Thr Asn Ser Met  Thr Ser Ser
    1445                 1450                 1455

Glu Arg  Asn Ile Ser Glu Leu  Glu Ser Phe Glu Glu  Leu Glu Asn
    1460                 1465                 1470

His Asp  Thr Asp Ile Phe Asn  Thr Val Val Asn Gly  Gly Glu Gln
    1475                 1480                 1485

Ala Thr  Glu Glu Leu Ile Gln  Glu Glu Val Glu Ala  Ser Lys Thr
    1490                 1495                 1500

Leu Glu  Leu Ile Asp Ile Ser  Ser Lys Asn Ile Met  Glu Glu Lys
    1505                 1510                 1515

Arg Met  Asn Gly Ile Ile Tyr  Glu Ile Ile Ser Lys  Arg Leu Ala
    1520                 1525                 1530

Thr Pro  Pro Ser Leu Asp Phe  Cys Tyr Asp Ser Lys  Gln Asn Ser
    1535                 1540                 1545

Glu Lys  Glu Thr Asn Glu Gly  Glu Thr Lys Met Val  Lys Met Met
    1550                 1555                 1560

Val Lys  Thr Met Glu Thr Gly  Ser Tyr Ser Glu Ser  Ser Pro Asp
    1565                 1570                 1575

Leu Lys  Lys Cys Ile Lys Ser  Pro Val Thr Ser Asp  Trp Ser Asp
    1580                 1585                 1590

Tyr Arg  Pro Asp Ser Asp Ser  Glu Gln Pro Tyr Lys  Thr Ser Ser
```

```
    1595                1600                1605

Asp Asp  Pro Asn Asp Ser Gly  Glu Leu Thr Gln Glu  Lys Glu Tyr
    1610                1615                1620

Asn Ile  Gly Phe Val Lys Arg  Ala Ile Glu Lys Leu  Tyr Gly Lys
    1625                1630                1635

Ala Asp  Ile Ile Lys Pro Ser  Phe Phe Pro Gly Ser  Thr Arg Lys
    1640                1645                1650

Ser Gln  Val Cys Pro Tyr Asn  Ser Val Glu Phe Gln  Cys Ser Arg
    1655                1660                1665

Lys Ala  Ser Leu Tyr Asp Ser  Glu Gly Gln Ser Phe  Gly Ser Ser
    1670                1675                1680

Glu Gln  Val Ser Ser Ser Ser  Ser Met Leu Gln Glu  Phe Gln Glu
    1685                1690                1695

Glu Arg  Gln Asp Lys Cys Asp  Val Ser Ala Val Arg  Asp Asn Tyr
    1700                1705                1710

Cys Arg  Gly Asp Ile Val Glu  Pro Gly Thr Lys Gln  Asn Asp Asp
    1715                1720                1725

Ser Arg  Ile Leu Thr Asp Ile  Glu Glu Gly Val Leu  Ile Asp Lys
    1730                1735                1740

Gly Lys  Trp Leu Leu Lys Glu  Asn His Leu Leu Arg  Met Ser Ser
    1745                1750                1755

Glu Asn  Pro Gly Met Cys Gly  Asn Ala Asp Thr Thr  Ser Val Asp
    1760                1765                1770

Thr Leu  Leu Asp Asn Asn Ser  Ser Glu Val Pro Tyr  Ser His Phe
    1775                1780                1785

Gly Asn  Leu Ala Pro Gly Pro  Thr Met Asp Glu Leu  Ser Ser Ser
    1790                1795                1800

Glu Leu  Glu Glu Leu Thr Gln  Pro Leu Glu Leu Lys  Cys Asn Tyr
    1805                1810                1815

Phe Asn  Met Pro His Gly Ser  Asp Ser Glu Pro Phe  His Glu Asp
    1820                1825                1830

Leu Leu  Asp Val Arg Asn Glu  Thr Cys Ala Lys Glu  Arg Ile Ala
    1835                1840                1845

Asn His  His Thr Glu Glu Lys  Gly Ser His Gln Ser  Glu Arg Val
    1850                1855                1860

Cys Thr  Ser Val Thr His Ser  Phe Ile Ser Ala Gly  Asn Lys Val
    1865                1870                1875

Tyr Pro  Val Ser Asp Asp Ala  Ile Lys Asn Gln Pro  Leu Pro Gly
    1880                1885                1890

Ser Asn  Met Ile His Gly Thr  Leu Gln Glu Ala Asp  Ser Leu Asp
    1895                1900                1905

Lys Leu  Tyr Ala Leu Cys Gly  Gln His Cys Pro Ile  Leu Thr Val
    1910                1915                1920

Ile Ile  Gln Pro Met Asn Glu  Glu Asp Arg Gly Phe  Ala Tyr Arg
    1925                1930                1935

Lys Glu  Ser Asp Ile Glu Asn  Phe Leu Gly Phe Tyr  Leu Trp Met
    1940                1945                1950

Lys Ile  His Pro Tyr Leu Leu  Gln Thr Asp Lys Asn  Val Phe Arg
    1955                1960                1965

Glu Glu  Asn Asn Lys Ala Ser  Met Arg Gln Asn Leu  Ile Asp Asn
    1970                1975                1980

Ala Ile  Gly Asp Ile Phe Asp  Gln Phe Tyr Phe Ser  Asn Thr Phe
    1985                1990                1995
```

```
Asp Leu  Met Gly Lys Arg Arg  Lys Gln Lys Arg Ile  Asn Phe Leu
    2000                 2005                 2010

Gly Leu  Glu Glu Glu Gly Asn  Leu Lys Lys Phe Gln  Pro Asp Leu
    2015                 2020                 2025

Lys Glu  Arg Phe Cys Met Asn  Phe Leu His Thr Ser  Leu Leu Val
    2030                 2035                 2040

Val Gly  Asn Val Asp Ser Asn  Thr Gln Asp Leu Ser  Gly Gln Thr
    2045                 2050                 2055

Asn Glu  Ile Phe Lys Ala Val  Asp Glu Asn Asn Asn  Leu Leu Asn
    2060                 2065                 2070

Asn Arg  Phe Gln Gly Ser Arg  Thr Asn Leu Asn Gln  Val Val Arg
    2075                 2080                 2085

Glu Asn  Ile Asn Cys His Tyr  Phe Phe Glu Met Leu  Gly Gln Ala
    2090                 2095                 2100

Cys Leu  Leu Asp Ile Cys Gln  Val Glu Thr Ser Leu  Asn Ile Ser
    2105                 2110                 2115

Asn Arg  Asn Ile Leu Glu Leu  Cys Met Phe Glu Gly  Glu Asn Leu
    2120                 2125                 2130

Phe Ile  Trp Glu Glu Glu Asp  Ile Leu Asn Leu Thr  Asp Leu Glu
    2135                 2140                 2145

Ser Ser  Arg Glu Gln Glu Asp  Leu
    2150                 2155


<210> SEQ ID NO 36
<211> LENGTH: 3950
<212> TYPE: DNA
<213> ORGANISM: Homo sapiens

<400> SEQUENCE: 36

atgtcacatc tggtggaccc tacatcagga gacttgccag ttagagacat agatgctata     60

cctctggtgc taccagcctc aaaaggtaag aatatgaaaa ctcaaccacc cttgagcagg    120

atgaaccggg aggaattgga ggacagtttc tttcgacttc gcgaagatca catgttggtg    180

aaggagcttt cttggaagca acaggatgag atcaaaaggc tgaggaccac cttgctgcgg    240

ttgaccgctg ctggccggga cctgcgggtc gcggaggagg cggcgccgct ctcggagacc    300

gcaaggcgcg ggcagaaggc gggatggcgg cagcgcctct ccatgcacca gcgcccccag    360

atgcaccgac tgcaagggca tttccactgc gtcggccctg ccagcccccg ccgcgcccag    420

cctcgcgtcc aagtgggaca cagacagctc cacacagccg gtgcaccggt gccggagaaa    480

cccaagaggg ggccaaggga caggctgagc tacacagccc ctccatcgtt taaggagcat    540

gcgacaaatg aaaacagagg tgaagtagcc agtaaaccca gtgaacttgt ttctggttct    600

aacagcataa tttctttcag cagtgtcata agtatggcta aacccattgg tctatgcatg    660

cctaacagtg cccacatcat ggccagcaat accatgcaag tggaagagcc acccaagtct    720

cctgagaaaa tgtggcctaa agatgaaaat tttgaacaga gaagctcatt ggagtgtgct    780

cagaaggctg cagagcttcg agcttccatt aaagagaagg tagagctgat tcgacttaag    840

aagctcttac atgaaagaaa tgcttcattg gttatgacaa aagcacaatt aacagaagtt    900

caagaggcat acgaaacctt gctccagaag aatcagggaa tcctgagtgc agcccatgag    960

gccctcctca agcaagtgaa tgagctcagg gcagagctga aggaagaaag caagaaggct   1020

gtgagcttga agagccaact ggaagatgtg tctatcttgc agatgactct gaaggagttt   1080

caggagagag ttgaagattt ggaaaaagaa cgaaaattgc tgaatgacaa ttatgacaaa   1140
```

```
ctcttagaaa gcatgctgga cagcagtgac agctccagtc agccccactg gagcaacgag   1200
ctcatagcgg aacagctaca gcagcaagtc tctcagctgc aggatcagct ggatgctgag   1260
ctggaggaca agagaaaagt tttacttgag ctgtccaggg agaaagccca aaatgaggat   1320
ctgaagcttg aagtcaccaa catacttcag aagcataaac aggaagtaga gctcctccaa   1380
aatgcagcca caatttccca acctcctgac aggcaatctg aaccagccac tcacccagct   1440
gtattgcaag agaacactca gatcgagcca agtgaaccca aaaaccaaga agaaaagaaa   1500
ctgtcccagg tgctaaatga gttgcaagta tcacacgcag agaccacatt ggaactagaa   1560
aagaccaggg acatgcttat tctgcagcgc aaaatcaacg tgtgttatca ggaggaactg   1620
gaggcaatga tgacaaaagc tgacaatgat aatagagatc acaaagaaaa gctggagagg   1680
ttgactcgac tactagacct caagaataac cgtatcaagc agctggaagg tattttaaga   1740
agccatgacc ttccaacatc tgaacagctc aaagatgttg cttatggcac ccgaccgttg   1800
tcgttatgtt tggaaacact gccagcccat ggagatgagg ataaagtgga tatttctctg   1860
ctgcatcagg gtgagaatct tttgaactg cacatccacc aggccttcct gacatctgcc    1920
gccctagctc aggctggaga tacccaacct accactttct gcacctattc cttctatgac   1980
tttgaaaccc actgtacccc attatctgtg gggccacagc cctctatga cttcacctcc    2040
cagtatgtga tggagacaga ttcgcttttc ttacactacc ttcaagaggc ttcagcccgg   2100
cttgacatac accaggccat ggccagtgaa cacagcactc ttgctgcagg atggatttgc   2160
tttgacaggg tgctagagac tgtggagaaa gtccatggct tggccacact gattggagct   2220
ggtggagaag agttcggggt tctagagtac tggatgaggc tgcgtttccc cataaaaccc   2280
agcctacagg cgtgcaataa acgaaagaaa gcccaggtct acctgtcaac cgatgtgctt   2340
ggaggccgga aggcccagga agaggagttc agatcggagt cttgggaacc tcagaacgag   2400
ctgtggattg aaatcaccaa gtgctgtggc ctccggagtc gatggctggg aactcaaccc   2460
agtccatatg ctgtgtaccg cttcttcacc ttttctgacc atgacactgc catcattcca   2520
gccagtaaca acccctactt tagagaccag gctcgattcc cagtgcttgt gacctctgac   2580
ctggaccatt atctgagacg ggaggccttg tctatacatg tttttgatga tgaagactta   2640
gagcctggct cgtatcttgg ccgagcccga gtgcctttac tgcctcttgc aaaaaatgaa   2700
tctatcaaag gtgattttaa cctcactgac cctgcagaga aacccaacgg atctattcaa   2760
gtgcaactgg attggaagtt tccctacata cccctgaga gcttcctgaa accagaagct    2820
cagactaagg ggaaggatac caaggacagt tcaaagatct catctgaaga ggaaaaggct   2880
tcatttcctt cccaggatca gatggcatct cctgaggttc ccattgaagc tggccagtat   2940
cgatctaaga gaaaacctcc tcatgggga gaaagaaagg agaaggagca ccaggttgtg    3000
agctactcaa gaagaaaaca tggcaaaaga ataggtgttc aaggaaagaa tagaatggag   3060
tatcttagcc ttaacatctt aaatggaaat acaccagagc aggtgaatta cactgagtgg   3120
aagttctcag agactaacag cttcataggt gatggcttta aaaatcagca cgaggaagag   3180
gaaatgacat tatcccattc agcactgaaa cagaaggaac ctctacatcc tgtaaatgac   3240
aaagaatcct ctgaacaagg ttctgaagtc agtgaagcac aaactaccga cagtgatgat   3300
gtcatagtgc cacccatgtc tcagaaatat cctaaggcag attcagagaa gatgtgcatt   3360
gaaattgtct ccctggcctt ctacccagag gcagaagtga tgtctgatga gaacataaaa   3420
caggtgtatg tggagtacaa attctacgac ctacccttgt cggagacaga gactccagtg   3480
```

```
tccctaagga agcctagggc aggagaagaa atccactttc actttagcaa ggtaatagac   3540

ctggacccac aggagcagca aggccgaagg cggtttctgt tcgacatgct gaatggacaa   3600

gatcctgatc aaggacattt aaagtttaca gtggtaagtg atcctctgga tgaagaaaag   3660

aaagaatgtg aagaagtggg atatgcatat cttcaactgt ggcagatcct ggagtcagga   3720

agagatattc tagagcaaga gctagacatt gttagccctg aagatctggc taccccaata   3780

ggaaggctga aggtttccct tcaagcagct gctgtcctcc atgctattta caaggagatg   3840

actgaagatt tgttttcatg aaggaacaag tgctattcca atctaaaagt ctctgaggga   3900

accatagtaa aaagtctctt ataaagttag cttgctataa catgaaaaaa              3950


<210> SEQ ID NO 37
<211> LENGTH: 1286
<212> TYPE: PRT
<213> ORGANISM: Homo sapiens

<400> SEQUENCE: 37

Met Ser His Leu Val Asp Pro Thr Ser Gly Asp Leu Pro Val Arg Asp
1               5                   10                  15

Ile Asp Ala Ile Pro Leu Val Leu Pro Ala Ser Lys Gly Lys Asn Met
            20                  25                  30

Lys Thr Gln Pro Pro Leu Ser Arg Met Asn Arg Glu Glu Leu Glu Asp
        35                  40                  45

Ser Phe Phe Arg Leu Arg Glu Asp His Met Leu Val Lys Glu Leu Ser
    50                  55                  60

Trp Lys Gln Gln Asp Glu Ile Lys Arg Leu Arg Thr Thr Leu Leu Arg
65                  70                  75                  80

Leu Thr Ala Ala Gly Arg Asp Leu Arg Val Ala Glu Glu Ala Ala Pro
                85                  90                  95

Leu Ser Glu Thr Ala Arg Arg Gly Gln Lys Ala Gly Trp Arg Gln Arg
            100                 105                 110

Leu Ser Met His Gln Arg Pro Gln Met His Arg Leu Gln Gly His Phe
        115                 120                 125

His Cys Val Gly Pro Ala Ser Pro Arg Arg Ala Gln Pro Arg Val Gln
    130                 135                 140

Val Gly His Arg Gln Leu His Thr Ala Gly Ala Pro Val Pro Glu Lys
145                 150                 155                 160

Pro Lys Arg Gly Pro Arg Asp Arg Leu Ser Tyr Thr Ala Pro Pro Ser
                165                 170                 175

Phe Lys Glu His Ala Thr Asn Glu Asn Arg Gly Glu Val Ala Ser Lys
            180                 185                 190

Pro Ser Glu Leu Val Ser Gly Ser Asn Ser Ile Ile Ser Phe Ser Ser
        195                 200                 205

Val Ile Ser Met Ala Lys Pro Ile Gly Leu Cys Met Pro Asn Ser Ala
    210                 215                 220

His Ile Met Ala Ser Asn Thr Met Gln Val Glu Glu Pro Pro Lys Ser
225                 230                 235                 240

Pro Glu Lys Met Trp Pro Lys Asp Glu Asn Phe Glu Gln Arg Ser Ser
                245                 250                 255

Leu Glu Cys Ala Gln Lys Ala Ala Glu Leu Arg Ala Ser Ile Lys Glu
            260                 265                 270

Lys Val Glu Leu Ile Arg Leu Lys Lys Leu Leu His Glu Arg Asn Ala
        275                 280                 285

Ser Leu Val Met Thr Lys Ala Gln Leu Thr Glu Val Gln Glu Ala Tyr
```

```
    290                 295                 300

Glu Thr Leu Leu Gln Lys Asn Gln Gly Ile Leu Ser Ala Ala His Glu
305                 310                 315                 320

Ala Leu Leu Lys Gln Val Asn Glu Leu Arg Ala Glu Leu Lys Glu Glu
                325                 330                 335

Ser Lys Lys Ala Val Ser Leu Lys Ser Gln Leu Glu Asp Val Ser Ile
            340                 345                 350

Leu Gln Met Thr Leu Lys Glu Phe Gln Glu Arg Val Glu Asp Leu Glu
        355                 360                 365

Lys Glu Arg Lys Leu Leu Asn Asp Asn Tyr Asp Lys Leu Leu Glu Ser
    370                 375                 380

Met Leu Asp Ser Ser Asp Ser Ser Ser Gln Pro His Trp Ser Asn Glu
385                 390                 395                 400

Leu Ile Ala Glu Gln Leu Gln Gln Gln Val Ser Gln Leu Gln Asp Gln
                405                 410                 415

Leu Asp Ala Glu Leu Glu Asp Lys Arg Lys Val Leu Leu Glu Leu Ser
            420                 425                 430

Arg Glu Lys Ala Gln Asn Glu Asp Leu Lys Leu Glu Val Thr Asn Ile
        435                 440                 445

Leu Gln Lys His Lys Gln Glu Val Glu Leu Leu Gln Asn Ala Ala Thr
    450                 455                 460

Ile Ser Gln Pro Pro Asp Arg Gln Ser Glu Pro Ala Thr His Pro Ala
465                 470                 475                 480

Val Leu Gln Glu Asn Thr Gln Ile Glu Pro Ser Glu Pro Lys Asn Gln
                485                 490                 495

Glu Glu Lys Lys Leu Ser Gln Val Leu Asn Glu Leu Gln Val Ser His
            500                 505                 510

Ala Glu Thr Thr Leu Glu Leu Glu Lys Thr Arg Asp Met Leu Ile Leu
        515                 520                 525

Gln Arg Lys Ile Asn Val Cys Tyr Gln Glu Glu Leu Glu Ala Met Met
    530                 535                 540

Thr Lys Ala Asp Asn Asp Asn Arg Asp His Lys Glu Lys Leu Glu Arg
545                 550                 555                 560

Leu Thr Arg Leu Leu Asp Leu Lys Asn Asn Arg Ile Lys Gln Leu Glu
                565                 570                 575

Gly Ile Leu Arg Ser His Asp Leu Pro Thr Ser Glu Gln Leu Lys Asp
            580                 585                 590

Val Ala Tyr Gly Thr Arg Pro Leu Ser Leu Cys Leu Glu Thr Leu Pro
        595                 600                 605

Ala His Gly Asp Glu Asp Lys Val Asp Ile Ser Leu Leu His Gln Gly
    610                 615                 620

Glu Asn Leu Phe Glu Leu His Ile His Gln Ala Phe Leu Thr Ser Ala
625                 630                 635                 640

Ala Leu Ala Gln Ala Gly Asp Thr Gln Pro Thr Thr Phe Cys Thr Tyr
                645                 650                 655

Ser Phe Tyr Asp Phe Glu Thr His Cys Thr Pro Leu Ser Val Gly Pro
            660                 665                 670

Gln Pro Leu Tyr Asp Phe Thr Ser Gln Tyr Val Met Glu Thr Asp Ser
        675                 680                 685

Leu Phe Leu His Tyr Leu Gln Glu Ala Ser Ala Arg Leu Asp Ile His
    690                 695                 700

Gln Ala Met Ala Ser Glu His Ser Thr Leu Ala Ala Gly Trp Ile Cys
705                 710                 715                 720
```

```
Phe Asp Arg Val Leu Glu Thr Val Glu Lys Val His Gly Leu Ala Thr
                725                 730                 735

Leu Ile Gly Ala Gly Gly Glu Glu Phe Gly Val Leu Glu Tyr Trp Met
            740                 745                 750

Arg Leu Arg Phe Pro Ile Lys Pro Ser Leu Gln Ala Cys Asn Lys Arg
        755                 760                 765

Lys Lys Ala Gln Val Tyr Leu Ser Thr Asp Val Leu Gly Gly Arg Lys
    770                 775                 780

Ala Gln Glu Glu Glu Phe Arg Ser Glu Ser Trp Glu Pro Gln Asn Glu
785                 790                 795                 800

Leu Trp Ile Glu Ile Thr Lys Cys Cys Gly Leu Arg Ser Arg Trp Leu
                805                 810                 815

Gly Thr Gln Pro Ser Pro Tyr Ala Val Tyr Arg Phe Phe Thr Phe Ser
            820                 825                 830

Asp His Asp Thr Ala Ile Ile Pro Ala Ser Asn Asn Pro Tyr Phe Arg
        835                 840                 845

Asp Gln Ala Arg Phe Pro Val Leu Val Thr Ser Asp Leu Asp His Tyr
    850                 855                 860

Leu Arg Arg Glu Ala Leu Ser Ile His Val Phe Asp Asp Glu Asp Leu
865                 870                 875                 880

Glu Pro Gly Ser Tyr Leu Gly Arg Ala Arg Val Pro Leu Leu Pro Leu
                885                 890                 895

Ala Lys Asn Glu Ser Ile Lys Gly Asp Phe Asn Leu Thr Asp Pro Ala
            900                 905                 910

Glu Lys Pro Asn Gly Ser Ile Gln Val Gln Leu Asp Trp Lys Phe Pro
        915                 920                 925

Tyr Ile Pro Pro Glu Ser Phe Leu Lys Pro Glu Ala Gln Thr Lys Gly
    930                 935                 940

Lys Asp Thr Lys Asp Ser Ser Lys Ile Ser Ser Glu Glu Glu Lys Ala
945                 950                 955                 960

Ser Phe Pro Ser Gln Asp Gln Met Ala Ser Pro Glu Val Pro Ile Glu
                965                 970                 975

Ala Gly Gln Tyr Arg Ser Lys Arg Lys Pro Pro His Gly Gly Glu Arg
            980                 985                 990

Lys Glu Lys Glu His Gln Val Val  Ser Tyr Ser Arg Arg  Lys His Gly
        995                 1000                 1005

Lys Arg  Ile Gly Val Gln Gly  Lys Asn Arg Met Glu  Tyr Leu Ser
    1010                 1015                 1020

Leu Asn  Ile Leu Asn Gly Asn  Thr Pro Glu Gln Val  Asn Tyr Thr
    1025                 1030                 1035

Glu Trp  Lys Phe Ser Glu Thr  Asn Ser Phe Ile Gly  Asp Gly Phe
    1040                 1045                 1050

Lys Asn  Gln His Glu Glu Glu  Glu Met Thr Leu Ser  His Ser Ala
    1055                 1060                 1065

Leu Lys  Gln Lys Glu Pro Leu  His Pro Val Asn Asp  Lys Glu Ser
    1070                 1075                 1080

Ser Glu  Gln Gly Ser Glu Val  Ser Glu Ala Gln Thr  Thr Asp Ser
    1085                 1090                 1095

Asp Asp  Val Ile Val Pro Pro  Met Ser Gln Lys Tyr  Pro Lys Ala
    1100                 1105                 1110

Asp Ser  Glu Lys Met Cys Ile  Glu Ile Val Ser Leu  Ala Phe Tyr
    1115                 1120                 1125
```

```
Pro Glu  Ala Glu Val Met Ser  Asp Glu Asn Ile Lys  Gln Val Tyr
    1130                 1135                 1140

Val Glu  Tyr Lys Phe Tyr Asp  Leu Pro Leu Ser Glu  Thr Glu Thr
    1145                 1150                 1155

Pro Val  Ser Leu Arg Lys Pro  Arg Ala Gly Glu Glu  Ile His Phe
    1160                 1165                 1170

His Phe  Ser Lys Val Ile Asp  Leu Asp Pro Gln Glu  Gln Gln Gly
    1175                 1180                 1185

Arg Arg  Arg Phe Leu Phe Asp  Met Leu Asn Gly Gln  Asp Pro Asp
    1190                 1195                 1200

Gln Gly  His Leu Lys Phe Thr  Val Val Ser Asp Pro  Leu Asp Glu
    1205                 1210                 1215

Glu Lys  Lys Glu Cys Glu Glu  Val Gly Tyr Ala Tyr  Leu Gln Leu
    1220                 1225                 1230

Trp Gln  Ile Leu Glu Ser Gly  Arg Asp Ile Leu Glu  Gln Glu Leu
    1235                 1240                 1245

Asp Ile  Val Ser Pro Glu Asp  Leu Ala Thr Pro Ile  Gly Arg Leu
    1250                 1255                 1260

Lys Val  Ser Leu Gln Ala Ala  Ala Val Leu His Ala  Ile Tyr Lys
    1265                 1270                 1275

Glu Met  Thr Glu Asp Leu Phe  Ser
    1280                 1285
```

<210> SEQ ID NO 38
<211> LENGTH: 7221
<212> TYPE: DNA
<213> ORGANISM: Homo sapiens

<400> SEQUENCE: 38

```
cgggcggcct cttgtgtgag ggcctgtggg attctccgga tatggccgga gtgtttcctt     60

atcgagggcc gggtaacccg gtgcctggcc ctctagcccc gctaccggac tacatgtcgg    120

aggagaagct gcaggagaaa gctcgaaaat ggcagcaatt gcaggccaag cgctatgcag    180

aaaagcggaa gtttgggttt gtggatgccc agaaggaaga catgccccca gaacatgtca    240

gggagatcat tcgagaccat ggagacatga ccaacaggaa gttccgccat gacaaaaggg    300

tttacttggg tgccctaaag tacatgcccc acgcagtcct caaactcctg gagaacatgc    360

ctatgccttg ggagcagatt cgggatgtgc ccgtgctgta ccacatcact ggagccattt    420

ccttcgtcaa tgagattccc tgggtcattg aacctgtcta catctcccag tgggggtcaa    480

tgtggattat gatgcgccga gaaaaaagag ataggaggca tttcaagaga atgcgttttc    540

ccccttttga tgatgaggag ccgcccttgg actatgctga caacatccta aatgttgagc    600

cactggaggc cattcagcta gagctggacc ctgaggagga cgcccctgtg ttggactggt    660

tctatgacca ccagccgttg agggacagca ggaagtatgt aaatggctcc acttaccagc    720

gctggcagtt cacactacct atgatgtcaa ctctctaccg cctggctaat cagctcctga    780

cagacttggt ggatgacaac tacttctacc tgtttgattt gaaggccttc tttacgtcca    840

aggcactcaa tatggccatt cctggaggcc ccaaatttga acctcttgtt cgagacatca    900

acctacagga tgaagactgg aatgaattca atgatattaa caagattatc atccggcagc    960

ctatccggac tgagtacaag attgcttttc cttacttgta caacaatctt ccacaccatg   1020

tccacctcac ctggtaccat actcccaatg ttgtattcat caaaactgaa gatcctgact   1080

tgccagcttt ctactttgac cctttgatca acccaatctc ccataggcac tcagtcaaga   1140
```

```
gccaggaacc attgccggat gatgatgagg aatttgagct cccggagttt gtggagccct   1200
tcctgaagga cacacccctc tatacagaca atacagccaa tggcattgcc ctgctctggg   1260
ccccgcggcc cttcaaccta cgctctggtc gcacccgtcg ggccctggac ataccccttg   1320
tcaagaactg gtatcgggag cattgtcctg ccgggcagcc tgtgaaagtg agggtctcct   1380
accagaagct gcttaagtac tatgtgctga atgccctgaa gcatcggccc cctaaggctc   1440
aaaagaagag gtatttgttc cgctccttca aagccaccaa attctttcag tccacaaagc   1500
tggactgggt ggagggttgg ctccaggttt gccgccaggg ctacaacatg ctcaaccttc   1560
tcattcaccg caaaaacctc aactacctgc acctggacta caacttcaac ctcaagcctg   1620
tgaaaacgct caccaccaag gaaagaaaga aatctcgttt tgggaatgct ttccacctgt   1680
gtcgggaagt tctgcgtttg actaagctgg tggtggatag tcacgtgcag tatcggctgg   1740
gcaatgtgga tgccttccag ctggcagatg gattgcagta tatatttgcc catgttgggc   1800
agttgacggg catgtatcga tacaaataca agctgatgcg acagattcgc gtgtgcaagg   1860
acctgaagca tctcatctat tatcgtttca acacaggccc tgtagggaag ggtcctggct   1920
gtggcttctg ggctgccggt tggcgagtct ggctcttttt catgcgtggc attacccctt   1980
tattagagcg atggcttggc aacctcctgg cccggcagtt tgaaggtcga cactcaaagg   2040
gggtggcaaa gacagtaaca aagcagcgag tggagtcaca ttttgacctt gagctgcggg   2100
cagctgtgat gcatgatatt ctggacatga tgcctgaggg gatcaagcag aacaaggccc   2160
ggacaatcct gcagcacctc agtgaagcct ggcgctgctg gaaagccaac attccctgga   2220
aggtccctgg gctgccgacg cccatagaga atatgatcct tcgatacgtg aaggccaagg   2280
ctgactggtg gaccaacact gcccactaca accgagaacg gatccgccga ggggccactg   2340
tggacaagac tgtttgtaaa aagaatctgg gccgcctcac ccggctctat ctgaaggcag   2400
aacaggagcg gcagcacaac tacctgaagg acgggcctta catcacagcg gaggaaacag   2460
tggcagtata taccaccaca gtgcattggt tggaaagccg caggttttca cccatcccat   2520
tcccccccact ctcctataag catgacacca agttgctcat cttggcattg gagcggctca   2580
aggaagctta tagtgtgaag tctcggttga accagtctca gagggaggag ctaggtctga   2640
tcgagcaggc ctacgataac ctccacgagg cgctgtcccg cataaagcgt cacctcctca   2700
cacagagagc cttcaaagag gtgggcattg agttcatgga tctgtatagc cacctcgttc   2760
cagtatatga tgttgagccc ctggagaaga taactgatgc ttacctggac cagtacctgt   2820
ggtatgaagc cgacaagcgc cgcctgttcc caccctggat taagcctgca gacacagaac   2880
cacctccact gcttgtttac aagtggtgtc aaggcatcaa taacctgcag gacgtgtggg   2940
agacgagtga aggcgagtgc aatgtcatgc tggaatcccg ctttgagaag atgtatgaga   3000
agatcgactt gactctgctc aacaggctcg tgcgcctcat cgtggaccac aacatagccg   3060
actacatgac agccaagaac aacgtcgtca tcaactataa ggacatgaac catacgaatt   3120
catatgggat catcagaggc ctgcagtttg cctcattcat agtgcagtat tatggcctgg   3180
tgatggattt gcttgtattg ggattgcacc gggccagtga gatggctggg ccccctcaga   3240
tgccaaatga ctttctcagt ttccaggaca tagccactga ggctgcccac cccatccgtc   3300
tcttctgcag atacattgat cgcatccata ttttttttcag gttcacagca gatgaggctc   3360
gggacctgat tcaacgttac ctgacagagc accctgaccc caataatgaa aacatcgttg   3420
gctataataa caagaagtgc tggccccgag atgcccgcat gcgcctcatg aaacatgatg   3480
ttaacttagg ccgggcggta ttctgggaca tcaagaaccg cttgccacgg tcagtgacta   3540
```

```
cagttcagtg ggagaacagc ttcgtgtctg tgtacagtaa ggacaacccc aacctgctgt   3600
tcaacatgtg tggcttcgag tgccgcatcc tgcctaagtg ccgcaccagc tatgaggagt   3660
tcacccacaa ggacggggtc tggaacctgc agaatgaggt tactaaggag cgcacagctc   3720
agtgtttcct gcgtgtggac gatgagtcaa tgcagcgctt ccacaaccgc gtgcgtcaga   3780
ttctcatggc ctctgggtcc accaccttca ccaagattgt gaataagtgg aatacagctc   3840
tcattggcct tatgacatac tttcgggagg ctgtggtgaa cacccaagag ctcttggact   3900
tactggtgaa gtgtgagcac aaaatccaga cacgtatcaa gattggactc aactccaaga   3960
tgccaagtcg gttccccccg gttgtgttct acacccctaa ggagttgggt ggactcggca   4020
tgctctcaat gggccatgtg ctcatccccc aatccgacct caggtggtcc aaacagacag   4080
atgtaggtat cacacacttt cgttcaggaa tgagccatga agaagaccag ctcattccca   4140
acttgtaccg ctacatacag ccatgggaga gcgagttcat tgattctcag cgggtctggg   4200
ctgagtactc actcaagaga caagaggcca ttgctcagaa cagacgcctg actttagaag   4260
acctagaaga ttcatgggat cgtggcattc ctcgaatcaa taccctcttc cagaaggacc   4320
ggcacacact ggcttatgat aagggctggc gtgtcagaac tgactttaag cagtatcagg   4380
ttttgaagca gaatccgttc tggtggacac accagcggca tgatgggaag ctctggaacc   4440
tgaacaacta ccgtacagac atgatccagg ccctgggcgg tgtggaaggc attctggaac   4500
acacactctt taagggcact tacttcccta cctgggaggg gcttttctgg gagaaggcca   4560
gtggctttga ggaatctatg aagtggaaga agctaactaa tgctcagcga tcaggactga   4620
accagattcc caatcgtaga ttcaccctct ggtggtcccc gaccattaat cgagccaatg   4680
tatatgtagg ctttcaggtg cagctagacc tgacgggtat cttcatgcac ggcaagatcc   4740
ccacgctgaa gatctctctc atccagatct tccgagctca cttgtggcag aagatccatg   4800
agagcattgt tatggactta tgtcaggtgt ttgaccagga acttgatgca ctggaaattg   4860
agacagtaca aaaggagaca atccatcccc gaaagtcata taagatgaac tcttcctgtg   4920
cagatatcct gctctttgcc tcctataagt ggaatgtctc ccggccctca ttgctggctg   4980
actccaagga tgtgatggac agcaccacca cccagaaata ctggattgac atccagttgc   5040
gctgggggga ctatgattcc cacgacattg agcgctacgc ccgggccaag ttcctggact   5100
acaccaccga caacatgagt atctaccctt cgcccacagg tgtactcatc gccattgacc   5160
tggcctataa cttgcacagt gcctatggaa actggttccc aggcagcaag cctctcatac   5220
aacaggccat ggccaagatc atgaaggcaa accctgccct gtatgtgtta cgtgaacgga   5280
tccgcaaggg gctacagctc tattcatctg aacccactga gccttatttg tcttctcaga   5340
actatggtga gctcttctcc aaccagatta tctggtttgt ggatgacacc aacgtctaca   5400
gagtgactat tcacaagacc tttgaaggga acttgacaac caagcccatc aacggagcca   5460
tcttcatctt caacccacgc acagggcagc tgttcctcaa gataatccac acgtccgtgt   5520
gggcgggaca gaagcgtttg ggcagttggg ctaagtggaa gacagctgag gaggtggccg   5580
ccctgatccg atctctgcct gtggaggagc agcccaagca gatcattgtc accaggaagg   5640
acatgctgga cccactggag gtgcacttac tggacttccc caatattgtc atcaaaggat   5700
cggagctcca actccctttc caggcgtgtc tcaaggtgga aaaattcggg gatctcatcc   5760
ttaaagccac tgagccccag atggttctct tcaacctcta tgacgactgg ctcaagacta   5820
tttcatctta cacggccttc tcccgtctca tcctgattct gcgtgcccta catgtgaaca   5880
```

```
acgatcgggc aaaagtgatc ctgaagccag acaagactac tattacagaa ccacaccaca   5940

tctggcccac tctgactgac gaagaatgga tcaaggtcga ggtgcagctc aaggatctga   6000

tcttggctga ctacggcaag aaaaacaatg tgaacgtggc atcactgaca caatcagaaa   6060

ttcgagacat catcctgggt atggagatct cggcaccgtc acagcagcgg cagcagatcg   6120

ctgagatcga gaagcagacc aaggaacaat cgcagctgac ggcaacacag actcgcactg   6180

tcaacaagca tggcgatgag atcatcacct ccaccaccag caactatgag acccagactt   6240

tctcatccaa gactgagtgg agggtcaggg ccatctctgc tgccaacctg cacctaagga   6300

ccaatcacat ctatgtttca tctgacgaca tcaaggagac tggctacacc tacatccttc   6360

ccaagaatgt gcttaagaag ttcatctgca tatctgacct tcgggcccaa attgcaggat   6420

acctatatgg ggtgagccca ccagataacc cccaggtgaa ggagatccgc tgcattgtga   6480

tggtgccgca gtggggcact caccagaccg tgcacctgcc tggccagctg ccccagcatg   6540

agtacctcaa ggagatggaa cccttaggtt ggatccacac tcagcccaat gagtccccgc   6600

agttatcacc ccaggatgtc accacccatg ccaagatcat ggctgacaac ccatcttggg   6660

atggcgagaa gaccattatc atcacatgca gcttcacgcc aggctcctgt acactgacgg   6720

cctacaagct gacccctagt ggctacgaat ggggccgcca gaacacagac aagggcaaca   6780

accccaaggg ctacctgcct tcacactatg agagggtgca gatgctgctg tcggaccgtt   6840

tccttggctt cttcatggtc cctgcccagt cctcgtggaa ctacaacttc atgggtgttc   6900

ggcatgaccc caacatgaaa tatgagctac agctggcgaa ccccaaagag ttctaccacg   6960

aggtgcacag gccctctcac ttcctcaact ttgctctcct gcaggagggg gaggtttact   7020

ctgcggatcg ggaggacctg tatgcctgac cgtttccctg cctcctgctt cagcctcccg   7080

aggccgaagc ctcagcccct ccagacaggc cgctgacatt cagcagtttg gcctctttcc   7140

ctctgtctgt gcttgtgttg ttgacctcct gatggcttgt catcctgaat aaaatataat   7200

aataaatttt gtataaatag g                                             7221
```

<210> SEQ ID NO 39
<211> LENGTH: 2335
<212> TYPE: PRT
<213> ORGANISM: Homo sapiens

<400> SEQUENCE: 39

```
Met Ala Gly Val Phe Pro Tyr Arg Gly Pro Gly Asn Pro Val Pro Gly
1               5                   10                  15

Pro Leu Ala Pro Leu Pro Asp Tyr Met Ser Glu Glu Lys Leu Gln Glu
            20                  25                  30

Lys Ala Arg Lys Trp Gln Gln Leu Gln Ala Lys Arg Tyr Ala Glu Lys
        35                  40                  45

Arg Lys Phe Gly Phe Val Asp Ala Gln Lys Glu Asp Met Pro Pro Glu
    50                  55                  60

His Val Arg Glu Ile Ile Arg Asp His Gly Asp Met Thr Asn Arg Lys
65                  70                  75                  80

Phe Arg His Asp Lys Arg Val Tyr Leu Gly Ala Leu Lys Tyr Met Pro
                85                  90                  95

His Ala Val Leu Lys Leu Leu Glu Asn Met Pro Met Pro Trp Glu Gln
            100                 105                 110

Ile Arg Asp Val Pro Val Leu Tyr His Ile Thr Gly Ala Ile Ser Phe
        115                 120                 125

Val Asn Glu Ile Pro Trp Val Ile Glu Pro Val Tyr Ile Ser Gln Trp
```

```
130                 135                 140

Gly Ser Met Trp Ile Met Met Arg Arg Glu Lys Arg Asp Arg Arg His
145                 150                 155                 160

Phe Lys Arg Met Arg Phe Pro Pro Phe Asp Asp Glu Glu Pro Pro Leu
                165                 170                 175

Asp Tyr Ala Asp Asn Ile Leu Asn Val Glu Pro Leu Glu Ala Ile Gln
            180                 185                 190

Leu Glu Leu Asp Pro Glu Glu Asp Ala Pro Val Leu Asp Trp Phe Tyr
        195                 200                 205

Asp His Gln Pro Leu Arg Asp Ser Arg Lys Tyr Val Asn Gly Ser Thr
    210                 215                 220

Tyr Gln Arg Trp Gln Phe Thr Leu Pro Met Met Ser Thr Leu Tyr Arg
225                 230                 235                 240

Leu Ala Asn Gln Leu Leu Thr Asp Leu Val Asp Asp Asn Tyr Phe Tyr
                245                 250                 255

Leu Phe Asp Leu Lys Ala Phe Phe Thr Ser Lys Ala Leu Asn Met Ala
            260                 265                 270

Ile Pro Gly Gly Pro Lys Phe Glu Pro Leu Val Arg Asp Ile Asn Leu
        275                 280                 285

Gln Asp Glu Asp Trp Asn Glu Phe Asn Asp Ile Asn Lys Ile Ile Ile
    290                 295                 300

Arg Gln Pro Ile Arg Thr Glu Tyr Lys Ile Ala Phe Pro Tyr Leu Tyr
305                 310                 315                 320

Asn Asn Leu Pro His His Val His Leu Thr Trp Tyr His Thr Pro Asn
                325                 330                 335

Val Val Phe Ile Lys Thr Glu Asp Pro Asp Leu Pro Ala Phe Tyr Phe
            340                 345                 350

Asp Pro Leu Ile Asn Pro Ile Ser His Arg His Ser Val Lys Ser Gln
        355                 360                 365

Glu Pro Leu Pro Asp Asp Asp Glu Glu Phe Glu Leu Pro Glu Phe Val
    370                 375                 380

Glu Pro Phe Leu Lys Asp Thr Pro Leu Tyr Thr Asp Asn Thr Ala Asn
385                 390                 395                 400

Gly Ile Ala Leu Leu Trp Ala Pro Arg Pro Phe Asn Leu Arg Ser Gly
                405                 410                 415

Arg Thr Arg Arg Ala Leu Asp Ile Pro Leu Val Lys Asn Trp Tyr Arg
            420                 425                 430

Glu His Cys Pro Ala Gly Gln Pro Val Lys Val Arg Val Ser Tyr Gln
        435                 440                 445

Lys Leu Leu Lys Tyr Tyr Val Leu Asn Ala Leu Lys His Arg Pro Pro
    450                 455                 460

Lys Ala Gln Lys Lys Arg Tyr Leu Phe Arg Ser Phe Lys Ala Thr Lys
465                 470                 475                 480

Phe Phe Gln Ser Thr Lys Leu Asp Trp Val Glu Gly Trp Leu Gln Val
                485                 490                 495

Cys Arg Gln Gly Tyr Asn Met Leu Asn Leu Leu Ile His Arg Lys Asn
            500                 505                 510

Leu Asn Tyr Leu His Leu Asp Tyr Asn Phe Asn Leu Lys Pro Val Lys
        515                 520                 525

Thr Leu Thr Thr Lys Glu Arg Lys Lys Ser Arg Phe Gly Asn Ala Phe
    530                 535                 540

His Leu Cys Arg Glu Val Leu Arg Leu Thr Lys Leu Val Val Asp Ser
545                 550                 555                 560
```

```
His Val Gln Tyr Arg Leu Gly Asn Val Asp Ala Phe Gln Leu Ala Asp
                565                 570                 575

Gly Leu Gln Tyr Ile Phe Ala His Val Gly Gln Leu Thr Gly Met Tyr
            580                 585                 590

Arg Tyr Lys Tyr Lys Leu Met Arg Gln Ile Arg Val Cys Lys Asp Leu
        595                 600                 605

Lys His Leu Ile Tyr Tyr Arg Phe Asn Thr Gly Pro Val Gly Lys Gly
    610                 615                 620

Pro Gly Cys Gly Phe Trp Ala Ala Gly Trp Arg Val Trp Leu Phe Phe
625                 630                 635                 640

Met Arg Gly Ile Thr Pro Leu Leu Glu Arg Trp Leu Gly Asn Leu Leu
                645                 650                 655

Ala Arg Gln Phe Glu Gly Arg His Ser Lys Gly Val Ala Lys Thr Val
            660                 665                 670

Thr Lys Gln Arg Val Glu Ser His Phe Asp Leu Glu Leu Arg Ala Ala
        675                 680                 685

Val Met His Asp Ile Leu Asp Met Met Pro Glu Gly Ile Lys Gln Asn
    690                 695                 700

Lys Ala Arg Thr Ile Leu Gln His Leu Ser Glu Ala Trp Arg Cys Trp
705                 710                 715                 720

Lys Ala Asn Ile Pro Trp Lys Val Pro Gly Leu Pro Thr Pro Ile Glu
                725                 730                 735

Asn Met Ile Leu Arg Tyr Val Lys Ala Lys Ala Asp Trp Trp Thr Asn
            740                 745                 750

Thr Ala His Tyr Asn Arg Glu Arg Ile Arg Arg Gly Ala Thr Val Asp
        755                 760                 765

Lys Thr Val Cys Lys Lys Asn Leu Gly Arg Leu Thr Arg Leu Tyr Leu
    770                 775                 780

Lys Ala Glu Gln Glu Arg Gln His Asn Tyr Leu Lys Asp Gly Pro Tyr
785                 790                 795                 800

Ile Thr Ala Glu Glu Thr Val Ala Val Tyr Thr Thr Thr Val His Trp
                805                 810                 815

Leu Glu Ser Arg Arg Phe Ser Pro Ile Pro Phe Pro Pro Leu Ser Tyr
            820                 825                 830

Lys His Asp Thr Lys Leu Leu Ile Leu Ala Leu Glu Arg Leu Lys Glu
        835                 840                 845

Ala Tyr Ser Val Lys Ser Arg Leu Asn Gln Ser Gln Arg Glu Glu Leu
    850                 855                 860

Gly Leu Ile Glu Gln Ala Tyr Asp Asn Leu His Glu Ala Leu Ser Arg
865                 870                 875                 880

Ile Lys Arg His Leu Leu Thr Gln Arg Ala Phe Lys Glu Val Gly Ile
                885                 890                 895

Glu Phe Met Asp Leu Tyr Ser His Leu Val Pro Val Tyr Asp Val Glu
            900                 905                 910

Pro Leu Glu Lys Ile Thr Asp Ala Tyr Leu Asp Gln Tyr Leu Trp Tyr
        915                 920                 925

Glu Ala Asp Lys Arg Arg Leu Phe Pro Pro Trp Ile Lys Pro Ala Asp
    930                 935                 940

Thr Glu Pro Pro Pro Leu Leu Val Tyr Lys Trp Cys Gln Gly Ile Asn
945                 950                 955                 960

Asn Leu Gln Asp Val Trp Glu Thr Ser Glu Gly Glu Cys Asn Val Met
                965                 970                 975
```

```
Leu Glu Ser Arg Phe Glu Lys Met Tyr Glu Lys Ile Asp Leu Thr Leu
            980                 985                 990

Leu Asn Arg Leu Val Arg Leu Ile  Val Asp His Asn Ile  Ala Asp Tyr
        995                 1000                1005

Met Thr  Ala Lys Asn Asn Val  Val Ile Asn Tyr Lys  Asp Met Asn
    1010                 1015                1020

His Thr  Asn Ser Tyr Gly Ile  Ile Arg Gly Leu Gln  Phe Ala Ser
    1025                 1030                1035

Phe Ile  Val Gln Tyr Tyr Gly  Leu Val Met Asp Leu  Leu Val Leu
    1040                 1045                1050

Gly Leu  His Arg Ala Ser Glu  Met Ala Gly Pro Pro  Gln Met Pro
    1055                 1060                1065

Asn Asp  Phe Leu Ser Phe Gln  Asp Ile Ala Thr Glu  Ala Ala His
    1070                 1075                1080

Pro Ile  Arg Leu Phe Cys Arg  Tyr Ile Asp Arg Ile  His Ile Phe
    1085                 1090                1095

Phe Arg  Phe Thr Ala Asp Glu  Ala Arg Asp Leu Ile  Gln Arg Tyr
    1100                 1105                1110

Leu Thr  Glu His Pro Asp Pro  Asn Asn Glu Asn Ile  Val Gly Tyr
    1115                 1120                1125

Asn Asn  Lys Lys Cys Trp Pro  Arg Asp Ala Arg Met  Arg Leu Met
    1130                 1135                1140

Lys His  Asp Val Asn Leu Gly  Arg Ala Val Phe Trp  Asp Ile Lys
    1145                 1150                1155

Asn Arg  Leu Pro Arg Ser Val  Thr Thr Val Gln Trp  Glu Asn Ser
    1160                 1165                1170

Phe Val  Ser Val Tyr Ser Lys  Asp Asn Pro Asn Leu  Leu Phe Asn
    1175                 1180                1185

Met Cys  Gly Phe Glu Cys Arg  Ile Leu Pro Lys Cys  Arg Thr Ser
    1190                 1195                1200

Tyr Glu  Glu Phe Thr His Lys  Asp Gly Val Trp Asn  Leu Gln Asn
    1205                 1210                1215

Glu Val  Thr Lys Glu Arg Thr  Ala Gln Cys Phe Leu  Arg Val Asp
    1220                 1225                1230

Asp Glu  Ser Met Gln Arg Phe  His Asn Arg Val Arg  Gln Ile Leu
    1235                 1240                1245

Met Ala  Ser Gly Ser Thr Thr  Phe Thr Lys Ile Val  Asn Lys Trp
    1250                 1255                1260

Asn Thr  Ala Leu Ile Gly Leu  Met Thr Tyr Phe Arg  Glu Ala Val
    1265                 1270                1275

Val Asn  Thr Gln Glu Leu Leu  Asp Leu Leu Val Lys  Cys Glu His
    1280                 1285                1290

Lys Ile  Gln Thr Arg Ile Lys  Ile Gly Leu Asn Ser  Lys Met Pro
    1295                 1300                1305

Ser Arg  Phe Pro Pro Val Val  Phe Tyr Thr Pro Lys  Glu Leu Gly
    1310                 1315                1320

Gly Leu  Gly Met Leu Ser Met  Gly His Val Leu Ile  Pro Gln Ser
    1325                 1330                1335

Asp Leu  Arg Trp Ser Lys Gln  Thr Asp Val Gly Ile  Thr His Phe
    1340                 1345                1350

Arg Ser  Gly Met Ser His Glu  Glu Asp Gln Leu Ile  Pro Asn Leu
    1355                 1360                1365

Tyr Arg  Tyr Ile Gln Pro Trp  Glu Ser Glu Phe Ile  Asp Ser Gln
```

```
    1370                1375                1380

Arg Val  Trp Ala Glu Tyr Ser  Leu Lys Arg Gln Glu  Ala Ile Ala
    1385                1390                1395

Gln Asn  Arg Arg Leu Thr Leu  Glu Asp Leu Glu Asp  Ser Trp Asp
    1400                1405                1410

Arg Gly  Ile Pro Arg Ile Asn  Thr Leu Phe Gln Lys  Asp Arg His
    1415                1420                1425

Thr Leu  Ala Tyr Asp Lys Gly  Trp Arg Val Arg Thr  Asp Phe Lys
    1430                1435                1440

Gln Tyr  Gln Val Leu Lys Gln  Asn Pro Phe Trp Trp  Thr His Gln
    1445                1450                1455

Arg His  Asp Gly Lys Leu Trp  Asn Leu Asn Asn Tyr  Arg Thr Asp
    1460                1465                1470

Met Ile  Gln Ala Leu Gly Gly  Val Glu Gly Ile Leu  Glu His Thr
    1475                1480                1485

Leu Phe  Lys Gly Thr Tyr Phe  Pro Thr Trp Glu Gly  Leu Phe Trp
    1490                1495                1500

Glu Lys  Ala Ser Gly Phe Glu  Glu Ser Met Lys Trp  Lys Lys Leu
    1505                1510                1515

Thr Asn  Ala Gln Arg Ser Gly  Leu Asn Gln Ile Pro  Asn Arg Arg
    1520                1525                1530

Phe Thr  Leu Trp Trp Ser Pro  Thr Ile Asn Arg Ala  Asn Val Tyr
    1535                1540                1545

Val Gly  Phe Gln Val Gln Leu  Asp Leu Thr Gly Ile  Phe Met His
    1550                1555                1560

Gly Lys  Ile Pro Thr Leu Lys  Ile Ser Leu Ile Gln  Ile Phe Arg
    1565                1570                1575

Ala His  Leu Trp Gln Lys Ile  His Glu Ser Ile Val  Met Asp Leu
    1580                1585                1590

Cys Gln  Val Phe Asp Gln Glu  Leu Asp Ala Leu Glu  Ile Glu Thr
    1595                1600                1605

Val Gln  Lys Glu Thr Ile His  Pro Arg Lys Ser Tyr  Lys Met Asn
    1610                1615                1620

Ser Ser  Cys Ala Asp Ile Leu  Leu Phe Ala Ser Tyr  Lys Trp Asn
    1625                1630                1635

Val Ser  Arg Pro Ser Leu Leu  Ala Asp Ser Lys Asp  Val Met Asp
    1640                1645                1650

Ser Thr  Thr Thr Gln Lys Tyr  Trp Ile Asp Ile Gln  Leu Arg Trp
    1655                1660                1665

Gly Asp  Tyr Asp Ser His Asp  Ile Glu Arg Tyr Ala  Arg Ala Lys
    1670                1675                1680

Phe Leu  Asp Tyr Thr Thr Asp  Asn Met Ser Ile Tyr  Pro Ser Pro
    1685                1690                1695

Thr Gly  Val Leu Ile Ala Ile  Asp Leu Ala Tyr Asn  Leu His Ser
    1700                1705                1710

Ala Tyr  Gly Asn Trp Phe Pro  Gly Ser Lys Pro Leu  Ile Gln Gln
    1715                1720                1725

Ala Met  Ala Lys Ile Met Lys  Ala Asn Pro Ala Leu  Tyr Val Leu
    1730                1735                1740

Arg Glu  Arg Ile Arg Lys Gly  Leu Gln Leu Tyr Ser  Ser Glu Pro
    1745                1750                1755

Thr Glu  Pro Tyr Leu Ser Ser  Gln Asn Tyr Gly Glu  Leu Phe Ser
    1760                1765                1770
```

```
Asn Gln  Ile Ile Trp Phe Val  Asp Asp Thr Asn Val  Tyr Arg Val
    1775                 1780                 1785

Thr Ile  His Lys Thr Phe Glu  Gly Asn Leu Thr Thr  Lys Pro Ile
    1790                 1795                 1800

Asn Gly  Ala Ile Phe Ile Phe  Asn Pro Arg Thr Gly  Gln Leu Phe
    1805                 1810                 1815

Leu Lys  Ile Ile His Thr Ser  Val Trp Ala Gly Gln  Lys Arg Leu
    1820                 1825                 1830

Gly Gln  Leu Ala Lys Trp Lys  Thr Ala Glu Glu Val  Ala Ala Leu
    1835                 1840                 1845

Ile Arg  Ser Leu Pro Val Glu  Glu Gln Pro Lys Gln  Ile Ile Val
    1850                 1855                 1860

Thr Arg  Lys Asp Met Leu Asp  Pro Leu Glu Val His  Leu Leu Asp
    1865                 1870                 1875

Phe Pro  Asn Ile Val Ile Lys  Gly Ser Glu Leu Gln  Leu Pro Phe
    1880                 1885                 1890

Gln Ala  Cys Leu Lys Val Glu  Lys Phe Gly Asp Leu  Ile Leu Lys
    1895                 1900                 1905

Ala Thr  Glu Pro Gln Met Val  Leu Phe Asn Leu Tyr  Asp Asp Trp
    1910                 1915                 1920

Leu Lys  Thr Ile Ser Ser Tyr  Thr Ala Phe Ser Arg  Leu Ile Leu
    1925                 1930                 1935

Ile Leu  Arg Ala Leu His Val  Asn Asn Asp Arg Ala  Lys Val Ile
    1940                 1945                 1950

Leu Lys  Pro Asp Lys Thr Thr  Ile Thr Glu Pro His  His Ile Trp
    1955                 1960                 1965

Pro Thr  Leu Thr Asp Glu Glu  Trp Ile Lys Val Glu  Val Gln Leu
    1970                 1975                 1980

Lys Asp  Leu Ile Leu Ala Asp  Tyr Gly Lys Lys Asn  Asn Val Asn
    1985                 1990                 1995

Val Ala  Ser Leu Thr Gln Ser  Glu Ile Arg Asp Ile  Ile Leu Gly
    2000                 2005                 2010

Met Glu  Ile Ser Ala Pro Ser  Gln Gln Arg Gln Gln  Ile Ala Glu
    2015                 2020                 2025

Ile Glu  Lys Gln Thr Lys Glu  Gln Ser Gln Leu Thr  Ala Thr Gln
    2030                 2035                 2040

Thr Arg  Thr Val Asn Lys His  Gly Asp Glu Ile Ile  Thr Ser Thr
    2045                 2050                 2055

Thr Ser  Asn Tyr Glu Thr Gln  Thr Phe Ser Ser Lys  Thr Glu Trp
    2060                 2065                 2070

Arg Val  Arg Ala Ile Ser Ala  Ala Asn Leu His Leu  Arg Thr Asn
    2075                 2080                 2085

His Ile  Tyr Val Ser Ser Asp  Asp Ile Lys Glu Thr  Gly Tyr Thr
    2090                 2095                 2100

Tyr Ile  Leu Pro Lys Asn Val  Leu Lys Lys Phe Ile  Cys Ile Ser
    2105                 2110                 2115

Asp Leu  Arg Ala Gln Ile Ala  Gly Tyr Leu Tyr Gly  Val Ser Pro
    2120                 2125                 2130

Pro Asp  Asn Pro Gln Val Lys  Glu Ile Arg Cys Ile  Val Met Val
    2135                 2140                 2145

Pro Gln  Trp Gly Thr His Gln  Thr Val His Leu Pro  Gly Gln Leu
    2150                 2155                 2160
```

```
Pro Gln  His Glu Tyr Leu Lys  Glu Met Glu Pro Leu  Gly Trp Ile
    2165                 2170                 2175

His Thr  Gln Pro Asn Glu Ser  Pro Gln Leu Ser Pro  Gln Asp Val
    2180                 2185                 2190

Thr Thr  His Ala Lys Ile Met  Ala Asp Asn Pro Ser  Trp Asp Gly
    2195                 2200                 2205

Glu Lys  Thr Ile Ile Ile Thr  Cys Ser Phe Thr Pro  Gly Ser Cys
    2210                 2215                 2220

Thr Leu  Thr Ala Tyr Lys Leu  Thr Pro Ser Gly Tyr  Glu Trp Gly
    2225                 2230                 2235

Arg Gln  Asn Thr Asp Lys Gly  Asn Asn Pro Lys Gly  Tyr Leu Pro
    2240                 2245                 2250

Ser His  Tyr Glu Arg Val Gln  Met Leu Leu Ser Asp  Arg Phe Leu
    2255                 2260                 2265

Gly Phe  Phe Met Val Pro Ala  Gln Ser Ser Trp Asn  Tyr Asn Phe
    2270                 2275                 2280

Met Gly  Val Arg His Asp Pro  Asn Met Lys Tyr Glu  Leu Gln Leu
    2285                 2290                 2295

Ala Asn  Pro Lys Glu Phe Tyr  His Glu Val His Arg  Pro Ser His
    2300                 2305                 2310

Phe Leu  Asn Phe Ala Leu Leu  Gln Glu Gly Glu Val  Tyr Ser Ala
    2315                 2320                 2325

Asp Arg  Glu Asp Leu Tyr Ala
    2330                 2335


<210> SEQ ID NO 40
<211> LENGTH: 7972
<212> TYPE: DNA
<213> ORGANISM: Homo sapiens

<400> SEQUENCE: 40

atttgaagtc ctcgttccac gccttctcat catcctgaac accgagctct gggactccgg     60

cggagaatct aaacgtaaag catcacccac ggtcgtgaac tgtaggctct cctggcatcc    120

gggatcttat tctggccttg gcggagttgg ggatggtgtc gcctagcagc cgctgccgct    180

ttggcttgct cgggaccatt tggctggacc cagagtccgc gtggaaccgc gatagggatc    240

tgtcagggcc cgcggccggg tccagcttgg tggttgcggt agtgagaggc ctccgctggt    300

tgccaggctt ggtctagagg tggagcacag tgaaagaatt caagatgcca cctaatataa    360

actggaaaga aataatgaaa gttgacccag atgacctgcc ccgtcaagaa gaactggcag    420

ataatttatt gatttcctta tccaaggtgg aagtaaatga gctaaaaagt gaaaagcaag    480

aaaatgtgat acaccttttc agaattactc agtcactaat gaagatgaaa gctcaagaag    540

tggagctggc tttggaagaa gtagaaaaag ctggagaaga acaagcaaaa tttgaaaatc    600

aattaaaaac taaagtaatg aaactggaaa atgaactgga gatggctcag cagtctgcag    660

gtggacgaga tactcggttt ttacgtaatg aaatttgcca acttgaaaaa caattagaac    720

aaaaagatag agaattggag gacatggaaa aggagttgga gaaagagaag aaagttaatg    780

agcaattggc tcttcgaaat gaggaggcag aaaatgaaaa cagcaaatta agaagagaga    840

acaaacgtct aaagaaaaag aatgaacaac tttgtcagga tattattgac taccagaaac    900

aaatagattc acagaaagaa acacttttat caagaagagg ggaagacagt gactaccgat    960

cacagttgtc taaaaaaaac tatgagctta tccaatatct tgatgaaatt cagactttaa   1020

cagaagctaa tgagaaaatt gaagttcaga atcaagaaat gagaaaaaat ttagaagagt   1080
```

```
ctgtacagga aatggagaag atgactgatg aatataatag aatgaaagct attgtgcatc   1140
agacagataa tgtaatagat cagttaaaaa aagaaaacga tcattatcaa cttcaagtgc   1200
aggagcttac agatcttctg aaatcaaaaa atgaagaaga tgatccaatt atggtagctg   1260
tcaatgcaaa agtagaagaa tggaagctaa ttttgtcttc taaagatgat gaaattattg   1320
agtatcagca aatgttacat aacctaaggg agaaacttaa gaatgctcag cttgatgctg   1380
ataaaagtaa tgttatggct ctacagcagg gtatacagga acgagacagt caaattaaga   1440
tgctcaccga acaagtagaa caatatacaa aagaaatgga aaagaatact tgtattattg   1500
aagatttgaa aaatgagctc caaagaaaca aaggtgcttc aaccctttct caacagactc   1560
atatgaaaat tcagtcaacg ttagacattt taaaagagaa aactaaagag gctgagagaa   1620
cagctgaact ggctgaggct gatgctaggg aaaaggataa agaattagtt gaggctctga   1680
agaggttaaa agattatgaa tcgggagtat atggtttaga agatgctgtc gttgaaataa   1740
agaattgtaa aaaccaaatt aaaataagag atcgagagat tgaaatatta acaaaggaaa   1800
tcaataaact tgaattgaag atcagtgatt tccttgatga aaatgaggca cttagagagc   1860
gtgtgggcct tgaaccaaag acaatgattg atttaactga atttagaaat agcaaacact   1920
taaaacagca gcagtacaga gctgaaaacc agattctttt gaaagagatt gaaagtctag   1980
aggaagaacg acttgatctg aaaaaaaaaa ttcgtcaaat ggctcaagaa agaggaaaaa   2040
gaagtgcaac ttcaggatta accactgagg acctgaacct aactgaaaac atttctcaag   2100
gagatagaat aagtgaaaga aaattggatt tattgagcct caaaaatatg agtgaagcac   2160
aatcaaagaa tgaatttctt tcaagagaac taattgaaaa agaaagagat ttagaaagga   2220
gtaggacagt gatagccaaa tttcagaata aattaaaaga attagttgaa gaaaataagc   2280
aacttgaaga aggtatgaaa gaaatattgc aagcaattaa ggaaatgcag aaagatcctg   2340
atgttaaagg aggagaaaca tctctaatta tccctagcct tgaaagacta gttaatgcta   2400
tagaatcaaa gaatgcagaa ggaatctttg atgcgagtct gcatttgaaa gcccaagttg   2460
atcagcttac cggaagaaat gaagaattaa gacaggagct cagggaatct cggaaagagg   2520
ctataaatta ttcacagcag ttggcaaaag ctaatttaaa gatagaccat cttgaaaaag   2580
aaactagtct tttacgacaa tcagaaggat cgaatgttgt ttttaaagga attgacttac   2640
ctgatgggat agcaccatct agtgccagta tcattaattc tcagaatgaa tatttaatac   2700
atttgttaca ggaactagaa aataaagaaa aaaagttaaa gaatttagaa gattctcttg   2760
aagattacaa cagaaaattt gctgtaattc gtcatcaaca aagtttgttg tataaagaat   2820
acctaagtga aaaggagacc tggaaaacag aatctaaaac aataaaagag gaaaagagaa   2880
aacttgagga tcaagtccaa caagatgcta taaaagtaaa agaatataat aatttgctca   2940
atgctcttca gatggattcg gatgaaatga aaaaaatact tgcagaaaat agtaggaaaa   3000
ttactgtttt gcaagtgaat gaaaaatcac ttataaggca atatacaacc ttagtagaat   3060
tggagcgaca acttagaaaa gaaaatgaga agcaaaagaa tgaattgttg tcaatggagg   3120
ctgaagtttg tgaaaaaatt gggtgtttgc aaagatttaa ggaaatggcc attttcaaga   3180
ttgcagctct ccaaaaagtt gtagataata gtgtttcttt gtctgaacta gaactggcta   3240
ataaacagta caatgaactg actgctaagt acagggacat cttgcaaaaa gataatatgc   3300
ttgttcaaag aacaagtaac ttggaacacc tggagtgtga aaacatctcc ttaaaagaac   3360
aagtggagtc tataaataaa gaactggaga ttaccaagga aaaacttcac actattgaac   3420
```

```
aagcctggga acaggaaact aaattaggta atgaatctag catggataag gcaaagaaat   3480
caataaccaa cagtgacatt gtttccattt caaaaaaaat aactatgctg gaaatgaagg   3540
aattaaatga aaggcagcgg gctgaacatt gtcaaaaaat gtatgaacac ttacggactt   3600
cgttaaagca aatggaggaa cgtaattttg aattggaaac caaatttgct gagcttacca   3660
aaatcaattt ggatgcacag aaggtggaac agatgttaag agatgaatta gctgatagtg   3720
tgagcaaggc agtaagtgat gctgataggc aacggattct agaattagag aagaatgaaa   3780
tggaactaaa agttgaagtg tcaaaactga gagagatttc tgatattgcc agaagacaag   3840
ttgaaatttt gaatgcacaa caacaatcta gggacaagga agtagagtcc ctcagaatgc   3900
aactgctaga ctatcaggca cagtctgatg aaaagtcgct cattgccaag ttgcaccaac   3960
ataatgtctc tcttcaactg agtgaggcta ctgctcttgg taagttggag tcaattacat   4020
ctaaactgca gaagatggag gcctacaact tgcgcttaga gcagaaactt gatgaaaaag   4080
aacaggctct ctattatgct cgtttggagg gaagaaacag agcaaaacat ctgcgccaaa   4140
caattcagtc tctacgacga cagtttagtg gagctttacc cttggcacaa caggaaaagt   4200
tctccaaaac aatgattcaa ctacaaaatg acaaacttaa gataatgcaa gaaatgaaaa   4260
attctcaaca agaacataga aatatggaga acaaaacatt ggagatggaa ttaaaattaa   4320
agggcctgga agagttaata agcactttaa aggataccaa aggagcccaa aaggtaatca   4380
actggcatat gaaaatagaa gaacttcgtc ttcaagaact taaactaaat cgggaattag   4440
tcaaggataa agaagaaata aaatatttga ataacataat ttctgaatat gaacgtacaa   4500
tcagcagtct tgaagaagaa attgtgcaac agaacaagtt tcatgaagaa agacaaatgg   4560
cctgggatca aagagaagtt gacctggaac gccaactaga catttttgac cgtcagcaaa   4620
atgaaatact aaatgcggca caaaagtttg aagaagctac aggatcaatc cctgacccta   4680
gtttgcccct tccaaatcaa cttgagatcg ctctaaggaa aattaaggag aacattcgaa   4740
taattctaga aacacgggca acttgcaaat cactagaaga gaaactaaaa gagaaagaat   4800
ctgctttaag gttagcagaa caaaatatac tgtcaagaga caaagtaatc aatgaactga   4860
ggcttcgatt gcctgccact gcagaaagag aaaagctcat agctgagcta ggcagaaaag   4920
agatggaacc aaaatctcac cacacattga aaattgctca tcaaaccatt gcaaacatgc   4980
aagcaaggtt aaatcaaaaa gaagaagtat taaagaagta tcaacgtctt ctagaaaaag   5040
ccagagagga gcaaagagaa attgtgaaga aacatgagga agaccttcat attcttcatc   5100
acagattaga actacaggct gatagttcac taaataaatt caaacaaacg gcttgggatt   5160
taatgaaaca gtctcccact ccagttccta ccaacaagca ttttattcgt ctggctgaga   5220
tggaacagac agtagcagaa caagatgact ctctttcctc actcttggtc aaactaaaga   5280
aagtatcaca agatttggag agacaaagag aaatcactga attaaaagta aaagaatttg   5340
aaaatatcaa attacagctt caagaaaacc atgaagatga agtgaaaaaa gtaaaagcgg   5400
aagtagagga tttaaagtat cttctggacc agtcacaaaa ggagtcacag tgtttaaaat   5460
ctgaacttca ggctcaaaaa gaagcaaatt caagagctcc aacaactaca atgagaaatc   5520
tagtagaacg gctaaagagc caattagcct tgaaggagaa acaacagaaa gcacttagtc   5580
gggcactttt agaactccgg gcagaaatga cagcagctgc tgaagaacgt attatttctg   5640
caacttctca aaaagaggcc catctcaatg ttcaacaaat cgttgatcga catactagag   5700
agctaaagac acaagttgaa gatttaaatg aaaatctttt aaaattgaaa gaagcactta   5760
aaacaagtaa aaacagagaa aactcactaa ctgataattt gaatgactta aataatgaac   5820
```

```
tgcaaaagaa acaaaaagcc tataataaaa tacttagaga gaaagaggaa attgatcaag   5880
agaatgatga actgaaaagg caaattaaaa gactaaccag tggattacag ggcaaacccc   5940
tgacagataa taaacaaagt ctaattgaag aactccaaag gaaagttaaa aaactagaga   6000
accaattaga gggaaaggtg gaggaagtag acctaaaacc tatgaaagaa aagaatgcta   6060
aagaagaatt aattaggtgg gaagaaggta aaaagtggca agccaaaata gaaggaattc   6120
gaaacaagtt aaaagagaaa gagggggaag tctttacttt aacaaagcag ttgaatactt   6180
tgaaggatct tttgccaaa gccgataaag agaaacttac tttgcagagg aaactaaaaa   6240
caactggcat gactgttgat caggttttgg gaatacgagc tttggagtca gaaaaagaat   6300
tggaagaatt aaaaaagaga aatcttgact tagaaaatga tatattgtat atgagggccc   6360
accaagctct tcctcgagat tctgttgtag aagatttaca tttacaaaat agatacctcc   6420
aagaaaaact tcatgcttta gaaaaacagt tttcaaagga tacatattct aagccttcaa   6480
tttcaggaat agagtcagat gatcattgtc agagagaaca ggagcttcag aaggaaaact   6540
tgaagttgtc atctgaaaat attgaactga aatttcagct tgaacaagca aataaagatt   6600
tgccaagatt aaagaatcaa gtcagagatt tgaaggaaat gtgtgaattt cttaagaaag   6660
aaaaagcaga agttcagcgg aaacttggcc atgttagagg gtctggtaga agtggaaaga   6720
caatcccaga actggaaaaa accattggtt taatgaaaaa agtagttgaa aaagtccaga   6780
gagaaaatga acagttgaaa aaagcatcag gaatattgac tagtgaaaaa atggctaata   6840
ttgagcagga aaatgaaaaa ttgaaggctg aattagaaaa acttaaagct catcttgggc   6900
atcagttgag catgcactat gaatccaaga ccaaaggcac agaaaaaatt attgctgaaa   6960
atgaaaggct tcgtaaagaa cttaaaaaag aaactgatgc tgcagagaaa ttacggatag   7020
caaagaataa tttagagata ttaaatgaga agatgacagt tcaactagaa gagactggta   7080
agagattgca gtttgcagaa agcagaggtc cacagcttga aggtgctgac agtaagagct   7140
ggaaatccat tgtggttaca agaatgtatg aaaccaagtt aaaagaattg gaaactgata   7200
ttgccaaaaa aaatcaaagc attactgacc ttaaacagct tgtaaaagaa gcaacagaga   7260
gagaacaaaa agttaacaaa tacaatgaag accttgaaca acagattaag attcttaaac   7320
atgttcctga aggtgctgag acagagcaag gccttaaacg ggagcttcaa gttcttagat   7380
tagctaatca tcagctggat aaagagaaag cagaattaat ccatcagata gaagctaaca   7440
aggaccaaag tggagctgaa agcaccatac ctgatgctga tcaactaaag gaaaaaataa   7500
aagatctaga gacacagctc aaaatgtcag atctagaaaa gcagcatttg aaggaggaaa   7560
taaagaagct gaaaaaagaa ctggaaaatt ttgatccttc attttttgaa gaaattgaag   7620
atcttaagta taattacaag gaagaagtga agaagaatat tctcttagaa gagaaggtaa   7680
aaaaactttc agaacaattg ggagttgaat taactagccc tgttgctgct tctgaagagt   7740
ttgaagatga agaagaaagt cctgttaatt tccccattta ctaaaggtca cctataaact   7800
ttgtttcatt taactattta ttaactttat aagttaaata tacttggaaa taagcagttc   7860
tccgaactgt agtatttcct tctcactacc ttgtaccttt atacttagat tggaattctt   7920
aataaataaa attatatgaa attttcaact tattaaaaaa aaaaaaaaaa aa           7972
```

<210> SEQ ID NO 41
<211> LENGTH: 2479
<212> TYPE: PRT
<213> ORGANISM: Homo sapiens

<400> SEQUENCE: 41

```
Met Pro Pro Asn Ile Asn Trp Lys Glu Ile Met Lys Val Asp Pro Asp
1               5                   10                  15

Asp Leu Pro Arg Gln Glu Glu Leu Ala Asp Asn Leu Leu Ile Ser Leu
            20                  25                  30

Ser Lys Val Glu Val Asn Glu Leu Lys Ser Glu Lys Gln Glu Asn Val
        35                  40                  45

Ile His Leu Phe Arg Ile Thr Gln Ser Leu Met Lys Met Lys Ala Gln
    50                  55                  60

Glu Val Glu Leu Ala Leu Glu Glu Val Glu Lys Ala Gly Glu Glu Gln
65                  70                  75                  80

Ala Lys Phe Glu Asn Gln Leu Lys Thr Lys Val Met Lys Leu Glu Asn
                85                  90                  95

Glu Leu Glu Met Ala Gln Gln Ser Ala Gly Gly Arg Asp Thr Arg Phe
            100                 105                 110

Leu Arg Asn Glu Ile Cys Gln Leu Glu Lys Gln Leu Glu Gln Lys Asp
        115                 120                 125

Arg Glu Leu Glu Asp Met Glu Lys Glu Leu Glu Lys Glu Lys Lys Val
    130                 135                 140

Asn Glu Gln Leu Ala Leu Arg Asn Glu Glu Ala Glu Asn Glu Asn Ser
145                 150                 155                 160

Lys Leu Arg Arg Glu Asn Lys Arg Leu Lys Lys Lys Asn Glu Gln Leu
                165                 170                 175

Cys Gln Asp Ile Ile Asp Tyr Gln Lys Gln Ile Asp Ser Gln Lys Glu
            180                 185                 190

Thr Leu Leu Ser Arg Arg Gly Glu Asp Ser Asp Tyr Arg Ser Gln Leu
        195                 200                 205

Ser Lys Lys Asn Tyr Glu Leu Ile Gln Tyr Leu Asp Glu Ile Gln Thr
    210                 215                 220

Leu Thr Glu Ala Asn Glu Lys Ile Glu Val Gln Asn Gln Glu Met Arg
225                 230                 235                 240

Lys Asn Leu Glu Glu Ser Val Gln Glu Met Glu Lys Met Thr Asp Glu
                245                 250                 255

Tyr Asn Arg Met Lys Ala Ile Val His Gln Thr Asp Asn Val Ile Asp
            260                 265                 270

Gln Leu Lys Lys Glu Asn Asp His Tyr Gln Leu Gln Val Gln Glu Leu
        275                 280                 285

Thr Asp Leu Leu Lys Ser Lys Asn Glu Glu Asp Asp Pro Ile Met Val
    290                 295                 300

Ala Val Asn Ala Lys Val Glu Glu Trp Lys Leu Ile Leu Ser Ser Lys
305                 310                 315                 320

Asp Asp Glu Ile Ile Glu Tyr Gln Gln Met Leu His Asn Leu Arg Glu
                325                 330                 335

Lys Leu Lys Asn Ala Gln Leu Asp Ala Asp Lys Ser Asn Val Met Ala
            340                 345                 350

Leu Gln Gln Gly Ile Gln Glu Arg Asp Ser Gln Ile Lys Met Leu Thr
        355                 360                 365

Glu Gln Val Glu Gln Tyr Thr Lys Glu Met Glu Lys Asn Thr Cys Ile
    370                 375                 380

Ile Glu Asp Leu Lys Asn Glu Leu Gln Arg Asn Lys Gly Ala Ser Thr
385                 390                 395                 400

Leu Ser Gln Gln Thr His Met Lys Ile Gln Ser Thr Leu Asp Ile Leu
                405                 410                 415
```

```
Lys Glu Lys Thr Lys Glu Ala Glu Arg Thr Ala Glu Leu Ala Glu Ala
            420                 425                 430

Asp Ala Arg Glu Lys Asp Lys Glu Leu Val Glu Ala Leu Lys Arg Leu
        435                 440                 445

Lys Asp Tyr Glu Ser Gly Val Tyr Gly Leu Glu Asp Ala Val Val Glu
    450                 455                 460

Ile Lys Asn Cys Lys Asn Gln Ile Lys Ile Arg Asp Arg Glu Ile Glu
465                 470                 475                 480

Ile Leu Thr Lys Glu Ile Asn Lys Leu Glu Leu Lys Ile Ser Asp Phe
                485                 490                 495

Leu Asp Glu Asn Glu Ala Leu Arg Glu Arg Val Gly Leu Glu Pro Lys
            500                 505                 510

Thr Met Ile Asp Leu Thr Glu Phe Arg Asn Ser Lys His Leu Lys Gln
        515                 520                 525

Gln Gln Tyr Arg Ala Glu Asn Gln Ile Leu Leu Lys Glu Ile Glu Ser
    530                 535                 540

Leu Glu Glu Glu Arg Leu Asp Leu Lys Lys Lys Ile Arg Gln Met Ala
545                 550                 555                 560

Gln Glu Arg Gly Lys Arg Ser Ala Thr Ser Gly Leu Thr Thr Glu Asp
                565                 570                 575

Leu Asn Leu Thr Glu Asn Ile Ser Gln Gly Asp Arg Ile Ser Glu Arg
            580                 585                 590

Lys Leu Asp Leu Leu Ser Leu Lys Asn Met Ser Glu Ala Gln Ser Lys
        595                 600                 605

Asn Glu Phe Leu Ser Arg Glu Leu Ile Glu Lys Glu Arg Asp Leu Glu
    610                 615                 620

Arg Ser Arg Thr Val Ile Ala Lys Phe Gln Asn Lys Leu Lys Glu Leu
625                 630                 635                 640

Val Glu Glu Asn Lys Gln Leu Glu Glu Gly Met Lys Glu Ile Leu Gln
                645                 650                 655

Ala Ile Lys Glu Met Gln Lys Asp Pro Asp Val Lys Gly Gly Glu Thr
            660                 665                 670

Ser Leu Ile Ile Pro Ser Leu Glu Arg Leu Val Asn Ala Ile Glu Ser
        675                 680                 685

Lys Asn Ala Glu Gly Ile Phe Asp Ala Ser Leu His Leu Lys Ala Gln
    690                 695                 700

Val Asp Gln Leu Thr Gly Arg Asn Glu Glu Leu Arg Gln Glu Leu Arg
705                 710                 715                 720

Glu Ser Arg Lys Glu Ala Ile Asn Tyr Ser Gln Gln Leu Ala Lys Ala
                725                 730                 735

Asn Leu Lys Ile Asp His Leu Glu Lys Glu Thr Ser Leu Leu Arg Gln
            740                 745                 750

Ser Glu Gly Ser Asn Val Val Phe Lys Gly Ile Asp Leu Pro Asp Gly
        755                 760                 765

Ile Ala Pro Ser Ser Ala Ser Ile Ile Asn Ser Gln Asn Glu Tyr Leu
    770                 775                 780

Ile His Leu Leu Gln Glu Leu Glu Asn Lys Glu Lys Lys Leu Lys Asn
785                 790                 795                 800

Leu Glu Asp Ser Leu Glu Asp Tyr Asn Arg Lys Phe Ala Val Ile Arg
                805                 810                 815

His Gln Gln Ser Leu Leu Tyr Lys Glu Tyr Leu Ser Glu Lys Glu Thr
            820                 825                 830
```

```
Trp Lys Thr Glu Ser Lys Thr Ile Lys Glu Glu Lys Arg Lys Leu Glu
        835                 840                 845

Asp Gln Val Gln Gln Asp Ala Ile Lys Val Lys Glu Tyr Asn Asn Leu
    850                 855                 860

Leu Asn Ala Leu Gln Met Asp Ser Asp Glu Met Lys Lys Ile Leu Ala
865                 870                 875                 880

Glu Asn Ser Arg Lys Ile Thr Val Leu Gln Val Asn Glu Lys Ser Leu
                885                 890                 895

Ile Arg Gln Tyr Thr Thr Leu Val Glu Leu Glu Arg Gln Leu Arg Lys
            900                 905                 910

Glu Asn Glu Lys Gln Lys Asn Glu Leu Leu Ser Met Glu Ala Glu Val
        915                 920                 925

Cys Glu Lys Ile Gly Cys Leu Gln Arg Phe Lys Glu Met Ala Ile Phe
    930                 935                 940

Lys Ile Ala Ala Leu Gln Lys Val Val Asp Asn Ser Val Ser Leu Ser
945                 950                 955                 960

Glu Leu Glu Leu Ala Asn Lys Gln Tyr Asn Glu Leu Thr Ala Lys Tyr
                965                 970                 975

Arg Asp Ile Leu Gln Lys Asp Asn Met Leu Val Gln Arg Thr Ser Asn
            980                 985                 990

Leu Glu His Leu Glu Cys Glu Asn  Ile Ser Leu Lys Glu  Gln Val Glu
        995                 1000                 1005

Ser Ile  Asn Lys Glu Leu Glu  Ile Thr Lys Glu Lys  Leu His Thr
    1010                 1015                 1020

Ile Glu  Gln Ala Trp Glu Gln  Glu Thr Lys Leu Gly  Asn Glu Ser
    1025                 1030                 1035

Ser Met  Asp Lys Ala Lys Lys  Ser Ile Thr Asn Ser  Asp Ile Val
    1040                 1045                 1050

Ser Ile  Ser Lys Lys Ile Thr  Met Leu Glu Met Lys  Glu Leu Asn
    1055                 1060                 1065

Glu Arg  Gln Arg Ala Glu His  Cys Gln Lys Met Tyr  Glu His Leu
    1070                 1075                 1080

Arg Thr  Ser Leu Lys Gln Met  Glu Glu Arg Asn Phe  Glu Leu Glu
    1085                 1090                 1095

Thr Lys  Phe Ala Glu Leu Thr  Lys Ile Asn Leu Asp  Ala Gln Lys
    1100                 1105                 1110

Val Glu  Gln Met Leu Arg Asp  Glu Leu Ala Asp Ser  Val Ser Lys
    1115                 1120                 1125

Ala Val  Ser Asp Ala Asp Arg  Gln Arg Ile Leu Glu  Leu Glu Lys
    1130                 1135                 1140

Asn Glu  Met Glu Leu Lys Val  Glu Val Ser Lys Leu  Arg Glu Ile
    1145                 1150                 1155

Ser Asp  Ile Ala Arg Arg Gln  Val Glu Ile Leu Asn  Ala Gln Gln
    1160                 1165                 1170

Gln Ser  Arg Asp Lys Glu Val  Glu Ser Leu Arg Met  Gln Leu Leu
    1175                 1180                 1185

Asp Tyr  Gln Ala Gln Ser Asp  Glu Lys Ser Leu Ile  Ala Lys Leu
    1190                 1195                 1200

His Gln  His Asn Val Ser Leu  Gln Leu Ser Glu Ala  Thr Ala Leu
    1205                 1210                 1215

Gly Lys  Leu Glu Ser Ile Thr  Ser Lys Leu Gln Lys  Met Glu Ala
    1220                 1225                 1230

Tyr Asn  Leu Arg Leu Glu Gln  Lys Leu Asp Glu Lys  Glu Gln Ala
```

```
    1235                1240                1245

Leu Tyr  Tyr Ala Arg Leu Glu  Gly Arg Asn Arg Ala  Lys His Leu
    1250                1255                1260

Arg Gln  Thr Ile Gln Ser Leu  Arg Arg Gln Phe Ser  Gly Ala Leu
    1265                1270                1275

Pro Leu  Ala Gln Gln Glu Lys  Phe Ser Lys Thr Met  Ile Gln Leu
    1280                1285                1290

Gln Asn  Asp Lys Leu Lys Ile  Met Gln Glu Met Lys  Asn Ser Gln
    1295                1300                1305

Gln Glu  His Arg Asn Met Glu  Asn Lys Thr Leu Glu  Met Glu Leu
    1310                1315                1320

Lys Leu  Lys Gly Leu Glu Glu  Leu Ile Ser Thr Leu  Lys Asp Thr
    1325                1330                1335

Lys Gly  Ala Gln Lys Val Ile  Asn Trp His Met Lys  Ile Glu Glu
    1340                1345                1350

Leu Arg  Leu Gln Glu Leu Lys  Leu Asn Arg Glu Leu  Val Lys Asp
    1355                1360                1365

Lys Glu  Glu Ile Lys Tyr Leu  Asn Asn Ile Ile Ser  Glu Tyr Glu
    1370                1375                1380

Arg Thr  Ile Ser Ser Leu Glu  Glu Glu Ile Val Gln  Gln Asn Lys
    1385                1390                1395

Phe His  Glu Glu Arg Gln Met  Ala Trp Asp Gln Arg  Glu Val Asp
    1400                1405                1410

Leu Glu  Arg Gln Leu Asp Ile  Phe Asp Arg Gln Gln  Asn Glu Ile
    1415                1420                1425

Leu Asn  Ala Ala Gln Lys Phe  Glu Glu Ala Thr Gly  Ser Ile Pro
    1430                1435                1440

Asp Pro  Ser Leu Pro Leu Pro  Asn Gln Leu Glu Ile  Ala Leu Arg
    1445                1450                1455

Lys Ile  Lys Glu Asn Ile Arg  Ile Ile Leu Glu Thr  Arg Ala Thr
    1460                1465                1470

Cys Lys  Ser Leu Glu Glu Lys  Leu Lys Glu Lys Glu  Ser Ala Leu
    1475                1480                1485

Arg Leu  Ala Glu Gln Asn Ile  Leu Ser Arg Asp Lys  Val Ile Asn
    1490                1495                1500

Glu Leu  Arg Leu Arg Leu Pro  Ala Thr Ala Glu Arg  Glu Lys Leu
    1505                1510                1515

Ile Ala  Glu Leu Gly Arg Lys  Glu Met Glu Pro Lys  Ser His His
    1520                1525                1530

Thr Leu  Lys Ile Ala His Gln  Thr Ile Ala Asn Met  Gln Ala Arg
    1535                1540                1545

Leu Asn  Gln Lys Glu Glu Val  Leu Lys Lys Tyr Gln  Arg Leu Leu
    1550                1555                1560

Glu Lys  Ala Arg Glu Glu Gln  Arg Glu Ile Val Lys  Lys His Glu
    1565                1570                1575

Glu Asp  Leu His Ile Leu His  His Arg Leu Glu Leu  Gln Ala Asp
    1580                1585                1590

Ser Ser  Leu Asn Lys Phe Lys  Gln Thr Ala Trp Asp  Leu Met Lys
    1595                1600                1605

Gln Ser  Pro Thr Pro Val Pro  Thr Asn Lys His Phe  Ile Arg Leu
    1610                1615                1620

Ala Glu  Met Glu Gln Thr Val  Ala Glu Gln Asp Asp  Ser Leu Ser
    1625                1630                1635
```

```
Ser Leu  Leu Val Lys Leu Lys  Lys Val Ser Gln Asp  Leu Glu Arg
    1640                 1645                 1650

Gln Arg  Glu Ile Thr Glu Leu  Lys Val Lys Glu Phe  Glu Asn Ile
    1655                 1660                 1665

Lys Leu  Gln Leu Gln Glu Asn  His Glu Asp Glu Val  Lys Lys Val
    1670                 1675                 1680

Lys Ala  Glu Val Glu Asp Leu  Lys Tyr Leu Leu Asp  Gln Ser Gln
    1685                 1690                 1695

Lys Glu  Ser Gln Cys Leu Lys  Ser Glu Leu Gln Ala  Gln Lys Glu
    1700                 1705                 1710

Ala Asn  Ser Arg Ala Pro Thr  Thr Thr Met Arg Asn  Leu Val Glu
    1715                 1720                 1725

Arg Leu  Lys Ser Gln Leu Ala  Leu Lys Glu Lys Gln  Gln Lys Ala
    1730                 1735                 1740

Leu Ser  Arg Ala Leu Leu Glu  Leu Arg Ala Glu Met  Thr Ala Ala
    1745                 1750                 1755

Ala Glu  Glu Arg Ile Ile Ser  Ala Thr Ser Gln Lys  Glu Ala His
    1760                 1765                 1770

Leu Asn  Val Gln Gln Ile Val  Asp Arg His Thr Arg  Glu Leu Lys
    1775                 1780                 1785

Thr Gln  Val Glu Asp Leu Asn  Glu Asn Leu Leu Lys  Leu Lys Glu
    1790                 1795                 1800

Ala Leu  Lys Thr Ser Lys Asn  Arg Glu Asn Ser Leu  Thr Asp Asn
    1805                 1810                 1815

Leu Asn  Asp Leu Asn Asn Glu  Leu Gln Lys Lys Gln  Lys Ala Tyr
    1820                 1825                 1830

Asn Lys  Ile Leu Arg Glu Lys  Glu Glu Ile Asp Gln  Glu Asn Asp
    1835                 1840                 1845

Glu Leu  Lys Arg Gln Ile Lys  Arg Leu Thr Ser Gly  Leu Gln Gly
    1850                 1855                 1860

Lys Pro  Leu Thr Asp Asn Lys  Gln Ser Leu Ile Glu  Glu Leu Gln
    1865                 1870                 1875

Arg Lys  Val Lys Lys Leu Glu  Asn Gln Leu Glu Gly  Lys Val Glu
    1880                 1885                 1890

Glu Val  Asp Leu Lys Pro Met  Lys Glu Lys Asn Ala  Lys Glu Glu
    1895                 1900                 1905

Leu Ile  Arg Trp Glu Glu Gly  Lys Lys Trp Gln Ala  Lys Ile Glu
    1910                 1915                 1920

Gly Ile  Arg Asn Lys Leu Lys  Glu Lys Glu Gly Glu  Val Phe Thr
    1925                 1930                 1935

Leu Thr  Lys Gln Leu Asn Thr  Leu Lys Asp Leu Phe  Ala Lys Ala
    1940                 1945                 1950

Asp Lys  Glu Lys Leu Thr Leu  Gln Arg Lys Leu Lys  Thr Thr Gly
    1955                 1960                 1965

Met Thr  Val Asp Gln Val Leu  Gly Ile Arg Ala Leu  Glu Ser Glu
    1970                 1975                 1980

Lys Glu  Leu Glu Glu Leu Lys  Lys Arg Asn Leu Asp  Leu Glu Asn
    1985                 1990                 1995

Asp Ile  Leu Tyr Met Arg Ala  His Gln Ala Leu Pro  Arg Asp Ser
    2000                 2005                 2010

Val Val  Glu Asp Leu His Leu  Gln Asn Arg Tyr Leu  Gln Glu Lys
    2015                 2020                 2025
```

```
Leu His  Ala Leu Glu Lys Gln  Phe Ser Lys Asp Thr  Tyr Ser Lys
    2030                 2035                 2040

Pro Ser  Ile Ser Gly Ile Glu  Ser Asp Asp His Cys  Gln Arg Glu
    2045                 2050                 2055

Gln Glu  Leu Gln Lys Glu Asn  Leu Lys Leu Ser Ser  Glu Asn Ile
    2060                 2065                 2070

Glu Leu  Lys Phe Gln Leu Glu  Gln Ala Asn Lys Asp  Leu Pro Arg
    2075                 2080                 2085

Leu Lys  Asn Gln Val Arg Asp  Leu Lys Glu Met Cys  Glu Phe Leu
    2090                 2095                 2100

Lys Lys  Glu Lys Ala Glu Val  Gln Arg Lys Leu Gly  His Val Arg
    2105                 2110                 2115

Gly Ser  Gly Arg Ser Gly Lys  Thr Ile Pro Glu Leu  Glu Lys Thr
    2120                 2125                 2130

Ile Gly  Leu Met Lys Lys Val  Val Glu Lys Val Gln  Arg Glu Asn
    2135                 2140                 2145

Glu Gln  Leu Lys Lys Ala Ser  Gly Ile Leu Thr Ser  Glu Lys Met
    2150                 2155                 2160

Ala Asn  Ile Glu Gln Glu Asn  Glu Lys Leu Lys Ala  Glu Leu Glu
    2165                 2170                 2175

Lys Leu  Lys Ala His Leu Gly  His Gln Leu Ser Met  His Tyr Glu
    2180                 2185                 2190

Ser Lys  Thr Lys Gly Thr Glu  Lys Ile Ile Ala Glu  Asn Glu Arg
    2195                 2200                 2205

Leu Arg  Lys Glu Leu Lys Lys  Glu Thr Asp Ala Ala  Glu Lys Leu
    2210                 2215                 2220

Arg Ile  Ala Lys Asn Asn Leu  Glu Ile Leu Asn Glu  Lys Met Thr
    2225                 2230                 2235

Val Gln  Leu Glu Glu Thr Gly  Lys Arg Leu Gln Phe  Ala Glu Ser
    2240                 2245                 2250

Arg Gly  Pro Gln Leu Glu Gly  Ala Asp Ser Lys Ser  Trp Lys Ser
    2255                 2260                 2265

Ile Val  Val Thr Arg Met Tyr  Glu Thr Lys Leu Lys  Glu Leu Glu
    2270                 2275                 2280

Thr Asp  Ile Ala Lys Lys Asn  Gln Ser Ile Thr Asp  Leu Lys Gln
    2285                 2290                 2295

Leu Val  Lys Glu Ala Thr Glu  Arg Glu Gln Lys Val  Asn Lys Tyr
    2300                 2305                 2310

Asn Glu  Asp Leu Glu Gln Gln  Ile Lys Ile Leu Lys  His Val Pro
    2315                 2320                 2325

Glu Gly  Ala Glu Thr Glu Gln  Gly Leu Lys Arg Glu  Leu Gln Val
    2330                 2335                 2340

Leu Arg  Leu Ala Asn His Gln  Leu Asp Lys Glu Lys  Ala Glu Leu
    2345                 2350                 2355

Ile His  Gln Ile Glu Ala Asn  Lys Asp Gln Ser Gly  Ala Glu Ser
    2360                 2365                 2370

Thr Ile  Pro Asp Ala Asp Gln  Leu Lys Glu Lys Ile  Lys Asp Leu
    2375                 2380                 2385

Glu Thr  Gln Leu Lys Met Ser  Asp Leu Glu Lys Gln  His Leu Lys
    2390                 2395                 2400

Glu Glu  Ile Lys Lys Leu Lys  Lys Glu Leu Glu Asn  Phe Asp Pro
    2405                 2410                 2415

Ser Phe  Phe Glu Glu Ile Glu  Asp Leu Lys Tyr Asn  Tyr Lys Glu
```

```
    2420                2425                2430

Glu Val  Lys Lys Asn Ile Leu  Leu Glu Glu Lys Val  Lys Lys Leu
    2435                2440                2445

Ser Glu  Gln Leu Gly Val Glu  Leu Thr Ser Pro Val  Ala Ala Ser
    2450                2455                2460

Glu Glu  Phe Glu Asp Glu Glu  Glu Ser Pro Val Asn  Phe Pro Ile
    2465                2470                2475

Tyr


<210> SEQ ID NO 42
<211> LENGTH: 2625
<212> TYPE: DNA
<213> ORGANISM: Homo sapiens

<400> SEQUENCE: 42

actcgaccgg gctgcgctca ctgcccagcc ggggccccgg gagcctccag gctcccgccc     60

gccctgagct gcggcctccg catggagggg ccactcactc caccaccgct gcagggaggc    120

ggagccgccg ctgttccgga gcccggagcc cggcaacacc cgggacacga gacggcggcg    180

cagcggtaca gcgcccgact gctgcaggcc ggctacgagc ccgagagccc tagattggac    240

ctcgctacac acccgacgac accccgttca gaactatctt cagtggtctt actggcaggt    300

gttggtgtcc agatggatcg ccttcgcagg gctagcatgg cggactacct gatcagcggc    360

ggcaccggct acgtgcccga ggatgggctc accgcgcagc agctcttcgc cagcgccgac    420

ggcctcacct acaacgactt cctgattctc ccaggattca tagacttcat agctgatgag    480

gtggacctga cctcagccct gacccggaag atcacgctga agacgccact gatctcctcc    540

cccatggaca ctgtgacaga ggctgacatg gccattgcca tggctctgat gggaggtatt    600

ggtttcattc accacaactg caccccagag ttccaggcca acgaggtgcg gaaggtcaag    660

aagtttgaac agggcttcat cacggaccct gtggtgctga gcccctcgca cactgtgggc    720

gatgtgctgg aggccaagat gcggcatggc ttctctggca tccccatcac tgagacgggc    780

accatgggca gcaagctggt gggcatcgtc acctcccgag acatcgactt tcttgctgag    840

aaggaccaca ccaccctcct cagtgaggtg atgacgccaa ggattgaact ggtggtggct    900

ccagcaggtg tgacgttgaa agaggcaaat gagatcctgc agcgtagcaa gaaagggaag    960

ctgcctatcg tcaatgattg cgatgagctg gtggccatca tcgcccgcac cgacctgaag   1020

aagaaccgag actaccctct ggcctccaag gattcccaga agcagctgct ctgtggggca   1080

gctgtgggca cccgtgagga tgacaaatac cgtctggacc tgctcaccca ggcgggcgtc   1140

gacgtcatag tcttggactc gtcccaaggg aattcggtgt atcagatcgc catggtgcat   1200

tacatcaaac agaagtaccc ccacctccag gtgattgggg ggaacgtggt gacagcagcc   1260

caggccaaga acctgattga tgctggtgtg gacgggctgc gcgtgggcat gggctgcggc   1320

tccatctgca tcacccagga agtgatggcc tgtggtcggc cccagggcac tgctgtgtac   1380

aaggtggctg agtatgcccg gcgctttggt gtgcccatca tagccgatgg cggcatccag   1440

accgtgggac acgtggtcaa ggccctggcc cttggagcct ccacagtgat gatgggctcc   1500

ctgctggccg ccactacgga ggcccctggc gagtacttct tctcagacgg ggtgcggctc   1560

aagaagtacc ggggcatggg ctcactggat gccatggaga agagcagcag cagccagaaa   1620

cgatacttca gcgaggggga taaagtgaag atcgcgcagg gtgtctcggg ctccatccag   1680

gacaaaggat ccattcagaa gttcgtgccc tacctcatag caggcatcca acacggctgc   1740
```

```
caggatatcg gggcccgcag cctgtctgtc cttcggtcca tgatgtactc aggagagctc   1800

aagtttgaga agcggaccat gtcggcccag attgagggtg gtgtccatgg cctgcactct   1860

tacgaaaagc ggctgtactg aggacagcgg tggaggccga ggtggtggag gggatgcacc   1920

ccagtgtcca cttttgggca cagcctccct ccataactga gtggtccaca gatttgcact   1980

acgggttctc cagctccttt ccaggcagag aggaggggag gtcctgaggg gactgctgcc   2040

cctcactcgg catcccctgc agagtcagga ctgctcccgg ggccaggctg ccctgggagc   2100

cccctccga gcccagccag ccaggctctc aggccctgcg cctgcctcag gtctttcttg   2160

ctgcagcctg ctccagcctg gcccccaccc caggggcagg cggcccctcc tggcttctcc   2220

tgtagggcac ctccctgccc ctagcctccc aggaaatggt gctctcctgg ccctgcctct   2280

ggcccttccc gggccgctgc ccctcagcca tgtggcactt ctgagctcct gacctaggcc   2340

aaggggaggt ctctgccccc ttccccggcc ctgggctacc cttgggtcct gctcctcagg   2400

ccgctcccct gtccctggcc atgggtagga gactgccctg gtcatggccg cctgcctgtc   2460

attcctgact caccaccgtc cccaggtgaa ccattcctcc cttctcctca gctgcagtcg   2520

aaggctttaa ctttgcacac ttgggatcac agttgcgtca ttgtgtatta aatacttgga   2580

ataaatcaag caggtctcaa cgcctccact aaaaaaaaaa aaaaa                   2625


<210> SEQ ID NO 43
<211> LENGTH: 599
<212> TYPE: PRT
<213> ORGANISM: Homo sapiens

<400> SEQUENCE: 43

Met Glu Gly Pro Leu Thr Pro Pro Pro Leu Gln Gly Gly Gly Ala Ala
1               5                   10                  15

Ala Val Pro Glu Pro Gly Ala Arg Gln His Pro Gly His Glu Thr Ala
            20                  25                  30

Ala Gln Arg Tyr Ser Ala Arg Leu Leu Gln Ala Gly Tyr Glu Pro Glu
        35                  40                  45

Ser Pro Arg Leu Asp Leu Ala Thr His Pro Thr Thr Pro Arg Ser Glu
    50                  55                  60

Leu Ser Ser Val Val Leu Leu Ala Gly Val Gly Val Gln Met Asp Arg
65                  70                  75                  80

Leu Arg Arg Ala Ser Met Ala Asp Tyr Leu Ile Ser Gly Gly Thr Gly
                85                  90                  95

Tyr Val Pro Glu Asp Gly Leu Thr Ala Gln Gln Leu Phe Ala Ser Ala
            100                 105                 110

Asp Gly Leu Thr Tyr Asn Asp Phe Leu Ile Leu Pro Gly Phe Ile Asp
        115                 120                 125

Phe Ile Ala Asp Glu Val Asp Leu Thr Ser Ala Leu Thr Arg Lys Ile
    130                 135                 140

Thr Leu Lys Thr Pro Leu Ile Ser Ser Pro Met Asp Thr Val Thr Glu
145                 150                 155                 160

Ala Asp Met Ala Ile Ala Met Ala Leu Met Gly Gly Ile Gly Phe Ile
                165                 170                 175

His His Asn Cys Thr Pro Glu Phe Gln Ala Asn Glu Val Arg Lys Val
            180                 185                 190

Lys Lys Phe Glu Gln Gly Phe Ile Thr Asp Pro Val Val Leu Ser Pro
        195                 200                 205

Ser His Thr Val Gly Asp Val Leu Glu Ala Lys Met Arg His Gly Phe
    210                 215                 220
```

```
Ser Gly Ile Pro Ile Thr Glu Thr Gly Thr Met Gly Ser Lys Leu Val
225                 230                 235                 240

Gly Ile Val Thr Ser Arg Asp Ile Asp Phe Leu Ala Glu Lys Asp His
                245                 250                 255

Thr Thr Leu Leu Ser Glu Val Met Thr Pro Arg Ile Glu Leu Val Val
            260                 265                 270

Ala Pro Ala Gly Val Thr Leu Lys Glu Ala Asn Glu Ile Leu Gln Arg
        275                 280                 285

Ser Lys Lys Gly Lys Leu Pro Ile Val Asn Asp Cys Asp Glu Leu Val
    290                 295                 300

Ala Ile Ile Ala Arg Thr Asp Leu Lys Lys Asn Arg Asp Tyr Pro Leu
305                 310                 315                 320

Ala Ser Lys Asp Ser Gln Lys Gln Leu Leu Cys Gly Ala Ala Val Gly
                325                 330                 335

Thr Arg Glu Asp Asp Lys Tyr Arg Leu Asp Leu Leu Thr Gln Ala Gly
            340                 345                 350

Val Asp Val Ile Val Leu Asp Ser Ser Gln Gly Asn Ser Val Tyr Gln
        355                 360                 365

Ile Ala Met Val His Tyr Ile Lys Gln Lys Tyr Pro His Leu Gln Val
    370                 375                 380

Ile Gly Gly Asn Val Val Thr Ala Ala Gln Ala Lys Asn Leu Ile Asp
385                 390                 395                 400

Ala Gly Val Asp Gly Leu Arg Val Gly Met Gly Cys Gly Ser Ile Cys
                405                 410                 415

Ile Thr Gln Glu Val Met Ala Cys Gly Arg Pro Gln Gly Thr Ala Val
            420                 425                 430

Tyr Lys Val Ala Glu Tyr Ala Arg Arg Phe Gly Val Pro Ile Ile Ala
        435                 440                 445

Asp Gly Gly Ile Gln Thr Val Gly His Val Val Lys Ala Leu Ala Leu
    450                 455                 460

Gly Ala Ser Thr Val Met Met Gly Ser Leu Leu Ala Ala Thr Thr Glu
465                 470                 475                 480

Ala Pro Gly Glu Tyr Phe Phe Ser Asp Gly Val Arg Leu Lys Lys Tyr
                485                 490                 495

Arg Gly Met Gly Ser Leu Asp Ala Met Glu Lys Ser Ser Ser Ser Gln
            500                 505                 510

Lys Arg Tyr Phe Ser Glu Gly Asp Lys Val Lys Ile Ala Gln Gly Val
        515                 520                 525

Ser Gly Ser Ile Gln Asp Lys Gly Ser Ile Gln Lys Phe Val Pro Tyr
    530                 535                 540

Leu Ile Ala Gly Ile Gln His Gly Cys Gln Asp Ile Gly Ala Arg Ser
545                 550                 555                 560

Leu Ser Val Leu Arg Ser Met Met Tyr Ser Gly Glu Leu Lys Phe Glu
                565                 570                 575

Lys Arg Thr Met Ser Ala Gln Ile Glu Gly Gly Val His Gly Leu His
            580                 585                 590

Ser Tyr Glu Lys Arg Leu Tyr
        595
```

<210> SEQ ID NO 44
<211> LENGTH: 2981
<212> TYPE: DNA
<213> ORGANISM: Homo sapiens

<400> SEQUENCE: 44

```
gctgggtaaa tcccagagtc tcagccgcct aagtgtcttc cccggaggtg agattatctc     60
cgcctgtgct ggacacctcc ctttctcctg cagccatgga tgccgctctg ctcctgaacg    120
tggaaggggt caagaaaacc attctgcacg ggggcacggg cgagctccca aacttcatca    180
ccggatcccg agtgatcttt catttccgca ccatgaaatg tgatgaggag cggacagtca    240
ttgacgacag tcggcaggtg ggccagccca tgcacatcat catcggaaac atgttcaagc    300
tcgaggtctg ggagatcctg cttacctcca tgcgggtgca cgaggtggcc gagttctggt    360
gcgacaccat ccacacgggg gtctacccca tcctatcccg gagcctgagg cagatggccc    420
agggcaagga ccccacagag tggcacgtgc acacgtgcgg gctggccaac atgttcgcct    480
accacacgct gggctacgag gacctggacg agctgcagaa ggagcctcag cctctggtct    540
ttgtgatcga gctgctgcag gttgatgccc cgagtgatta ccagagggag acctggaacc    600
tgagcaatca tgagaagatg aaggcggtgc ccgtcctcca cggagaggga aatcggctct    660
tcaagctggg ccgctacgag gaggcctctt ccaagtacca ggaggccatc atctgcctaa    720
ggaacctgca gaccaaggag aagccatggg aggtgcagtg gctgaagctg gagaagatga    780
tcaatactct gatcctcaac tactgccagt gcctgctgaa gaaggaggag tactatgagg    840
tgctggagca caccagtgat attctccggc accacccagg catcgtgaag gcctactacg    900
tgcgtgcccg ggctcacgca gaggtgtgga atgaggccga ggccaaggcg gacctccaga    960
aagtgctgga gctggagccg tccatgcaga aggcggtgcg cagggagctg aggctgctgg   1020
agaaccgcat ggcggagaag caggaggagg agcggctgcg ctgccggaac atgctgagcc   1080
agggtgccac gcagcctccc gcagagccac ccacagagcc acccgcacag tcatccacag   1140
agccacctgc agagccaccc acagcaccat ctgcagagct gtccgcaggg ccccctgcag   1200
agccagccac agagccaccc ccgtccccag ggcactcgct gcagcactga gccccctgag   1260
gcccacagcc acccaggcag ggagcaagtg gcctggtcac ttctggttcg attgaccagg   1320
atcgtggtgt cactttttaa aatttaaaat taatttttga aatcaaagtc agacacaccc   1380
atggtaaaaa aaaaaaaaaa aacaatccca agggtacaga agagcttatg aataaaagta   1440
gttttctcct ctacccctct cattccttcc gtgccatggt tttaattgac cctgttttta   1500
attcttctgg tagttttctc tatttccaag taatctgttt aaatcagttt ctagatttta   1560
ccccatgtca atgacaaatg aggatttgat gctctgatcc tttctcatgc ctgatacccc   1620
tccctgtctc cccattttgg atagttacat ttgggggtca tctcggtgat ttttgtaact   1680
ttacgcagga cacttagagc tctctagaat cccactgact ttagtgggtc ttgatgtagg   1740
gtgggcaagc cccgacactg gagcttagcc tgagagggtt cttggcctcc cccaggaaag   1800
atttcaaagg caagcgccag tggtagggta gaagaaaaca gctgtggtcg ggcacggtgg   1860
ctcacgccta taatcccagc actttgggag gccgaggcgg gtggatcacc tgaggtcagg   1920
agttccagac cagcctggcc aacatggtga aacctcatct ctactaaaaa tacaaaaaaa   1980
ctagctgggc gtggtggcgg gcgcctataa tcccagctac ttgggaggct gaggcaggag   2040
aattgattga acctgggagg cggaggttgc agtgagccaa gatcacgtca ttgcactcca   2100
gcctggtcaa caagagtaaa acttcatctc aaaaaacaaa acaaaacaaa aacaacaaca   2160
aaaaacaaaa gaaaaacaaa caaaaccaaa accaaaacag ctgtattgaa gctgcagtgt   2220
tgcagctctg tgactgccct gcagagcagg gctaccccat aggcagcgag cagcagctca   2280
gggcagttct gcagtcagat ttatacccac ttttaattac atgtagatta aggagctgca   2340
```

```
tatacaaaga tttctaggga aggagtagta acttctgggt cctggggtct ttgccacgga   2400

acagggcagt atgccagggt gttgccacgg caatggtaaa ctgacatggc accctggggg   2460

tcatgcctta gggaaagccg cttccactcg cccctgtttt agctcatctt caagttagtc   2520

tggtgtccaa gctccaccgc ctgcctcagt ctggtgacct ccttctgtgt ctgatgagca   2580

tggcagcgtt gggaccttcc ccttccaact ctctccctcc tcttcgtcct ccctaaagga   2640

cgggtacgag gaggggctat cacgccagcg acatcctcta gcaccaccca ggtgtgtggg   2700

gtggggcagg ggggcgacga agtatccagc ccagggccac gtagtcaact gccaagggct   2760

tcctgggctt ctcttctgcc ccagagcttg tctccaccca gcaggggttc ccccagcgct   2820

aactgtatcc ctaaagttct gatgtacttt acttttccat cttccttgtt gttaacatct   2880

accttctgct ctgtaagcaa aactaaatct tctgtgcttt gtccataggt tgattctaca   2940

atctgaaaat caataaacag catttgcatg aaaaaaaaaa a                       2981
```

<210> SEQ ID NO 45
<211> LENGTH: 384
<212> TYPE: PRT
<213> ORGANISM: Homo sapiens

<400> SEQUENCE: 45

```
Met Asp Ala Ala Leu Leu Leu Asn Val Glu Gly Val Lys Lys Thr Ile
1               5                   10                  15

Leu His Gly Gly Thr Gly Glu Leu Pro Asn Phe Ile Thr Gly Ser Arg
            20                  25                  30

Val Ile Phe His Phe Arg Thr Met Lys Cys Asp Glu Glu Arg Thr Val
        35                  40                  45

Ile Asp Asp Ser Arg Gln Val Gly Gln Pro Met His Ile Ile Ile Gly
    50                  55                  60

Asn Met Phe Lys Leu Glu Val Trp Glu Ile Leu Leu Thr Ser Met Arg
65                  70                  75                  80

Val His Glu Val Ala Glu Phe Trp Cys Asp Thr Ile His Thr Gly Val
                85                  90                  95

Tyr Pro Ile Leu Ser Arg Ser Leu Arg Gln Met Ala Gln Gly Lys Asp
            100                 105                 110

Pro Thr Glu Trp His Val His Thr Cys Gly Leu Ala Asn Met Phe Ala
        115                 120                 125

Tyr His Thr Leu Gly Tyr Glu Asp Leu Asp Glu Leu Gln Lys Glu Pro
    130                 135                 140

Gln Pro Leu Val Phe Val Ile Glu Leu Leu Gln Val Asp Ala Pro Ser
145                 150                 155                 160

Asp Tyr Gln Arg Glu Thr Trp Asn Leu Ser Asn His Glu Lys Met Lys
                165                 170                 175

Ala Val Pro Val Leu His Gly Glu Gly Asn Arg Leu Phe Lys Leu Gly
            180                 185                 190

Arg Tyr Glu Glu Ala Ser Ser Lys Tyr Gln Glu Ala Ile Ile Cys Leu
        195                 200                 205

Arg Asn Leu Gln Thr Lys Glu Lys Pro Trp Glu Val Gln Trp Leu Lys
    210                 215                 220

Leu Glu Lys Met Ile Asn Thr Leu Ile Leu Asn Tyr Cys Gln Cys Leu
225                 230                 235                 240

Leu Lys Lys Glu Glu Tyr Tyr Glu Val Leu Glu His Thr Ser Asp Ile
                245                 250                 255
```

```
Leu Arg His His Pro Gly Ile Val Lys Ala Tyr Tyr Val Arg Ala Arg
            260                 265                 270

Ala His Ala Glu Val Trp Asn Glu Ala Glu Ala Lys Ala Asp Leu Gln
        275                 280                 285

Lys Val Leu Glu Leu Glu Pro Ser Met Gln Lys Ala Val Arg Arg Glu
    290                 295                 300

Leu Arg Leu Leu Glu Asn Arg Met Ala Glu Lys Gln Glu Glu Glu Arg
305                 310                 315                 320

Leu Arg Cys Arg Asn Met Leu Ser Gln Gly Ala Thr Gln Pro Pro Ala
                325                 330                 335

Glu Pro Pro Thr Glu Pro Pro Ala Gln Ser Ser Thr Glu Pro Pro Ala
            340                 345                 350

Glu Pro Pro Thr Ala Pro Ser Ala Glu Leu Ser Ala Gly Pro Pro Ala
        355                 360                 365

Glu Pro Ala Thr Glu Pro Pro Pro Ser Pro Gly His Ser Leu Gln His
    370                 375                 380
```

<210> SEQ ID NO 46
<211> LENGTH: 1934
<212> TYPE: DNA
<213> ORGANISM: Homo sapiens

<400> SEQUENCE: 46

```
gggcacaagc aatcctccct tctcagcttc ctgagtggcc aggactacag aggactgtat      60

gctgttctta aggactctct gcttcctgga caagctcaag ctaaggacta catctcccag     120

caggctgtgc tctgacagct cttggattta aataggattc tgggctctgc tcagagtcag     180

gctgctgctc agcacccagg acggagagga gcagagaagc agcagaagca gccaagagct     240

ggagccagac caggaacctg agccagagct ggggttgaag ctggagcagc agcaaaagca     300

acagcagcta cagaagttgg aacgatgctg gtcaccttgg gactgctcac ctccttcttc     360

tcgttcctgt atatggtagc tccatccatc aggaagttct ttgctggtgg agtgtgtaga     420

acaaatgtgc agcttcctgg caaggtagtg gtgatcactg gcgccaacac gggcattggc     480

aaggagacgg ccagagagct cgctagccga ggagcccgag tctatattgc ctgcagagat     540

gtactgaagg gggagtctgc tgccagtgaa atccgagtgg atacaaagaa ctcccaggtg     600

ctggtgcgga aattggacct atccgacacc aaatctatcc gagcctttgc tgagggcttt     660

ctggcagagg aaaagcagct ccatattctg atcaacaatg cgggagtaat gatgtgtcca     720

tattccaaga cagctgatgg ctttgaaacc cacctgggag tcaaccacct gggccacttc     780

ctcctcacct acctgctcct ggagcggcta aaggtgtctg cccctgcacg ggtggttaat     840

gtgtcctcgg tggctcacca cattggcaag attcccttcc acgacctcca gagcgagaag     900

cgctacagca ggggttttgc ctattgccac agcaagctgg ccaatgtgct tttactcgt      960

gagctggcca agaggctcca aggcaccggg gtcaccacct acgcagtgca cccaggcgtc    1020

gtccgctctg agctggtccg gcactcctcc ctgctctgcc tgctctggcg gctcttctcc    1080

ccctttgtca agacggcacg ggagggggcg cagaccagcc tgcactgcgc cctggctgag    1140

ggcctggagc ccctgagtgg caagtacttc agtgactgca agaggacctg ggtgtctcca    1200

agggcccgaa ataacaaaac agctgagcgc ctatggaatg tcagctgtga gcttctagga    1260

atccggtggg agtagctggt ggaagagctg cagctttatc aggcccaatc catgccataa    1320

tgaacaggga ccaaggagaa ggccaaccct aaaggattgt cctcttggcc agctggtgct    1380

gcgaatcctg cctgctctga tcctcttgac ccttctggga atgtttgcac acctgacact    1440
```

```
cttgtgagac tggcttatgg catgagttgt ggacacctat agagtgttct tctctaagac   1500

ctggaaagtc agcaaccctc tgggggcagc aggactgggc agatcccagg ctgggcatgg   1560

gggtggcaga agagcccgag aaattgggtc agttccctca tcagcaccag aggctcagct   1620

gaggcaagaa gagcaccatc actgcctatt tctaggggct atacactcca actcttggtt   1680

gatctctttc tttttaaaaa tatttgccac caccctggag tctagaccaa cacacaaaga   1740

tcctggctaa ccctggccta tttagattcc ttcctctcac ctggaccttc ccatttcaat   1800

catgcagatg gtttcttttt gtaaagagtt ccgtttgcct ttcaattttt agagaaaata   1860

aagactgcat tcatctcaaa aaaaaaaaaa aaaaaaaaaa aaaaaaaaaa aaaaaaaaaa   1920

aaaaaaaaaa aaaa                                                     1934
```

<210> SEQ ID NO 47
<211> LENGTH: 316
<212> TYPE: PRT
<213> ORGANISM: Homo sapiens

<400> SEQUENCE: 47

```
Met Leu Val Thr Leu Gly Leu Leu Thr Ser Phe Phe Ser Phe Leu Tyr
1               5                   10                  15

Met Val Ala Pro Ser Ile Arg Lys Phe Phe Ala Gly Gly Val Cys Arg
            20                  25                  30

Thr Asn Val Gln Leu Pro Gly Lys Val Val Val Ile Thr Gly Ala Asn
        35                  40                  45

Thr Gly Ile Gly Lys Glu Thr Ala Arg Glu Leu Ala Ser Arg Gly Ala
    50                  55                  60

Arg Val Tyr Ile Ala Cys Arg Asp Val Leu Lys Gly Glu Ser Ala Ala
65                  70                  75                  80

Ser Glu Ile Arg Val Asp Thr Lys Asn Ser Gln Val Leu Val Arg Lys
                85                  90                  95

Leu Asp Leu Ser Asp Thr Lys Ser Ile Arg Ala Phe Ala Glu Gly Phe
            100                 105                 110

Leu Ala Glu Glu Lys Gln Leu His Ile Leu Ile Asn Asn Ala Gly Val
        115                 120                 125

Met Met Cys Pro Tyr Ser Lys Thr Ala Asp Gly Phe Glu Thr His Leu
    130                 135                 140

Gly Val Asn His Leu Gly His Phe Leu Leu Thr Tyr Leu Leu Leu Glu
145                 150                 155                 160

Arg Leu Lys Val Ser Ala Pro Ala Arg Val Val Asn Val Ser Ser Val
                165                 170                 175

Ala His His Ile Gly Lys Ile Pro Phe His Asp Leu Gln Ser Glu Lys
            180                 185                 190

Arg Tyr Ser Arg Gly Phe Ala Tyr Cys His Ser Lys Leu Ala Asn Val
        195                 200                 205

Leu Phe Thr Arg Glu Leu Ala Lys Arg Leu Gln Gly Thr Gly Val Thr
    210                 215                 220

Thr Tyr Ala Val His Pro Gly Val Val Arg Ser Glu Leu Val Arg His
225                 230                 235                 240

Ser Ser Leu Leu Cys Leu Leu Trp Arg Leu Phe Ser Pro Phe Val Lys
                245                 250                 255

Thr Ala Arg Glu Gly Ala Gln Thr Ser Leu His Cys Ala Leu Ala Glu
            260                 265                 270

Gly Leu Glu Pro Leu Ser Gly Lys Tyr Phe Ser Asp Cys Lys Arg Thr
```

```
        275                 280                 285

Trp Val Ser Pro Arg Ala Arg Asn Asn Lys Thr Ala Glu Arg Leu Trp
    290                 295                 300

Asn Val Ser Cys Glu Leu Leu Gly Ile Arg Trp Glu
305                 310                 315


<210> SEQ ID NO 48
<211> LENGTH: 4729
<212> TYPE: DNA
<213> ORGANISM: Homo sapiens

<400> SEQUENCE: 48

agtctaggcc tccgcctccg ttaccctgga gcccaggtta ccgccgctgc cacccaggag      60

ccccgatcct cgcctctgtc ccatccttgt gttcaaacct cccgcatctc ggcaacctcg     120

gcacccgccc ggcagcctcc gcaggaacca ggcacccgct ctttggcggt cagacgccga     180

ggccccagct gggagtttgg tcctaagagg gaaggcaagg aggcgggacg ccgcatcggc     240

tctgctgaag agcctgcggg ttggaggtgg gctttgaagt gggcgtggag acggcggggg     300

aggtggaggt gcgagtataa atgatcaacc agaaattatc ttcaaaggaa taaaaccaga     360

agtatgtaaa taaaaagccc aagataaaga aacagaaaag ctgacactac atgaagcaga     420

gggcaaaaaa gtttatcttc tggatgccaa tgtgaattgt ggtctacaaa tacattgtgg     480

agaaaataga ttgcacagaa atgaatatta tcaggatctg aagactgtga aaatgttttt     540

cagtattgtc atagtctcct ctggagaaaa taatctgtga aattatgtga atagagacca     600

tttttcaaaa caatggggga aagagcagga agtccaggta ctgatcaaga aagaaaggca     660

ggcaaacacc attattctta cttatctgat tttgaaacgc cacagtcttc tggccgatca     720

tcgctggtca gttcttcacc tgcaagtgtt aggagaaaaa atcctaaaag acaaacttca     780

gatggccaag tacatcacca agcccctcgg aaaccaagcc ctaagggtct accaaacaga     840

aagggagtcc gagtgggatt tcgctcccag agcctcaata gagagccact tcggaaagat     900

actgatcttg ttacaaaacg gattctgtct gcaagactgc taaaaatcaa tgagttgcag     960

aatgaagtat ctgaactcca ggtcaagtta gctgagctgc taaaagaaaa taaatctttg    1020

aaaaggcttc agtacagaca ggagaaagcc ctgaataagt ttgaagatgc cgaaaatgaa    1080

atctcacaac ttatatttcg tcataacaat gagattacag cactcaaaga acgcttaaga    1140

aaatctcaag agaaagaacg ggcaactgag aaaagggtaa aagatacaga aagtgaacta    1200

tttaggacaa aattttcctt acagaaactg aaagagatct ctgaagctag acacctacct    1260

gaacgagatg atttggcaaa gaaactagtt tcagcagagt taaagttaga tgacaccgag    1320

agaagaatta aggagctatc gaaaaacctt gaactgagta ctaacagttt ccaacgacag    1380

ttgcttgctg aaaggaaaag ggcatatgag gctcatgatg aaaataaagt tcttcaaaag    1440

gaggtacagc gactatatca caaattaaag gaaaaggaga gagaactgga tataaaaaat    1500

atatattcta atcgtctgcc aaagtcctct ccaaataaag agaaagaact tgcattaaga    1560

aaaaatgctg catgccagag tgattttgca gacctgtgta caaaaggagt acaaaccatg    1620

gaagacttca agccagaaga atatccttta actccagaaa caattatgtg ttacgaaaac    1680

aaatgggaag aaccaggaca tcttactttg gacttgcaat ctcaaaagca agacaggcat    1740

ggagaagcag ggattctaaa cccaattatg gaaagagaag aaaaatttgt tacagatgaa    1800

gaactccatg tcgtaaaaca ggaggttgaa aagctggagg atgaatggga aagagaagaa    1860

cttgataaaa agcaaaaaga aaaggcatct ttactggaaa gagaagaaaa gccagagtgg    1920
```

```
gaaactggaa ggtaccaact aggaatgtat ccaattcaga atatggataa attgcaagga   1980
gaggaagaag aaagactgaa gagagaaatg ctacttgcta aactgaatga aattgacaga   2040
gaactccaag attctcgaaa tctaaaatac cctgttttgc cattgttacc tgattttgaa   2100
tcaaaactac actccccaga gagaagcccc aaaacataca ggttctctga atcctcagag   2160
agattattta atgggcatca tttgcaagac atcagtttct caactccaaa aggagaaggt   2220
cagaattcag gaaatgttag aagtccagcc tcccctaatg agttcgcatt tggtagctac   2280
gtgccttcgt ttgcaaaaac atcagagagg tcaaatccat ttagtcaaaa aagtagtttt   2340
ttggatttcc aaagaaacag tatggaaaaa cttagtaaag atggtgtaga tttaattaca   2400
agaaaagaga aaaaagctaa tttgatggaa cagttatttg gtgccagtgg tagcagcacc   2460
atttcctcca aaagcagtga cccaaattct gtggcttcca gtaaaggaga cattgaccct   2520
ctaaattttc tccctgggaa taaaggcagc agagatcaag aacatgatga agatgaaggc   2580
tttttcctca gtgaaggaag aagttttaat ccaaataggc accgattaaa acatgcagac   2640
gataaaccag cagtaaaagc agctgattct gtagaagatg aaattgaaga agtagcactg   2700
agatgactga ctagagtata catttttttct aattgtaaat attgaaatat tttaatacag   2760
tatttattat aaacatttag actttttaat gctaaaatgt ccttattaag gaatgatttt   2820
taatagctaa atacaatgca gttaaaaaga agtagatcat acatacacca catagatagt   2880
ttgccaagaa tgaaggaggc ttttttgaat gaaaccaaaa ataaaaaatat gtcttgaaaa   2940
atgaaataga ttttaactct tcatccagtg ctatggcaag tttaactgca ctggaggtgg   3000
tattcctttt ctacttttat tcctatttat gtatttattt ttaatcatat tctcactgtg   3060
ctaaatacag tcttcccact aattgttgaa tgaaaattaa gggtgaaagt ctgtgttggg   3120
aagtgtagct ccggatggtg gagaaccagt gcttcttagg agcccttccc tttatggata   3180
gggccagggg tccctatctt acgtggcagt cctaagctac tcttgagtga tagcagtcac   3240
aacattggga tttcccattc ctctgaaagt acccacagct aaacactact catttcccaa   3300
tttcagtatt tactgaaatc acttacctac aattctgtta gaatattatg ttgagttcgg   3360
aagacatttc tctgtttgca aggacagtta gttgctctct gtcatagccc gcagaagctt   3420
ggctacagtg taattcctct ccttgttctc ctacactctt tgtatctcag tgactgggtg   3480
taagatttca tgccaaatgc aaggaatagt ggaaatacat accaactgca aagaatagaa   3540
aaactttatc ccaatatatt atagaaagat cttcagttca attatgtcca gagtaatata   3600
atttggcaat gttaatgctt ttaagatttg aacttgtcct caaaccaagg agacaacaat   3660
agtgtaatac tattggactt acaggattag ttttaaagca actttgaata gaagtgtttc   3720
agacatagga cttctgcctt gttgactaga gtggatagtt ttctgtttaa atgcattggt   3780
cttttggctg tttgtaattc acttcagctt atagagaagt tgatgacctt ggatcatgct   3840
gggtatgatt ggtctttaaa aagcagtaat ataccaccag cccaaggaga aaacattgtt   3900
aaaatgaaga gtggtggaaa tagtgtgttg ggaagaataa aaaatttaga ttggcactta   3960
ttctaaagtg agctgttttt ttcaagaatt tactagcatt tgctcgtagt atgatttctg   4020
acgccagtca tatatactga tgaggggaag gagttactgt gttattctga gttcttataa   4080
atgcatatta ttgaatttca ttgcatgact atttgtcaag acttacctgg ttaggtctcc   4140
aattaaaaga tgtaccacct gtcatcttct aaattgtgtt cctttcattt attgggaaca   4200
gaatctctca aaagtgctaa actatattaa aaagttttct taatagattt gtatgtctga   4260
```

```
tatgtataac catttactat aatatgttgc aaatcattct aatatatgta aaacaatatt   4320

atttgtaatg cagttattgg taaaatatta tgtaatgtta attttgttcc tagctgctaa   4380

tttttctgcc aaaagtattc taattttcag gttgttttaa aggcttttaa aactttttag   4440

ttaagttttt tattcacgtc atttaaatta gtttttgct tttttctac ctgataatct     4500

ctttaacaag atgcaacaag acagaattat taaaattaaa cctaaagtta agttacagat   4560

ttaaaggcat tatgatatta agcattaaaa ttggagatta aaatgtacaa aacagggttt   4620

tccttatgaa caaaccttac agggtaaatt gttttttttt ctaaatgtca ttaaatttat   4680

ttgtactcag aactgttact aataaaaatt aaaaatgcaa aaaaaaaaa               4729
```

```
<210> SEQ ID NO 49
<211> LENGTH: 697
<212> TYPE: PRT
<213> ORGANISM: Homo sapiens

<400> SEQUENCE: 49

Met Gly Glu Arg Ala Gly Ser Pro Gly Thr Asp Gln Glu Arg Lys Ala
1               5                   10                  15

Gly Lys His His Tyr Ser Tyr Leu Ser Asp Phe Glu Thr Pro Gln Ser
            20                  25                  30

Ser Gly Arg Ser Ser Leu Val Ser Ser Ser Pro Ala Ser Val Arg Arg
        35                  40                  45

Lys Asn Pro Lys Arg Gln Thr Ser Asp Gly Gln Val His His Gln Ala
    50                  55                  60

Pro Arg Lys Pro Ser Pro Lys Gly Leu Pro Asn Arg Lys Gly Val Arg
65                  70                  75                  80

Val Gly Phe Arg Ser Gln Ser Leu Asn Arg Glu Pro Leu Arg Lys Asp
                85                  90                  95

Thr Asp Leu Val Thr Lys Arg Ile Leu Ser Ala Arg Leu Leu Lys Ile
            100                 105                 110

Asn Glu Leu Gln Asn Glu Val Ser Glu Leu Gln Val Lys Leu Ala Glu
        115                 120                 125

Leu Leu Lys Glu Asn Lys Ser Leu Lys Arg Leu Gln Tyr Arg Gln Glu
    130                 135                 140

Lys Ala Leu Asn Lys Phe Glu Asp Ala Glu Asn Glu Ile Ser Gln Leu
145                 150                 155                 160

Ile Phe Arg His Asn Asn Glu Ile Thr Ala Leu Lys Glu Arg Leu Arg
                165                 170                 175

Lys Ser Gln Glu Lys Glu Arg Ala Thr Glu Lys Arg Val Lys Asp Thr
            180                 185                 190

Glu Ser Glu Leu Phe Arg Thr Lys Phe Ser Leu Gln Lys Leu Lys Glu
        195                 200                 205

Ile Ser Glu Ala Arg His Leu Pro Glu Arg Asp Asp Leu Ala Lys Lys
    210                 215                 220

Leu Val Ser Ala Glu Leu Lys Leu Asp Asp Thr Glu Arg Arg Ile Lys
225                 230                 235                 240

Glu Leu Ser Lys Asn Leu Glu Leu Ser Thr Asn Ser Phe Gln Arg Gln
                245                 250                 255

Leu Leu Ala Glu Arg Lys Arg Ala Tyr Glu Ala His Asp Glu Asn Lys
            260                 265                 270

Val Leu Gln Lys Glu Val Gln Arg Leu Tyr His Lys Leu Lys Glu Lys
        275                 280                 285

Glu Arg Glu Leu Asp Ile Lys Asn Ile Tyr Ser Asn Arg Leu Pro Lys
```

```
    290                 295                 300

Ser Ser Pro Asn Lys Glu Lys Glu Leu Ala Leu Arg Lys Asn Ala Ala
305                 310                 315                 320

Cys Gln Ser Asp Phe Ala Asp Leu Cys Thr Lys Gly Val Gln Thr Met
                325                 330                 335

Glu Asp Phe Lys Pro Glu Glu Tyr Pro Leu Thr Pro Glu Thr Ile Met
            340                 345                 350

Cys Tyr Glu Asn Lys Trp Glu Glu Pro Gly His Leu Thr Leu Asp Leu
        355                 360                 365

Gln Ser Gln Lys Gln Asp Arg His Gly Glu Ala Gly Ile Leu Asn Pro
    370                 375                 380

Ile Met Glu Arg Glu Glu Lys Phe Val Thr Asp Glu Glu Leu His Val
385                 390                 395                 400

Val Lys Gln Glu Val Glu Lys Leu Glu Asp Glu Trp Glu Arg Glu Glu
                405                 410                 415

Leu Asp Lys Lys Gln Lys Glu Lys Ala Ser Leu Leu Glu Arg Glu Glu
            420                 425                 430

Lys Pro Glu Trp Glu Thr Gly Arg Tyr Gln Leu Gly Met Tyr Pro Ile
        435                 440                 445

Gln Asn Met Asp Lys Leu Gln Gly Glu Glu Glu Glu Arg Leu Lys Arg
    450                 455                 460

Glu Met Leu Leu Ala Lys Leu Asn Glu Ile Asp Arg Glu Leu Gln Asp
465                 470                 475                 480

Ser Arg Asn Leu Lys Tyr Pro Val Leu Pro Leu Leu Pro Asp Phe Glu
                485                 490                 495

Ser Lys Leu His Ser Pro Glu Arg Ser Pro Lys Thr Tyr Arg Phe Ser
            500                 505                 510

Glu Ser Ser Glu Arg Leu Phe Asn Gly His His Leu Gln Asp Ile Ser
        515                 520                 525

Phe Ser Thr Pro Lys Gly Glu Gly Gln Asn Ser Gly Asn Val Arg Ser
    530                 535                 540

Pro Ala Ser Pro Asn Glu Phe Ala Phe Gly Ser Tyr Val Pro Ser Phe
545                 550                 555                 560

Ala Lys Thr Ser Glu Arg Ser Asn Pro Phe Ser Gln Lys Ser Ser Phe
                565                 570                 575

Leu Asp Phe Gln Arg Asn Ser Met Glu Lys Leu Ser Lys Asp Gly Val
            580                 585                 590

Asp Leu Ile Thr Arg Lys Glu Lys Lys Ala Asn Leu Met Glu Gln Leu
        595                 600                 605

Phe Gly Ala Ser Gly Ser Ser Thr Ile Ser Ser Lys Ser Ser Asp Pro
    610                 615                 620

Asn Ser Val Ala Ser Ser Lys Gly Asp Ile Asp Pro Leu Asn Phe Leu
625                 630                 635                 640

Pro Gly Asn Lys Gly Ser Arg Asp Gln Glu His Asp Glu Asp Glu Gly
                645                 650                 655

Phe Phe Leu Ser Glu Gly Arg Ser Phe Asn Pro Asn Arg His Arg Leu
            660                 665                 670

Lys His Ala Asp Asp Lys Pro Ala Val Lys Ala Ala Asp Ser Val Glu
        675                 680                 685

Asp Glu Ile Glu Glu Val Ala Leu Arg
    690                 695
```

<210> SEQ ID NO 50

<211> LENGTH: 3771
<212> TYPE: DNA
<213> ORGANISM: Homo sapiens

<400> SEQUENCE: 50

```
ccagggtgag attatgaggc tgagctgaga atatcaagac tgtaccgagt agggggcctt     60
ggcaagtgtg gagagcccgg cagctggggc agagggcgga gtacggtgtg cgtttacgga    120
cctcttcaaa cgaggtagga aggtcagaag tcaaaaaggg aacaaatgat gtttaaccac    180
acaaaaatga aaatccaatg gttggatatc cattccaaat acacaaaggc aacggataag    240
tgatccgggc caggcacaga aggccatgca cccgtaggat tgcactcaga gctcccaaat    300
gcataggaat agaagggtgg gtgcaggagg ctgaggggtg gggaaagggc atgggtgttt    360
catgaggaca gagcttccgt ttcatgcaat gaaaagagtt tggagacgga tggtggtgac    420
tggactatac acttacacac ggtagcgatg gtacactttg tattatgtat attttaccac    480
gatcttttta aagtgtcaaa ggcaaatggc caaatggttc cttgtcctat agctgtagca    540
gccatcggct gttagtgaca aagcccctga gtcaagatga cagcagcccc cataactcct    600
aatcggctct cccgcgtgga gtcatttagg agtagtcgca ttagagacaa gtccaacatc    660
taatcttcca ccctggccag ggccccagct ggcagcgagg gtgggagact ccgggcagag    720
cagagggcgc tgacattggg gcccggcctg gcttgggtcc ctctggcctt tccccagggg    780
ccctctttcc ttggggcttt cttgggccgc cactgctccc gctcctctcc ccccatccca    840
ccccctcacc ccctcgttct tcatatcctt ctctagtgct ccctccactt tcatccaccc    900
ttctgcaaga gtgtgggacc acaaatgagt tttcacctgg cctggggaca cacgtgcccc    960
cacaggtgct gagtgacttt ctaggacagt aatctgcttt aggctaaaat gggacttgat   1020
cttctgttag ccctaatcat caattagcag agccggtgaa ggtgcagaac ctaccgcctt   1080
tccaggcctc ctcccacctc tgccacctcc actctccttc ctgggatgtg ggggctggca   1140
cacgtgtggc ccagggcatt ggtgggattg cactgagctg ggtcattagc gtaatcctgg   1200
acaagggcag acagggcgag cggagggcca gctccggggc tcaggcaagg ctgggggctt   1260
cccccagaca ccccactcct cctctgctgg acccccactt catagggcac ttcgtgttct   1320
caaagggctt ccaaatagca tggtggcctt ggatgcccag ggaagcctca gagttgctta   1380
tctccctcta gacagaaggg gaatctcggt caagagggag aggtcgccct gttcaaggcc   1440
acccagccag ctcatggcgg taatgggaca aggctggcca gccatcccac cctcagaagg   1500
gacccggtgg ggcaggtgat ctcagaggag gctcacttct gggtctcaca ttcttggatc   1560
cggttccagg cctcggccct aaatagtctc cctgggcttt caagagaacc acatgagaaa   1620
ggaggattcg ggctctgagc agtttcacca cccacccccc agtctgcaaa tcctgacccg   1680
tgggtccacc tgccccaaag gcggacgcag gacagtagaa gggaacagag aacacataaa   1740
cacagagagg gccacagcgg ctcccacagt caccgccacc ttcctggcgg ggatgggtgg   1800
ggcgtctgag tttggttccc agcaaatccc tctgagccgc ccttgcgggc tcgcctcagg   1860
agcaggggag caagaggtgg gaggaggagg tctaagtccc aggcccaatt aagagatcag   1920
gtagtgtagg gtttgggagc ttttaaggtg aagaggcccg ggctgatccc acaggccagt   1980
ataaagcgcc gtgaccctca ggtgatgcgc cagggccggc tgccgtcggg gacagggctt   2040
tccatagcca tgctagagga tccggtactc gaggaactga aaaaccagaa agttaactgg   2100
taagtttagt ctttttgtct tttatttcag gtcccggatc cggtggtggt gcaaatcaaa   2160
gaactgctcc tcagtggatg ttgcctttac ttctaggcct gtacggaagt gttacttctg   2220
```

```
ctctaaaagc tgcggaattg tacccgcggc cgcgggacag ggctttccat agccatggcc   2280

cagcagtgga gcctccaaag gctcgcaggc cgccatccgc aggacagcta tgaggacagc   2340

acccagtcca gcatcttcac ctacaccaac agcaactcca ccagaggccc cttcgaaggc   2400

ccgaattacc acatcgctcc cagatgggtg taccacctca ccagtgtctg gatgatcttt   2460

gtggtcactg catccgtctt cacaaatggg cttgtgctgg cggccaccat gaagttcaag   2520

aagctgcgcc acccgctgaa ctggatcctg gtgaacctgg cggtcgctga cctagcagag   2580

accgtcatcg ccagcactat cagcattgtg aaccaggtct ctggctactt cgtgctgggc   2640

caccctatgt gtgtcctgga gggctacacc gtctccctgt gtgggatcac aggtctctgg   2700

tctctggcca tcatttcctg ggagagatgg atggtggtct gcaagccctt tggcaatgtg   2760

agatttgatg ccaagctggc catcgtgggc attgccttct cctggatctg gtctgctgtg   2820

tggacagccc cgcccatctt tggttggagc aggtactggc cccacggcct gaagacttca   2880

tgcggcccag acgtgttcag cggcagctcg taccccgggg tgcagtctta catgattgtc   2940

ctcatggtca cctgctgcat catcccactc gctatcatca tgctctgcta cctccaagtg   3000

tggctggcca tccgagcggt ggcaaagcag cagaaagagt ctgaatccac ccagaaggca   3060

gagaaggaag tgacgcgcat ggtggtggtg atgatctttg cgtactgcgt ctgctgggga   3120

ccctacacct tcttcgcatg ctttgctgct gccaaccctg gttacgcctt ccaccctttg   3180

atggctgccc tgccggccta ctttgccaaa agtgccacta tctacaaccc cgttatctat   3240

gtctttatga accggcagtt tcgaaactgc atcttgcagc ttttcgggaa gaaggttgac   3300

gatggctctg aactctccag cgcctccaaa acggaggtct caactgtgtc ctcgacccag   3360

gtagggccta actgaggtct gcctcctacc catcccgccc accggggctt tggccacctc   3420

tcctttcccc ctccttctcc atccctgtaa aataaatgta atttatcttt gccaaaacca   3480

aaaaaaacgg aattcgtaat catgtcatag ctgtttcctg tgtgaaattg ttatccgctc   3540

acaattccac acaacatacg aggcggccgc gcggatccag acatgataag atacattgat   3600

gagtttggac aaaccacaac tagaatgcag tgaaaaaaat gctttatttg tgaaatttgt   3660

gatgctattg ctttatttgt aaccattata agctgcaata aacaagttaa caacaacaat   3720

tgcattcatt ttatgtttca ggttcagggg gaggtgtggg aggtttttta g            3771
```

<210> SEQ ID NO 51
<211> LENGTH: 36
<212> TYPE: DNA
<213> ORGANISM: Artificial Sequence
<220> FEATURE:
<223> OTHER INFORMATION: Synthetic

<400> SEQUENCE: 51

```
gacttgatct tctgttagcc ctaatcatca attagc                               36
```

REAGENTS AND METHODS FOR MODULATING CONE PHOTORECEPTOR ACTIVITY

RELATED APPLICATIONS

This application is a continuation of U.S. patent application Ser. No. 15/939,674, filed Mar. 29, 2018, which is a continuation of U.S. patent application Ser. No. 14/837,448 filed Aug. 27, 2015, which is a continuation of U.S. patent application Ser. No. 14/075,415 filed Nov. 8, 2013 now U.S. Pat. No. 9,198,595 issued Dec. 1, 2015, which is a continuation of U.S. patent application Ser. No. 13/395,609 filed Mar. 12, 2012, which is a U.S. National Phase of International Application No. PCT/US2010/048964, filed Sep. 15, 2010, which claims priority to U.S. Provisional Application No. 61/242,587, filed Sep. 15, 2009, the disclosures of which are hereby incorporated by reference in their entireties.

STATEMENT OF U.S. GOVERNMENT SUPPORT

This work was supported by the National Institutes of Health grants R01EY016861, R01EY11123, and P30EY01730. The U.S. government has certain rights in the invention.

BACKGROUND

Classic visual deprivation experiments have led to the expectation that neural connections established during development would not appropriately process an input that was not present from birth. Therefore, it was believed that treatment of congenital vision disorders would be ineffective unless administered to the very young.

SUMMARY OF THE INVENTION

In a first aspect, the present invention provides methods for cone cell gene therapy in a primate, comprising administering to the eye of a primate in need of cone cell gene therapy a recombinant gene delivery vector comprising:

(a) a promoter region, wherein the promoter region is specific for retinal cone cells; and (b) a gene encoding a therapeutic, wherein the gene is operatively linked to the promoter region;

wherein in vivo expression of the therapeutic in cone cells of the primate serves to treat the primate in need of cone cell gene therapy.

The method of this aspect of the invention can be used, for example, to treat a cone cell disorder, including but not limited to color blindness, blue cone monochomacy, achromatopsia, incomplete achromatopsia, rod-cone degeneration, retinitis pigmentosa (RP), macular degeneration, cone dystrophy, blindness, Stargardt's Disease, and Leber's congenital amaurosis. In one embodiment, the methods restore visual capacity in the primate; in another embodiment, the primate is able to visualize new colors as a result of the therapy. In another embodiment, the primate has a vision disorder in which its photoreceptors are healthy. In a further embodiment, the primate is an adult primate.

In another aspect, the present invention provides isolated nucleic acid expression vector comprising:

(a) a promoter region, wherein the promoter region is specific for primate retinal cone cells; and (b) a gene encoding a therapeutic, wherein the gene is operatively linked to the promoter region. In various embodiments, the vectors further comprise an enhancer element upstream of the promoter, wherein the gene is operatively linked to the enhancer element, and/or an intron comprising a splice donor/acceptor region, wherein the intron is located downstream of the promoter region and is located upstream of the gene. The vectors can be used, for example, in the methods of the invention.

In another aspect, the present invention provides color multi-focal electroretinogram (mf-ERG) comprising:

(a) an electroretinogram (ERG) comprising (i) a recording electrode that is (A) designed for placement on at least one of a cornea and a sclera of at least one eye of a subject and (B) arranged to output at least one signal generated by the at least one eye; and (ii) a computing system communicatively coupled to the recording electrode, the computing system comprising (A) at least one processor and (B) data storage containing instructions executable by the at least one processor to carry out a set of functions, the set of functions including processing and saving the at least one signal generated by the at least one eye;

(b) a retinal stimulator comprising matched light sources selected from the group consisting of red, green, blue, and ultraviolet light sources, wherein the matched light sources are connected to the ERG and in operation can be independently frequency modulated at rates between about 1 Hz and about 60 Hz, inclusive, wherein the stimulator in operation is capable of stimulating a retinal field of a subject throughout an operating radius of at least about 70 degrees;

(c) one or more constant current integrated circuit chips arranged to drive the stimulator; and (d) a pulse-frequency modulator connected to the retinal stimulator, wherein in operation the pulse-frequency modulator is capable of controlling individual stimulator segments while keeping relative spectral content of the light constant. In various preferred embodiments, the matched light sources are paired red and green light sources;

triplets of red, green, and blue light sources; or quartets of red, green, blue, and ultraviolet light sources. In another preferred embodiment the retinal stimulator comprises a concave surface comprising a series of trapezoidal-shaped circuit boards placed edge-to-edge, wherein the concave surface positions the matched light sources so in operation they are held equidistantly from and pointing toward a single focal point where a subject's pupil can be positioned.

BRIEF DESCRIPTION OF THE FIGURES

FIG. 6. The signal to noise ratio (SNR) for as a function of degrees of eccentricity for a typical (averaged) subject and for the highest subject recorded.

DETAILED DESCRIPTION OF THE INVENTION

Figure 1:
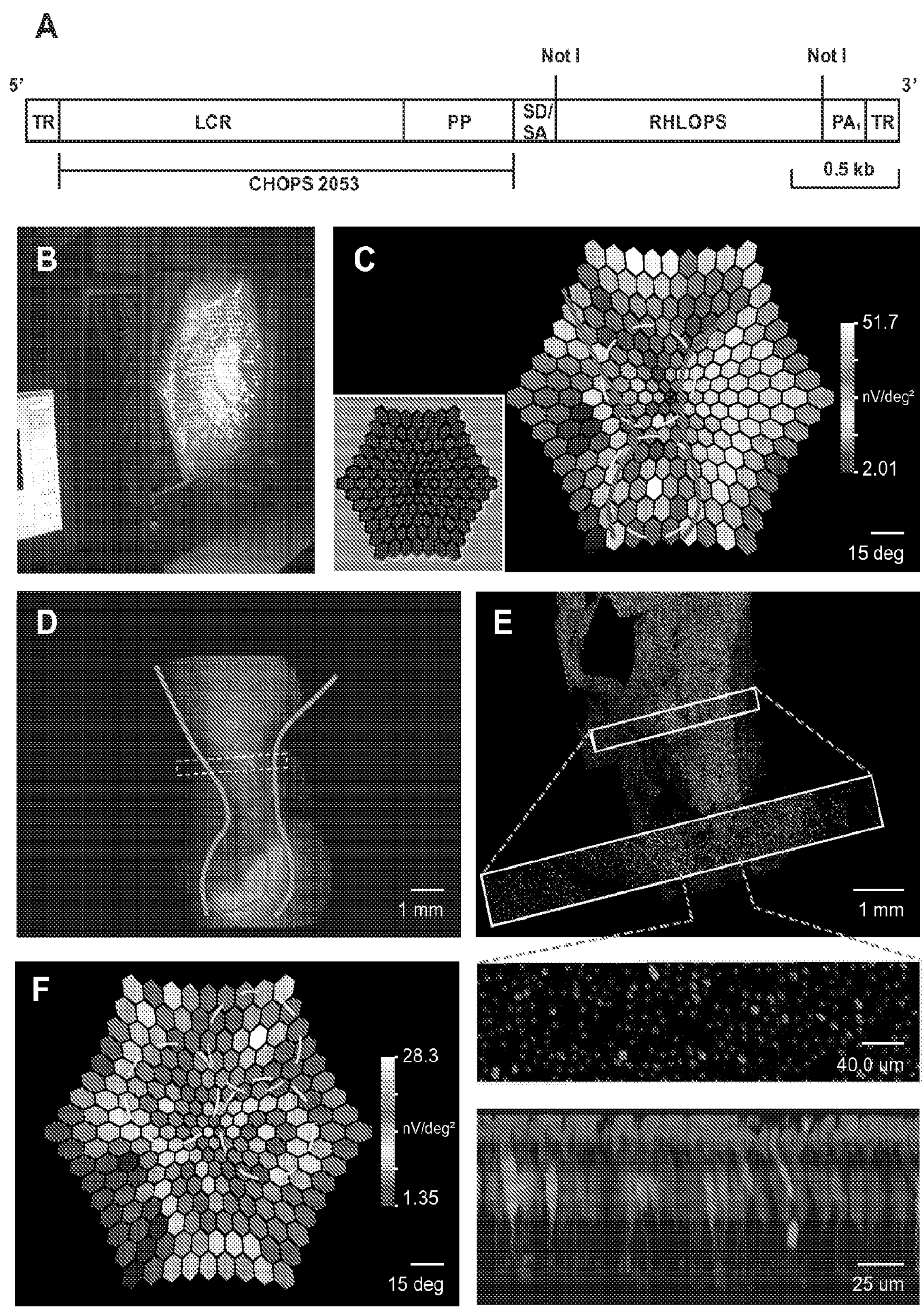
FIG. 1. rAAV2/5 vector produced functional L-opsin in primate retina. a) Molecular map; TR=terminal repeats; LCR=locus control region; PP=proximal promoter; SD/SA=splice donor/acceptor; RHLOPS=recombinant human L opsin cDNA; $PA_1$=polyadenylation signal. b) Red light Multi-focal electroretinogram (Mf-ERG) stimulus. c) mf-ERG 40 weeks after two injections (yellow circles) of a mixture of L-opsin- and green fluorescent protein (GFP)-coding viruses. Grey lines show borders of highest response; for comparison, inset=mfERG 16 weeks post-injection; there was no reliable signal from L-opsin, unchanged from baseline. High responses in far peripheral retina were measured reliably and may have originated from offshoot of one of the injections. d) Fluorescence photographs from a similar retinal area as c; grey lines from c were copied in d. e) Confocal microscopy revealed a mosaic pattern of GFP expression in 5-12% of cones. Because GFP-coding virus was diluted to ⅓ compared to L-opsin virus, an estimated 15-36% of cones in behaviourally tested animals express L-opsin. f) Mf-ERG from a behaviourally tested animal 70 weeks after 3 injections of L-opsin virus.

In a first aspect, the present invention provides methods for cone cell gene therapy in a primate, comprising administering to the eye of a primate in need of cone cell gene therapy a recombinant gene delivery vector comprising:

(a) a promoter region, wherein the promoter region is specific for retinal cone cells; and (b) a gene encoding a therapeutic, wherein the gene is operatively linked to the promoter region;

wherein in vivo expression of the therapeutic in cone cells of the primate serves to treat the primate in need of cone cell gene therapy.

Cone cells are photoreceptor cells in the retina of the eye that function best in relatively bright light. The cone cells gradually become sparser towards the periphery of the retina. The methods of the present invention can be used for treatment of any condition that can be addressed, at least in part, by gene therapy of retinal cone photoreceptor cells. The inventors have demonstrated effective treatment of congenital vision disorders in adult primates, a result that is completely unexpected in the art.

In one preferred embodiment, the gene therapy serves to treat a cone cell disorder. As used herein, a "cone cell disorder" is any disorder impacting retinal cone cells, including but not limited to color blindness, blue cone monochomacy, achromatopsia, incomplete achromatopsia, rod-cone degeneration, retinitis pigmentosa (RP), macular degeneration, cone dystrophy, blindness, Stargardt's Disease, and Leber's congenital amaurosis.

The gene encoding a therapeutic to be expressed in the cone cells can comprise or consist of any gene or cDNA that encodes a polypeptide or RNA-based therapeutic (siRNA, antisense, ribozyme, shRNA, etc.) that can be used as a therapeutic for treating a cone cell disorder. In a preferred embodiment, the primate is of the Parvorder Catarrhini. As is known in the art, Catarrhini is one of the two subdivisions of the higher primates (the other being the New World monkeys), and includes Old World monkeys and the apes, which in turn are further divided into the lesser apes or gibbons and the great apes, consisting of the orangutans, gorillas, chimpanzees, bonobos, and humans. In a further preferred embodiment, the primate is a human.

A "promoter" is a DNA sequence that directs the binding of RNA polymerase and thereby promotes RNA synthesis, i.e., a minimal sequence sufficient to direct transcription. Any suitable promoter region can be used in the gene therapy vectors, so long as it specifically promotes expression of the gene in retinal cone cells. In a preferred embodiment, the promoter specifically promotes expression of the gene in primate retinal cone cells; more preferably in Catarrhini retinal cone cells; even more preferably in human retinal cone cells. As used herein, "specifically" means that the promoter predominately promotes expression of the gene in retinal cone cells compared to other cell types, such that at least 80%, and preferably 85%, 90%, 91%, 92%, 93%, 94%, 95%, 96%, 97%, 97%, 98%, 99%, 99.5%, or more of expression of the gene after delivery of the vector to the eye will be in cone cells. Exemplary suitable promoter regions include the promoter region for any cone-specific gene, such as the L opsin promoter (SEQ ID NO:1), the M opsin promoter (SEQ ID NO:2), and the S opsin promoter (SEQ ID NO:3), or portions thereof suitable to promote expression in a cone-specific manner. Any suitable method for identifying promoter sequences capable of driving expression in primate cone cells can be used to identify such promoters, as will be understood by those of skill in the art based on the teachings herein.

In a preferred embodiment, the gene delivery vector further comprises an enhancer element upstream of the promoter, wherein the gene is operatively linked to the enhancer element. Enhancers are cis-acting elements that stimulate transcription of adjacent genes. Any suitable enhancer element can be used in the gene therapy vectors, so long as it enhances expression of the gene when used in combination with the promoter. In a preferred embodiment, the enhancer element is specific for retinal cone cells; more preferably, it is specific for primate retinal cone cells; more preferably in Catarrhini retinal cone cells; even more preferably in human retinal cone cells. As used herein, “specifically” means that the enhancer predominately enhances expression of the gene in retinal cone cells compared to other cell types, such that at least 80%, and preferably 85%, 90%, 91%, 92%, 93%, 94%, 95%, 96%, 97%, 97%, 98%, 99%, 99.5%, or more of expression of the gene after delivery of the vector to the eye will be in cone cells. Exemplary suitable enhancer regions comprise or consist of the enhancer region for any cone-specific gene, such as the L/M minimal opsin enhancer (SEQ ID NO: 51), L/M enhancer elements of 100, 200, 300, 400, 500, 600, 700, 800, 900, 1000, 1100, 1200, 1300, 1400, 1500, 1600, 1700, 1800, 1900, 2000, or more nucleotides that comprise one or more copies of the L/M minimal opsin enhancer, and the full L/M opsin enhancer (SEQ ID NO:4), or other portions thereof suitable to promote expression in a cone-specific manner. Any suitable method for identifying enhancer sequences capable of driving expression in primate cone cells can be used to identify such enhancers, as will be understood by those of skill in the art based on the teachings herein.

The length of the promoter and enhancer regions can be of any suitable length for their intended purpose, and the spacing between the promoter and enhancer regions can be any suitable spacing to promote cone-specific expression of the gene product. In various preferred embodiments, the enhancer is located 0-1500; 0-1250; 0-1000; 0-750; 0-600; 0-500; 0-400; 0-300; 0-200; 0-100; 0-90; 0-80; 0-70; 0-60; 0-50; 0-40; 0-30; 0-20; or 0-10 nucleotides upstream of the promoter. The promoter can be any suitable distance upstream of the encoded gene.

In a further preferred embodiment that can be combined with any other embodiment in any aspect of the present invention, the enhancer comprises or consists of a sequence selected from the group consisting of the L/M minimal opsin enhancer (SEQ ID NO: 51), L/M enhancer elements of 100, 200, 300, 400, 500, 600, 700, 800, 900, 1000, 1100, 1200, 1300, 1400, 1500, 1600, 1700, 1800, 1900, 2000, or more nucleotides that comprise one or more copies of the L/M minimal opsin enhancer, and the full L/M opsin enhancer (SEQ ID NO:4), or other portions thereof suitable to promote expression in a cone-specific manner, and the promoter comprises or consists of a sequence selected from the group consisting of L opsin promoter (SEQ ID NO: 1), the M opsin promoter (SEQ ID NO:2), and the S opsin promoter (SEQ ID NO:3).

In a further preferred embodiment, the gene delivery vector further comprises an intron comprising a splice donor/acceptor region, wherein the intron is located downstream of the promoter region and is located upstream of the gene. Any intron can be used, so long as it comprises a splice donor/acceptor region recognized in primate cone cells, so that the intron can be spliced out of the resulting mRNA product. In one embodiment, the intron comprises or consists of an SV40 intron according to SEQ ID NO:5. In various preferred embodiments, the 3' end of the intron is 0-20; 0-15; 0-10; 0-9; 0-8; 0-7; 0-6; or 0-5 nucleotides upstream of the gene, and its 5' end is 0-20; 0-15; 0-10; 0-9; 0-8; 0-7; 0-6; or 0-5 nucleotides downstream of the proximal promoter region.

The gene is operatively linked to the promoter region and the enhancer element, such that the promoter and enhancer elements are capable of driving expression of the gene or cDNA in cone cells of the subject.

The gene encoding a therapeutic to be expressed in the cone cells can be any gene or cDNA that encodes a polypeptide or RNA-based therapeutic (siRNA, antisense, ribozyme, shRNA, etc.) that can be used as a therapeutic for treating a cone cell disorder, or as a means to otherwise enhance vision, including but not limited to promoting tetrachromatic color vision. In various preferred embodiments, the gene encodes a therapeutic protein selected from the group consisting of (a) SEQ ID NO: 7 (SEQ ID NO: 6) Homo sapiens opsin 1 (cone pigments), short-wave-sensitive (OPN1SW), mRNA NCBI Reference Sequence: NM_001708.2;

(b) SEQ ID NO: 9 (SEQ ID NO: 8) Homo sapiens opsin 1 (cone pigments), medium-wave-sensitive (OPN1MW), mRNA NCBI Reference Sequence: NM_000513.2;

(c) SEQ ID NO: 11 (SEQ ID NO: 10) Homo sapiens opsin 1 (cone pigments), long-wave-sensitive (OPN1LW), mRNA NCBI Reference Sequence: NM_020061.4;

(d) SEQ ID NO: 13 (SEQ ID NO: 12) ATP binding cassette retina gene (ABCR) gene (NM_000350);

(e) SEQ ID NO: 15 (SEQ ID NO: 14) retinal pigmented epithelium-specific 65 kD protein gene (RPE65) (NM_000329);

(f) SEQ ID NO: 17 (SEQ ID NO: 16) retinal binding protein 1 gene (RLBP1) (NM_000326);

(g) SEQ ID NO: 19 (SEQ ID NO: 18) peripherin/retinal degeneration slow gene, (NM_000322);

(h) SEQ ID NO: 21 (SEQ ID NO: 20) arrestin (SAG) (NM_000541);

(i) SEQ ID NO: 23 (SEQ ID NO: 22) alpha-transducin (GNAT1) (NM_000172);

(j) SEQ ID NO: 24 guanylate cyclase activator 1A (GUCA1A) (NP_000400.2);

(k) SEQ ID NO: 25 retina specific guanylate cyclase (GUCY2D), (NP_000171.1); (l) SEQ ID NO: 26 & 27 alpha subunit of the cone cyclic nucleotide gated cation channel (CNGA3) (NP_001073347.1 or NP_001289.1);

(m) SEQ ID NO: 28 Human cone transducin alpha subunit (incomplete achromotopsia);

(n) SEQ ID NO: 29 cone cGMP-specific 3',5'-cyclic phosphodiesterase subunit alpha', protein (cone dystrophy type 4);

(o) SEQ ID NO: 30 retinal cone rhodopsin-sensitive cGMP 3',5'-cyclic phosphodiesterase subunit gamma, protein (retinal cone dystrophy type 3A);

(p) SEQ ID NO: 31 cone rod homeobox, protein (Cone-rod dystrophy);

(q) SEQ ID NO: 32 cone photoreceptor cyclic nucleotide-gated channel beta subunit, protein (achromatopsia);

(r) SEQ ID NO: 33 cone photoreceptor cGMP-gated cation channel beta-subunit, protein (total color blindness, for example, among Pingelapese Islanders);

(s) SEQ ID NO: 35 (SEQ ID NO: 34) retinitis pigmentosa 1 (autosomal dominant) (RP1);

(t) SEQ ID NO: 37 (SEQ ID NO: 36) retinitis pigmentosa GTPase regulator interacting protein 1 (RPGRIP1);

(u) SEQ ID NO: 39 (SEQ ID NO: 38) PRP8;

(v) SEQ ID NO: 41 (SEQ ID NO: 40) centrosomal protein 290 kDa (CEP290);

(w) SEQ ID NO: 43 (SEQ ID NO: 42) IMP (inosine 5'-monophosphate) dehydrogenase 1 (IMPDH1), transcript variant 1;

(x) SEQ ID NO: 45 (SEQ ID NO: 44) aryl hydrocarbon receptor interacting protein-like 1 (AIPL1), transcript variant 1;

(y) SEQ ID NO: 47 (SEQ ID NO: 46) retinol dehydrogenase 12 (all-trans/9-cis/11-cis) (RDH12);

(z) SEQ ID NO: 49 (SEQ ID NO: 48) Leber congenital amaurosis 5 (LCAS), transcript variant 1; and (aa) exemplary OPN1LW/OPN1MW2 polymorphs (compared to OPN1LW (L opsin) polypeptide sequence; the amino acid to the left of the number is the residue present in the L opsin sequence; the number is the reside number in L opsin, and the reside to the right of the number is the variation from L opsin. Polymorphs according to these embodiments may comprise one or more of the amino acid substitutions in Table 1 below:

TABLE 1

| | |
|---|---|
| (i) | Thr65Ile |
| (ii) | Ile111Val |
| (iii) | Ser116Tyr |
| (iv) | Leu153Met |
| (v) | Ile171Val |
| (vi) | Ala174Val |
| (vii) | Ile178Val |
| (viii) | Ser180Ala |
| (ix) | Ile230Thr |
| (x) | Ala233Ser |
| (xi) | Val236Met |
| (xii) | Ile274Val |
| (xiii) | Phe275Leu |
| (xiv) | Tyr277Phe |
| (xv) | Val279Phe |
| (xvi) | Thr285Ala |
| (xvii) | Pro298Ala |
| (xviii) | Tyr309Phe. |

The proteins recited in (a)-(c) and (aa) are all involved in color vision. The exemplary polymorphs include ones at positions 65, 116, 180, 230, 233, 277, 285, and 309 that affect the spectra of the pigments in cone cells expressing them. Positions 274, 275, 277, 279, 285, 298 and 309 together distinguish L opsin from M opsin.

The proteins recited (d)-(z) are exemplary eye disease-associated gene, such as in retinitis pigmentosa (polypeptides “e”-“l”, “s”-“y”), incomplete achromatopsia (polypeptide “m”), Stargardt’s (polypeptide “d”); Leber congenital amaurosis (polypeptide “z”); cone dystrophy, such as cone dystrophy type 4 (polypeptide “n”); retinal cone dystrophy; for example, retinal cone dystrophy type 3A (polypeptide “o”) ; Cone-rod dystrophy (polypeptide “p”); achromatopsia (polypeptide “q’); and total color blindness, for example, among Pingelapese Islanders (polypeptide “r”).

Exemplary nucleic acids encoding these polypeptides are shown by SEQ ID NO in parenthesis. Thus, in a further preferred embodiment, the genes comprise or consist of a nucleic acid sequence according to one or more of the nucleic acid sequences recited above. In a further preferred embodiment, the vector comprises the sequence shown in SEQ ID NO: 50

Any suitable gene therapy vector that can be used for cone cell delivery can be used in the methods of the present invention; the vector may comprise single or double stranded nucleic acid; preferably single stranded or double stranded DNA. In a preferred embodiment that can be combined with any of the above embodiments, the gene delivery vector comprises a recombinant adeno-associated virus (AAV) gene delivery vector. Prior to the present invention, rAAV vectors had not been shown capable of transducing primate cone cells. In this embodiment, the gene delivery vector is bounded on the 5' and 3' end by functional AAV inverted terminal repeat (ITR) sequences. By “functional AAV ITR sequences” is meant that the ITR sequences function as intended for the rescue, replication and packaging of the AAV virion. Hence, AAV ITRs for use in the vectors of the invention need not have a wild-type nucleotide sequence, and may be altered by the insertion, deletion or substitution of nucleotides or the AAV ITRs may be derived from any of several AAV serotypes. The rAAV vector may be derived from an adeno-associated virus serotype, including without limitation, AAV-1, AAV-2, AAV-3, AAV-4, AAV-5, AAV-6, AAV-7, AAV-8, etc. Preferred AAV vectors have the wild type REP and CAP genes deleted in whole or part, but retain functional flanking ITR sequences. In a further preferred embodiment, the AAV vector comprises rAAV$^{2}/_{5}$, a “pseudotyped” version of AAV2 created by using rep from AAV2 and cap from A AV5 or AAV2 , A AV3, AAV4, AAV6, AAV7, AA V8 together with a plasmid containing a vector based on AAV2. Preferably, the rAAV is replication defective, in that the AAV vector cannot independently further replicate and package its genome. For example, when cone cells are transduced with rAAV virions, the gene is expressed in the transduced cone cells, however, due to the fact that the transduced cone cells lack AAV rep and cap genes and accessory function genes, the rAAV is not able to replicate.

Recombinant AAV (rAAV) virions encapsidating the vectors recited above for use in transducing cone cells may be produced using standard methodology. In one embodiment, an AAV expression vector according to the invention is introduced into a producer cell, followed by introduction of an AAV helper construct, where the helper construct includes AAV coding regions capable of being expressed in the producer cell and which complement AAV helper functions absent in the AAV vector. This is followed by introduction of helper virus and/or additional vectors into the producer cell, wherein the helper virus and/or additional vectors provide accessory functions capable of supporting efficient rAAV virus production. The producer cells are then cultured to produce rAAV. These steps are carried out using standard methodology. Replication-defective AAV virions encapsulating the recombinant AAV vectors of the instant invention are made by standard techniques known in the art using AAV packaging cells and packaging technology. Examples of these methods may be found, for example, in U.S. Pat. Nos. 5,436,146; 5,753,500, 6,040,183, 6,093,570 and 6,548,286, expressly incorporated by reference herein in their entirety. Further compositions and methods for packaging are described in Wang et al. (US 2002/0168342), also incorporated by reference herein in its entirety.

Any suitable method for producing viral particles for delivery can be used, including but not limited to those described in the examples that follow. Any concentration of viral particles suitable to effectively transducer cone cells can be administered to the eye. In one preferred embodiment, viral particles are delivered in a concentration of at least $10^{10}$ vector genome containing particles per mL; in various preferred embodiments, the viral particles are delivered in a concentration of at least $7.5\times10^{10}$; $10^{11}$; $5\times10^{11}$; $10^{12}$; $5\times10^{12}$; $10^{13}$; $1.5\times10^{13}$; $3\times10^{13}$; $5\times10^{13}$; $7.5\times9\times10^{13}$; or $9\times10^{13}$ vector genome containing particles per mL. Similarly, any total number of viral particles suitable to provide appropriate transduction of retinal cone cells can be administered to the primate's eye. In various preferred embodiments, at least $10^{10}$; $5\times10^{10}$; $10^{11}$; $5\times10^{11}$; $10^{12}$; $1.5\times10^{12}$; $3\times10^{12}$; $5\times10^{12}$; $7.5\times10^{12}$; $10^{13}$; $1.5\times10^{13}$; or $2.7'10^{13}$ viral particles are injected per eye. Any suitable number of administrations of the vector to the primate eye can be made. In one embodiment, the methods comprise a single administration; in other embodiments, multiple administrations are made over time as deemed appropriate by an attending clinician.

The viral stock for delivery to the primate eye can be treated as appropriate for delivery. The viral stock can be combined with pharmaceutically-acceptable carriers, diluents and reagents useful in preparing a formulation that is generally safe, non-toxic, and desirable, and includes excipients that are acceptable for primate use. Such excipients can be solid, liquid, semisolid, or, in the case of an aerosol composition, gaseous. Examples of such carriers or diluents include, but are not limited to, water, saline, Ringer's solutions, dextrose solution, and 5% human serum albumin. Supplementary active compounds can also be incorporated into the formulations. Solutions or suspensions used for the formulations can include a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates; detergents such as Tween 20 to prevent aggregation; and compounds for the adjustment of tonicity such as sodium chloride or dextrose. The pH can be adjusted with acids or bases, such as hydrochloric acid or sodium hydroxide.

In a further preferred embodiment that can be combined with any other embodiment, the methods of the invention restore visual capacity in the primate. As used herein, "restoring visual capacity" means that some benefit to vision is provided, including but not limited to a reduction or slowing of vision loss; improved visual acuity; decrease in abnormal sensitivity to bright lights; and/or an increase in one or more visual attributes, such as improved color perception (ie: monochromatic to dichromatic vision; dichromatic to trichromatic vision; trichromatic to tetrachromatic vision; etc.). The primate is preferably of the Parvorder Catarrhini, and more preferably is a human.

In a further preferred embodiment that can be combined with all of the above embodiments, the primate suffers from color blindness, and the primate is able to visualize new colors as a result of the therapy. In this embodiment, it is preferred that the enhancer (if present) comprises or consists of a sequence selected from the group consisting of the L/M minimal opsin enhancer (SEQ ID NO: 51), L/M enhancer elements of 100, 200, 300, 400, 500, 600, 700, 800, 900, 1000, 1100, 1200, 1300, 1400, 1500, 1600, 1700, 1800, 1900, 2000, or more nucleotides that comprise one or more copies of the L/M minimal opsin enhancer, and the full L/M opsin enhancer (SEQ ID NO:4), or other portions thereof suitable to promote expression in a cone-specific manner, and the promoter comprises or consists of a sequence selected from the group consisting of L opsin promoter (SEQ ID NO: 1), the M opsin promoter (SEQ ID NO:2), and the S opsin promoter (SEQ ID NO:3), while the gene encodes one or more polypeptides comprising or consisting of a sequence selected from the group consisting of SEQ ID NO: 7 (OPN1SW), SEQ ID NO: 9 (OPN1MW), SEQ ID NO: 11 (OPN1LW), mRNA; and exemplary OPN1LW/OPN1MW2 polymorphs as described in Table 1 above. It is further preferred that the vector comprises a rAAV vector as described above.

The color blindness may be acquired or inherited, and can be full (monochromatic) or partial. In a preferred embodiment, the primate has partial color blindness selected from the group consisting of red-green and blue-yellow color blindness. The partial color blindness can comprise, for example, dichromacy or anomalous trichromasy. These methods result in the primate improved color perception (ie: monochromatic to dichromatic vision; dichromatic to trichromatic vision; trichromatic to tetrachromatic vision; etc.). The primate is preferably of the Parvorder Catarrhini, and more preferably is a human.

As described in detail below, the methods may be used to improve color perception in primates from dichromatic to trichromatic. Dichromats who are missing either the L- or the M-photopigment fail to distinguish from grey:colours near the so-called 'spectral neutral point' located in the bluegreen region of color space (near dominant wavelength of 490 nm) and complementary colors near the 'extra-spectral neutral point' in the red-violet region (near dominant wavelength of 499 nm). Co-expressing the L-opsin transgene within a subset of endogenous M-cones shifted their spectral sensitivity to respond to long wavelength light, thus producing two distinct cone types absorbing in the middle-to-long wavelengths, as required for trichromasy. These results demonstrate that gene therapy changed the spectral sensitivity of a subset of the cones, and the results further demonstrate the unexpected result that adult monkeys gained new color vision capacities because of the gene therapy.

In a further preferred embodiment of all of the above embodiments, the primate has a vision disorder in which its photoreceptors are healthy, such as color blindness. As used herein, "healthy" means that the cells being treated are functioning but simply do not provide for the desired color perception, in contrast to gene therapy in which the target cells are degenerating or dying. The studies reported herein are the first to use gene therapy in primates to address a vision disorder in which all photoreceptors are intact and healthy, making it possible to assess the full potential of gene therapy to restore visual capacities. The methods of the present invention thus will allow many opportunities for functions to be added or restored in the eye.

In a further preferred embodiment that can be combined with any of the other embodiments herein, the primate is an adult primate, such as an adult human (ie: at least 16 years of age; preferably at least 18 years of age or 21 years of age). Classic visual deprivation experiments have led to the expectation that neural connections established during development would not appropriately process an input that was not present from birth. Therefore, it was believed that treatment of congenital vision disorders would be ineffective unless administered to the very young. The present study thus provides significantly unexpected results in curing a visual disorder in an adult primate.

Those of skill in the art will readily appreciate, based on the teachings herein, the variety of treatment modalities that can be accomplished using the methods of the invention. In one embodiment, the gene encodes ABCR and is administered to the eye of a primate with Stargardt disease. In other embodiments, the gene encodes:

one or more of polypeptides "e"-"l" and "s"-"y" in Table 1, and is administered to the eye of a primate with retinitis pigmentosa;

polypeptide "m" in Table 1, and is administered to the eye of a primate with incomplete achromatopsia;

polypeptide "z" in Table 1, and is administered to the eye of a primate with Leber congenital amaurosis;

polypeptide "n" in Table 1, and is administered to the eye of a primate with cone dystrophy, such as cone dystrophy type 4;

polypeptide "o" in Table 1, and is administered to the eye of a primate with retinal cone dystrophy, for example, retinal cone dystrophy type 3A;

polypeptide "p" in Table 1, and is administered to the eye of a primate with cone-rod dystrophy;

polypeptide "q" in Table 1, and is administered to the eye of a primate with achromatopsia; and/or polypeptide "r" in Table 1, and is administered to the eye of a primate with total color blindness, for example, a native of the Pingelapese Islands.

Any suitable means for delivery of the gene therapy vector to the eye can be used, including but not limited to administering in a contact lens fluid, contact lens cleaning and rinsing solutions, eye drops, surgical irrigation solutions, ophthalmological devices, injection, iontophoresis, topical instillation on the eye, and topical instillation. The topical instillation can be administered, for example, in the form of a liquid solution, a paste, of a hydrogel. The topical instillation can be embedded, for example, in a foam matrix or supported in a reservoir. The injection into the primate eye can be, for example, an intracameral injection, an intracorneal injection, a subconjonctival injection, a subtenon injection, a subretinal injection, an intravitreal injection, and an injection into the anterior chamber.

The primate's progress in response to the treatment may be monitored by any suitable means. In embodiments where the methods are used to treat color blindness, monitoring or progress may comprise, for example, use of standard color vision tests, or the wide-field color multifocal electroretinogram (mf-ERG) system described below to detect spectral sensitivity shifts in the primate's vision. Thus, in another aspect, the present invention provides methods for use of the electroretinogram disclosed herein for monitoring changes in vision perception, such as color perception, of a primate undergoing gene therapy to treat a visual disorder. All embodiments of the methods disclosed above can be combined with all embodiments of the electroretinogram disclosed below.

In a second aspect, the present invention provides isolated nucleic acid expression vectors comprising:

(a) a promoter region, wherein the promoter region is specific for primate retinal cone cells; and (b) a gene encoding a therapeutic, wherein the gene is operatively linked to the promoter region.

All terms in this second aspect have the same meaning as disclosed above for the first aspect of the invention. Similarly, all embodiments and combinations thereof disclosed above in the first aspect of the invention can be used in this second aspect of the invention. The inventors have demonstrated effective treatment of congenital vision disorders in adult primates using the recombinant vectors of the invention, a result that is completely unexpected in the art.

Any suitable promoter region can be used in the isolated nucleic acid expression vector, so long as it specifically promotes expression of the gene in retinal cone cells. In a preferred embodiment, the promoter specifically promotes expression of the gene in Catarrhini retinal cone cells; even more preferably in human retinal cone cells. Exemplary suitable promoter regions include the promoter region for any cone-specific gene, such as the L opsin promoter (SEQ ID NO: 1), the M opsin promoter (SEQ ID NO: 2), and the S opsin promoter (SEQ ID NO: 3), or portions thereof suitable to promote expression in a cone-specific manner.

In a preferred embodiment, the isolated nucleic acid expression vector further comprises an enhancer element upstream of the promoter, wherein the gene is operatively linked to the enhancer element. Any suitable enhancer element can be used in the gene therapy vectors, so long as it enhances expression of the gene when used in combination with the promoter. In a preferred embodiment, the enhancer element is specific for retinal cone cells; more preferably, it is specific for primate retinal cone cells; more preferably in Catarrhini retinal cone cells; even more preferably in human retinal cone cells. Exemplary suitable enhancer regions comprise or consist of the enhancer region for any cone-specific gene, such as the L/M minimal opsin enhancer (SEQ ID NO: 51), L/M enhancer elements of 100, 200, 300, 400, 500, 600, 700, 800, 900, 1000, 1100, 1200, 1300, 1400, 1500, 1600, 1700, 1800, 1900, 2000, or more nucleotides that comprise one or more copies of the L/M minimal opsin enhancer, and the full L/M opsin enhancer (SEQ ID NO: 4), or other portions thereof suitable to promote expression in a cone-specific manner.

The length of the promoter and enhancer regions can be of any suitable length for their intended purpose, and the spacing between the promoter and enhancer regions can be any suitable spacing to promote cone-specific expression of the gene product. In various preferred embodiments, the enhancer is located 0-1500; 0-1250; 0-1000; 0-750; 0-600; 0-500; 0-400; 0-300; 0-200; 0-100; 0-90; 0-80; 0-70; 0-60; 0-50; 0-40; 0-30; 0-20; or 0-10 nucleotides upstream of the promoter. The promoter can be any suitable distance upstream of the encoded gene.

In a further preferred embodiment that can be combined with any other embodiment in any aspect of the present invention, the enhancer comprises or consists of a sequence selected from the group consisting of the L/M minimal opsin enhancer (SEQ ID NO: 51), L/M enhancer elements of 100, 200, 300, 400, 500, 600, 700, 800, 900, 1000, 1100, 1200, 1300, 1400, 1500, 1600, 1700, 1800, 1900, 2000, or more nucleotides that comprise one or more copies of the L/M minimal opsin enhancer, and the full L/M opsin enhancer (SEQ ID NO: 4), or other portions thereof suitable to promote expression in a cone-specific manner, and the promoter comprises or consists of a sequence selected from the group consisting of L opsin promoter (SEQ ID NO: 1), the M opsin promoter (SEQ ID NO: 2), and the S opsin promoter (SEQ ID NO: 3).

In a further preferred embodiment, the isolated nucleic acid expression vector further comprises an intron comprising a splice donor/acceptor region, wherein the intron is located downstream of the promoter region and is located upstream of the gene. Any intron can be used, so long as it comprises a splice donor/acceptor region recognized in primate cone cells, so that the intron can be spliced out of the resulting mRNA product. In one embodiment, the intron comprises or consists of an SV40 intron according to SEQ ID NO: 5. In various preferred embodiments, the 3' end of the intron is 0-20; 0-15; 0-10; 0-9; 0-8; 0-7; 0-6; or 0-5 nucleotides upstream of the gene, and its 5' end is 0-20; 0-15; 0-10; 0-9; 0-8; 0-7; 0-6; or 0-5 nucleotides downstream of the proximal promoter region.

The gene is operatively linked to the promoter region and the enhancer element, such that the promoter and enhancer elements are capable of driving expression of the gene or cDNA in cone cells of the subject.

The gene encoding a therapeutic to be expressed in the cone cells can be any gene or cDNA that encodes a polypeptide or RNA-based therapeutic (siRNA, antisense, ribozyme, shRNA, etc.) that can be used as a therapeutic for treating a cone cell disorder, or as a means to otherwise enhance vision, including but not limited to promoting tetrachromatic color vision. In various preferred embodiments, the gene encodes a therapeutic protein comprising or consisting of those disclosed above in the methods of the first aspect of the invention.

In a further preferred embodiment, the vector comprises the sequence shown in SEQ ID NO: 50, which details the vector used in at least some of the examples that follow.

In a further preferred embodiment that can be combined with any of the above embodiments, the gene delivery vector comprises a recombinant adeno-associated virus (AAV) gene delivery vector. In a further preferred embodiment, the AAV vector comprises rAAV2/5. Preferably, the rAAV is replication defective, in that the AAV vector cannot independently further replicate and package its genome. For example, when cone cells are transduced with rAAV virions, the gene is expressed in the transduced cone cells, however, due to the fact that the transduced cone cells lack AAV rep and cap genes and accessory function genes, the rAAV is not able to replicate.

In a third aspect, the present invention provides a formulation comprising packaged viral particles containing the nucleic acid expression vectors of the second aspect of the invention. In one preferred embodiment, viral particles are present in a concentration of at least $10^{10}$ vector genome containing particles per mL; in various preferred embodiments, the viral particles are delivered in a concentration of at least $7.5\times10^{10}$; $10^{11}$; $5\times10^{11}$; $10^{12}$; $5\times10^{12}$; $10^{13}$; $1.5\times10^{13}$; $3\times10^{13}$; $5\times10^{13}$; $7.5\times9\times10^{13}$; or 9'$10^{13}$ vector genome containing particles per mL. The formulation may further comprise pharmaceutically-acceptable carriers, diluents and reagents as described above in the first aspect of the invention. The formulation may be in the form of a liquid solution, a paste, a hydrogel, or may be embedded within a substrate, including but not limited to a foam matrix or supported in a reservoir.

In a fourth aspect, the present invention provides recombinant host cells transfected or transduced with the nucleic acid expression vector of the second aspect of the invention. The cells may be of any type that can be transfected with the expression vector. In one embodiment where the expression vector is a rAAV vector, the cells comprise producer cells transduced with a replication incompetent rAAV expression vector according to the second aspect of the invention, form which viral particles can be obtained by introduction of an AAV helper construct as described above and as is well known in the art.

In a fifth aspect, the present invention provides a color multifocal electroretinogram system, comprising:

(a) an electroretinogram (ERG) comprising (i) a recording electrode that is (A) designed for placement on at least one of a cornea and a sclera of at least one eye of a subject and (B) arranged to output at least one signal generated by the at least one eye; and (ii) a computing system communicatively coupled to the recording electrode, the computing system comprising (A) at least one processor and (B) data storage containing instructions executable by the at least one processor to carry out a set of functions, the set of functions including processing and saving the at least one signal generated by the at least one eye;

(b) a retinal stimulator comprising matched light sources selected from the group consisting of red, green, blue, and ultraviolet light sources, wherein the matched light sources are connected to the ERG and in operation can be independently frequency modulated at rates between about 1 Hz and about 60 Hz, inclusive, wherein the stimulator in operation is capable of stimulating a retinal field of a subject throughout an operating radius of at least about 70 degrees;

(c) one or more constant current integrated circuit chips arranged to drive the stimulator; and (d) a pulse-frequency modulator connected to the retinal stimulator, wherein in operation the pulse-frequency modulator is capable of controlling individual stimulator segments while keeping relative spectral content of the light constant.

The electroretinograms of the present invention can be used, for example, in characterizing the topography of expression of the different opsin transgenes in the eyes of living subjects treated with gene therapy, and thus can be used with the gene therapy methods of the invention disclosed above.

As used here, a "matched" light source is one that includes light stimulus of different wavelengths, wherein the number of pixels is approximately the same, or is the same, at each wavelength. One non-limiting example is a matched light source stimulus containing 1024 doublet pixels each containing a red (653 nm, half-bandwidth 22 nm) and a green (527 nm, half-bandwidth 33 nm) LED, with a resulting matched light source with 2,048 paired green and red LEDs.

In various preferred embodiments, the stimulator in operation is capable of stimulating a retinal field of a subject throughout an operating radius of at least about 80, 90, 100, 110, 120, 130, 140, 150, or more degrees.

In one preferred embodiment, the matched light sources are paired red and green light sources. In another preferred embodiment, the matched light sources are triplets of red, green, and blue light sources. In a further preferred embodiment, the matched light sources are quartets of red, green, blue, and ultraviolet light sources.

Any suitable matched light source can be used. In one preferred embodiment, the matched light sources comprise matched light emitting diodes (LEDs).

In another preferred embodiment, that can be combined with any of the embodiments herein, the retinal stimulator comprises a concave surface comprising a series of trapezoidal-shaped circuit boards placed edge-to-edge, wherein the concave surface positions the matched light sources so in operation they are held equidistantly from and pointing toward a single focal point where a subject's pupil can be positioned. This embodiment helps to limit SNR fall-off in peripheral retinal regions. Any suitable concave surface can be used; in a preferred embodiment, the concave surface comprises a geodesic dome.

In a further embodiment that can be combined with any of the above embodiments, the set of functions executable by the processor further comprises coding and decoding topographical regions on the recording electrode using a cyclic summation technique.

In a further preferred embodiment that can be combined with any of the embodiments herein, the ERG further comprises an amplifier; and wherein the computing system is communicatively coupled to the amplifier.

Further embodiments and details of the color multifocal electroretinogram system are provided in the Examples that follow.

In a further aspect, the present invention provides methods for determining a location of functioning opsin expression in a subject, comprising use of the mf-ERG of any embodiment or combination of embodiments of the fifth aspect of the invention, wherein the recording electrode is placed on at least one of a cornea and a sclera of at least one eye of a subject; stimulating the subject's retinal field with the retinal stimulator; and determining responses of different areas of the subject's retina to different stimulation frequencies to generate a map of retinal responses, wherein the map provides a location of functioning opsin expression in a subject. In one preferred embodiment, the subject has been treated according to the gene therapy methods for color blindness disclosed above according to any embodiment or combination of embodiments of the first aspect of the invention.

Unless the context clearly dictates otherwise, embodiments in one aspect of the invention may be used in other aspects of the invention, and can be combined with each other.

EXAMPLE 1

Red-green colour blindness, which results from the absence of either the long- (L) or middle- (M) wavelength-sensitive visual photopigments, is the most common single locus genetic disorder. Here, the possibility of curing colour blindness using gene therapy was explored in experiments on adult monkeys that had been colour blind since birth. A third type of cone pigment was added to dichromatic retinas, providing the receptoral basis for trichromatic colour vision. This opened a new avenue to explore the requirements for establishing the neural circuits for a new dimension of colour sensation. Classic visual deprivation experiments[1] have led to the expectation that neural connections established during development would not appropriately process an input that was not present from birth. Therefore, it was believed that treatment of congenital vision disorders would be ineffective unless administered to the very young. Here, however, addition of a third opsin in adult red-green colour-deficient primates was sufficient to produce trichromatic colour vision behaviour. Thus, trichromacy can arise from a single addition of a third cone class and it does not require an early developmental process. This provides a positive outlook for the potential of gene therapy to cure adult vision disorders.

Gene therapy was performed on adult squirrel monkeys (*Saimiri sciureus*) that were missing the L opsin gene. In this species, some females have trichromatic colour vision while males are red-green colour blind[2]. Serotype 2/5 recombinant adeno-associated virus (rAAV) containing a human L-opsin gene under control of the L/M opsin enhancer and promoter (FIG. 1*a*) was delivered to the photoreceptor layer via subretinal injections. Transcriptional regulatory elements were chosen to direct expression preferentially in M cones, but not short- (S) wavelength-sensitive cones or rods[3]. To provide the receptoral basis for trichromacy, animals received three 100 μL injections (containing a total of $2.7\times10^{13}$ viral particles) in each eye which produced a relatively uniform, third submosaic of approximately 15-36% of M cones that coexpressed the transgene (FIG. 1*e, f*).

Prior to treatment, monkeys were trained to perform a computer-based colour vision test, the Cambridge Colour Test[4,5], which was modified for use with animals[6] (FIG. 2*a*). Dichromats who are missing either the L- or M-photopigment fail to distinguish from grey: colours near the so-called "spectral neutral point" located in the blue-green region of colour space (near dominant wavelength (DW) 490 nm) and complementary colours near the "extra-spectral neutral point," in the red-violet region (near DW=-499 nm). While trichromats have four main hue percepts—blue, yellow, red, and green—dichromats have only two percepts, nominally blue and yellow. Before treatment, two dichromatic monkeys completed three colour vision tests consisting of 16 hues (FIG. 2*b, c*). Four-to-six months was required to test all 16 hues; thus, baseline results represent testing conducted for more than a year. As predicted, prior to treatment monkeys had low thresholds (averaging <0.03 units in u', v' colour space) for colours that represent blues and yellows to their eyes, but always failed to discriminate the blue-green (DW=490 nm) and red-violet hues (DW=−499 nm) with thresholds extrapolated from psychometric functions being orders of magnitude higher (FIG. 2*b, c*). Results were highly repeatable, with no improvement between the first and third tests, making us confident that animals would not spontaneously improve in the absence of treatment.

Co-expressing the L-opsin transgene within a subset of endogenous M-cones shifted their spectral sensitivity to respond to long wavelength light, thus producing two distinct cone types absorbing in the middle-to-long wavelengths, as required for trichromacy. The spectral sensitivity shift was readily detected using a custom-built wide-field colour multifocal electroretinogram (mf-ERG) system (FIG. 1*b, c, f*) (see ref 7 for details). In preliminary experiments, validity of the colour mf-ERG was tested using an animal that had received a mixture of the L-opsin-coding virus plus an identical virus, except that a green fluorescent protein (GFP) gene replaced the L-opsin gene. As reported previously, faint GFP fluorescence was first detected at 9 weeks post-injection, and it continued to increase in area and intensity through 24 weeks[8]. While faint signs of GFP were first detectable at 9 weeks, L-opsin levels sufficient to produce suprathreshold mf-ERG signals were still not present at 16 weeks post-injection (FIG. 1*c,* inset). After GFP fluorescence became robust, the red light mf-ERG, which indicates responses from the introduced L-opsin, showed highly elevated response amplitudes in two areas (FIG. 1*c*) corresponding to locations of subretinal injections (FIG. 1*d*).

The two dichromatic monkeys who participated in behavioural tests of colour vision were treated with only L-opsin-coding virus. While the elongated pattern produced by two injections in FIG. 1*c* and *d* allowed mf-ERG validation, the treatment goal was to produce a homogeneous region, as resulted from 3 injections shown in f, where the highest mf-ERG response covered about 80° of central retina, roughly the area for which humans have good red-green discrimination. These results demonstrate that gene therapy changed the spectral sensitivity of a subset of the cones. A priori, there were two possibilities for how a change in spectral sensitivity might change colour vision behaviour: 1) animals may have an increase in sensitivity to long-wavelength light, but if the neural circuitry for extracting colour information from the nascent "M+L cone" submosaic was absent, they would remain dichromatic, the hallmark of which is having two hues that are indistinguishable from grey (FIG. 2*d*). The spectral neutral point for individuals that have only S- and M-cones, (e.g. monkeys 1 and 2 pre-therapy), occurs near dominant wavelength (DW)=495 nm. At the limit, an increase in spectral sensitivity would shift the monkeys' neutral point toward that of individuals with only S and L cones, near DW=505 nm (dashed blue lines, FIG. 2*d*). 2) The second, more engaging possibility was that treatment would be sufficient to expand sensory capacity in monkeys, providing them with trichromatic vision. In this case, the animals' post-therapy results would appear similar to FIG. 2*e*, obtained from a trichromatic female control monkey.

Daily testing continued after treatment. After about 20 weeks post-injection (arrow, FIG. 3*a*), the trained monkeys' thresholds for blue-green and red-violet (DWs=490 and −499 nm, respectively, FIG. 3*b, c*) improved, reducing to an average of 0.08 units in u', v' colour space, indicating that they gained trichromatic vision. This time point corresponded to the same period in which robust levels of transgene expression were reported in the squirrel monkey[8]. A trichromatic female monkey and untreated dichromatic monkeys were tested in parallel. As expected, the female had low thresholds for all colours, averaging <0.03 units in u', v' colour space, but the untreated dichromats always failed to discriminate DWs=490 nm (triangle, FIG. 3*a*) and −499 nm, indicating a clear difference between treated and untreated monkeys.

Early experiments in which we obtained negative results served as "sham controls," demonstrating that acquiring a new dimension of colour vision requires a shift in spectral sensitivity that results from expression of an L pigment in a subset of M cones. Using similar subretinal injection procedures, we delivered fewer viral particles of an L-opsin-coding rAAV2/5 virus with an extra 146 base pair (bp) segment near the splice donor/acceptor site that had been carried over from the cloning vector and that was absent in the GFP-coding rAAV2/5 virus. The 146 bp segment contained an ATG and a duplicate mRNA start site that may have interfered with expression (see Full Methods online). Three monkeys received injections of this vector, containing an average of $1.7\times10^{12}$ virus particles per eye, and no reliable changes in spectral sensitivity were measured using the ERG. One animal was also tested behaviourally and his colour vision was unchanged from baseline 1 year after injection. In subsequent experiments reported here, we removed the extra 146 bp segment and also increased the amount of viral particles delivered per eye by approximately 16-fold, to $2.7\times10^{13}$. Negative results from earlier injections demonstrated that the subretinal injection procedure itself does not produce changes in the ERG or in colour vision.

Figure 2:
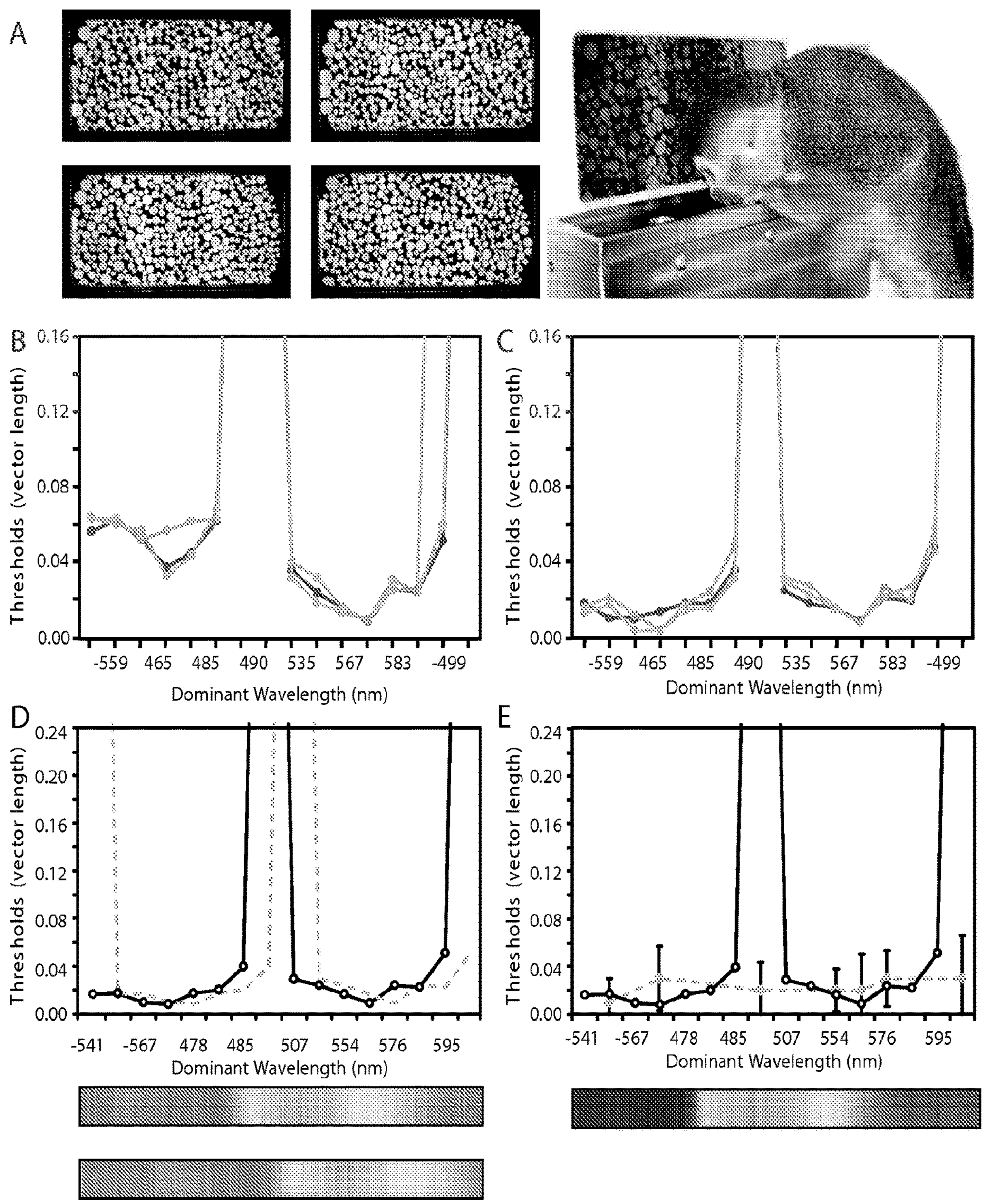
FIG. 2. Pre-therapy colour vision and possible treatment outcomes. a) Colour vision stimuli examples. b) Pre-therapy results, monkey 1. Hues tested are represented as dominant wavelengths (DWs) rather than u', v' coordinates. If a hue could not be reliably distinguished at even the highest saturation, the extrapolated threshold approached infinity. c) Pre-therapy results, monkey 2. d)-e), Possible experimental outcomes: Monkeys could have a relative increase in long-wavelength sensitivity, but remain dichromatic (dashed lines, d); theoretical colour spectrum appearances for a dichromat and a possible "spectral shift" are shown. Alternatively, dichromatic monkeys could become trichromatic. Results from a trichromatic female control monkey are plotted (dashed line, e; error bars=SEM and n varied from 7-11).
Figure 3:
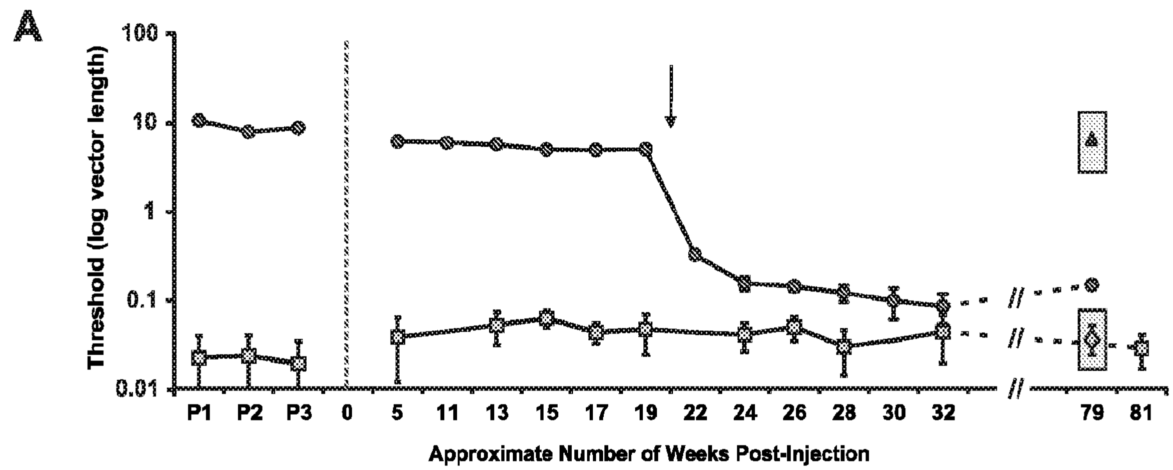
FIG. 3. Gene therapy produced trichromatic colour vision. a) Time course of thresholds for the blue-green confusion colour, DW=490 nm (circles), and a yellowish colour, DW=554 nm (squares). A logarithmic scale was used to fit high thresholds for DW=490 nm; significant improvement occurred after 20 weeks. Enclosed data points=untreated dichromatic monkey thresholds, DW=490 nm (triangle) and DW=554 nm (diamond). b)-c) Comparison of pre-therapy (open circles, solid line) and post-therapy thresholds (solid dots, dashed line). Enclosed data points are DW=490 nm thresholds when tested against a red-violet background (DW=−499 nm); pink triangles=trichromatic female control thresholds. Error bars=SEM; n varied from 7-11.
Figure 3:
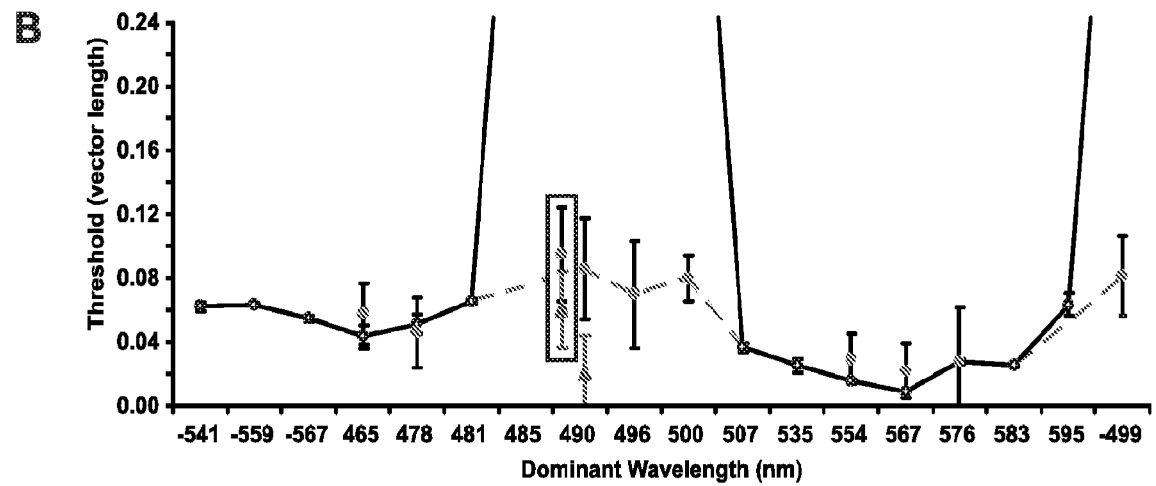
Figure 3:
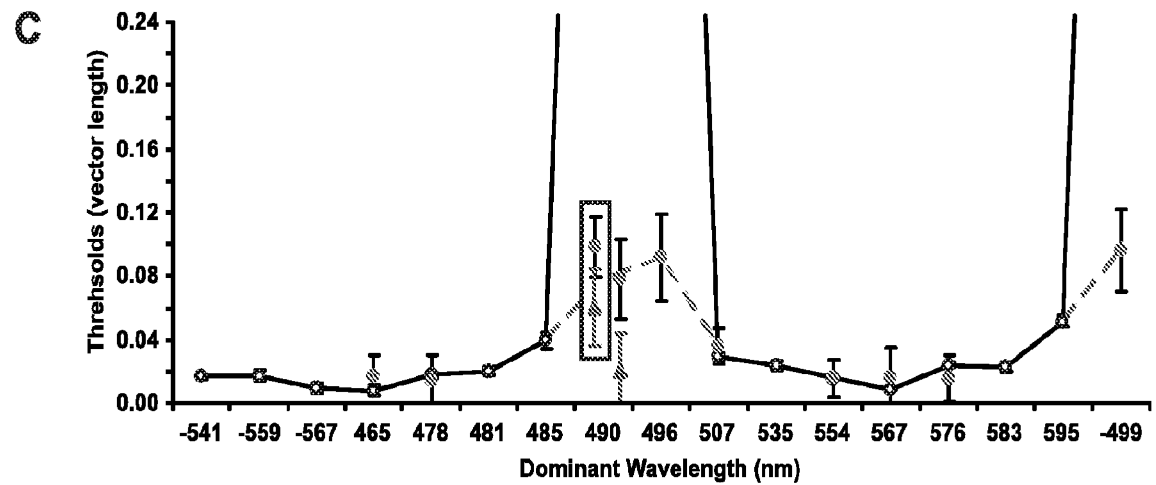
Figure 4:
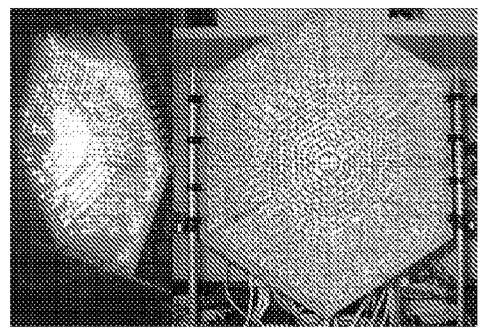
FIG. 4. a) The geodesic dome was created by placing trapezoidal-shaped circuit boards edge-to-edge. This structure holds the light emitting diodes (LEDs) so they converge on a single focal point. b) The circuit board takes the incoming control signals from the Retis-can mf-ERG and reroutes and modifies them to work with the new dome. The most frequent integrated circuit on the board are the constant current devices. c) The spectral composition of the red LED. d) The spectral composition of the green LED. e) The spectral sensitivity curves for the human M- (solid line) and L- (dashed line) cone photoreceptors. f) The activation of M-opsin (solid line) and the L-opsin (dashed line) in response to both the red and green LEDs.
Figure 4:
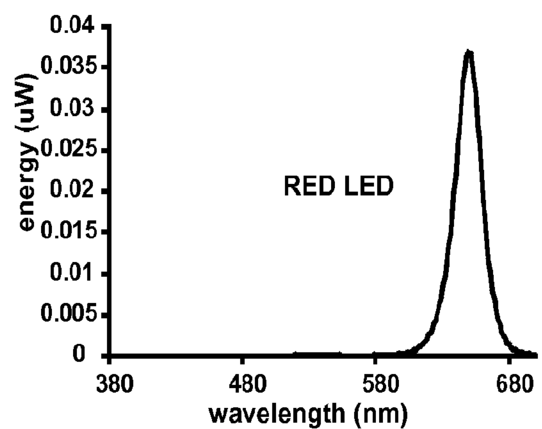
Figure 4:
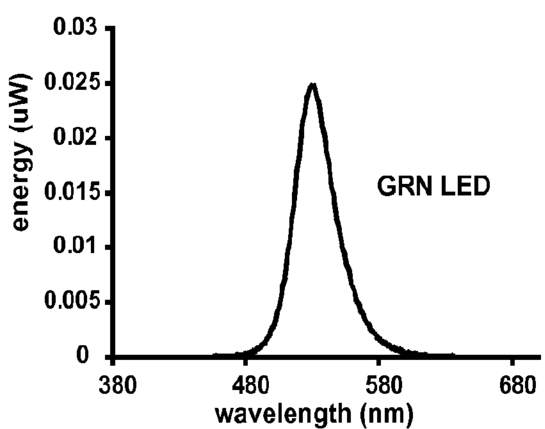
Figure 4:
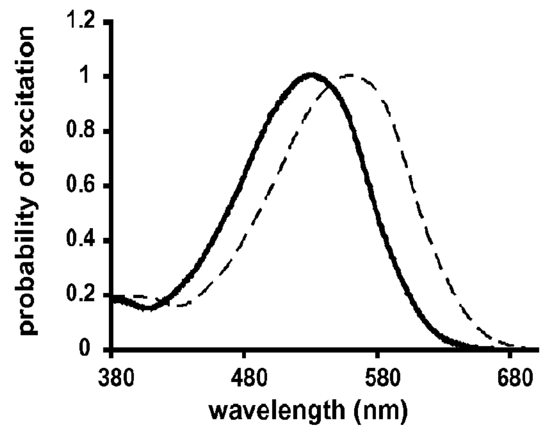
Figure 4:
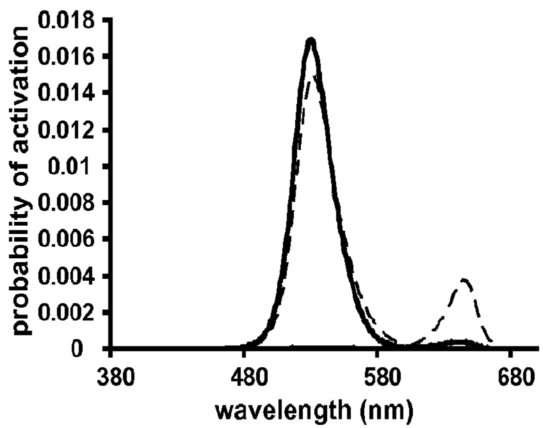
Figure 5:
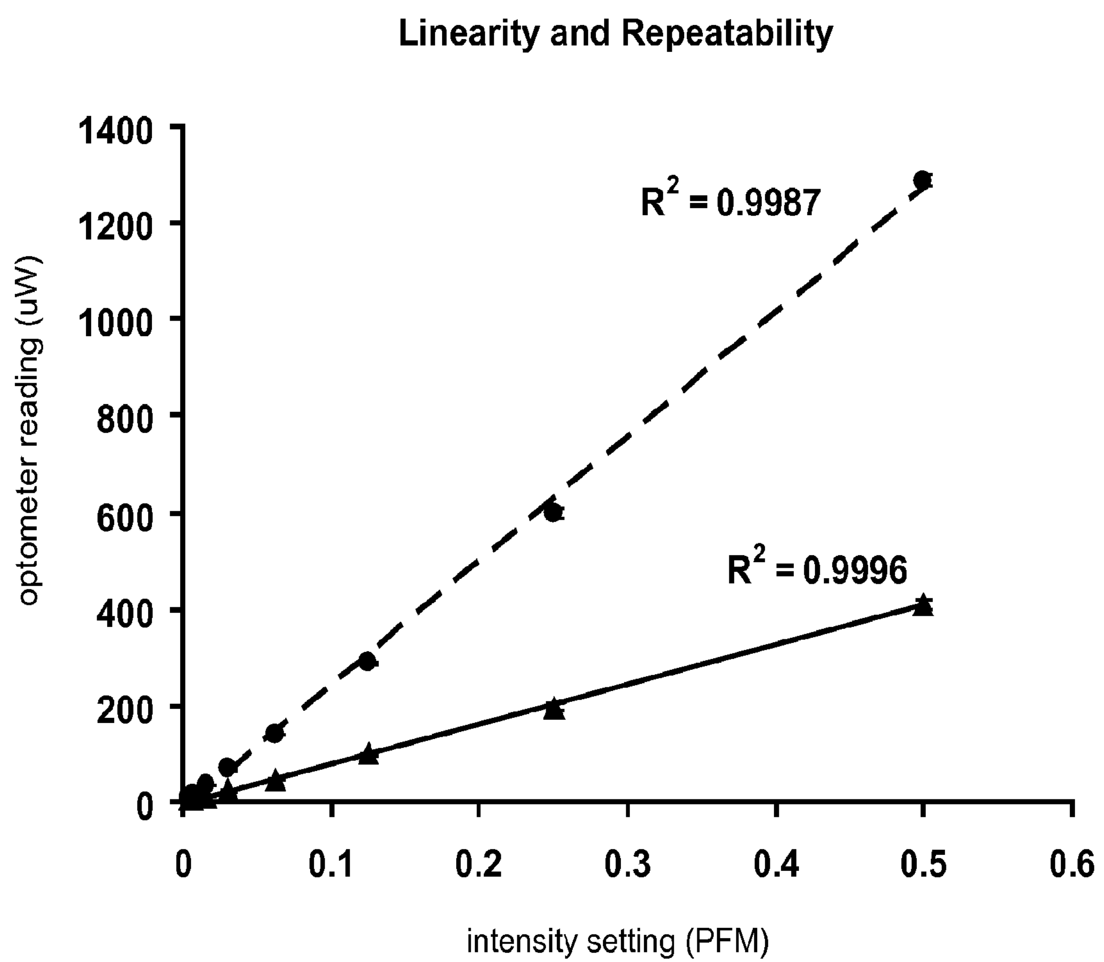
FIG. 5. Circles and dashed line represent the red LED out-puts in microwatts as a function of intensity; triangles and solid line represent the green LED outputs. Each data point represents an average of 3 measurements. Error bars are three standard deviations (99.7% confidence interval). To measure linearity, r2 values were computed for both the red and green LEDs.
Figure 7:
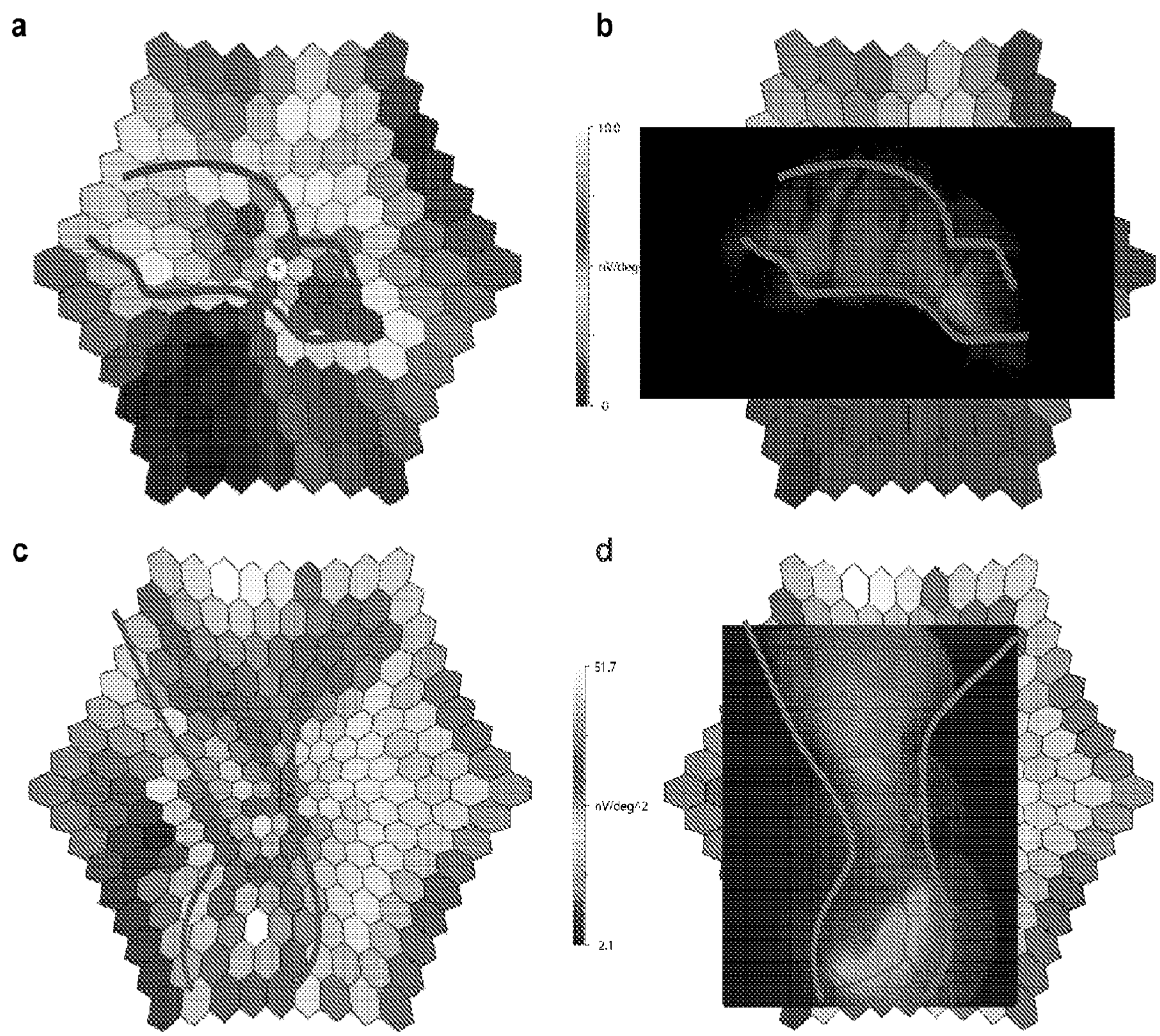
FIG. 7. a) Gerbil mf-ERG data in response to the L-cone isolating red stimulus. Locations of the retina that show a large amount of activity in response to stimulation by the red LEDs are indicated in red, while those areas that show the lowest amount of activation are indicated in blue (see scale). Gray lines show borders of the region where the mfERG response was highest. b) GFP fluorescence fundus image from the gerbil, scaled to the appropriate size, overlaid on the red-light mf-ERG data. The gray lines from (a) were copied into (b) to illustrate that areas of increased mf-ERG response corresponded to the same locations where robust GFP fluorescence was present. c) Red-light mf-ERG data from the squirrel monkey, which received two injections of the virus mixture, one superiorly and one inferiorly. d) A montage of GFP fluorescence images from the squirrel monkey, scaled to the appropriate size, overlaid on the mfERG data.
Figure 8:
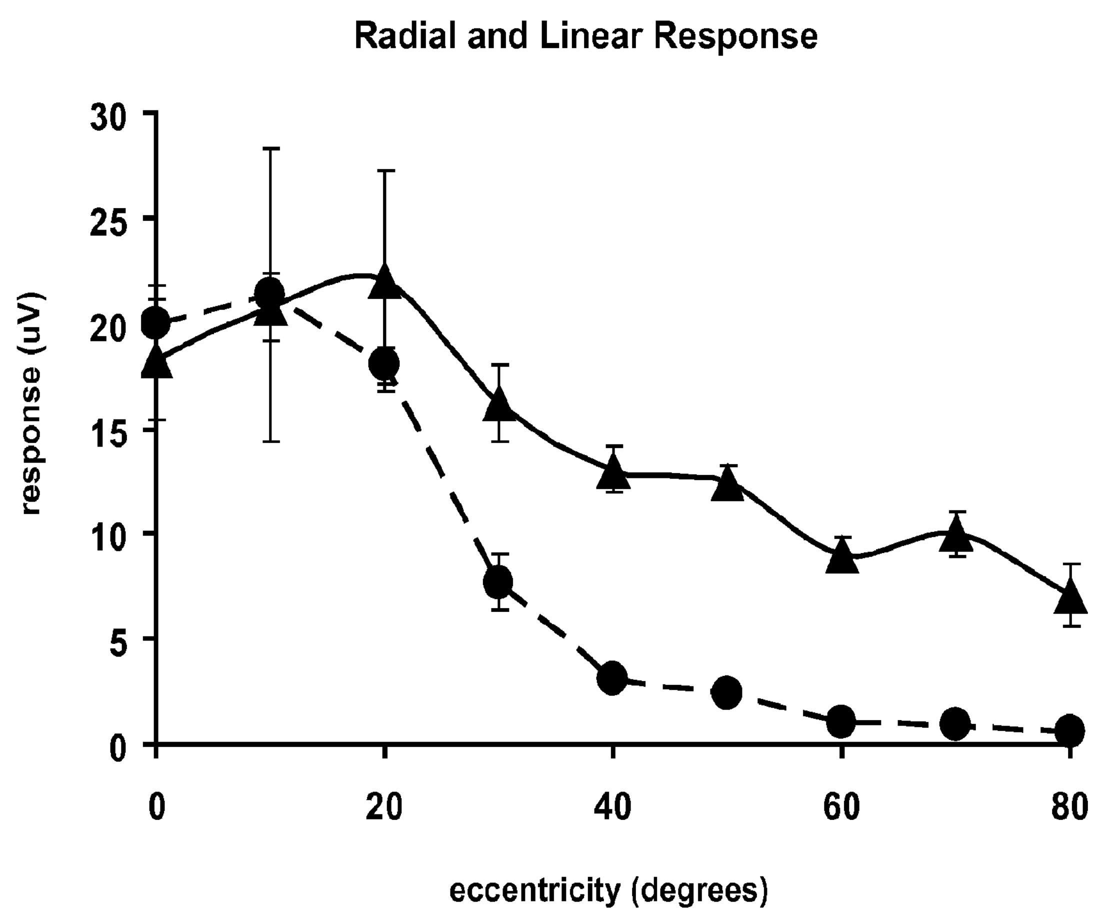
FIG. 8. The circles represent ERG response from LEDs that were moved on a linear path while the subject fixated forward. By 30 degrees, the signal is already less than half. In contrast, the triangles represent ERG response from LEDs that were fixed on a boom and rotated so that the LEDs always pointed at the pupil. Under this experimental protocol, −3 dB occurs first at 60 degrees.

The change in spectral sensitivity measured with the mf-ERG is necessary but not sufficient to produce a new colour vision capacity. For example, individuals with L but no M cones (termed deuteranopes) have a relatively enhanced sensitivity to red light but they are still as dichromatic as individuals with M but no L cones (protanopes), in that they are unable to distinguish particular "colours" from grey. To verify that the behavioural change observed in animals expressing the L pigment transgene was not purely a shift in spectral sensitivity (see FIG. 2*d*), monkey 1 was also tested on DWs=496 and 500 nm, and monkey 2 was tested on DWs 496 and 507 nm. Together, these DWs span the possible confusion points for deuteranopes and protanopes and for any intermediate dichromatic forms that could arise from expressing combinations of L and M pigments. As shown in FIG. 3*b* and *c,* both monkeys' measured thresholds for these additional hues were similar to their thresholds for DW=490 nm, demonstrating they now lacked a spectral neutral point and have become truly trichromatic. Furthermore, treated monkeys were able to discriminate blue-green (DW=490 nm) when it was tested against a red-violet background (DW=−499 nm), instead of the grey background, indicating that the monkeys' newly-acquired "green" and "red" percepts were distinct from one another. The treated monkeys' improvement in colour vision has remained stable for over 2 years and we plan to continue testing the animals to evaluate long term treatment effects.

Classic experiments in which visual deprivation of one eye during development caused permanent vision loss[1] led to the idea that inputs must be present during development for the formation of circuits to process them. From the clear change in behaviour associated with treatment, compared both between and within subjects, we conclude that adult monkeys gained new colour vision capacities because of gene therapy. These startling empirical results provide insight into the evolutionary question of what changes in the visual system are required for adding a new dimension of colour vision. Previously, it seemed possible that a transformation from dichromacy to trichromacy would require evolutionary/developmental changes, in addition to acquiring a third cone type. For example, L and M opsin-specific genetic regulatory elements might have been required to direct the opsins into distinct cone types[9] that would be recognized by L and M cone-specific retinal circuitry[10], and to account for cortical processing, multi-stage circuitry[11] might have evolved specifically for the purpose of trichromacy. However, our results demonstrate that trichromatic colour vision behaviour requires nothing more than a third cone type. As an alternative to the idea that the new dimension of colour vision arose by acquisition of a new L vs. M pathway, it is possible that it exploited the pre-existing blue-yellow circuitry. For example, if addition of the third cone class split the formerly S vs. M receptive fields into two types with differing spectral sensitivities, this would obviate the need for neural rewiring as part of the process of adopting new colour vision.

Some form of inherent plasticity in the mammalian visual system can be inferred from the acquisition of novel colour vision, as was also demonstrated in genetically engineered mice[12]; however, the point has been made that such plasticity need not imply that any rewiring of the neural circuitry has occurred[13]. Similarly, given the fact that new colour vision behaviour in adult squirrel monkeys corresponded to the same time interval as the appearance of robust levels of transgene expression, we conclude that rewiring of the visual system was not associated with the change from dichromatic to trichromatic vision.

Treated adult monkeys unquestionably respond to colours previously invisible to them. The internal experiences associated with the dramatic change in discrimination thresholds measured here cannot be determined; therefore, we cannot know whether the animals experience new internal sensations of "red" and "green." Nonetheless, we do know that evolution acts on behaviour, not on internalized experiences, and we suggest that gene therapy recapitulated what occurred during evolution of trichromasy in primates. These experiments demonstrate that a new colour vision capacity, as defined by new discrimination abilities, can be added by taking advantage of pre-existing neural circuitry and, internal experience aside, full colour vision could have evolved in the absence of any other change in the visual system except the addition of a third cone type.

Gene therapy trials are underway for Leber's congenital amaurosis[14-16]. Thus far, treatment has been administered to individuals who have suffered retinal degeneration from the disease. The experiments reported here are the first to use gene therapy in primates to address a vision disorder in which all photoreceptors are intact and healthy, making it possible to assess the full potential of gene therapy to restore visual capacities. Treatment allowing monkeys to see new colours in adulthood provides a striking counter-example to what occurs under conditions of monocular deprivation. For instance, it is impossible to restore vision in an adult who had grown up with a unilateral cataract. Future technologies will allow many opportunities for functions to be added or restored in the eye. While some changes may produce outcomes analogous to monocular deprivation, we predict that others, like gene therapy for red-green colour blindness, will provide vision where there was previously blindness.

Methods Summary for Example 1

Viral vector. CHOPS2053 was a 2.1 kb fragment containing the locus control region (LCR) and proximal promoter (PP) upstream of the human X-chromosome opsin gene array[9,17]. These elements (also known as pR2.1) have been shown to target transgene expression to mammalian L/M cones[3,18]. RHLOPS was a 1.2 kb fragment containing recombinant human L opsin cDNA. A clone of the human L opsin cDNA[19], known as hs7, was generously provided by J. Nathans. The QuickChange kit (Stratagene) was used to convert codon 180 so that it would encode a human L pigment maximally sensitive to 562 nm[20]. The virus was made using the genome from rAAV serotype 2 and the capsid from serotype 5, and the preparation had $9\times10^{13}$ DNase-resistant vector genome containing particles per mL. To prevent vector aggregation, 0.014% Tween 20 was added to the final vector preparation. A total of $2.7\times10^{13}$ viral particles was injected per eye.

An earlier version of the L-opsin coding rAAV2/5 used in previous unsuccessful experiments contained an extra 146 base pair segment between the splice donor/acceptor site and the translational start codon of the L-opsin gene that had been carried over from the cloning vector. Because we were concerned that this fragment may have interfered with transgene expression, a second version of L-opsin rAAV2/5 in which the extra 146 bp had been removed was used in later experiments described here. In addition to modifying the vector, we also increased the amount of viral particles delivered per eye by approximately 16-fold, from $1.7\times10^{12}$ to $2.7\times10^{13}$. Thus, we cannot conclude from this set of experiments what exact titer of viral particles was required to produce the effects on color vision behaviour, or exactly what effects, if any, the extra 146 bp had on transgene expression in earlier unsuccessful attempts.

The single-stranded DNA genome of conventional rAAV vectors, including rAAV2/5 used here, is devoid of Rep coding sequences. Thus, the vector genome is stabilized predominantly in an episomal form; however, the potential for integration exists[21]. According to NIH guidelines, the viral vector used here is rated biosafety level 1 (BSL1), and animal biosafety level 1 (ABSL1) meaning no special precautions were required in handling the virus or animals treated with the virus. Following treatment, squirrel monkeys had an increase in AAV antibody titers, ranging from 4-12 fold. Antibody titers remained unchanged in untreated control animals who were housed with treated animals.

Subretinal Injections. Subretinal injections were performed by a vitreo-retinal surgeon (T. B. C.) using a KDS model 210 syringe pump under a stereomicroscope. A 500 μL Hamilton Gastight (#1750TTL) Luer Lock syringe was connected to 88.9 cm of 30 gauge teflon tubing with male Luer Lock adapters at both ends (Hamilton 30TF double hub), which was then connected to a 30 gauge Becton Dickinson Yale regular bevel cannula (ref #511258) that was manually bent to produce a 135° angle 1.5 mm from the tip. All components were sterilized prior to use. The syringe and tubing were filled with sterile lactated Ringers solution to produce a dead volume of approximately 210 μL. Just prior to injection, 300 μL of rAAV was withdrawn using a rate of 100 μL/min.

Squirrel monkeys were anesthetized using intramuscular injections of ketamine (15 mg/kg) and xylazine (2 mg/kg); atropine (0.05 mg/kg) was also given to reduce airway secretions. The eye was dilated with 2-3 drops of tropicamide (1%) and treated with 1 drop each of betadine (5%), vigamox (0.5%), and proparacaine (1%). Subconjunctival injection of 0.1 mL of lidocaine (2%) was given and the anterior portion of the eye was exposed by performing a temporal canthotomy followed by limited conjuntival peritomy. Eyelids were held open with a speculum designed for premature infants. A temporal sclerotomy was made 1 mm posterior to the limbus with a 27 gauge needle, through which the injection cannula was inserted. Three subsequent 100 μL injections were made at different subretinal locations using an infusion rate of 1060 μL/min. Post-procedure, 0.05 mL each of decadron (10 mg/mL), kenalog (40 mg/mL), and cephazolin (100 mg/mL) were injected subconjunctivaly; 1 drop each of betadine (5%) and vigamox (0.5%) and a 0.6 cm strip of tobradex (0.3% tobramycin, 0.1% dexamethasone) ointment were applied topically; 10-20 mL of subcutaneous fluids (sterile lactated Ringers) were also given. Subsequent administration of steroids and analgesics were administered as needed post-procedure for potential inflammation or discomfort.

Confocal Microscopy. The animal in FIG. 1*c* and *d* succumbed to respiratory illness, unrelated to gene therapy, approximately 2 years and 3 months post-injection. The retina was fixed in 4% paraformaldehyde in phosphate buffered saline (PBS), and rinsed in PBS with 10% and 30% sucrose. It was sequentially incubated with 10% Normal Donkey Serum, rabbit monoclonal antibody to M/L opsin (Chemicon AB5405), and a Cy3 (red) conjugated donkey anti-rabbit antibody (Jackson Immunoresearch). Confocal images were analyzed using ImageJ (rsbweb.nih.gov). In the middle panel of FIG. 1*e,* magenta dots mark cone locations, and the red anti-M/L-opsin antibody staining was removed to show GFP-expressing (green) cells more clearly.

Behavioural Colour Vision Assessment. A three-alternative forced-choice paradigm in which position and saturation of the stimulus was randomized between trials was used. Monkeys had to discriminate the location of a coloured patch of dots that varied in size and brightness, surrounded by similarly varying grey dots. When animals touched the coloured target, a positive tone sounded and a juice reward was given; the next stimulus appeared immediately. (The squirrel monkey shown in FIG. 2*c* is drinking a reward from a previous trial.) If the wrong position was chosen, a negative tone sounded, and a 2-3 sec "penalty time" occurred before the next trial.

For each hue, monkeys were tested on up to 11 different saturations ranging from 0.01 to 0.11 in u', v' colour space (CIE 1976) and a threshold was calculated, which was taken as the saturation required to reach a criterion of 57% correct, the value determined to be significantly greater than chance (33% correct, P=0.05); see ref. 6 for full details.

References for Example 1

1. Wiesel, T. N. & Hubel, D. H. Single-cell responses in striate cortex of kittens deprived of vision in one eye. *J. Neurophysiol.* 26, 1003-1017 (1963).
2. Jacobs, G. H. A perspective on color vision in platyrrhine monkeys. *Vision Res.* 38, 3307-3313 (1998).
3. Li, Q., Timmers, A. M., Guy, J., Pang, J. & Hauswirth, W. W. Cone-specific expression using a human red opsin promoter in recombinant AAV. *Vision Res.* 48(2007).
4. Reffin, J. P., Astell, S. & Mollon, J. D. Trials of a computer-controlled colour vision test that preserves the advantages of pseudo-isochromatic plates. in *Colour Vision Deficiencies X*69-76 (Kluwer Academic Publishers, Dordrecht, 1991).
5. Regan, B. C., Reffin, J. P. & Mollon, J. D. Luminance noise and the rapid determination of discrimination ellipses in colour deficiency. *Vision Res.* 34, 1279-1299 (1994).
6. Mancuso, K., Neitz, M. & Neitz, J. An adaptation of the Cambridge Colour Test for use with animals. *Vis. Neurosci.* (2006).
7. Kuchenbecker, J., Sahay, M., Tait, D. M., Neitz, M. & Neitz, J. Topography of the long- to middle-wavelength sensitive cone ratio in the human retina assessed with a wide-field color multifocal electroretinogram. *Vis. Neurosci.* 25, 301-306 (2008).
8. Mancuso, K. et al. Recombinant adeno-associated virus targets passenger gene expression to cones in primate retina. *J. Opt. Soc. Am. A Opt. Image Sci. Vis.* 24, 1411-1416 (2007).
9. Nathans, J., Piantanida, T. P., Eddy, R. L., Shows, T. B. & Hogness, D. S. Molecular genetics of inherited variation in human color vision. *Science* 232, 203-210 (1986).
10. Shapley, R. Specificity of cone connections in the retina and color vision. Focus on "Specificity of cone inputs to macaque retinal ganglion cells". *J. Neurophysiol.* 95, 587-588 (2006).
11. DeValois, R. L. & DeValois, K. K. A multi-stage color model. *Vision Res.* 33, 1053-1065 (1993).
12. Jacobs, G. H., Williams, G .A., Cahill, H. & Nathans, J. Emergence of Novel Color Vision in Mice Engineered to Express a Human Cone Photopigment. *Science* 315, 1723-1725 (2007).
13. Makous, W. Comment on "Emergence of Novel Color Vision in Mice Engineered to Express a Human Cone Photopigment". *Science* 318, 196 (2007).
14. Maguire, A. M. et al. Safety and efficacy of gene transfer for Leber's congenital amaurosis. *N. Engl. J. Med.* 358, 2240-2248 (2008).
15. Bainbridge, J. W. & Ali, R. R. Success in sight: The eyes have it! Ocular gene therapy trials for LCA look promising. *Gene Ther.* 15, 1191-1192 (2008).
16. Cideciyan, A. V. et al. Human gene therapy for RPE65 isomerase deficiency activates the retinoid cycle of vision but with slow rod kinetics. *Proc. Natl. Acad. Sci. U. S. A.* 105, 15112-15117 (2008).
17. Wang, Y. et al. A locus control region adjacent to the human red and green visual pigment genes. *Neuron* 9, 429-440 (1992).
18. Mauck, M. C., Mauncuso, K., Kuchenbecher, J., Connor, T. B., Hauswirth, W. W., Neitz, J., Neitz, M. Longitudinal evaluation of expression of virally delivered transgenes in gerbil cone photoreceptors. *Vis. Neurosci.* 25, 273-282 (2008).
19. Nathans, J., Thomas, D. & Hogness, D. S. Molecular genetics of human color vision: the genes encoding blue, green, and red pigments. *Science* 232, 193-202 (1986).
20. Neitz, M., Neitz, J. & Jacobs, G. H. Spectral tuning of pigments underlying red-green color vision. *Science* 252, 971-974 (1991).
21. Büning, H., Perabo, L., Coutelle, O., Quadt-Humme, S. & Hallek, M. Recent developments in adeno-associated virus vector technology. *J. Gene Med.* 10, 717-733 (2008).

Example 2: Description and Validation of new LED-based, Wide-Field, Color mf-ERG The electroretinogram (ERG) is an electrophysiologic recording technique used to measure electrical activity of the entire retina. The electrochemical potential of retinal cells change in response to light, which in turn induces voltage on an electrode placed on the cornea and/or sclera. The first ERGs were recorded by a Swedish physiologist working in the mid-1800's in amphibian retina. Since this time the technique has been widely incorporated in clinical practice as a diagnostic tool. Marriage of physiology to engineering has led to a variety of stimuli and analysis paradigms which can tease out specific cellular responses or region specific information. The latter has been motivated by the fact that the topographical organization of the retina plays an important role in disease with different diseases being characterized by different affected retinal areas. Early attempts to evaluate the function of specific retinal regions using the ERG illuminated only a small patch of retina, however, such "focal ERGs" have the drawback that light reflected from the focal area onto other retinal regions produces an ERG response that cannot be uncoupled from that produced by the region of interest. The other problem is that obtaining any type of a topographical map of retinal function using the mono-focal approach is prohibited by the time required to obtain ERGs serially from many different retinal regions. Both problems have been solved with the development of the multifocal- (mf-) ERG, pioneered by Erich Sutter in the early 1990s (Sutter, 1991). Mf-ERGs perform a series of individual focal ERG experiments simultaneously by taking advantage of either (1) correlation techniques or (2) frequency encoding. In this way, a complete topographical map of electrical responses over a large retinal region is obtained in a relatively short period of time.

The typical ERG apparatus for mf-ERGs stimulates a hexagonal patch of retina with a 20 degree radius and uses video display. More recently a display that employs white light emitting diodes (LEDs) was designed for use with a frequency encoding method for obtaining mf-ERGs. Having a stimulus that could reach further into the periphery would be useful in the early detection of retinal diseases that progress from peripheral to central retina. Additionally, individuals with normal trichromatic color vision express three distinct photopigments, or opsins, in separate classes of cone photoreceptor: short- (S-), middle- (M-), and long- (L-) wavelength sensitive. The S-cones are maximally sensitive to short wavelengths of light near 420 nm; M-cones have their maximal response near 530 nm; and the L-cones are most sensitive near 560 nm. Thus, an mf-ERG stimulus containing LEDs of different wavelengths would have applications in characterizing the topography of expression of the different opsin transgenes in the eyes of living subjects treated with gene therapy.

In particular, in gene therapy treatments administering recombinant adeno-associated virus (rAAV) carrying a human L-opsin gene M-opsin gene or S-opsin gene to primates that have two cone types to produce trichromatic color vision. As such, a non-invasive objective method is needed to determine the locations of functioning opsin expression in vivo.

Here we describe a wide-field color mf-ERG capable of stimulating a radius greater than 70 degrees. The wide field mf-ERG has a colored LED-based stimulus that incorporates a new design capable of maintaining viable signal-to-noise ratio (SNR) out into the far peripheral retina.

mf-ERG and Stimulus Panel

An LEDs as a light source was chosen because new advancements in LED technology allow for a large number of focused photons to be emitted from a point source. Additionally, LEDs are available in a variety of single peak narrow-bandwidth packages. The stimulus contained 1024 doublet pixels each containing a red (653 nm, half-bandwidth 22 nm, FIG. 2.1*c*) and a green (527 nm, half-bandwidth 33 nm, FIG. 2.1*d*) LED. Thus, the new display had 2,048 paired green and red LEDs. LEDs have inherent manufacturing variations in their breakdown resistance. Since the amount of current is proportional to the number of photons per unit time, applying a constant voltage across the LEDs would result in varying photon output. To circumvent these issues and ensure repeatability and linearity, constant current integrated circuit chips (Allegro A6276) were used to drive the LEDs (FIG. 2.1*b*). These devices are designed to maintain constant current despite fluctuations in anode voltage. To prevent variation in peak wavelength over varied intensities, a pulse frequency modulation (PFM) signal was used (Swanson, Ueno, Smith, & Pokorny, 1987).

Using red and green LEDs, it is possible to isolate responses of L- or M-cones using silent substitution. Integrating the spectral composition of the green LED with the spectral sensitivity curves of the human M- and L-photopigments (FIG. 2.1*e*) yields that approximately equal quanta are caught by both photopigments (FIG. 2.1*f*). In contrast, the red LED is six times more effective at stimulating the L photopigment than it is the M (FIG. 2.1*f*). Isolation of responses that are due to transduction from an introduced L-opsin transgene, M-opsin transgene or S-opsin transgene are straightforward in primates because red, blue or green LEDs can be chosen that are much more effective for the L-opsin M-opsin or S-opsin transgene respectively than for the endogenous pigments of the untreated dichromatic primates. In the case of Squirrel monkeys, they have S-cones maximally sensitive near 430 nm, and they can express any of several variants of middle-to-long wavelength opsin including L or M. The monkey used in validation experiments had M-cones sensitive near 532 nm, in addition to his S-cones. Thus, following the administration of the L-opsin transgene via subretinal injection, the mf-ERGs of squirrel monkey were predicted to show elevations in mf-ERG amplitude to red light in regions corresponding areas of the retina transduced, and distal areas would show progressively lower amplitudes to the L-cone isolating stimulus.

Resolution of the stimulator was 1024 LED over a larger stimulating area of about 150 degrees of visual field. Sensitivity of the measurement can be increased by summing more retinal responses per unit area and by using ultra-bright LEDs. Other new techniques that were used to prevent peripheral SNR fall-off included the use of trapezoidal shaped printed circuit boards that when placed edge-to-edge created a geodesic dome (FIG. 2.1*a*). The advantage of this design was that LEDs were held equidistantly from and pointing toward a single focal point where the subject's pupil was positioned. Any variation in directionality caused by imperfect sphericity was corrected by aiming each LED individually. In the typical usage, LEDs from areas of the dome shaped stimulator were summed so that there were 37 individual segments, which together subtended the 150° of visual angle, thus allowing a wide-field functional map of an area covering almost the entire retina to be produced.

There are two mathematical methodologies available to code and decode the topographical regions on the recording electrode: One is a cross-correlation technique called m-sequence and the other is a frequency encoding technique called cyclic summation. Cyclic summation is preferred in our application because it has been empirically shown to provide higher signal-to-noise ratio than m-sequence (Lindenberg, Horn, & Korth, 2003). Also, cyclic summation cannot be done using any kind of conventional CRT or LCD video display. Cyclic summation requires independent control of every segment of the display. Conventional video displays update the entire screen with every video frame typically at 60 Hz. In cyclic summation, each segment being analyzed is updating at a slightly different frequency. Typically, the "center frequency" is 30 Hz but each segment fractionally different from 30 Hz, i.e., 30.00 Hz, 30.10 Hz, 30.20 . . . etc. In the analysis, responses to different areas of the retina to different segment frequencies are used to generate a map of retinal responses which are read out as electrophysiological "activity." For example, after gene therapy using an L opsin gene in a primate retina containing only M and S cones, areas of retina that express the newly introduced L opsin will have higher electrical activity in response to the red LED light relative to the green light than areas of the retina not expressing the transgene. This allows the effectiveness of the gene therapy in terms of areas responding their time course to be monitored with an objective measure.

In practice, we define the following parameters; $f_c$=center frequency, T=total time, Q=number of segments, and n=0 .. . (Q−1). The number of cycles per segment is given by $$cycles_n = f_c \cdot T - \left[\frac{Q-1}{2} + n\right]. \tag{2.1}$$

Then, $f_n$ represents the frequencies at which each segment is encoded into the stimulus is $$f_n = \frac{cycles_n}{T}. \tag{2.2}$$

Finally, by windowing and summing the recorded retinal waveform, defined as w(t), region specific signal, $Activity_n$, can be extracted in equation 2.3, $$Activity_n = \sum_{n=0}^{(Q-1)} \sum_{m=0}^{(cycles_n-1)} w\left(\frac{m}{f_n} \ \cdots \ \frac{(m+1)}{f_n}\right). \tag{2.3}$$

For our purposes, $f_c$=30 Hz, T=40 seconds, and Q=37. In the retina, an additional advantage of the cyclic summation method are that the intensity and temporal frequency of the LEDs can be specified to isolate cone photoreceptor responses and silence rod photoreceptor responses.

Repeatability, Linearity, and SNR

Measurements for repeatability and linearity were made using a UDT S370 Optometer (UDT Instruments, San Diego, CA). LED outputs were measured in microwatts (uW) at seven different intensity settings, in random order. Three complete sets of data were taken on three separate days. All measurements were taken after the instrument became equilibrated with the ambient room temperature, which reflects normal operation of the instrument.

Signal-to-noise ratio was measured using a human subject by first placing an opaque material in front of the stimulus and running successive mf-ERGs. Voltages received during the blocked trials were taken as the noise of the instrument. Signal was then measured by performing mf-ERGs on four human subjects with normal trichromatic color vision. To compare SNR as a function of eccentricity, signal and noise were broken into different eccentric rings. Best subject and the average of all subjects were calculated for each ring. Tests involving human subjects were done in accordance with the principles embodied in the Declaration of Helsinki.

Viral Vector and Subretinal Injections

To validate whether the instrument operated as expected, a mixture of two recombinant adeno-associated viruses was injected sub-retinally in a gerbil (*Meriones unguiculatus*) and a squirrel monkey (*Saimiri sciureus*). One virus, rAAV.CHOPS2053.GFP, carried a gene for green fluorescent protein (GFP) and the other virus, rAAV.CHOPS2053.RHLOPS, coded for human L-opsin. The L-opsin virus was identical to the GFP virus except that a Not I restriction fragment containing the coding sequence for green fluorescent protein was replaced with a 1.2 kb Not I restriction fragment containing recombinant human L opsin cDNA. The opsin gene encoded a human L pigment that is predicted from the deduced amino acid sequence to be maximally sensitive to 562 nm light. In order to provide a method for visualizing transduced cone photoreceptors using immunohistochemistry in future experiments, the sequence of the human L opsin transgene was changed so that the last 12 amino acids matched the known epitope for the monoclonal antibody OS-2. This antibody was previously shown to specifically label S or UV cones in mammalian and primate retina. The C-terminal 12 amino acids of human S opsin were demonstrated to be the epitope. The substitution of the C-terminal 12 amino acids of S-opsin into L-opsin is not predicted to change the spectral sensitivity of the L-opsin trans-gene product.

Subretinal injections were performed. Briefly, gerbils were anesthetized using a combination of Ketamine (50 mg/kg) and Xylazine (2 mg/kg), and it received two 5 uL subretinal injections of a 1:1 (volume:volume) mixture of rAAV.CHOPS2053.GFP and rAAV.CHOPS2053.RHLOPS that were placed in the superior retinal area. A color mf-ERG was then performed on this animal at 6 months post-injection. Squirrel monkeys was anesthetized using 15 mg/kg ketamine and 2 mg/kg xylazine, and they received two 100 uL subretinal injections of a virus mixture containing 110 uL of rAAV.CHOPS2053.GFP and 220 uL of rAAV.CHOPS2053.RHLOPS. Both injections were positioned near the fovea, with the first injection placed superiorly, and the second injection placed in the inferotemporal region of the retina. A color mf-ERG was performed on this animal about 42 weeks, or 10.5 months post-injection. All of these procedures were conducted in accordance with the experimental animal care and usage guidelines of the United States National Institutes of Health.

Fundus Exams

Both the gerbil and squirrel monkey had fundus images taken at multiple time points post-injection to observe expression of the GFP transgene over time. Fundus images were obtained using the fluorescein angiography mode of the RetCam II digital imaging system (Massie Laboratories, Pleasanton, CA. For the gerbil, images were taken with a lens designed for detecting retinopathy in premature infants, which provides a 130° field of view, and for the monkey, a high magnification 30° lens was used. Thus, multiple fundus images from the squirrel monkey were pieced together into a montage, in order to show a comparable retinal area.

Results

Measures of repeatability, linearity, and signal-to-noise ratio (SNR) were performed to evaluate the wide-field color ERG system. More properly, given n=2 . . . 8, m=½", and t=[0, ~3.5, 7] days, then intensity, $I_m(t)$, is said to be repeatable if $$s = 3 \cdot \sqrt{\frac{1}{2}\sum_{t=1}^{3}\left(I_m(t) - \overline{I_m(t)}\right)^2} \leq \varepsilon \quad (2.4)$$

where ε is defined as $$\varepsilon = 0.05 \cdot \max(\text{photon}_m). \quad (2.5)$$

The instrument was said to be linear if Pearson's $R^2$ was greater than 0.95. And finally, signal (in SNR) was is calculated by averaging response from four subjects, and noise was taken as the residual signal while an opaque material blocked stimulus.

Repeatability and linearity are demonstrated in FIG. 2.2. Each data point is an average of optometer measurements for the particular intensity setting taken on three separate days; error bars are the standard deviations with a 99.7% confidence interval. Pearson's R correlation was calculated and the coefficient of determination ($R^2$) values is shown. The red LEDs shared 0.9987 total variance and the green LEDs shared 0.9996 total variance demonstrating system is linear and repeatable over time. SNR values are shown in Table 2.1. The SNR was high for the inner segments of the stimulus panel; it decreased in more peripheral regions but remained high enough to allow measurements into the far periphery.

Because the GFP-coding virus and the L-opsin-coding virus were injected together at the same locations, fluorescence fundus images could be registered with mf-ERG data from the same animal in order to validate the redesigned wide-field color mf-ERG system. Areas of high GFP expression corresponded well to areas of high mf-ERG voltage in response to the L-cone isolating red stimulus (FIG. 2.3). Animals were insensitive to the red 653 nm wave-length light prior to injection, verifying that the signal measured in animals post-injection is true signal coming from the introduced L-opsin transgene product. In the squirrel monkey, the red-light mf-ERG data showed high voltage in the regions that corresponded to the fluorescence fundus images.

To evaluate whether the concave surface of the newly developed stimulator produces ERG amplitudes that are relatively constant with retinal eccentricity an experiment was performed in which flicker ERG responses were measured under two different conditions. In FIG. 2.4, the circles represent ERG responses from an LED traveling down a linear path while the subject fixated forward. On the same graph, triangles represent ERG responses from an LED traveling on a rotating boom while the subject fixated forward. The boom held the LEDs perpendicular to the cornea. Results from this experiment demonstrate the increase in signal given by the convex stimulator, compared to a traditional flat-panel LCD screen or CRT monitor. The curved stimulus design, in addition to the use of ultra-bright LEDs as the light source, increased the SNR sufficiently high in the far periphery to ensure viable signals were recorded from cone photoreceptors.

In the conventional mf-ERG, the signal amplitudes are greatly reduced in the periphery because the illumination from a flat screen falls off roughly as the cosine with increasing eccentricity. In our design, the redesigned stimulus had concave structure holding the LEDs such that the inner surface pointed perpendicular to the stimulated retinal area. In addition, similar to traditional mf-ERG stimulators, the number of LEDs in each segment was increased with eccentricity to compensate for the decrease in cone density.

If 40% of cones express the transgene the increase in red sensitivity should be that expected from a spectral ERG in which 20% of the total ERG contribution is from L opsin while 80% is from M opsin. This is consistent with the observed red sensitivity in both monkeys and gerbils.

This is the first time that measurements from cones in the far peripheral retina have been achieved. Results from these experiments indicate that the wide-field color mf-ERG system is a valid technique for measuring the topography of opsin expression in living subjects, and it will serve as an important tool for evaluating success of gene therapy in humans.

References for Example 2

Sutter, E. E. (1991). The Fast m-Transform: A Fast Computation of Cross-Correlations with Binary m-Sequences. *SIAM Journal on Computing,* 20(4), 686-694.

Swanson, W. H., Ueno, T., Smith, V. C., & Pokorny, J. (1987). Temporal modulation sensitivity and pulse-detection thresholds for chromatic and luminance perturbations. *Journal of the Optical Society of America A—Optics, Image Science and Vision,* 4(10), 13.

Lindenberg, T., Horn, F. K., & Korth, M. (2003). Cyclic summation versus m-sequence technique in the multifocal ERG. *Graefes Archive of Clinical Experimental Ophthalmology.,* 241(6), 505-510.

We claim:

1. An isolated nucleic acid expression vector comprising:

(a) a promoter region comprising an M opsin promoter comprising the nucleic acid sequence of SEQ ID NO: 2, wherein the promoter region is specific for primate retinal cone cells; and (b) a gene encoding a therapeutic protein comprising the amino acid sequence of SEQ ID NO: 11, wherein the gene is operatively linked to the promoter region.

2. The isolated nucleic acid expression vector of claim 1, wherein the expression vector is a recombinant adeno-associated virus (AAV) gene delivery vector.

3. The isolated nucleic acid expression vector of claim 1, wherein the therapeutic protein, when expressed in cone cells of a primate having color blindness and/or blue cone monochromacy (BCM), is capable of: 1) enabling the primate to visualize and to discriminate between red and green colors; and/or 2) restoring visual capacity in the primate.

4. The isolated nucleic acid expression vector of claim 3, wherein the visual capacity is selected from the group consisting of: a reduction or slowing of vision loss; improved visual acuity; and a decrease in abnormal sensitivity to bright lights.

5. The isolated nucleic acid expression vector of claim 1, further comprising an enhancer element upstream of the M opsin promoter, wherein the enhancer element comprises the nucleic acid sequence of SEQ ID NO: 51, and wherein the gene is operatively linked to the enhancer element.

6. The isolated nucleic acid expression vector of claim 1, further comprising an intron comprising a splice donor/acceptor region, wherein the intron is located downstream of the promoter region and is located upstream of the gene.

7. A formulation comprising packaged viral particles comprising the nucleic acid expression vectors of claim 1.

8. The formulation of claim 7, wherein the formulation is used to treat a cone cell disorder.

9. The formulation of claim 8, wherein the cone cell disorder is selected from the group consisting of color blindness, blue cone monochomacy, achromatopsia, incomplete achromatopsia, rod-cone degeneration, retinitis pigmentosa (RP), macular degeneration, cone dystrophy, blindness, Stargardt's Disease, and Leber's congenital amaurosis.

10. A recombinant host cells transfected or transduced with the nucleic acid expression vector of claim 1.

* * * * *